US007056687B2

(12) United States Patent
Lorens et al.

(10) Patent No.: US 7,056,687 B2
(45) Date of Patent: Jun. 6, 2006

(54) METHODS AND COMPOSITIONS FOR SCREENING FOR ALTERED CELLULAR PHENOTYPES

(75) Inventors: James Lorens, Portola Valley, CA (US); Todd M. Kinsella, Fayetteville, NC (US); Esteban Masuda, Menlo Park, CA (US); Yasumichi Hitoshi, Mountain View, CA (US); X. Charlene Liao, Palo Alto, CA (US); Denise Pearsall, Belmont, CA (US); Annabelle Freiro, South San Francisco, CA (US); Peter Chu, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 350 days.

(21) Appl. No.: 10/096,339

(22) Filed: Mar. 8, 2002

(65) Prior Publication Data

US 2003/0022196 A1 Jan. 30, 2003

Related U.S. Application Data

(63) Continuation-in-part of application No. 09/076,624, filed on May 12, 1998.

(51) Int. Cl.
*G01N 33/53* (2006.01)
*G01N 33/567* (2006.01)
*G01N 33/542* (2006.01)
*C12N 15/12* (2006.01)
*C12Q 1/66* (2006.01)

(52) U.S. Cl. .................. 435/7.2; 435/7.21; 435/7.8; 435/7.9; 435/8; 435/69.1

(58) Field of Classification Search ............... 435/7.2, 435/7.21, 7.8, 7.9, 8, 69.1
See application file for complete search history.

(56) References Cited

U.S. PATENT DOCUMENTS

| 5,219,752 | A | 6/1993 | Takazawa et al. |
| 5,654,150 | A | 8/1997 | King et al. |
| 5,773,731 | A | 6/1998 | Sakakura et al. |
| 5,804,387 | A | 9/1998 | Cormack et al. |
| 5,834,266 | A | 11/1998 | Crabtree et al. |
| 5,958,707 | A | 9/1999 | de Vries et al. |
| 6,280,937 | B1 * | 8/2001 | Luo et al. ............ 435/6 |
| 6,455,247 | B1 * | 9/2002 | Nolan et al. ......... 435/6 |
| 6,465,253 | B1 | 10/2002 | Wickham et al. |
| 6,613,563 | B1 | 9/2003 | Sosnowski et al. |
| 2002/0168649 | A1 | 11/2002 | Ferrick et al. |

FOREIGN PATENT DOCUMENTS

| DE | 4126414 | 2/1993 |
| WO | WO 92/14839 A1 | 9/1992 |
| WO | WO 95/25812 A2 | 9/1995 |
| WO | WO 95/25812 A3 | 9/1995 |
| WO | WO 96/30515 A1 | 10/1996 |
| WO | WO 96/38553 A1 | 12/1996 |
| WO | WO 96/40721 A1 | 12/1996 |

OTHER PUBLICATIONS

Adam, D., et al. "Signal transduction through a biomolecular receptor tyrosine protein kinase composed of a platelet-derived growth factor receptor-CD4 chimera and the nonreceptor tyrosine protein kinase Lck." *J Biol Chem*. Sep. 15, 1993; 268(26):19882-8.
Albrecht, B., et al. "A bifunctional control element in the human IgE germline promoter involved in repression and IL-4 activation." *Int Immunol*. Aug. 1994; 6(8):1143-51.
Allgood, V.E., et al. "Chimeric receptors as gene switches." *Curr Opin Biotechnol*. Aug. 1997; 8(4):474-9.
Amara, J.F., et al. "A versatile synthetic dimerizer for the regulation of protein—protein interactions." *Proc Natl Acad Sci USA*. Sep. 30, 1997; 94(20):10618-23.
Anders, R.A., et al. "Chimeric granulocyte/macrophage colony-stimulating factor/transforming growth factor-β (TGF-β) receptors define a model system for investigating the role of homomeric and heteromeric receptors in TGF-β signaling." *J Biol Chem*. Sep. 6, 1996; 271(36):21758-66.
Bazzoni, F., et al. "Chimeric tumor necrosis factor receptors with constitutive signaling activity." *Proc Natl Acad Sci USA*. Jun. 6, 1995; 92(12):5376-80.
Chaplin, P.J., et al. "Production of interleukin-12 as a self-processing 2A polypeptide." *Journal of Interferon and Cytokine Research*. 1999; 19:235-41.
Chen, L., et al. "Potentiation of cytochrome P450/cyclophosphamide-based cancer gene therapy by coexpression of the P450 reductase gene." *Cancer Res*. Nov. 1, 1997; 57(21):4830-7.
Claassen, J.L., et al. "Mechanism of pokeweed mitogen inhibition of rhIL-4-induced human IgE synthesis." *Cell Immunol*. Apr. 1992; 140(2):357-69.
Cormack, B.P., et al. "FACS-optimized mutants of the green fluorescent protein (GFP)." *Gene*. 1996; 173:33-8.
Declercq, W., et al. "Dimerization of chimeric erythropoietin/75 kDa tumour necrosis factor (TNF) receptors transduces TNF signals: necessity for the 75 kDa-TNF receptor transmembrane domain." *Cytokine*. Oct. 1995; 7(7):701-9.
De Felipe, P., et al. "Tricistronic and tetracistronic retroviral vectors for gene transfer." *Human Gene Therapy*. Sep. 1, 2000; 11:1921-31.

(Continued)

*Primary Examiner*—Joseph Murphy
(74) *Attorney, Agent, or Firm*—James S. Keddie; Carol L. Francis; James J. Diehl

(57) ABSTRACT

The invention relates to methods and compositions useful for screening for altered cellular phenotypes using an inducible expression system to enrich for and detect the altered phenotypes and, more particularly, relates to screening libraries of candidate bioactive agents, for example, nucleic acids and peptides, in cells using an regulatable expression system to enrich for a subpopulation of cells having an altered phenotype due to the presence of a candidate bioactive agent.

59 Claims, 67 Drawing Sheets

OTHER PUBLICATIONS

Desai, D.M., et al. "Ligand-mediated negative regulation of a chimeric transmembrane receptor tyrosine phosphatase." *Cell*. May 7, 1993; 73(3):541-54.

Donnelly, M.L., et al. "Analysis of the aphthovirus 2A/2B polyprotein 'cleavage' mechanism indicates not a proteolytic reaction, but a novel translational effect: a putative ribosomal 'skip'." *J Gen Virol*. May 2001; 82:1013-25.

Donnelly, M.L., et al. "The cleavage activities of aphthovirus and cardiovirus 2A proteins." *J Gen Virol*. Jan. 1997; 78:13-21.

Ezernieks, J., et al. "The human IgE germline promoter is regulated by interleukin-4, interleukin-13, interferon-alpha and interferon-γ via an interferon-γ-activated site and its flanking regions." *Eur J Biochem*. Sep. 15, 1996; 240(3):667-73.

Ferlin, W.G., et al. "CD40 signaling induces interleukin-4-independent IgE switching in vivo." *Eur J Immunol*. Dec. 1996; 26(12):2911-5.

Fiering, S., et al. "Single cell assay of a transcription factor reveals a threshold in transcription activated by signals emanating from the T-cell antigen receptor." *Genes Dev*. Oct. 1990; 4(10):1823-34.

Gauchat, J.F., et al. "Regulation of human IgE synthesis: the role of CD4+ and CD8+ T-cells and the inhibitory effects of interferon-alpha." *Eur Respir J Suppl*. Apr. 1991; 13:31s-38s.

Gauchat, J.F., et al. "Regulation of germ-line epsilon transcription and induction of epsilon switching in cloned EBV-transformed and malignant human B cell lines by cytokines and CD4+ T cells." *J Immunol*. Apr. 1, 1992; 148(7):2291-9.

Gauchat, F.F., et al. "Structure and expression of germline epsilon transcripts in human B cells induced by interleukin 4 to switch to IgE production." *J Exp Med*. Aug. 1, 1990; 172(2):463-73.

Gauchat, J.F., et al. "Modulation of IL-4 induced germline epsilon RNA synthesis in human B cells by tumor necrosis factor-α, anti-CD40 monoclonal antibodies or transforming growth factor-β correlates with levels of IgE production." *Int Immunol*. Mar. 1992; 4(3):397-406.

Ichiki, T., et al. "Regulation of the expression of human C epsilon germline transcript. Identification of a novel IL-4 responsive element." *J Immunol*. Jun. 15, 1993; 150(12):5408-17.

Jabara, H.H., et al. "Induction of germ-line and mature C epsilon transcripts in human B cells stimulated with rIL-4 and EBV." *J Immunol*. Nov. 15, 1990; 145(10):3468-73.

Jardieu, P. "Anti-IgE therapy." *Curr Opin Immunol*. Dec. 1995; 7(6):779-82.

Kawaguchi, Y., et al. "Expression of Fas-estrogen receptor fusion protein induces cell death in pancreatic cancer cell lines." *Cancer Lett*. Jun. 3, 1997; 116(1):53-9.

Kim, D.G., et al. "Construction of a bifunctional mRNA in the mouse by using the internal ribosomal entry site of the encephalomyocarditis virus." *Mol Cell Biol*. Aug. 1992; 12(8):3636-43.

Krishnan, K., et al. "Dimerization of a chimeric CD4-interferon-alpha receptor reconstitutes the signaling events preceding STAT phosphorylation." *Oncogene*. Jul. 4, 1996; 13(1):125-33.

Kumar, A., et al. "Human BCGF-12kD functions as an autocrine growth factor in transformed B cells." *Eur Cytokine Netw*. May-Jun. 1990; 1(2):109-13.

Loh, R.K., et al. "Role of protein tryosine kinases in CD40/interleukin-4-mediated isotype switching to IgE." *J Allergy Clin Immunol*. Oct. 1994; 94(4):784-92.

Loh, R.K., et al. "Mechanisms of inhibition of IgE synthesis by nedocromil sodium: nedocromil sodium inhibits deletional switch recombination in human B cells." *J Allergy Clin Immunol*. May 1996; 97(5):1141-50.

Luke, G.A., et al. "Translating the message." *Biologist*. Apr. 2001; 48(2):79-82.

Luo, H.Y., et al. "In vitro IgE production by Interleukin 4-stimulated human peripheral blood mononuclear cells is suppressed by rapamycin." *Clin Immunol Immunopathol*. Dec. 1991; 61(3):410-20.

Mares, J., et al. "A chimera between platelet-derived growth factor beta-receptor and fibroblast growth factor receptor-1 stimulates pancreatic beta-cell DNA synthesis in the presence of PDGF-BB." *Growth Factors*. 1992; 6(2):93-101.

McBratney, S., et al. "Internal initiation of translation." *Curr Opin Cell Biol*. Dec. 1993; 5(6):961-5.

Mikita, T., et al. "Requirements for interleukin-4-induced gene expression and functional characterization of Stat6." *Mol Cell Biol*. Oct. 1996; 16(10):5811-20.

Mizuguchi, H., et al. "IRES-dependent second gene expression is significantly lower than cap-dependent first gene expression in a bicistronic vector." *Mol Ther*. Apr. 2000; (1(4):376-82.

Ohashi, H., et al. "Ligand-induced activation of chimeric receptors between the erythropoietin receptor and receptor tyrosine kinases." *Proc Natl Acad Sci USA*. Jan. 4, 1994; 91(1):158-62.

Okuda, K., et al. "A chimeric receptor/oncogene that can be regulated by a ligand in vitro and in vivo." *J Clin Invest*. Oct. 1, 1997; 100(7):1708-15.

Qiu, G., et al. "Human IgE mRNA expression by peripheral blood lymphocytes stimulated with interleukin 4 and pokeweed mitogen." *Eur J Immunol*. Oct. 1990; 20(10):2191-9.

Rothman, P., et al. "Identification of a conserved lipopolysaccharide-plus-interleukin-4-responsive element located at the promoter of germ line epsilon transcripts." *Mol Cell Biol*. Nov. 1991; 11(11):5551-61.

Rothman, P., et al. "Structure and expression of germ line immunoglobulin heavy-chain epsilon transcripts: interleukin-4 plus lipopolysaccharide-directed switching to C epsilon." *Mol Cell Biol*. Apr. 1990; 10(4):1672-9.

Rudert, F., et al. "Apoptosis through CD95 (Fas/APO-1), but not a CD40/CD95 chimeric receptor, is inhibited by phorbol-12-myristate-13-acetate." *DNA Cell Biol*. Feb. 1997; 16(2):197-205.

Rudert, F., et al. "Apoptosis in L929 cells expressing a CD40/Fas chimeric receptor: dissociation of stimulatory from inhibitory death signalling functions." *Biochem Biophys Res Commun*. Nov. 15, 1994; 204(3):1102-10.

Ryan, M.D., et al. "Foot-and-mouth disease virus 2A oligopeptide mediated cleavage of an artificial polyprotein." *The EMBO Journal*. 1994; 13(4):928-33.

Ryan, M.D., et al. "Cleavage of foot-and-mouth disease virus polyprotein is mediated by residues located within a 19 amino acid sequence." *J Gen. Virol*. Nov. 1991; 72:2727-32.

Schneider, P., et al. "Characterization of Fas (Apo-1, CD95)-Fas ligand interaction." *J Biol Chem*. Jul. 25, 1997; 272(30):18827-33.

Seedorf, K., et al. "Analysis of platelet-derived growth factor receptor domain function using a novel chimeric receptor approach." *J Biol Chem*. Jul. 5, 1991; 266(19):12424-31.

Shields, R.L., et al. "Inhibition of allergic reactions with antibodies to IgE." *Int Arch Allergy Immunol*. May-Jun. 1995; 107(1-3):308-12.

Starling, G.C., et al, "Identification of amino acid residues important for ligand binding to Fas." *J Exp Med*. Apr. 21, 1997; 185(8):1487-92.

Stone, R. "Molecular 'surgery' for brain tumors." *Science*, Jun. 12, 1992; 256(5063):1513.

Takahasi, et al. "Swapping between fas and granulocyte colony-stimulating factor receptor." *J Biol Chem*. 1996; 271(29):17555-60.

Takebayashi, H., et al. "Hormone-induced apoptosis by Fas-nuclear receptor fusion proteins: novel biological tools for controlling apoptosis in vivo." *Cancer Res*. Sep. 15, 1996; 56(18):4164-70.

Vercelli, D., et al. "To E or not to E?" *Int. Arch. Allergy Immunol*. 1998; 116:1-4.

Wang, Q., et al. "UCN-01: a potent abrogator of G2 checkpoint function in cancer cells with disrupted p53." *J Natl Cancer Inst*. Jul. 17, 1996; 88(14):956-65.

Xu, L., et al. "Replacement of germ-line epsilon promoter by gene targeting alters control of immunoglobulin heavy chain class switching." *Proc Natl Acad Sci USA*. Apr. 15, 1993; 90(8):3705-9.

Grignani F, et al. High-efficiency gene transfer and slection of human hematopoietic progenitor cells with a hybrid EBV/retroviral vector expressing the green fluorescence protein. *Cancer Res*. Jan. 1, 1998;58(1):14-9.

Gonzalez-Cuadrado, et al. Agonistic anti-Fas Antibodies Induce Glomerular Cell Apoptosis in Mice In Vivo. *Kidney Intl*. 1997 51(6):1739-1746.

Harper et al. The p21 Cdk-Interactive Protein Cip1 is a potent inhibitor of G1 Cyclin-Dependent Kinases. *Cell* 1990 75:805-816.

Heidaran, et al. Chimeric a and b-Platelet-Derived Growth Factor (PDGF) Receptors Define Three Immunoglobulin-like Domains of the a-PDGF Receptor that Determine PDGF-AA Binding Specificity *J. Biol. Chem*. 1990 265(31):18741-18744.

Muruva, et al. Adenovirus-Mediated Expression of Fas Ligand Induces Hepatic Apoptosis after Systemic Administration and Apoptosis of Ex Vivo-Infected Pancreatic Islet Allografts and Isografts. *Hum. Gene Ther*. 1997 8(8):955.

Naviaux, et al. The pCL Vector System: Rapid Production of Helper-Free, High Titer, Recombinant Retroviruses. *J. Virol*. 1996 70(8):5701-5705.

Ramesh, et al. High-titer bicistronic retroviral vectors employing foot-and-mouth disease virus internal ribosome entry site. *Nuc. Acids Res*. 1996 24(14):2697-700.

Yan, et al. Two-amino acid molecular switch in an epithelial morphogen that regulates binding to two distinct receptors. *Science* 2000 290: 523-527.

Voet, et al. 1990 John Wiley & Sons, Inc. 126-128 and 228-234.

Mickel JE et al. Genotype-phenotype relationships in cystic fibrosis. *Med Clin. North Am*. 2000 84(3):597-607.

\* cited by examiner

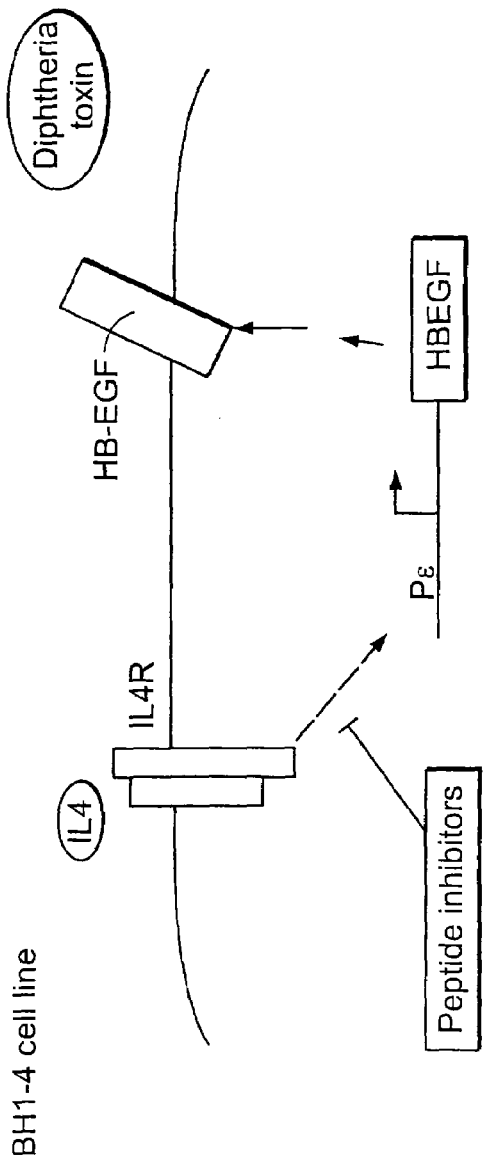

The HB-EGF/Diphtheria Toxin Selection (BH1-4)

- The new cell line generated contains a reporter driven by the germline ε promoter: The reporter HB-EGF functions as the receptor for diphtheria toxin and confers high sensitivity to diphtheria toxin killing following IL 4 induction (for use in survival screening strategies)

- The BH1-4 screening line consists of the B cell line BJAB engineered to contain the above reporter.

FIG. 1

SOCS1 and STAT6 Effects on IL4/dip Induced Death of BH1-4 Cells (Scatter)(Day 6)

SOCS1 and STAT6 Effects on IL4/dip Induced Death of BH1-4 Cells(day 6) Post Stimulation

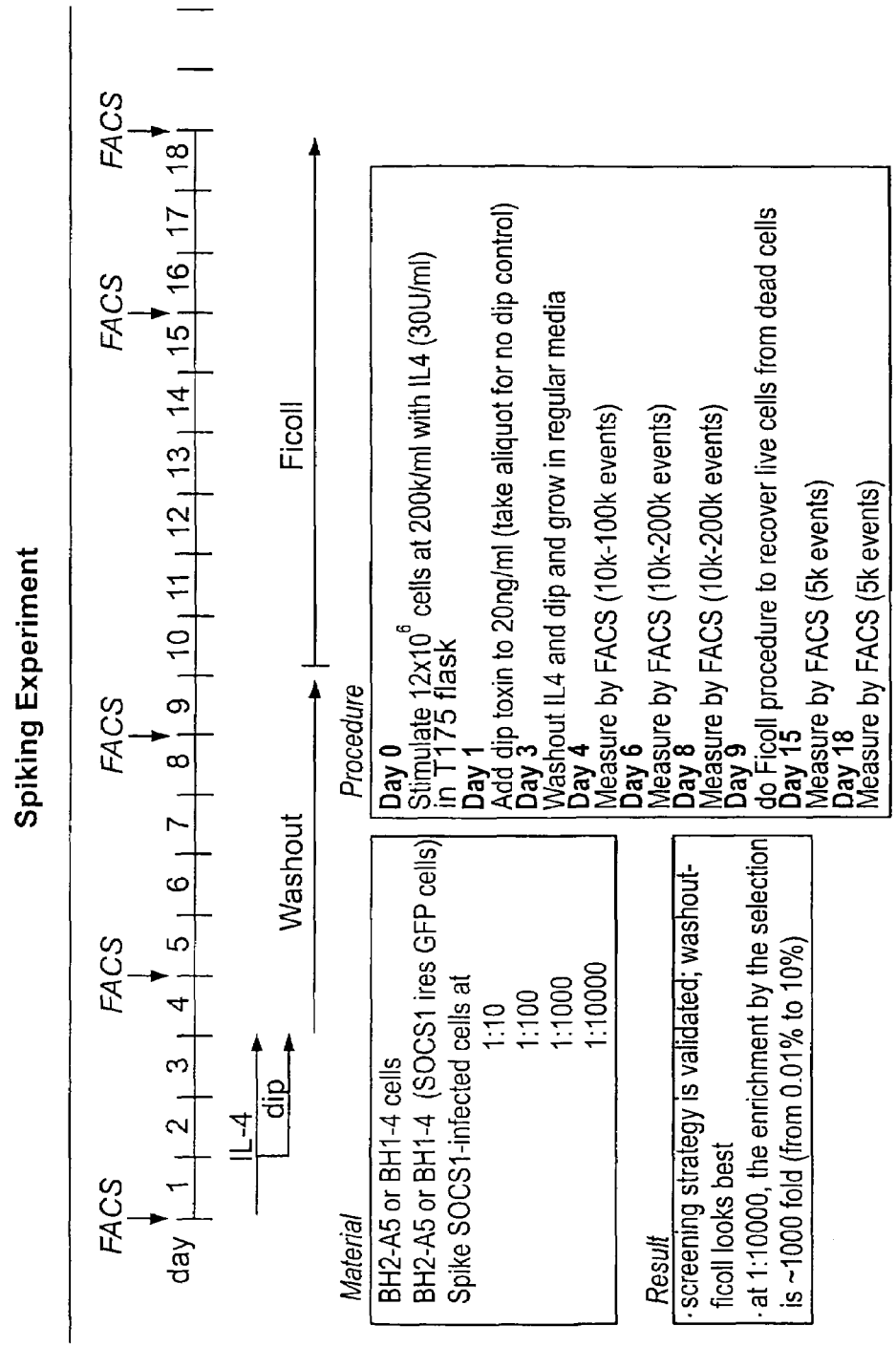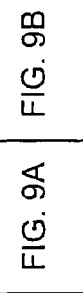
FIG. 8
FIG. 9

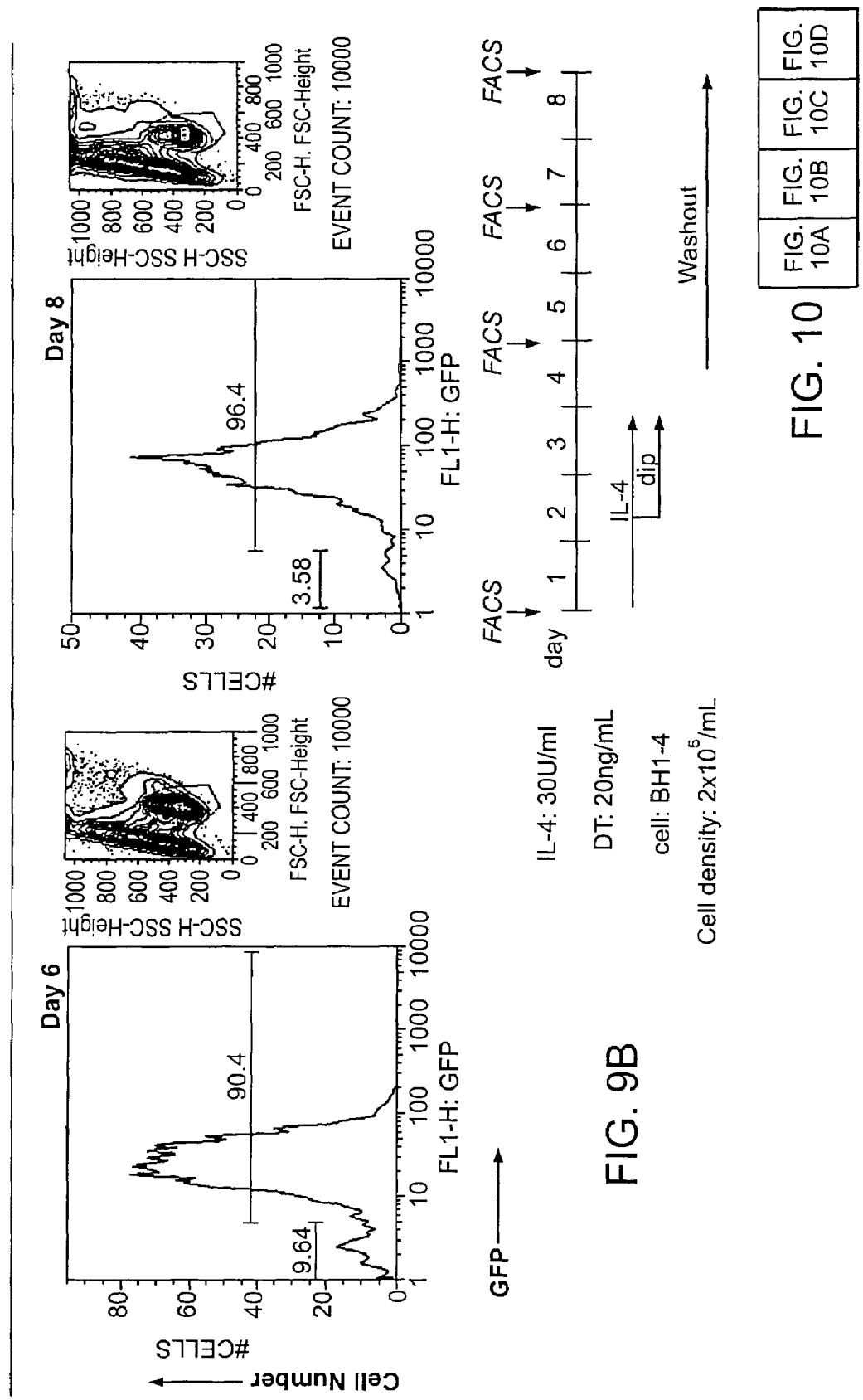

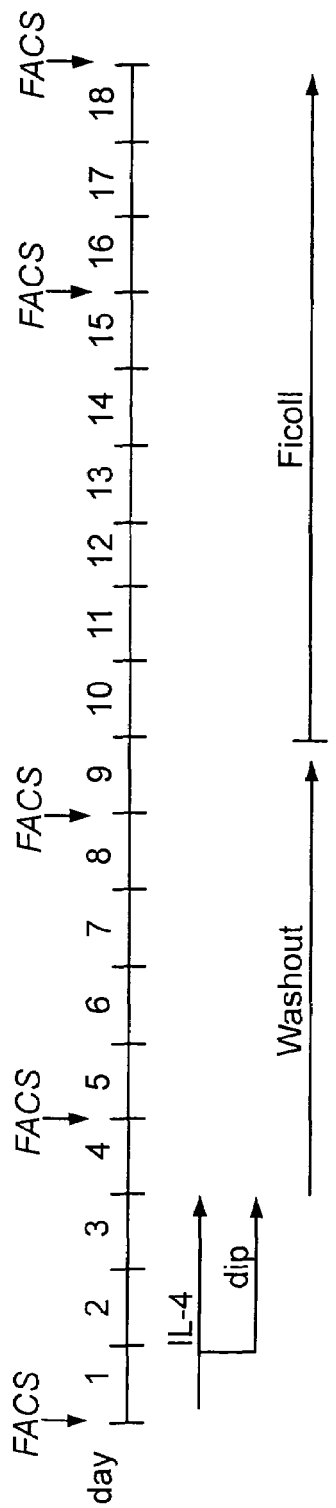
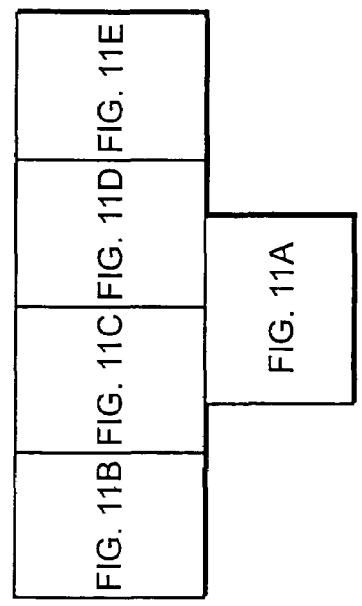

*data from the spike-in experiment in A5T-4 cells

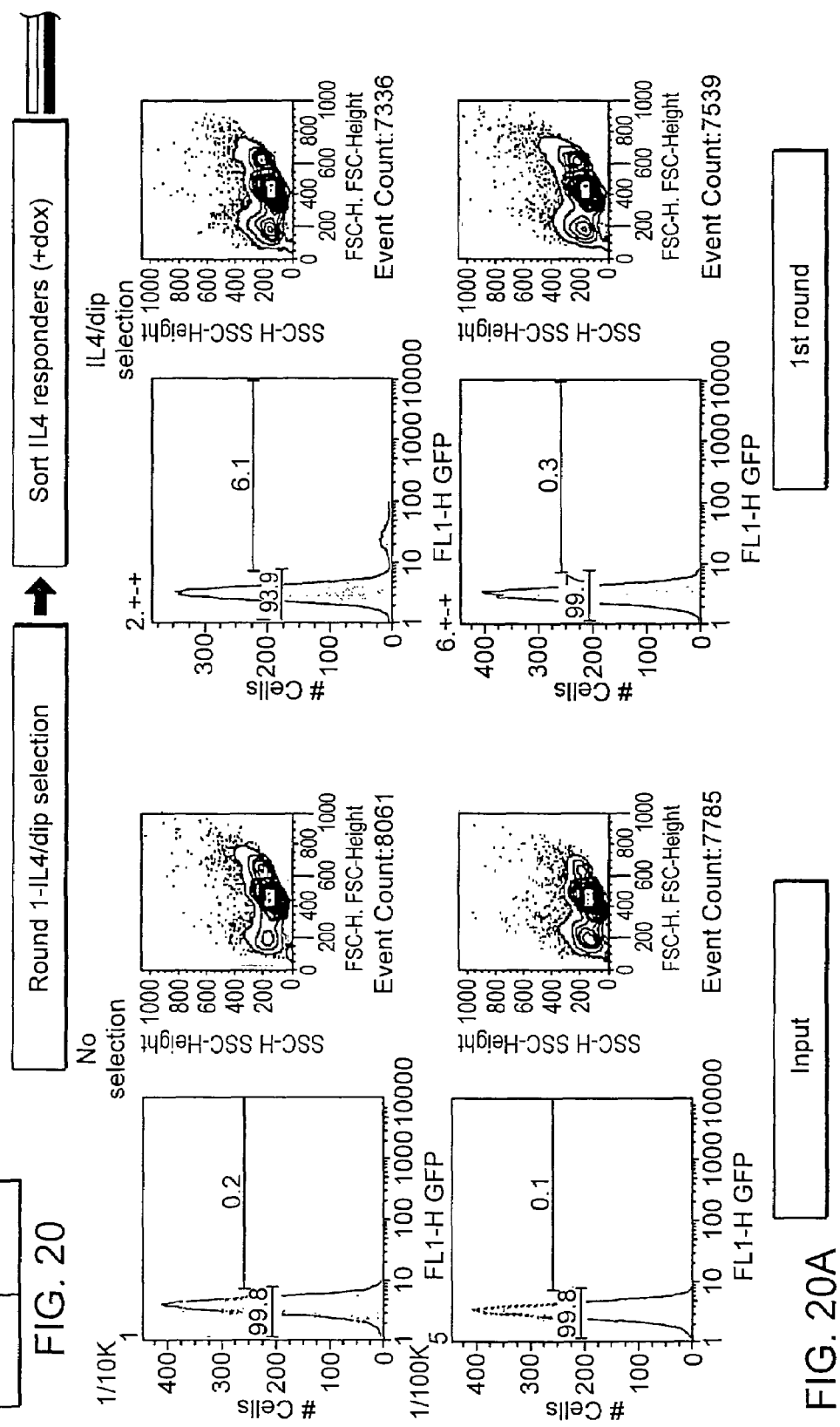

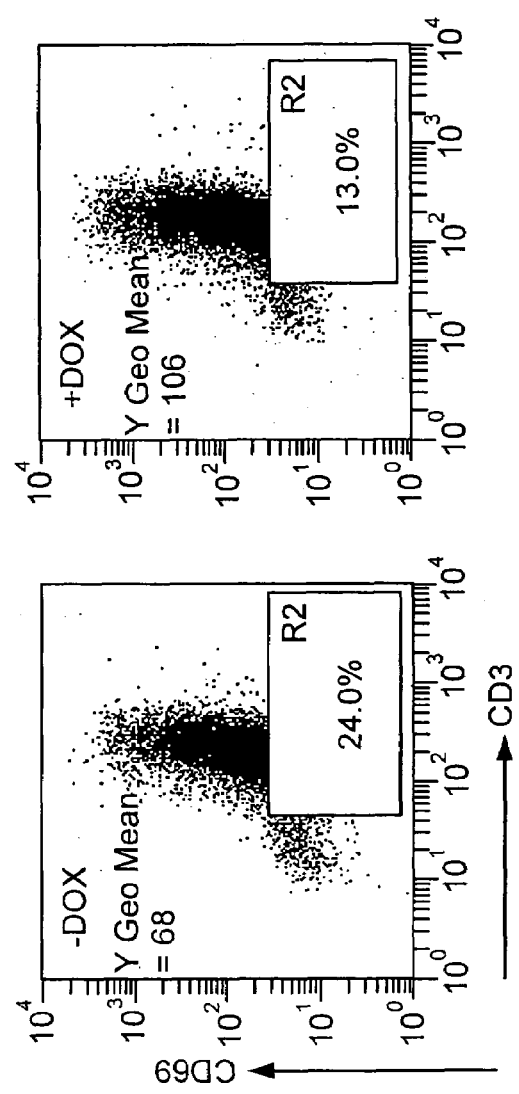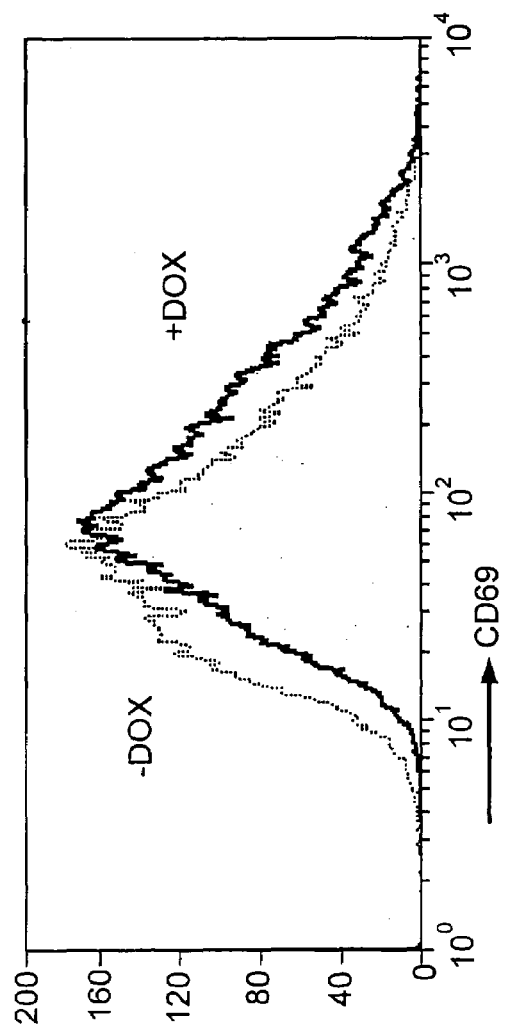
FIG. 28D

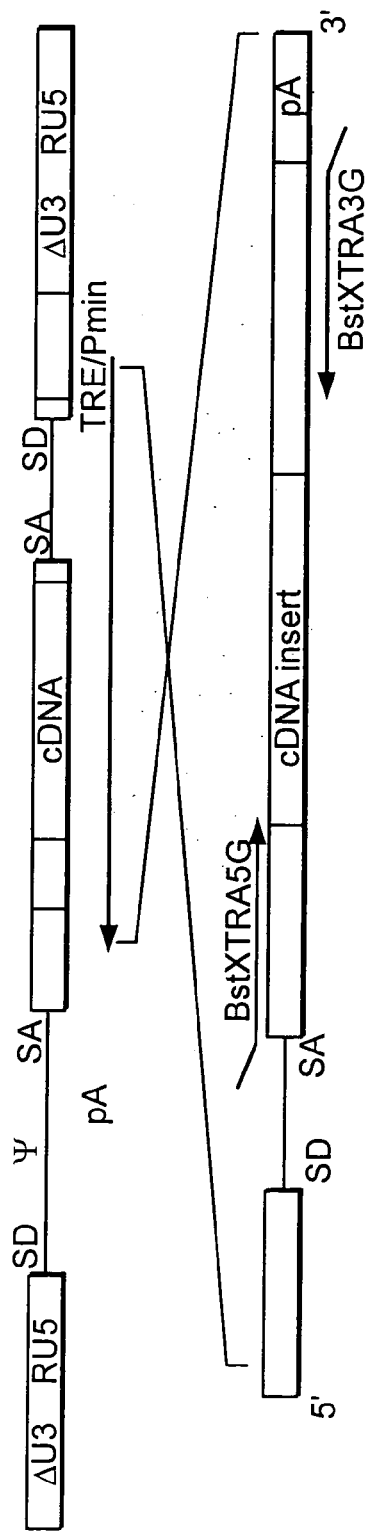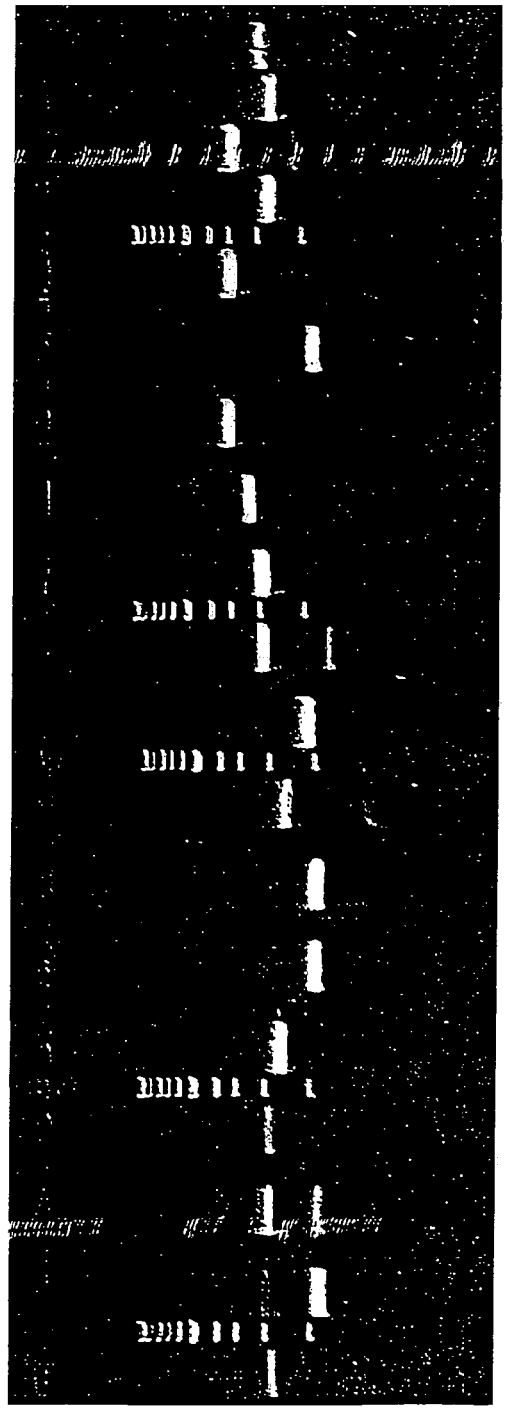
FIG. 29D

FIG. 33

| Table 2. Overview of identified molecular targets | | | | |
|---|---|---|---|---|
| gene | domain homology | accession# | Length | frequency |
| known to TCR pathway | | | | |
| TCRb | receptor | numerous | partial | 48 |
| Lck | Tyr kinase | U23852.1 | nt 1-859 | 4 |
| ZAP70 | Tyr kinase | L05148.1 | nt 63-997 | 12 |
| ZAP70 (long) | Tyr kinase | L05148.1 | nt 189-1019 | 19 |
| SYK | Tyr kinase | L28824.1 | nt 121-1160 | 2 |
| PLCg1 | Tyr kinase | 4505868 | nt 1485-235 | 4 |
| A-raf | Ser/Thr kinase | X04790.1 | nt 191-651 | 5 |
| PAG | transmembrane adaptor | AF240634.1 | nt 1-644 | 1 |
| SHP/PTP1C | protein-tyrosine phosphatase | X62055.1 | nt 746-1672 | 1 |
| CSK | tyrosine kinase | 4758077 | nt 405-726 | 1 |
| nucleolin (NCL) | RNA-binding | 4885510 | nt 88-361 | 1 |
| enzymes and receptors | | | | |
| TCPTP/PTPN2 | protein-tyrosine phosphatase | 4506290 | nt 3-1169 | 20 |
| IL10Ra | receptor | 4504632 | nt 750-1411 | 1 |
| integrin a2 | receptor | 6006008 | nt 3390-395 | 1 |
| Enolase 1a | phosphopyruvate hydratase | 4503570 | nt 797-1468 | 2 |
| DUSP1 | dual specificity phosphatase | 7108342 | nt 1065-136 | 1 |
| KIAA0251 | Pyridoxal-dependent decarboxylase | D87438 | nt 2098-237 | 2 |
| adaptors and transcription factors | | | | |
| GG2-1 | TNF-induced protein | AF070671.1 | nt 19-679 | 2 |
| Grb7 | adaptor | 4885354 | nt 1487-213 | 2 |
| SH2-B | adaptor | AF227968.1 | nt 1481-205 | 1 |
| STAT1 | signal transducing transcription fact | 6274551 | nt 113-737 | 1 |
| RERE | transcriptional factor | AB036737 | nt 1551-183 | 3 |
| sudD | Ser/Thr rich | 4507298 | nt 15-506 | 1 |
| Ku 70 | DNA-PKc subunit | 4503840 | nt 1085-170 | 1 |
| SCAMP2 | secretory carrier membrane protein | AF005038.2 | nt 25-863 | 1 |
| KIAA1228 | C2 domain (Ca2+ or IP binding) | AB033054 | nt 1080-180 | 1 |
| EST from clone 2108068 | LPP20 lipoprotein precursor | AL357532.1 | novel isoforr | 4 |
| cytoskeleton | | | | |
| vimentin (VIM) | intermediate filament | 4507894 | nt 25-496 | 1 |
| moesin (MSN) | moesin (MSN) | 4505256 | nt 8-326 | 1 |
| others | | | | |
| TIMP3 | inhibitor of metalloproteinase | 9257248 | nt 1225-146 | 1 |
| RNH | ribonuclease/angiogenin inhibitor | 4506564 | nt 339-1073 | 1 |
| HBA1 | hemoglobin, alpha 1 and 2 | | partial | 1 |
| MHCI | Ig superfamily | | partial | 1 |
| Ig light chain | Ig superfamily | | partial | 1 |

SEQUENCE LISTING

<160> NUMBER OF SEQ ID NOS: 39

<210> SEQ ID NO 1
<211> LENGTH: 61
<212> TYPE: PRT
<213> ORGANISM: Artificial sequence
<220> FEATURE:
<223> OTHER INFORMATION: coiled-coil presentation structure

<400> SEQUENCE: 1

-continued

```
Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 2
<211> LENGTH: 69
<212> TYPE: PRT
<213> ORGANISM: Artificial sequence
<220> FEATURE:
<223> OTHER INFORMATION: minibody presentation structure

<400> SEQUENCE: 2

Met Gly Arg Asn Ser Gln Ala Thr Ser Gly Phe Thr Phe Ser His Phe
1               5                   10                  15

Tyr Met Glu Trp Val Arg Gly Gly Glu Tyr Ile Ala Ala Ser Arg His
            20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Leu Gln Lys
    50                  55                  60

Lys Lys Gly Pro Pro
65

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
1               5

<210> SEQ ID NO 4
<211> LENGTH: 6
<212> TYPE: PRT
<213> ORGANISM: Homo sapiens

<400> SEQUENCE: 4

Ala Arg Arg Arg Arg Pro
1               5

<210> SEQ ID NO 5
<211> LENGTH: 10
<212> TYPE: PRT
<213> ORGANISM: Mus musculus

<400> SEQUENCE: 5

Glu Glu Val Gln Arg Lys Arg Gln Lys Leu
1               5                   10

<210> SEQ ID NO 6
<211> LENGTH: 9
<212> TYPE: PRT
<213> ORGANISM: Mus musculus

<400> SEQUENCE: 6
```

```
Glu Glu Lys Arg Lys Arg Thr Tyr Glu
 1               5
```

<210> SEQ ID NO 7
<211> LENGTH: 20
<212> TYPE: PRT
<213> ORGANISM: Xenopus laevis

<400> SEQUENCE: 7

```
Ala Val Lys Arg Pro Ala Ala Thr Lys Lys Ala Gly Gln Ala Lys Lys
 1               5                  10                  15

Lys Lys Leu Asp
            20
```

<210> SEQ ID NO 8
<211> LENGTH: 31
<212> TYPE: PRT
<213> ORGANISM: Mus musculus

<400> SEQUENCE: 8

```
Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
                20                  25                  30
```

<210> SEQ ID NO 9
<211> LENGTH: 21
<212> TYPE: PRT
<213> ORGANISM: Homo sapiens

<400> SEQUENCE: 9

```
Met Ser Ser Phe Gly Tyr Arg Thr Leu Thr Val Ala Leu Phe Thr Leu
 1               5                  10                  15

Ile Cys Cys Pro Gly
                20
```

<210> SEQ ID NO 10
<211> LENGTH: 51
<212> TYPE: PRT
<213> ORGANISM: Mus musculus

<400> SEQUENCE: 10

```
Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
                20                  25                  30

Ile Cys Val Ala Leu Leu Leu Ser Leu Ile Ile Thr Leu Ile Cys Tyr
            35                  40                  45

His Ser Arg
        50
```

<210> SEQ ID NO 11
<211> LENGTH: 33
<212> TYPE: PRT
<213> ORGANISM: Homo sapiens

<400> SEQUENCE: 11

```
Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
                20                  25                  30
```

Arg

<210> SEQ ID NO 12
<211> LENGTH: 37
<212> TYPE: PRT
<213> ORGANISM: Rattus sp.

<400> SEQUENCE: 12

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 13
<211> LENGTH: 14
<212> TYPE: PRT
<213> ORGANISM: Homo sapiens

<400> SEQUENCE: 13

Met Gly Ser Ser Lys Ser Lys Pro Lys Asp Pro Ser Gln Arg
1               5                   10

<210> SEQ ID NO 14
<211> LENGTH: 26
<212> TYPE: PRT
<213> ORGANISM: Homo sapiens

<400> SEQUENCE: 14

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 15
<211> LENGTH: 20
<212> TYPE: PRT
<213> ORGANISM: Rattus norvegicus

<400> SEQUENCE: 15

Lys Gln Phe Arg Asn Cys Met Leu Thr Ser Leu Cys Cys Gly Lys Asn
1               5                   10                  15

Pro Leu Gly Asp
            20

<210> SEQ ID NO 16
<211> LENGTH: 19
<212> TYPE: PRT
<213> ORGANISM: Homo sapiens

<400> SEQUENCE: 16

Leu Asn Pro Pro Asp Glu Ser Gly Pro Gly Cys Met Ser Cys Lys Cys
1               5                   10                  15

Val Leu Ser

<210> SEQ ID NO 17
<211> LENGTH: 5
<212> TYPE: PRT
<213> ORGANISM: Artificial sequence
<220> FEATURE:
<223> OTHER INFORMATION: lysosomal degradation seqeunce

```
<400> SEQUENCE: 17

Lys Phe Glu Arg Gln
1               5

<210> SEQ ID NO 18
<211> LENGTH: 36
<212> TYPE: PRT
<213> ORGANISM: Cricetulus griseus

<400> SEQUENCE: 18

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
                20                  25                  30

Tyr Gln Thr Ile
            35

<210> SEQ ID NO 19
<211> LENGTH: 35
<212> TYPE: PRT
<213> ORGANISM: Homo sapiens

<400> SEQUENCE: 19

Leu Val Pro Ile Ala Val Gly Ala Ala Leu Ala Gly Val Leu Ile Leu
1               5                   10                  15

Val Leu Leu Ala Tyr Phe Ile Gly Leu Lys His His His Ala Gly Tyr
                20                  25                  30

Glu Gln Phe
        35

<210> SEQ ID NO 20
<211> LENGTH: 27
<212> TYPE: PRT
<213> ORGANISM: Saccharomyces cerevisiae

<400> SEQUENCE: 20

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
                20                  25

<210> SEQ ID NO 21
<211> LENGTH: 25
<212> TYPE: PRT
<213> ORGANISM: Saccharomyces cerevisiae

<400> SEQUENCE: 21

Met Leu Ser Leu Arg Gln Ser Ile Arg Phe Phe Lys Pro Ala Thr Arg
1               5                   10                  15

Thr Leu Cys Ser Ser Arg Tyr Leu Leu
                20                  25

<210> SEQ ID NO 22
<211> LENGTH: 64
<212> TYPE: PRT
<213> ORGANISM: Saccharomyces cerevisiae

<400> SEQUENCE: 22

Met Phe Ser Met Leu Ser Lys Arg Trp Ala Gln Arg Thr Leu Ser Lys
1               5                   10                  15
```

```
Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60
```

<210> SEQ ID NO 23
<211> LENGTH: 41
<212> TYPE: PRT
<213> ORGANISM: Saccharomyces cerevisiae

<400> SEQUENCE: 23

```
Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40
```

<210> SEQ ID NO 24
<211> LENGTH: 4
<212> TYPE: PRT
<213> ORGANISM: Homo sapiens

<400> SEQUENCE: 24

```
Lys Asp Glu Leu
1
```

<210> SEQ ID NO 25
<211> LENGTH: 15
<212> TYPE: PRT
<213> ORGANISM: unidentified adenovirus

<400> SEQUENCE: 25

```
Leu Tyr Leu Ser Arg Arg Ser Phe Ile Asp Glu Lys Lys Met Pro
1               5                   10                  15
```

<210> SEQ ID NO 26
<211> LENGTH: 15
<212> TYPE: PRT
<213> ORGANISM: Homo sapiens

<400> SEQUENCE: 26

```
Leu Thr Glu Pro Thr Gln Pro Thr Arg Asn Gln Cys Cys Ser Asn
1               5                   10                  15
```

<210> SEQ ID NO 27
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 27

```
Arg Thr Ala Leu Gly Asp Ile Gly Asn
1               5
```

<210> SEQ ID NO 28
<211> LENGTH: 20
<212> TYPE: PRT
<213> ORGANISM: Unknown
<220> FEATURE:

<223> OTHER INFORMATION: signal sequence from Interleukin-2

<400> SEQUENCE: 28

Met Tyr Arg Met Gln Leu Leu Ser Cys Ile Ala Leu Ser Leu Ala Leu
1               5                   10                  15

Val Thr Asn Ser
            20

<210> SEQ ID NO 29
<211> LENGTH: 29
<212> TYPE: PRT
<213> ORGANISM: Homo sapiens

<400> SEQUENCE: 29

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 30
<211> LENGTH: 27
<212> TYPE: PRT
<213> ORGANISM: Homo sapiens

<400> SEQUENCE: 30

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 31
<211> LENGTH: 18
<212> TYPE: PRT
<213> ORGANISM: Influenza virus

<400> SEQUENCE: 31

Met Lys Ala Lys Leu Leu Val Leu Leu Tyr Ala Phe Val Ala Gly Asp
1               5                   10                  15

Gln Ile

<210> SEQ ID NO 32
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 32

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 33
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be any amino acid

```
<400> SEQUENCE: 33

Met Gly Xaa Xaa Xaa Xaa Gly Gly Pro Pro
1               5                   10

<210> SEQ ID NO 34
<211> LENGTH: 5
<212> TYPE: PRT
<213> ORGANISM: Artificial sequence
<220> FEATURE:
<223> OTHER INFORMATION: linker consensus sequence

<400> SEQUENCE: 34

Gly Ser Gly Gly Ser
1               5

<210> SEQ ID NO 35
<211> LENGTH: 4
<212> TYPE: PRT
<213> ORGANISM: Artificial sequence
<220> FEATURE:
<223> OTHER INFORMATION: linker consensus sequence

<400> SEQUENCE: 35

Gly Gly Gly Ser
1

<210> SEQ ID NO 36
<211> LENGTH: 20
<212> TYPE: PRT
<213> ORGANISM: Artificial sequence
<220> FEATURE:
<223> OTHER INFORMATION: consensus sequence for SH-3 domain binding
      protein
<220> FEATURE:
<221> NAME/KEY: MISC_FEATURE
<222> LOCATION: (3)..(7)
<223> OTHER INFORMATION: "Xaa" at positions 3 to 7 is a randomized
      residue which can be hydrophobically biased
<220> FEATURE:
<221> NAME/KEY: MISC_FEATURE
<222> LOCATION: (13)..(16)
<223> OTHER INFORMATION: "Xaa" at positions 13 and 15-16 indicates a
      bias toward a hydrophobic residue (i.e. Val, Ala, Gly, Leu, Pro,
      Arg).

<400> SEQUENCE: 36

Met Gly Xaa Xaa Xaa Xaa Xaa Arg Pro Leu Pro Pro Xaa Pro Xaa Xaa
1               5                   10                  15

Gly Gly Pro Pro
            20

<210> SEQ ID NO 37
<211> LENGTH: 63
<212> TYPE: DNA
<213> ORGANISM: Artificial sequence
<220> FEATURE:
<223> OTHER INFORMATION: oligonucleotide consensus sequence for SH-3
      domain binding protein
<220> FEATURE:
<221> NAME/KEY: misc_feature
<222> LOCATION: (7)..(20)
<223> OTHER INFORMATION: "n" at positions 7-8, 10-11, 13-14, 16-17, and
      19-20 can be any base.

<400> SEQUENCE: 37
atgggcnnkn nknnknnknn kagacctctg cctccasbkc ctsbksbkgg aggcccacct       60
taa                                                                    63
```

```
<210> SEQ ID NO 38
<211> LENGTH: 40
<212> TYPE: DNA
<213> ORGANISM: Artificial sequence
<220> FEATURE:
<223> OTHER INFORMATION: primer

<400> SEQUENCE: 38
ttgcagaacc accaccttgg gctcttaacc taggccgatc                                  40

<210> SEQ ID NO 39
<211> LENGTH: 41
<212> TYPE: DNA
<213> ORGANISM: Artificial sequence
<220> FEATURE:
<223> OTHER INFORMATION: primer

<400> SEQUENCE: 39
ttgcagaacc aatttaatgg cggccagtca ggccatcgtc g                                41
```

METHODS AND COMPOSITIONS FOR SCREENING FOR ALTERED CELLULAR PHENOTYPES

This application is a continuation-in-part of U.S. patent application Ser. No. 09/076,624, filed May 12, 1998, now abandoned.

FIELD OF THE INVENTION

The invention relates to methods and compositions useful for screening for altered cellular phenotypes using an inducible expression system to enrich for and detect the altered phenotypes. In particular, the invention relates to screening libraries of candidate bioactive agents, for example, nucleic acids and peptides, in cells using an regulatable expression system to enrich for a subpopulation of cells having an altered phenotype due to the presence of a candidate bioactive agent.

BACKGROUND OF THE INVENTION

Inducible expression systems have been developed to facilitate the analysis of gene function in cells and to facilitate the development of effective treatments using gene therapy. These expression systems attempt to control nucleic acid expression by using inducible eukaryotic promoters that are responsive to inducers such as hormones (Lee et al. (1981) Nature 294:228–232; Hynes et al. (1981) Proc. Natl. Acad. Sci. USA 78:2038–2042; Klock et al. (1987) Nature 329:734–736; Israel & Kaufman (1989) Nucl. Acids Res. 17:2589–2604); heavy metal ions (Mayo et al. (1982) Cell 29:99–108; Brinster et al. (1982) Nature 296:39–42; Searle et al. (1985) Mol. Cell. Biol. 5:1480–1489); or heat shock (Nouer et al. (1991) in Heat Shock Response, e.d. Nouer, L., CRC, Boca Raton, Fla., pp 167–220). However, these expression systems are problematic because the eukaryotic promoters can exhibit a high level of basal expression in the non-induced state; the inducers can promote pleiotropic effects; and the level of induction can be low.

In order to overcome these problems, inducible eukaryotic expression systems utilizing prokaryotic regulatory elements have been developed. The rationale for using prokaryotic regulatory elements in a eukaryotic expression system is based on the theory that effectors modulating the activity of such prokaryotic regulatory elements would not be responsive to eukaryotic cellular components. Therefore, pleiotropic effects would be eliminated. An example of such a system is the lac operator regulatable expression system. In this system, expression of sequences operably linked to the lac operator is constitutively induced (or "turned on") by a LacR-VP16 fusion protein and is repressed (or "turned off") in the presence of isopropyl-D-thiogalactopyranoside (IPTG) (Labow et al. (1990), cited supra). In another lac inducible system, the binding of LacR-VP16 to the operator sequence is enhanced by increasing the temperature of the cells. However, IPTG in eukaryotic cells is an inefficient inducer of nucleic acid expression and must be used at concentrations near cytotoxic levels. Furthermore, increasing the temperature of the cells is likely to promote pleiotropic effects in the cells. Thus, there is a need for a more efficient inducible regulatory system that exhibits rapid and high level induction of nucleic acid expression; is highly responsive to a specific exogenous inducer; and exhibits low levels of expression in the uninduced state.

The tetracycline (Tet) inducible system utilizes entirely prokaryotic components and, thus, pleiotropic effects are avoided (Gossen et al. (1992) Proc. Natl. Acad. Sci. USA 89:5547–5551; Gossen et al. (1995) Science 268:1766–1769). In this system, the inducer is an integral component of a transactivator that binds to the inducible promoter and drives expression of a nucleic acid of interest. Thus, the intermediate steps in the induction pathway are largely eliminated and the control of expression is highly specific and tightly controlled by contact with the inducer. The Tet-controlled expression system therefore provides an effective means for turning off and turning on nucleic acid expression in cells and, thereby, allowing for the regulated expression of a nucleic acid in cells.

With the advent of functional genomics, large numbers of nucleic acids encoding genes of unknown function have been isolated and cloned. Consequently, there is a critical need to develop rapid and highly efficient methods for screening large numbers of candidate nucleic acids for analysis of gene function and to identify potential targets for development of therapeutic agents.

One approach for studying gene function is to regulate the expression of a nucleic acid in cells and look for a corresponding alteration in cellular phenotype. Consequently, rapid and highly efficient methods of screening diverse populations of cells for an altered phenotype due to the inducible expression of a candidate nucleic acid is highly desirable and useful for the analysis of nucleic acid function and target discovery.

Thus, it is an object of the present invention to provide rapid and highly efficient methods of screening populations of cells for an altered cellular phenotype due to the presence of a candidate bioactive agent, using an inducible expression system that permits the regulated expression of candidate nucleic acids encoding a candidate bioactive agent and permits controlled expression of the candidate nucleic acid at a defined level.

SUMMARY OF THE INVENTION

In accordance with the objects described above, the present invention provides methods and compositions for screening for an altered cellular phenotype using an inducible expression system to enrich for and detect cells having an altered phenotype due to the presence of a candidate bioactive agent. In the methods of the present invention, detection of cells having an altered cellular phenotype is achieved by selection of cells responsive to the induction and repression of expression of a nucleic acid sequence encoding the candidate bioactive agent. The cells having an altered cellular phenotype are enriched by multiple rounds of selection.

The invention provides methods and compositions for screening candidate bioactive agents useful as targets for drug discovery, by accessing molecules and targets within living cells and provides for the direct selection of those bioactive agents with desired phenotypic effects. Further, the methods and compositions of the present invention are particularly useful for high throughput screening of candidate bioactive agents capable of altering a cellular phenotype.

The invention provides compositions for use in the methods of the present invention. Specifically, the invention provides populations of cells having a parent phenotype and comprising a nucleic acid encoding a first element expressed in the cells. The invention further provides libraries of fusion nucleic acids, where the fusion nucleic acids comprise a second element that is regulatable by the first element. The fusion nucleic acids further comprise a nucleic acid sequence operably linked to the second element. The nucleic acid sequence encodes a candidate bioactive agent. In addition, the invention provides a third element that induces or represses the expression of the nucleic acid sequence encoding the candidate bioactive agent. Thus, the invention provides two approaches for screening for an altered cellular phenotype: in a first approach the third element induces expression; and in a second approach the third element represses expression.

Using either approach, in the methods of the present invention, the cells having an altered phenotype due to the presence of the candidate bioactive agent are distinguished and detected based on their responsiveness to the induction and repression (in either order) of expression of the nucleic acid sequence encoding the candidate bioactive agent, by the third element. The responsive cells have the parent phenotype when expression of the nucleic acid sequence is repressed and have an altered phenotype when expression of the nucleic acid sequence is induced. The nonresponsive cells can be distinguished by having a phenotype that is not responsive to the induction and repression of expression of the nucleic acid sequence.

Using the first approach, the invention provides methods of screening for an altered cellular phenotype comprising the steps of: a) providing a population of cells having a parent phenotype and comprising a nucleic acid encoding a first element inducibly or constitutively expressed in the cells; b) introducing a library of fusion nucleic acids into the population of cells, where the fusion nucleic acids comprise a second element that is regulatable by the first element and further comprise a nucleic acid sequence encoding a candidate bioactive agent; c) inducing the expression of the nucleic acid sequence by contacting the cells with a third element; d) collecting a first subpopulation of cells having an altered phenotype; e) repressing the expression of the nucleic acid by modulating the contacting of the third element with the first subpopulation of cells; f) collecting a second population of cells having a parent phenotype; g) inducing the expression of the nucleic acid sequence by contacting the third element with the second subpopulation of cells; and g) detecting a third subpopulation of cells.

Using the second approach, the invention provides methods of screening for an altered cellular phenotype comprising the steps of: a) providing a population of cells having a parent phenotype and comprising a nucleic acid encoding a first element inducibly or constitutively expressed in the cells; b) introducing a library of fusion nucleic acids into the population of cells, where the fusion nucleic acids comprise a second element that is regulatable by the first element and further comprise a nucleic acid sequence encoding a candidate bioactive agent; c) inducing the expression of the nucleic acid sequence by expressing the first element; d) collecting a first subpopulation of cells having an altered phenotype; e) repressing the expression of the nucleic acid by contacting a third element with the first subpopulation of cells; f) collecting a second population of cells having a parent phenotype; g) inducing the expression of the nucleic acid sequence modulating the contacting the third element with the second subpopulation of cells; and h) detecting a third subpopulation of cells.

Using either approach, the invention provides methods of screening for an altered cellular phenotype further comprising collecting the responsive cells. The methods also further comprise repeating the induction or repression of expression and detecting the responsive cells and, further, collecting the cells to enrich for a subpopulation of cells having the altered phenotype. The inducing or repressing of expression, followed by detecting and, further, by collecting a subpopulation of cells responsive to the induction and represssion can be repeated multiple times to obtain a desired level of enrichment and detection of a subpopulation of cells having an altered cellular phenotype due to the presence of a candidate bioactive agent.

Examples of a first element include, but are not limited to, a transactivator. In one aspect, the first element comprises a tetracycline-dependent transactivator (tTA) or a reverse tetracycline-dependent transactivator (rtTA). The first element can be inducible; expressed constitutively, expressed stably or transiently; and expressed in trans or in cis relative to the nucleic acid sequence. In one aspect, the fusion nucleic acid further comprises the nucleic acid encoding the first element. Examples of a second element include, but are not limited to, an operator sequence. In one aspect, the operator sequence comprises a tetracycline operator sequence (TetO). In another aspect the second element is an oligomer of a TetO sequence. Examples of a third element include, but are not limited to, a molecule that induces or represses expression of the nucleic acid sequence. In one aspect, the molecule comprises tetracycline or analogues thereof, e.g., doxycycline (Dox).

In one aspect, the first element comprises a reverse tetracycline-dependent activator (rtTA) and expression of the nucleic acid sequence is induced by contacting the third element with the cells, and is repressed by modulating the contacting of the third element with the cells.

In another aspect, the first element comprises a tetracycline-dependent activator (tTA) and expression of the nucleic acid sequence is repressed by contacting the third element with the cells, and is induced by modulating the contacting of the third element with the cells.

Examples of candidate bioactive agents include, but are not limited to, nucleic acids and polypeptides. Further examples of bioactive agents are cyclic peptides, RNA, antisense RNA, and DNA. Additional examples of nucleic acid sequences encoding a candidate bioactive agent, include but are not limited to, random nucleic acid sequences, and biased random nucleic acid sequences. Examples of nucleic acid sequences encoding a candidate bioactive agent, also include but are not limited to, full-length cDNA sequences, subsequences of a full-length cDNA, and antisense sequences of a full-length cDNA. Another example of a nucleic acid sequence encoding a candidate bioactive agent is a nucleic acid sequence encoding an amino acid sequence that is in-frame or out-of-frame as compared to the open reading frame (ORF) encoded by the amino acid sequence of a full-length cDNA.

In one aspect, the present invention provides methods comprising the steps of: a) providing a population of cells having a parent phenotype and comprising a nucleic acid encoding a first element that is expressed in the cells, for example, a reverse tetracycline-dependent transactivator (rtTA); b) introducing into the population of cells a library of fusion nucleic acids, where the nucleic acids each comprise a second element that is regulatable by the first element, and a nucleic acid sequence that is operably linked to the first element, where the nucleic acid sequence encodes a candidate bioactive agent; c) inducing the expression of the nucleic acid sequence by contacting a third element with the population of cells, wherein the population of cells is expressing the first element; d) collecting a first subpopulation of cells having an altered phenotype; e) repressing the expression of the nucleic acid sequence by modulating the contacting of the third element with the first subpopulation of cells; f) collecting a second subpopulation of cells having the parent phenotype; g) inducing the expression of the nucleic acid sequence by contacting the third element with the second subpopulation of cells; and h) detecting a third subpopulation of cells having the altered phenotype.

In an additional aspect, the method further comprises: i) collecting the third subpopulation of cells having an altered phenotype; j) repressing the expression of the nucleic acid sequence by modulating the contacting of the third element with the third subpopulation of cells; and k) detecting a fourth subpopulation of cells having the parent phenotype.

In another additional aspect, the method further comprises: l) collecting the fourth subpopulation of cells having the parent phenotype; m) inducing the expression of the nucleic acid sequence by contacting the third element with the fourth subpopulation of cells; and n) detecting a fifth subpopulation of cells having the altered phenotype.

In another aspect, the invention provides a method of screening for cells having an altered phenotype comprising the steps of: a) providing a population of cells having a parent phenotype and comprising a nucleic acid encoding a first element, for example, a tetracycline-dependent transactivator; b) introducing into the population of cells a library of fusion nucleic acids, where the nucleic acids each comprise a second element that is regulatable by the first element, and a nucleic acid sequence that is operably linked to the first element, where the nucleic acid sequence encodes a candidate bioactive agent; c) inducing the expression of the nucleic acid sequence by expressing the first element in the population of cells; d) collecting a first subpopulation of cells having an altered phenotype; e) repressing the expression of the nucleic acid by contacting a third element with the first subpopulation of cells; f) collecting a second subpopulation of cells having the parent phenotype; g) inducing the expression of the nucleic acid sequence by modulating the contacting of the third element with the second subpopulation of cells; and h) detecting a third subpopulation of cells having the altered phenotype.

In an additional aspect, the method further comprises: i) collecting the third subpopulation of cells having the altered phenotype; j) repressing the expression of the nucleic acid sequence by contacting the third element with the third subpopulation of cells; and k) detecting a fourth subpopulation of cells having the parent phenotype.

In a further additional aspect, the method further comprises: l) collecting the fourth subpopulation of cells having the parent phenotype; m) inducing the expression of the nucleic acid sequence by modulating the contacting of the third element with the fourth subpopulation of cells; and n) detecting a fifth subpopulation of cells having said altered phenotype.

In one aspect, the first element comprises a reverse tetracycline-dependent activator (rtTA); the second element comprises an oligomer of a tetracycline operator sequence (TetO); and the third element comprises tetracycline or doxycycline.

In another aspect, the first element comprises a tetracycline-dependent activator (rtTA); said second element comprises an oligomer of a tetracycline operator sequence (TetO); and said third element comprises tetracycline (Tet) or doxycycline (Dox).

In a another aspect, the library of fusion nucleic acids comprises about $10^3$ to $10^9$ different said nucleic acid sequences, or $10^4$ to $10^8$ different random nucleic acid sequences. In a further aspect, the fusion nucleic acids are each a component of a retroviral vector.

In another aspect, the fusion nucleic acids further comprise a sequence encoding a reporter protein, and this sequence is operably linked to the nucleic acid sequence encoding the candidate bioactive agent. Examples of a reporter protein include, but are not limited to, an autofluorescent protein, for example, a green fluorescent protein (GFP) from Aqueorea, or a *Renilla* species.

In a further aspect, the cells are collected by fluorescence-activated cell sorting (FACS)

In a further aspect, the parent phenotype of the cells is due to the presence of a stimulator and the cells comprise a stimulator. In a preferred embodiment, the stimulator induces the parent phenotype. Examples of stimulators include, but are not limited to, cytokines, ligands or antibodies against cells surface receptors, growth factors, hormones, peptides, neuropeptides, drugs or compounds, LPS, viruses, bacteria, and so on. In a preferred embodiment, the stimulator is interleukin 4 (IL-4), a cytokine, that has various biological activities, for example, IL-4 induces germline epsilon promoter (transcription) in B cells. In another preferred embodiment, the stimulator is anti-TCR (T cell receptor), a stimulator that activates T cell activation as monitored by CD69 upregulation.

In another aspect, the cells having an altered phenotype are mammalian cells. Examples of mammalian cells having an altered phenotype, include but are not limited to, rodent cells and human cells.

In another aspect, the altered phenotype is the modulation of a T cell surface marker, for example, CD3, CD25, CD28, CD40L, CD69, CD95, or CD95L. Further examples of an altered phenotype, include but are not limited to, the modulation of cell cycle regulation, exocytosis, IgE secretion, IgE switching, antigen-induced B cell differentiation, antigen-induced B cell isotyping, apoptosis, angiogenesis, and T cell receptor (TCR) activation.

BRIEF DESCRIPTION OF THE FIGURES

FIG. 1 schematically depicts the cell line BH1-4 and HBEGF Diphtheria toxin selection in the cell line. The new cell line generated contains a reporter driven by the germline ε promoter: The reporter HB-EGF functions as the receptor for diphtheria toxin and confers high sensitivity to diphtheria toxin killing following IL4 induction (for use in survival screening strategies). The BH1-4 screening line consists of the B cell line BJAB engineered to contain the above reporter.

The BH2-A5 screening line consists of the B cell line BJAB engineered to contain the above dual-function reporter. Over 7500 single cell clones were screened to obtain this line.

Figure 3:
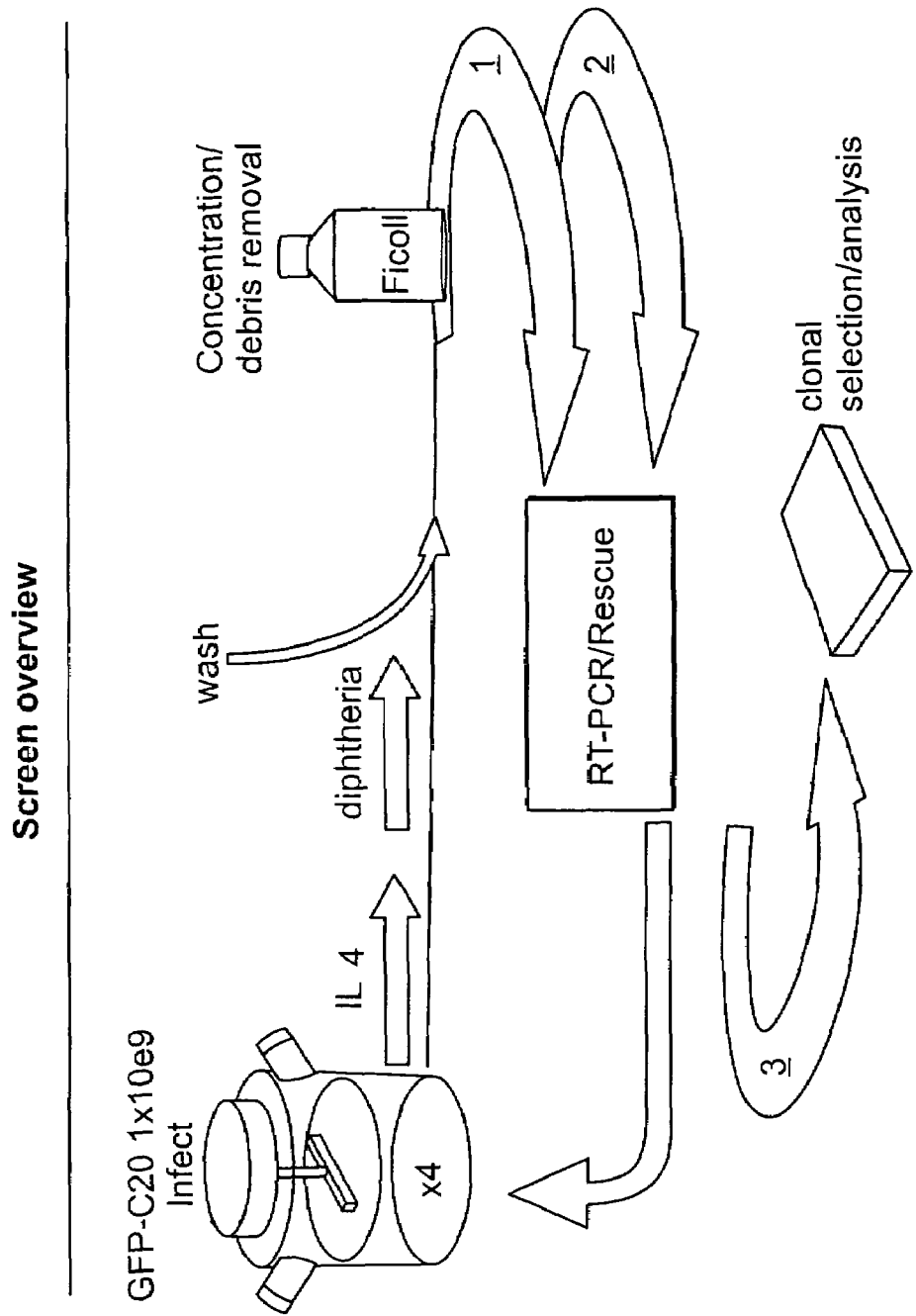

FIG. 3 depicts the conventional screening method.

Figure 4:
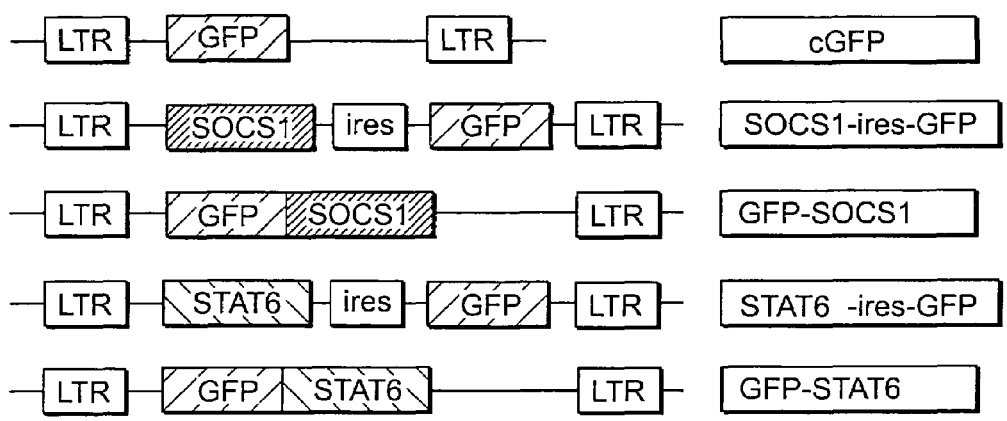

FIG. 4 schematically depicts five different retroviral vectors which were constructed as positive controls for the screening assay, and are the encoded GFP, SOCS1, STAT6Δ, and/or ires are operably linked to a promoter in the retroviral vector: the retroviral vector cGFP contains the GFP; the retroviral vector SOCS1-ires-GFP contains, from 5' to 3' (and operably linked), SOCS1, internal ribosomal entry site (IRES), and GFP; the retroviral vector GFP-SOCS1 contains, from 5' to 3' (and operably linked), GFP-SOCS1 fusion; the retroviral vector STAT6Δ-ires-GFP contains, from 5' to 3' (and operably linked), STAT6Δ, ires, and GFP; and the retroviral vector GFP-STAT6Δ contains, from 5' to 3' (and operably linked), GFP-STAT6Δ fusion.

Figure 5:
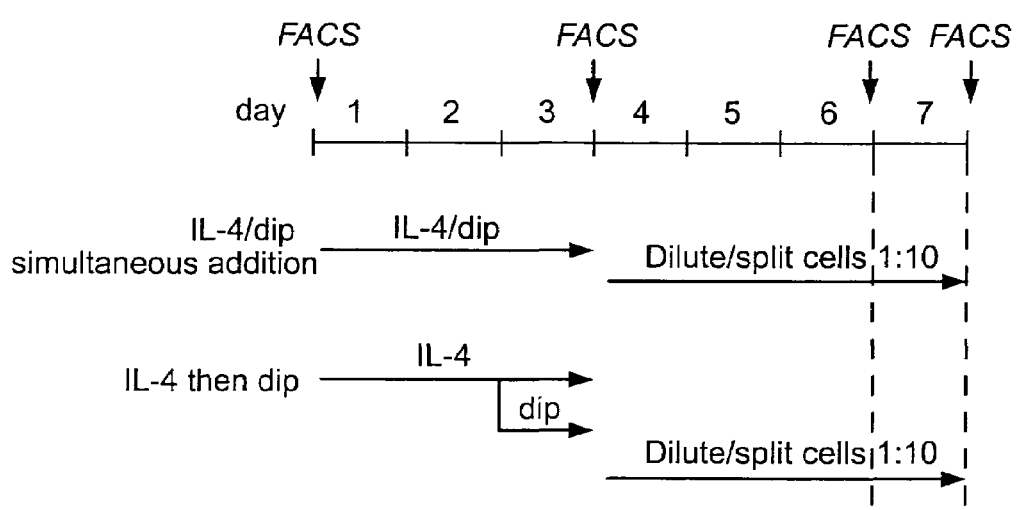

FIG. 5 depicts the assay of the five retroviral vectors described in FIG. 4, in BH1-4 cells.

Figures 6, 6A:
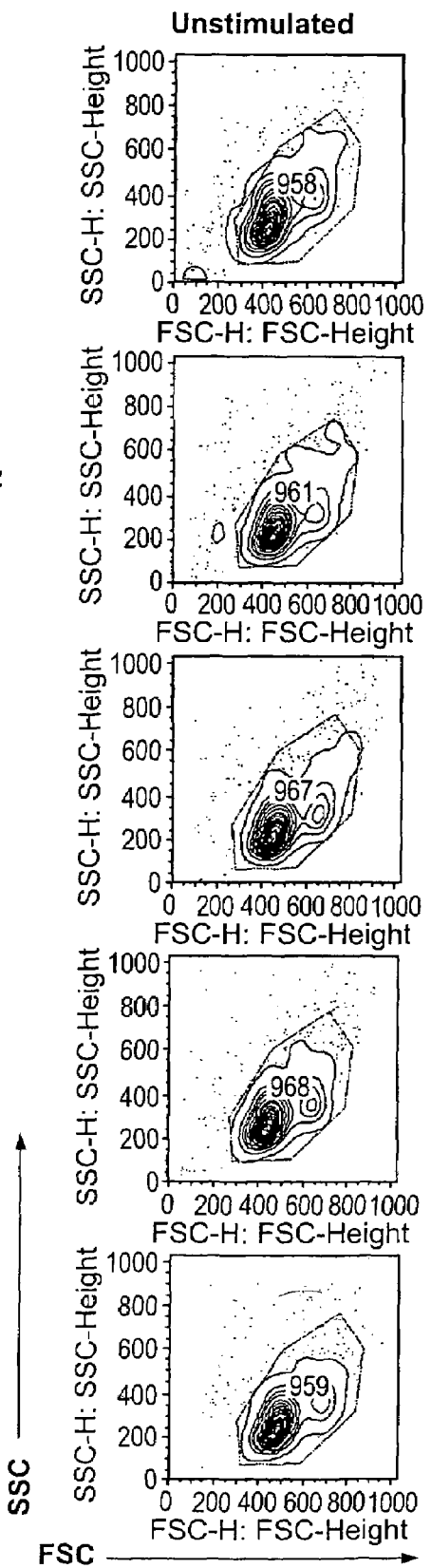
Figure 6B:
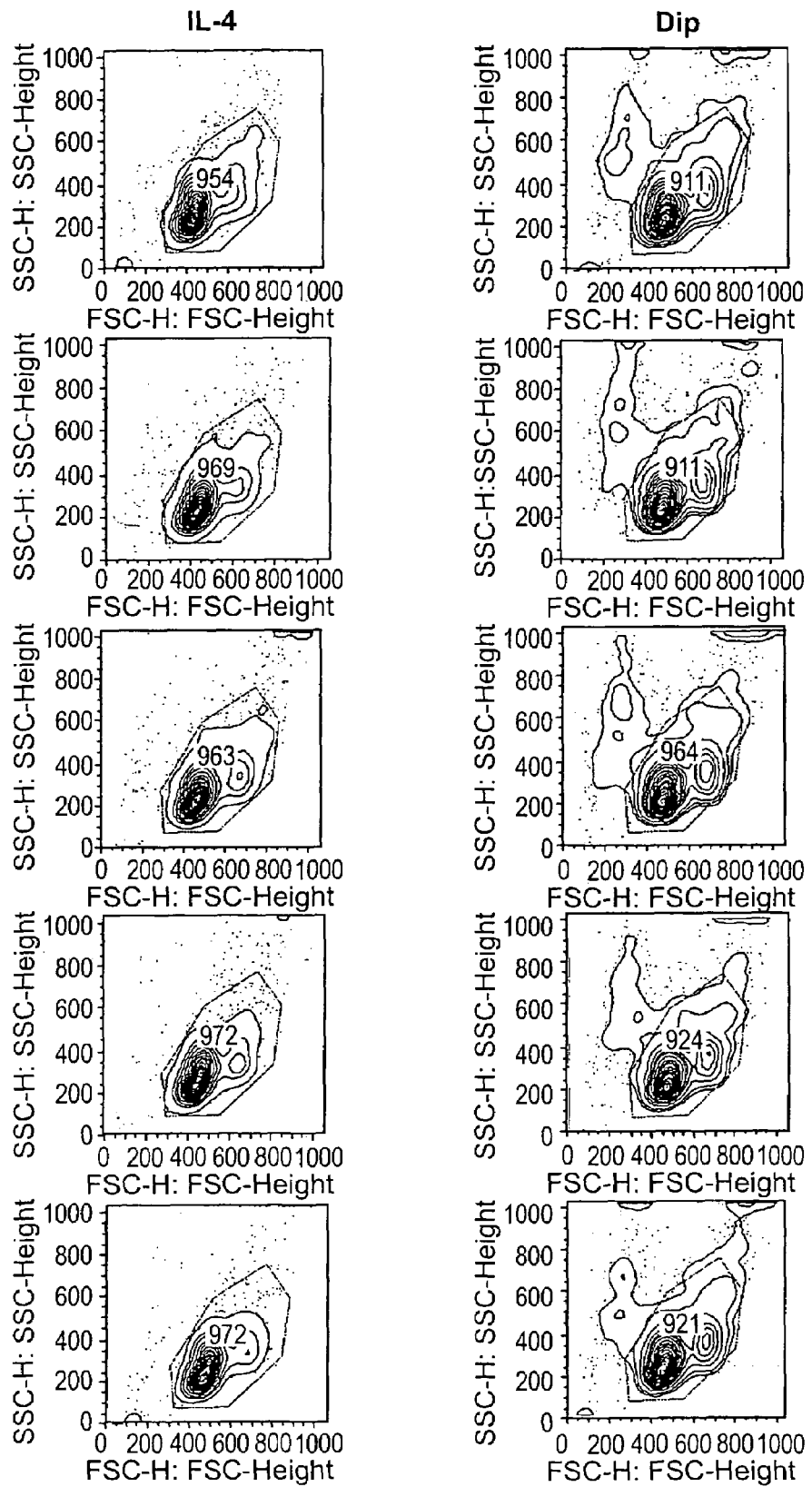
Figure 6C:
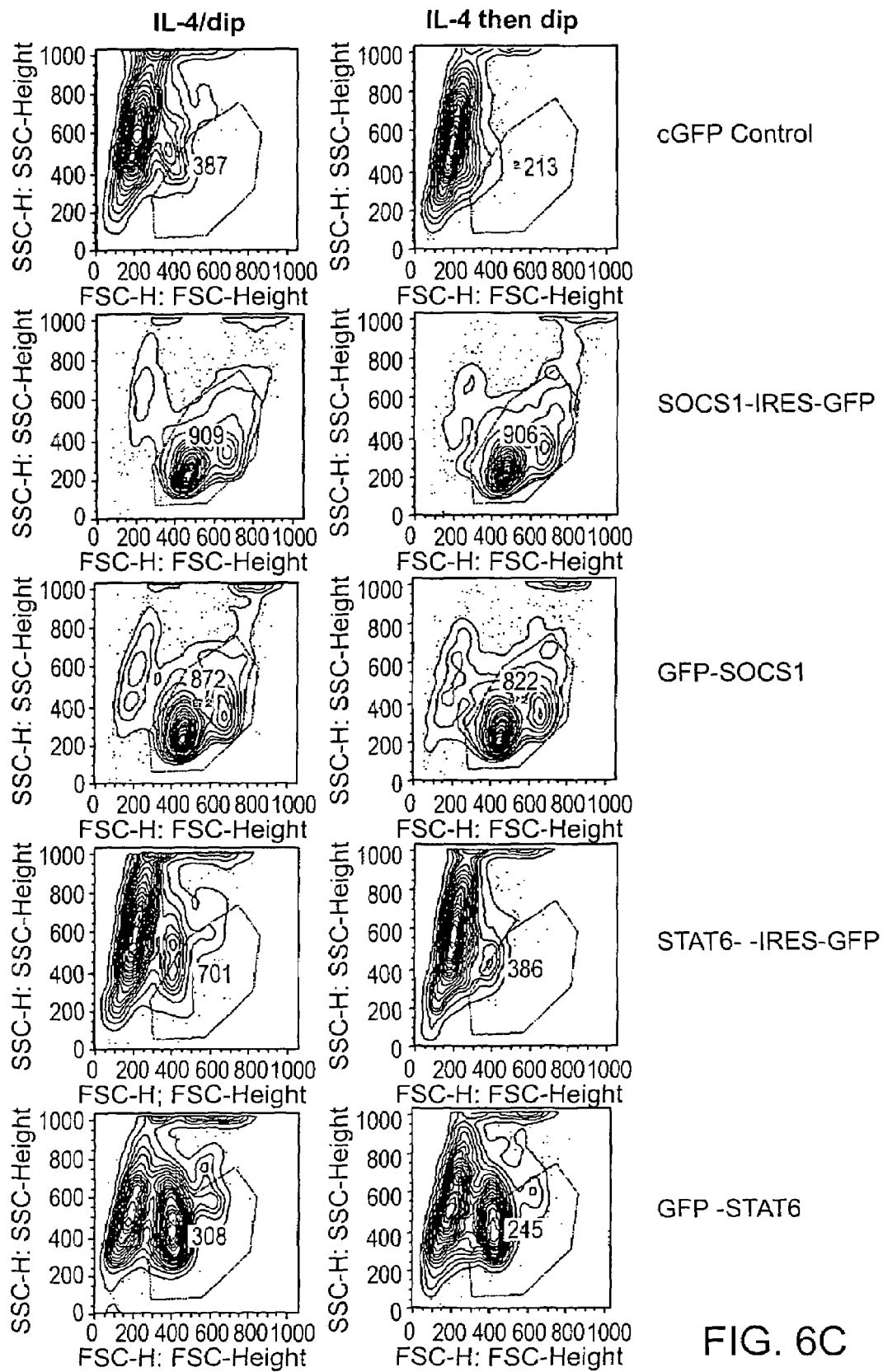

FIG. 6 depicts the effects of SOCS1 and STAT6 on IL4/diphtheria (IL4/dip) induced death of BH1-4 cells 6 days post infection for each of the five retroviral vectors described in FIG. 4.

Figures 7, 7A:
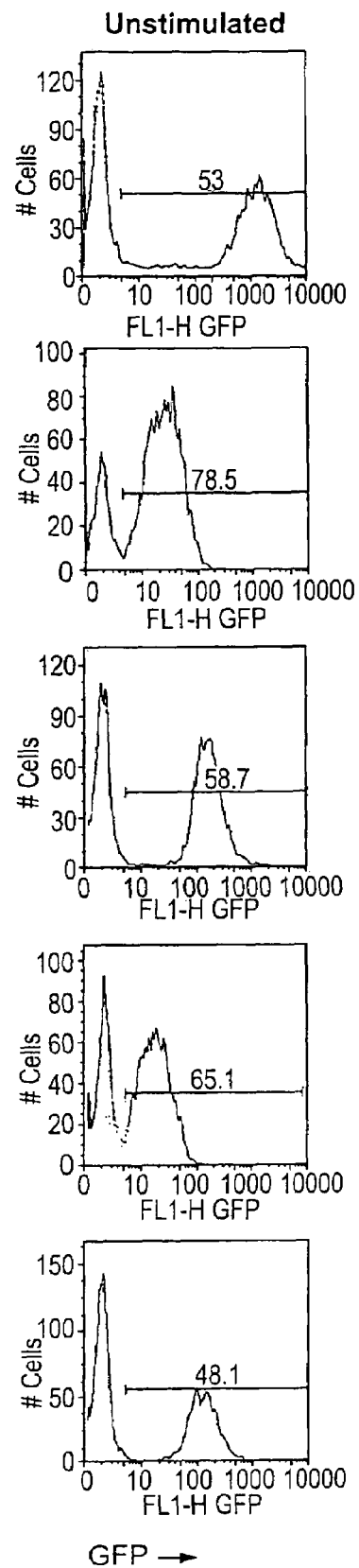
Figure 7B:
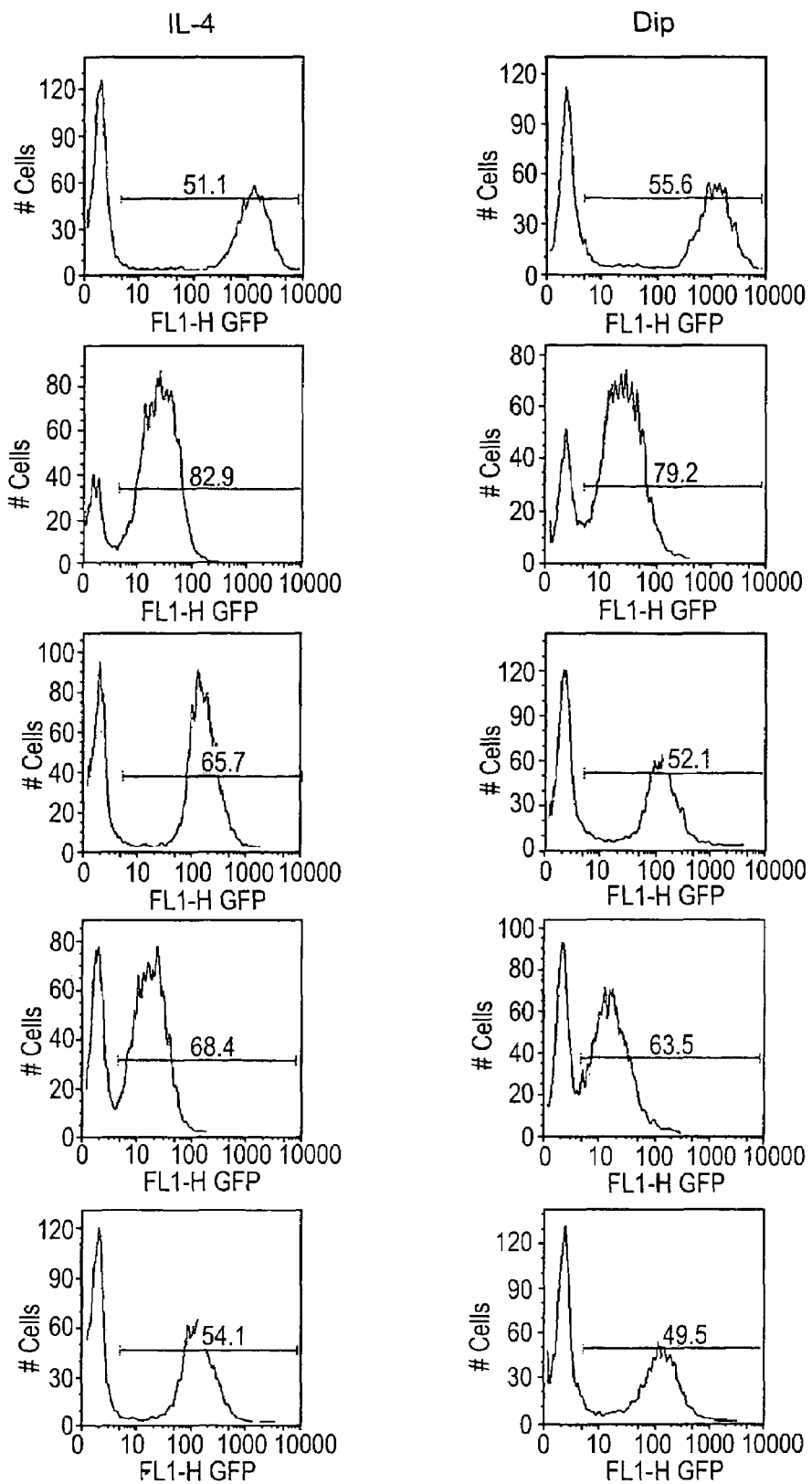
Figure 7C:
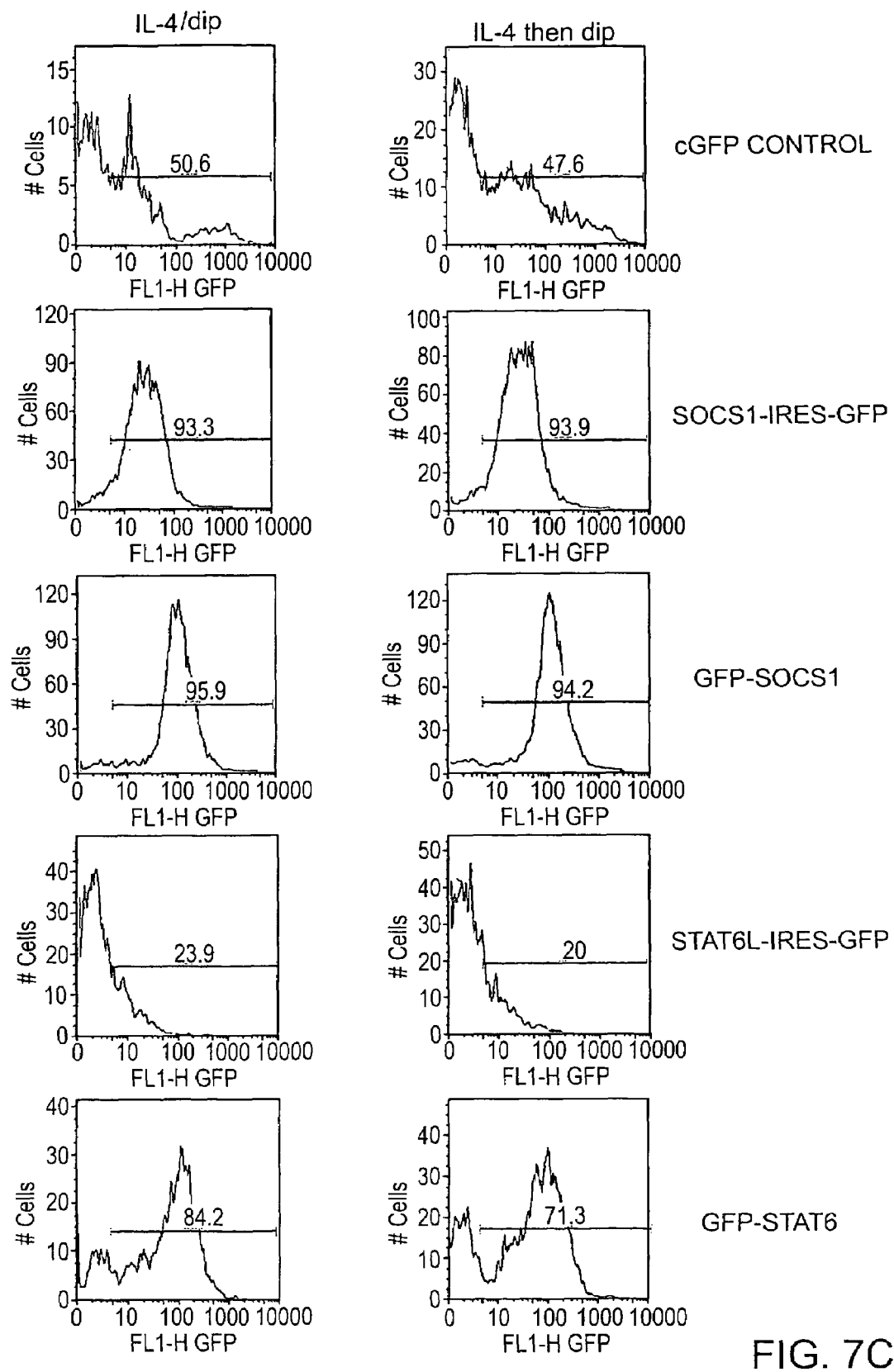

FIG. 7 depicts the same results as depicted in FIG. 6 except that the vertical axis indicates the number of cells, and the horizontal axis indicates the amount of GFP fluorescence.

FIG. 8 depicts a screening assaying using spiked cell.

Figure 9A:
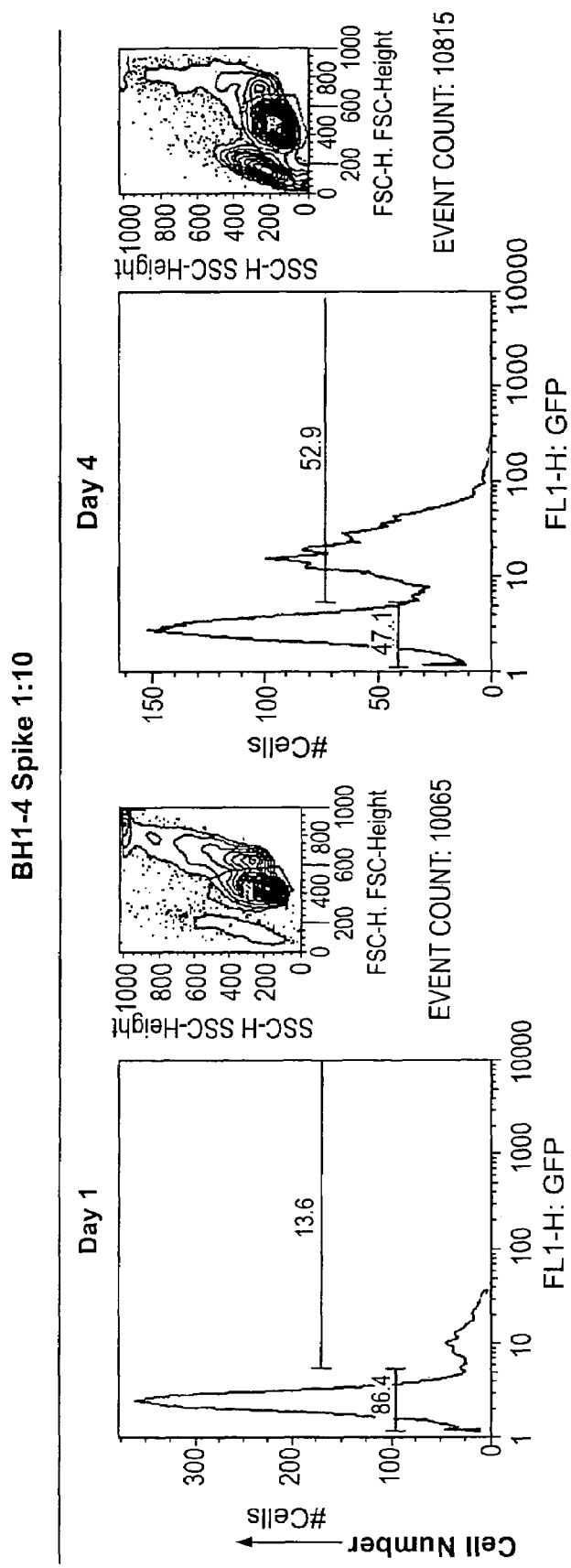
Figure 10A:
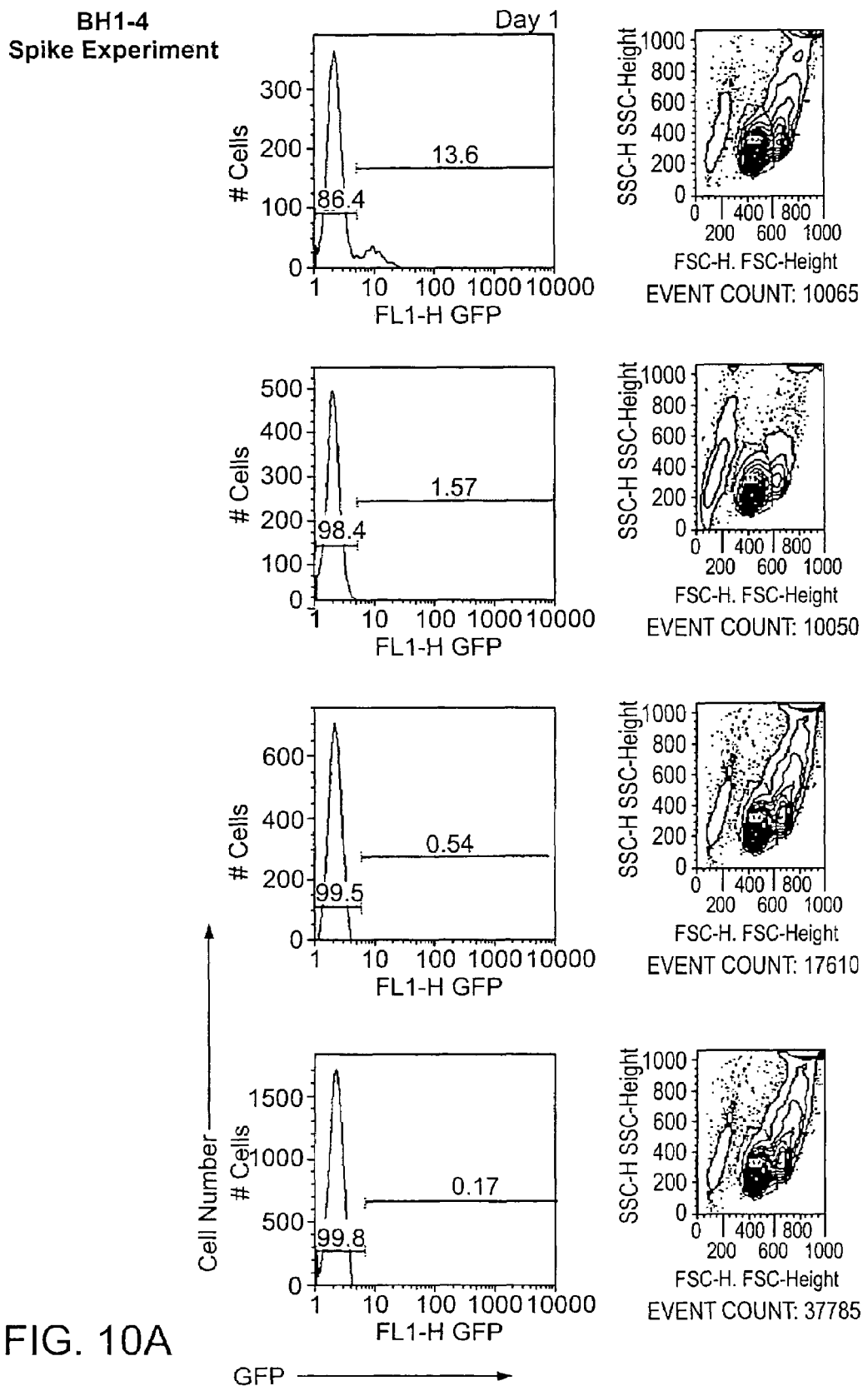
Figure 10B:
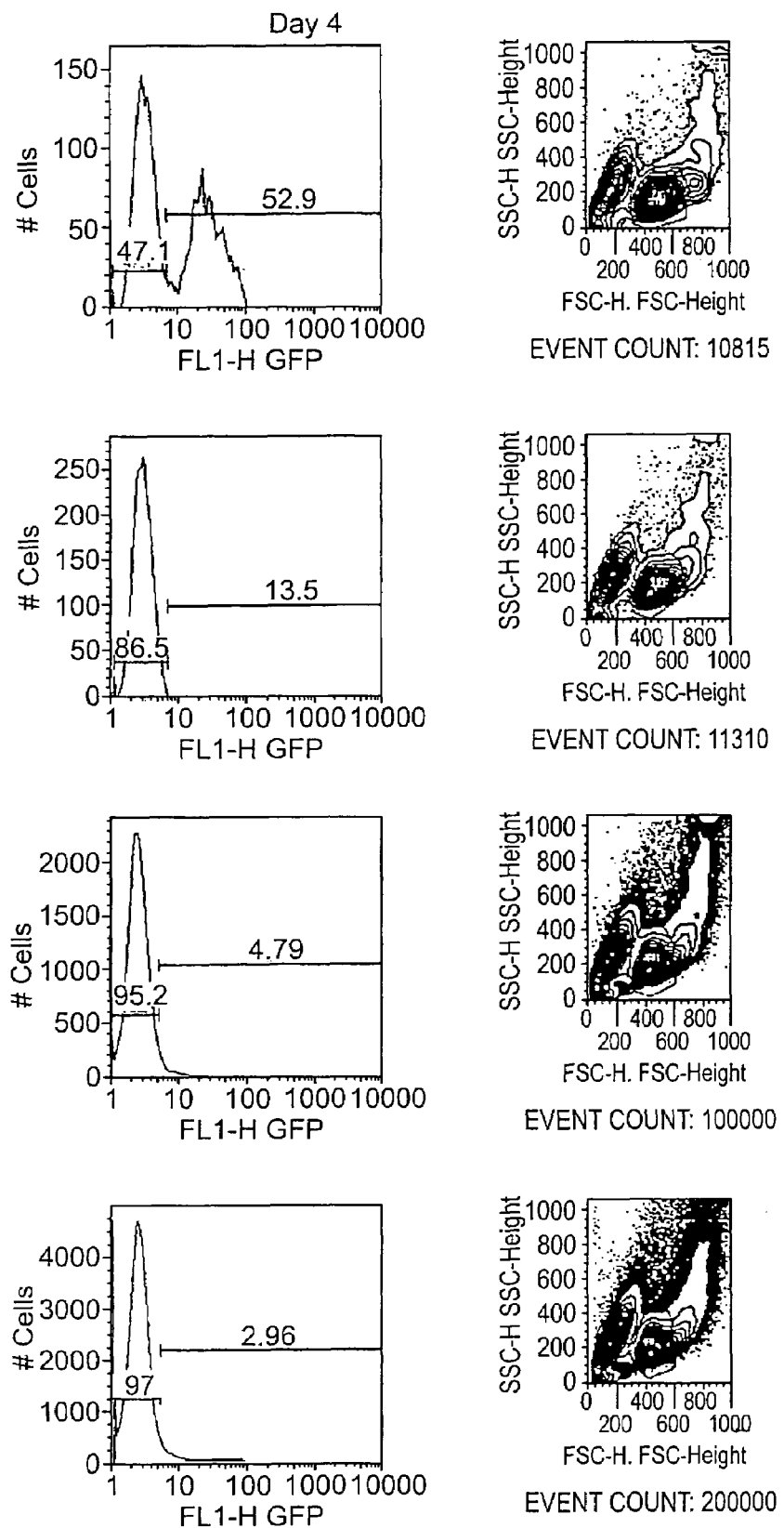
Figure 10C:
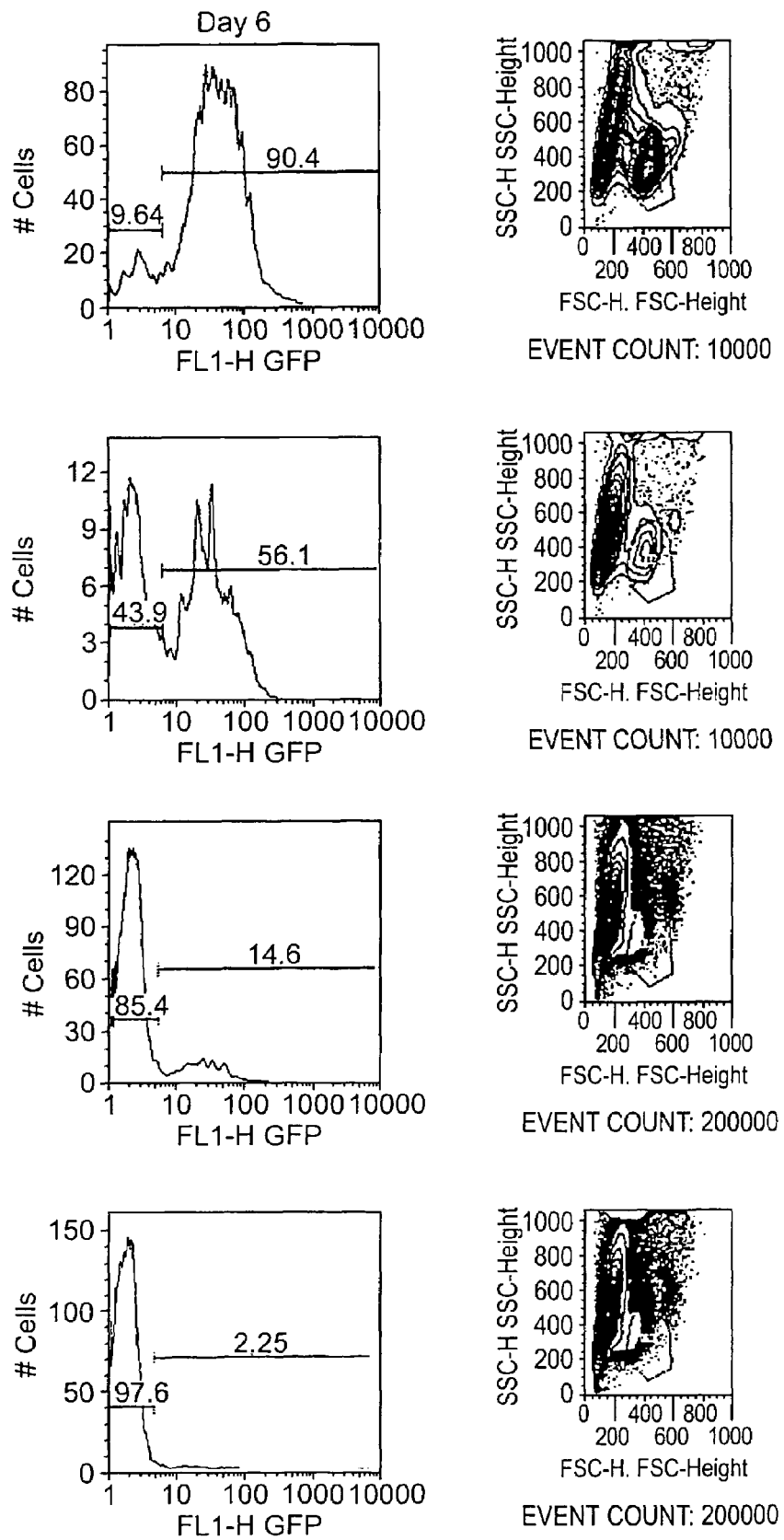
Figure 10D:
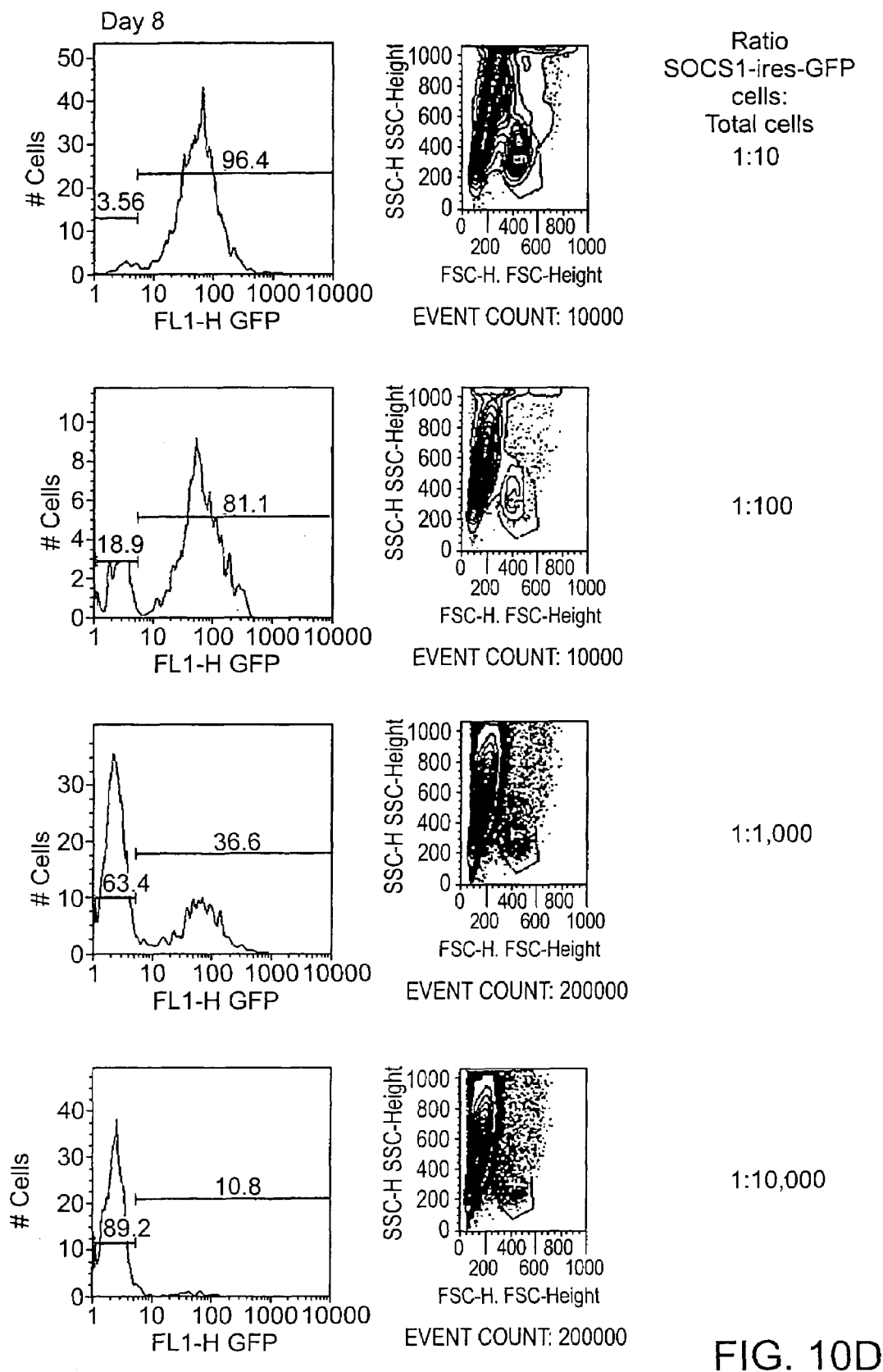
Figure 11B:
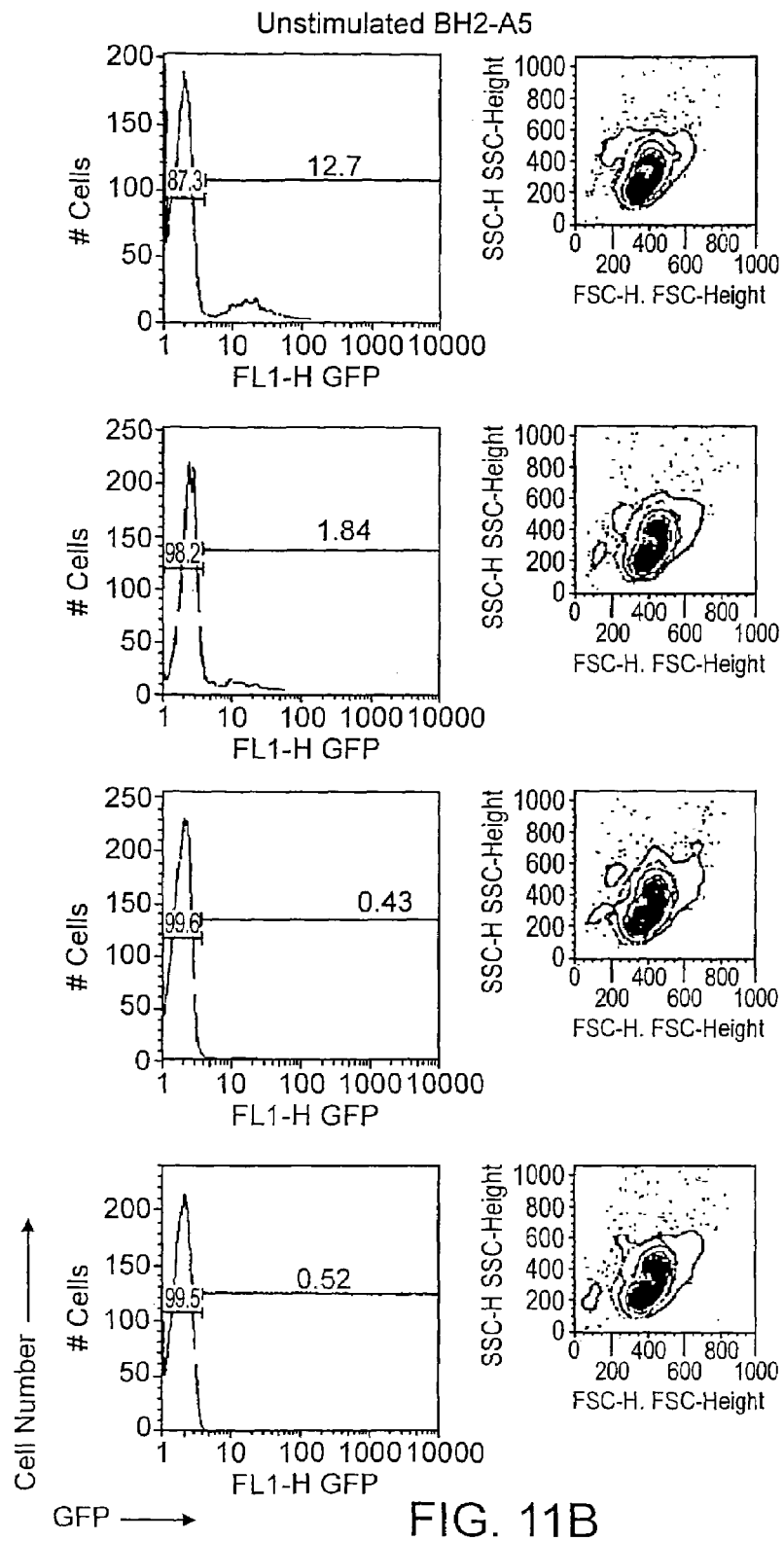
Figure 11C:
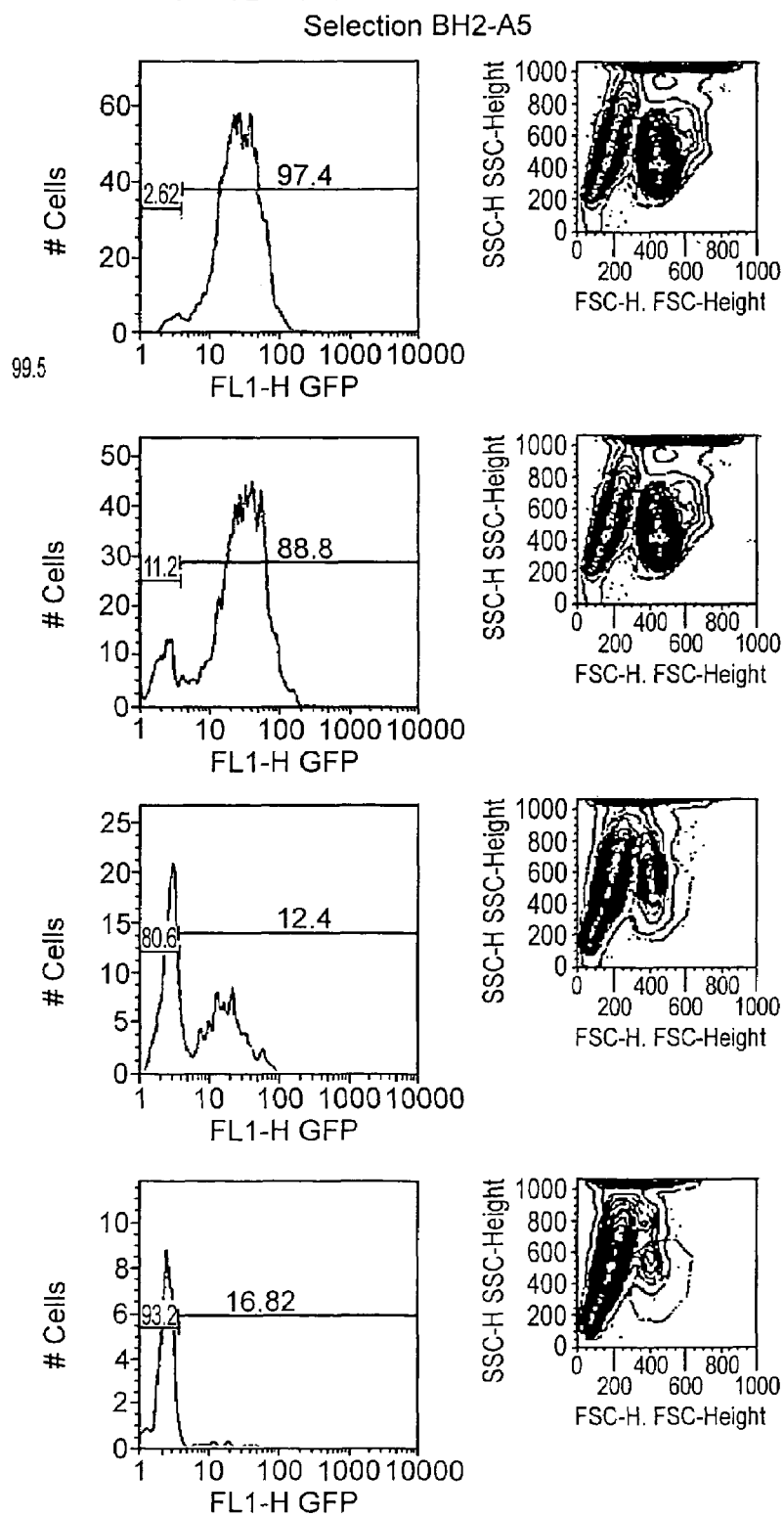
Figure 11D:
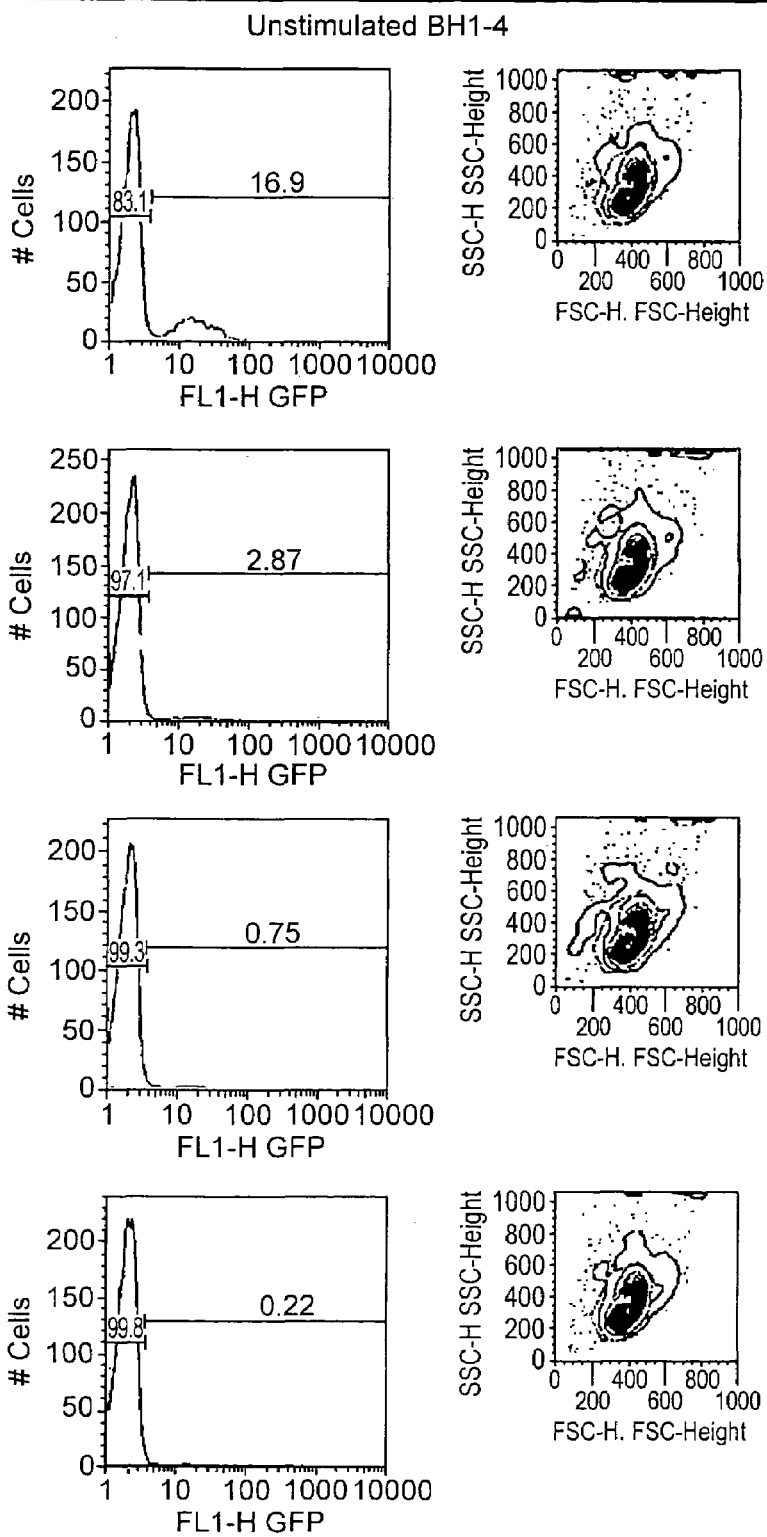
Figure 11E:
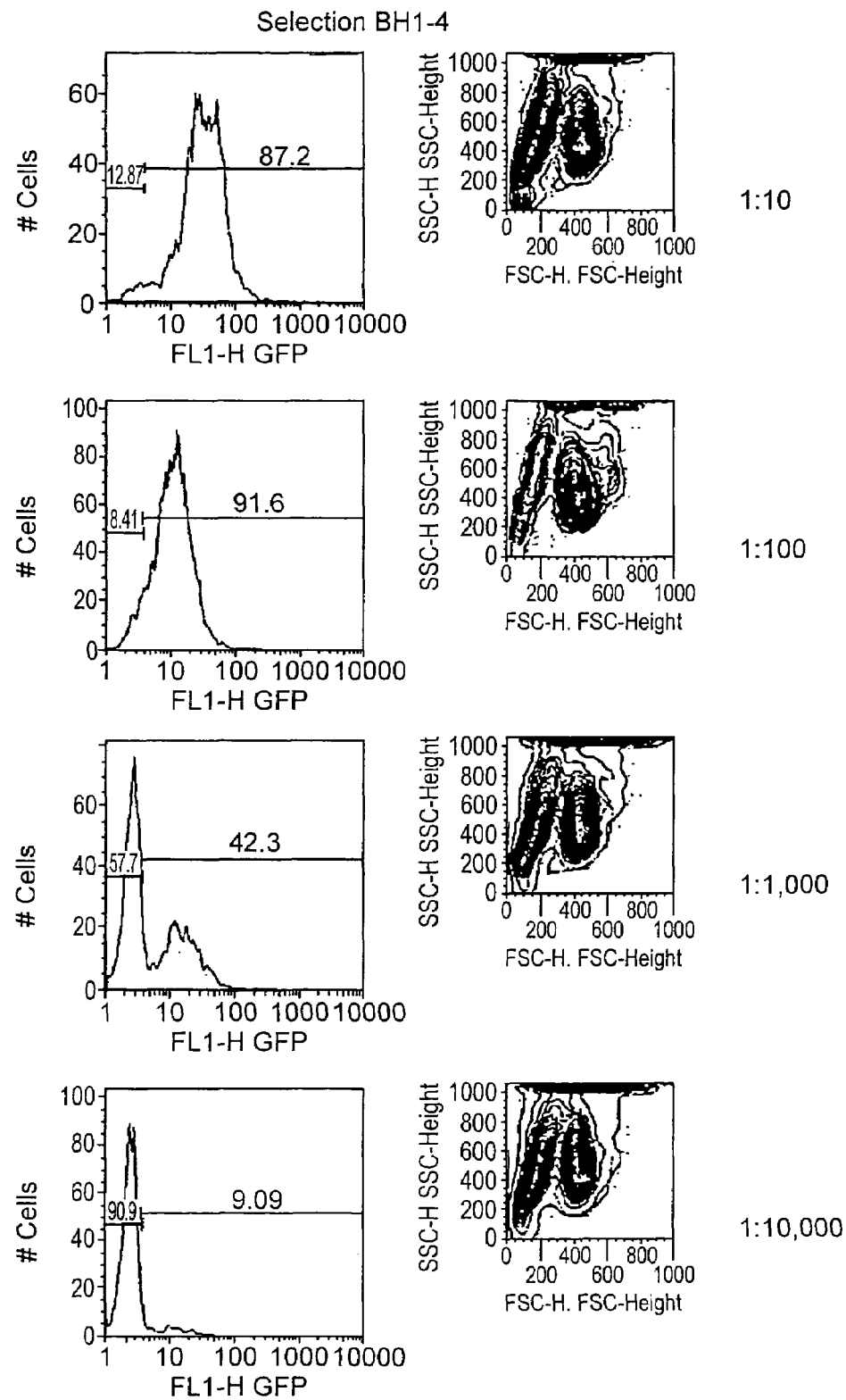

FIG. 9 schematically depicts the IL4-dip selection assay using BH1-4 cells and depicts the results of the assay starting with a 1:10 dilution of the SOCS1-infected cells.

FIG. 10 depicts the results for screening assays using BH1-4 cells starting with the 1:10, 1:100, 1:1,000, and 1:10,000 dilution of the SOCS1-infected cells.

FIG. 11 depicts the results of screening assays for BH1-4 and BH2-A5 cells starting with the 1:10, 1:100, 1:1,000, and 1:10,000 dilution of the spiked cells.

Figure 12:
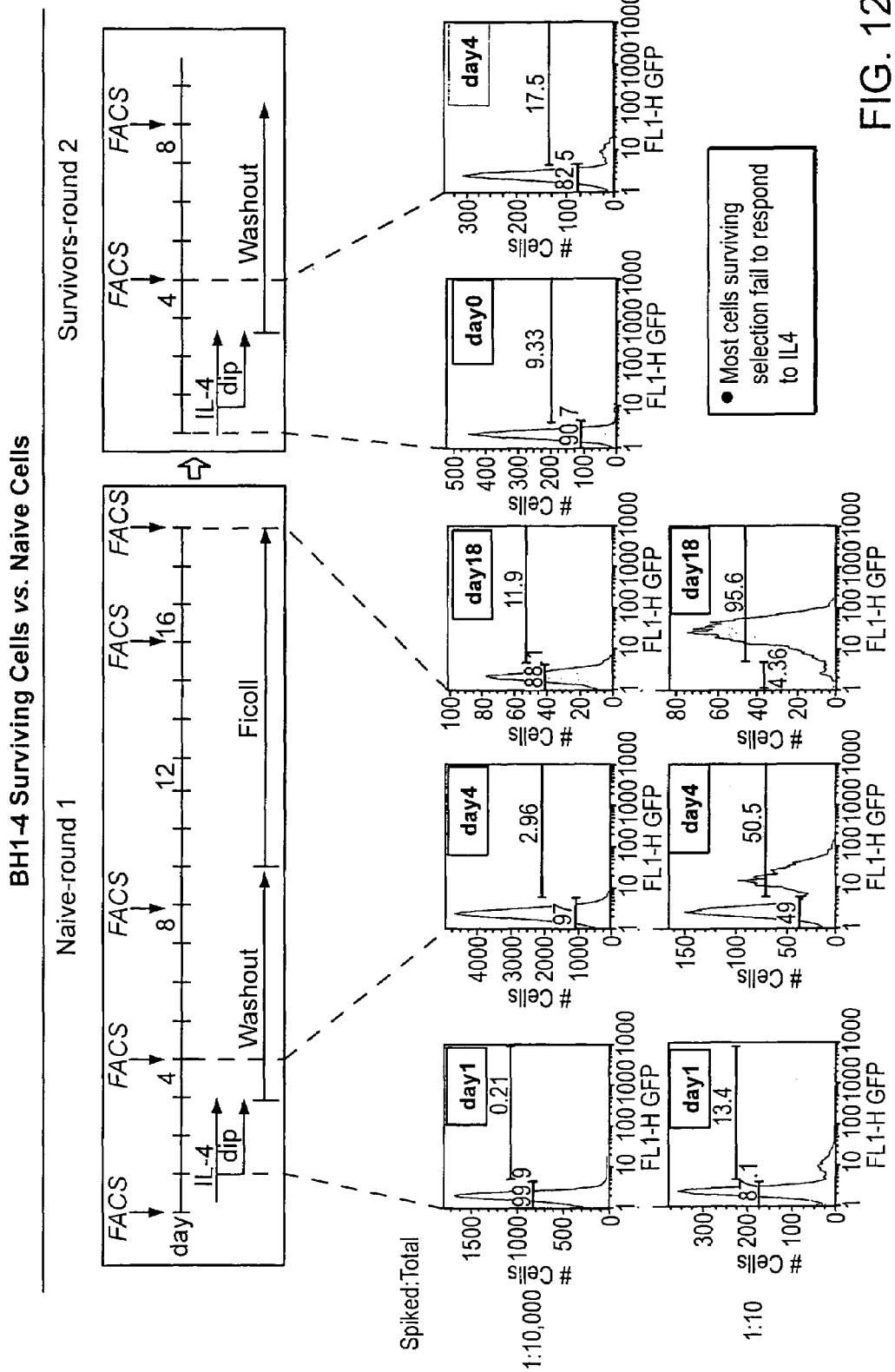

FIG. 12 depicts the results of selection beginning with naïve cells in a first round of selection with IL4-Dip and then subjecting the surviving cells from the first round of selection to a second round of selection with IL4-Dip.

Figure 13:
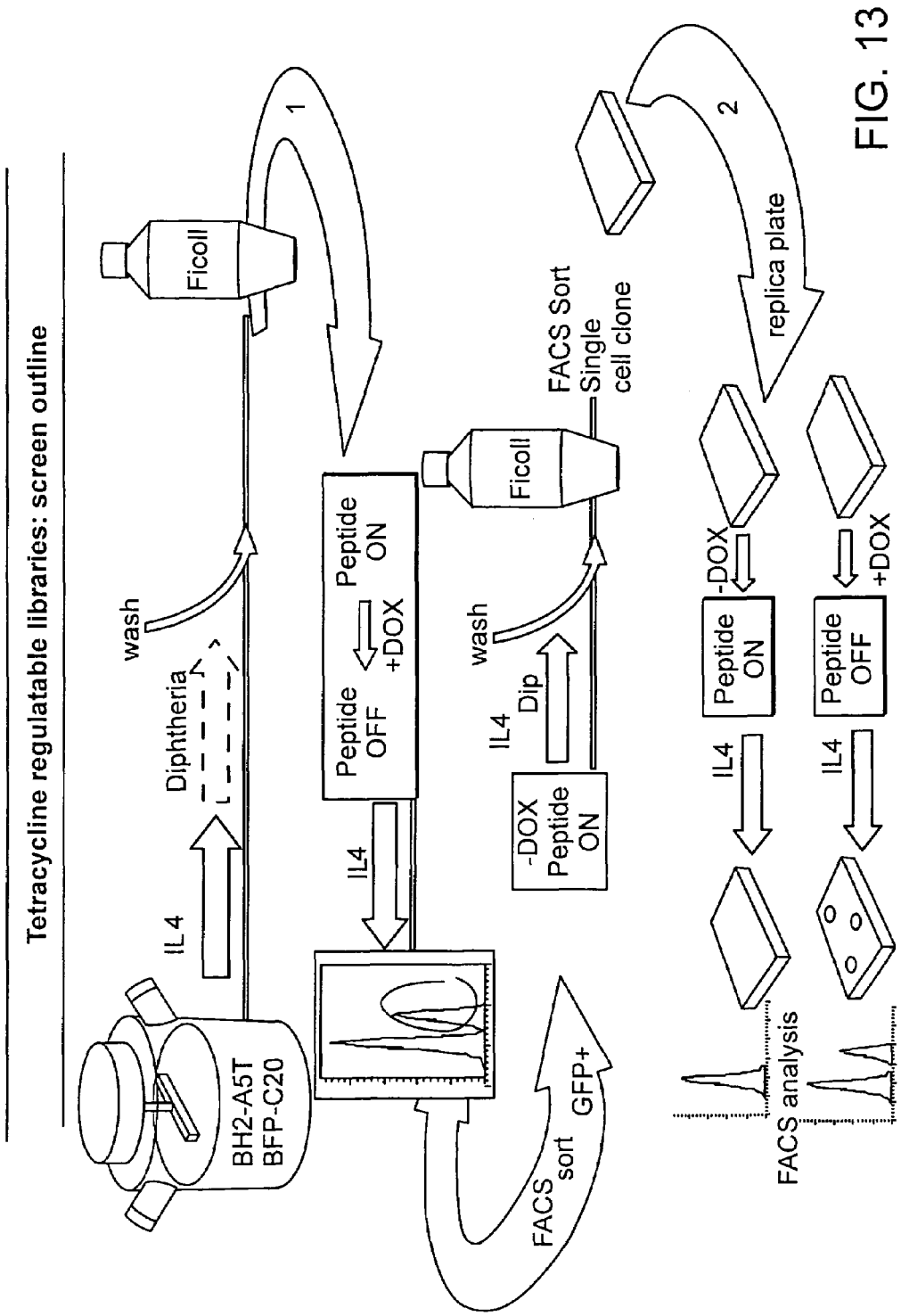

FIG. 13 depicts a screening assay using a novel cell line BH2-A5T with the peptide library BFP-C20 encoded by retroviral vectors.

Figure 14:
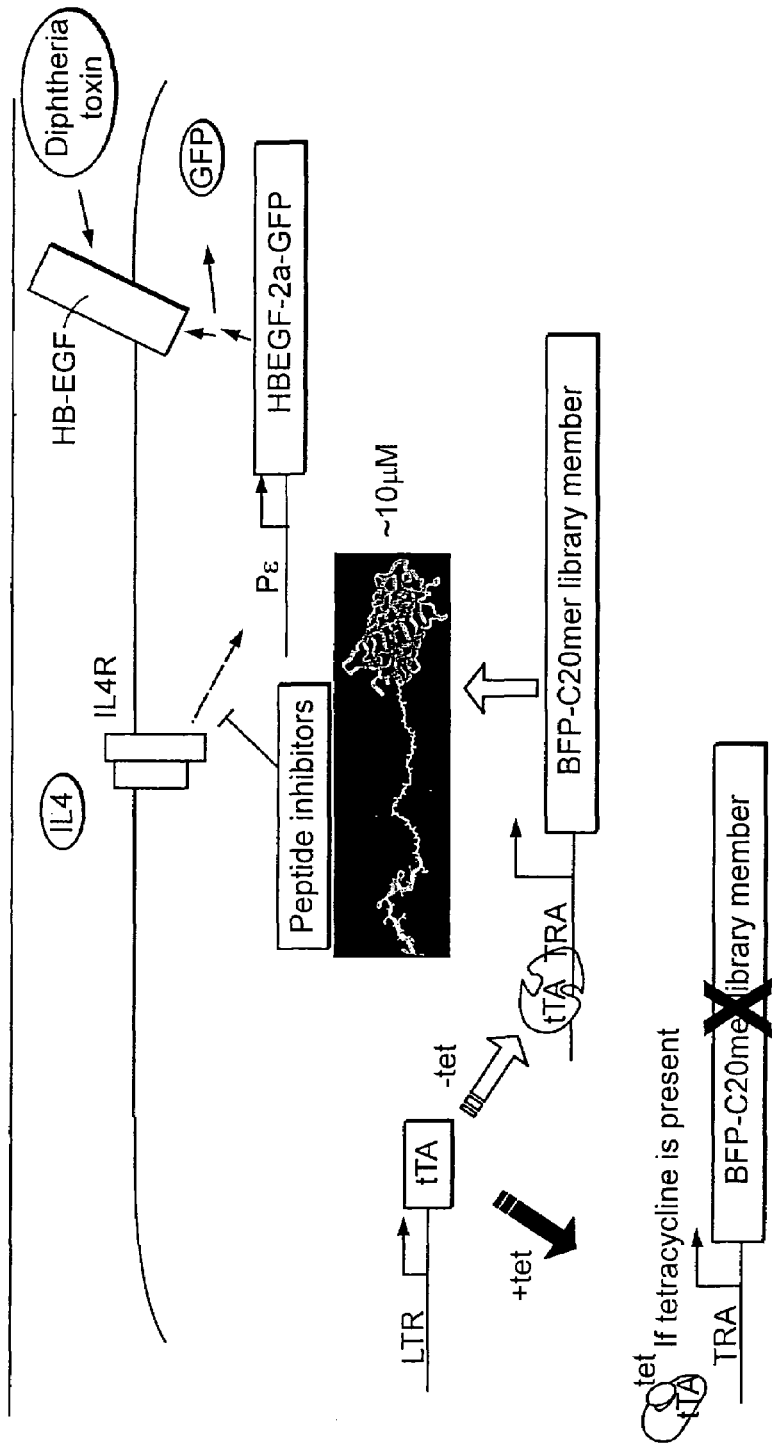

FIG. 14 depicts the cell line BH2-A5T (or "A5T" or "A5T-4") which expresses a Tet regulated transactivator (tTA or Tet transactivator) and allows for the Tet regulated expression of candidate bioactive agents introduced into the cells. The A5T-4 cell line was further engineered to express the tetracycline-regulated transactivator (tTA) allowing for regulation of peptide library expression. The 20 mer peptides are expressed as carboxy-terminal fusions to a BFP scaffold.

Figure 15:
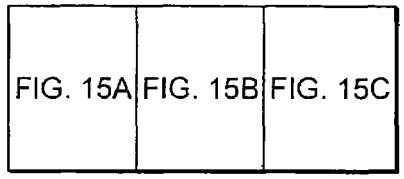
Figure 15A:
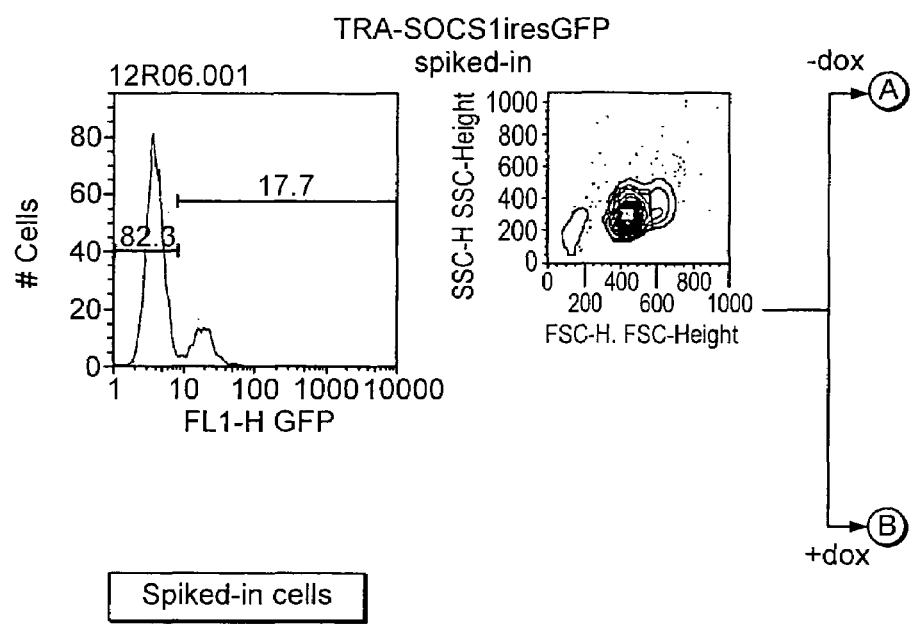
Figure 15B:
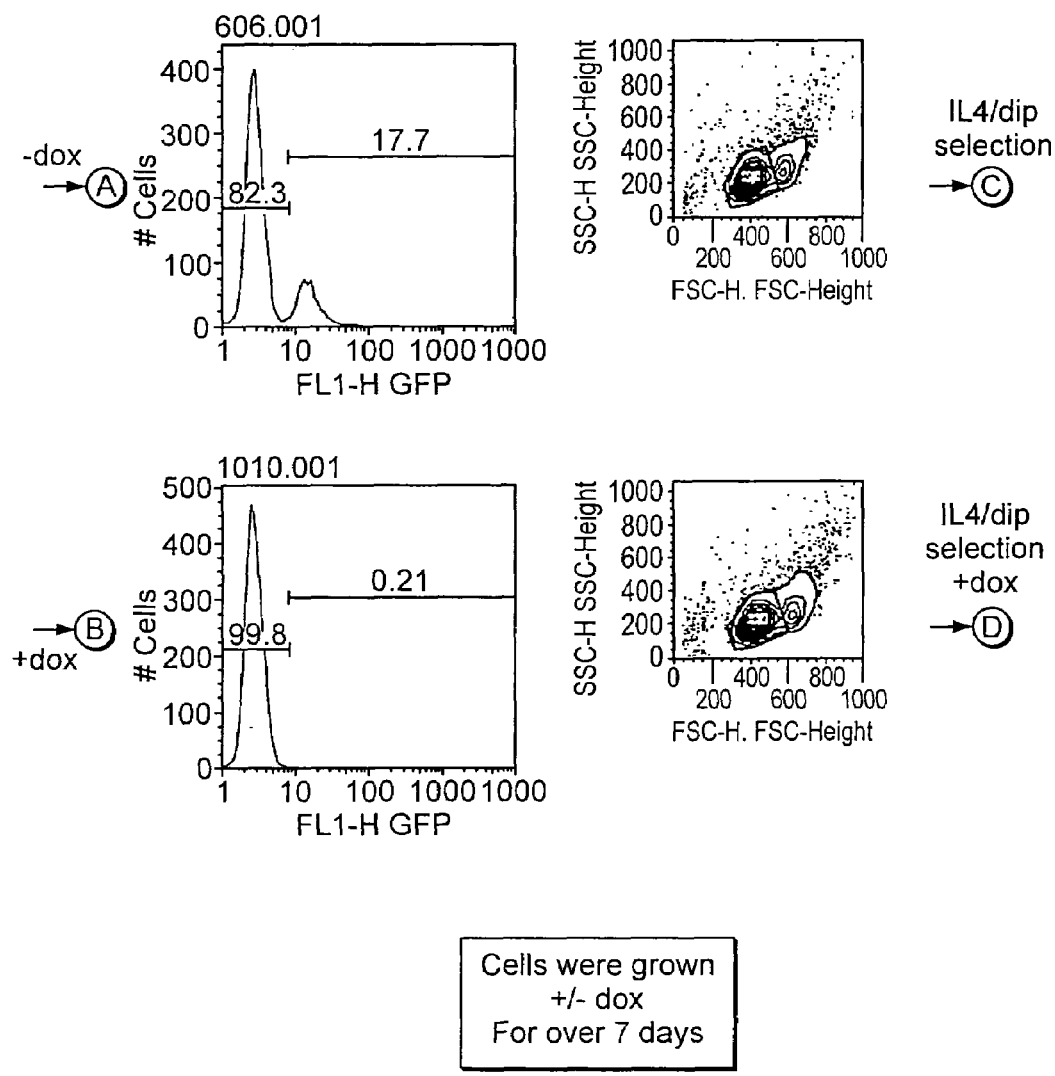
Figure 15C:
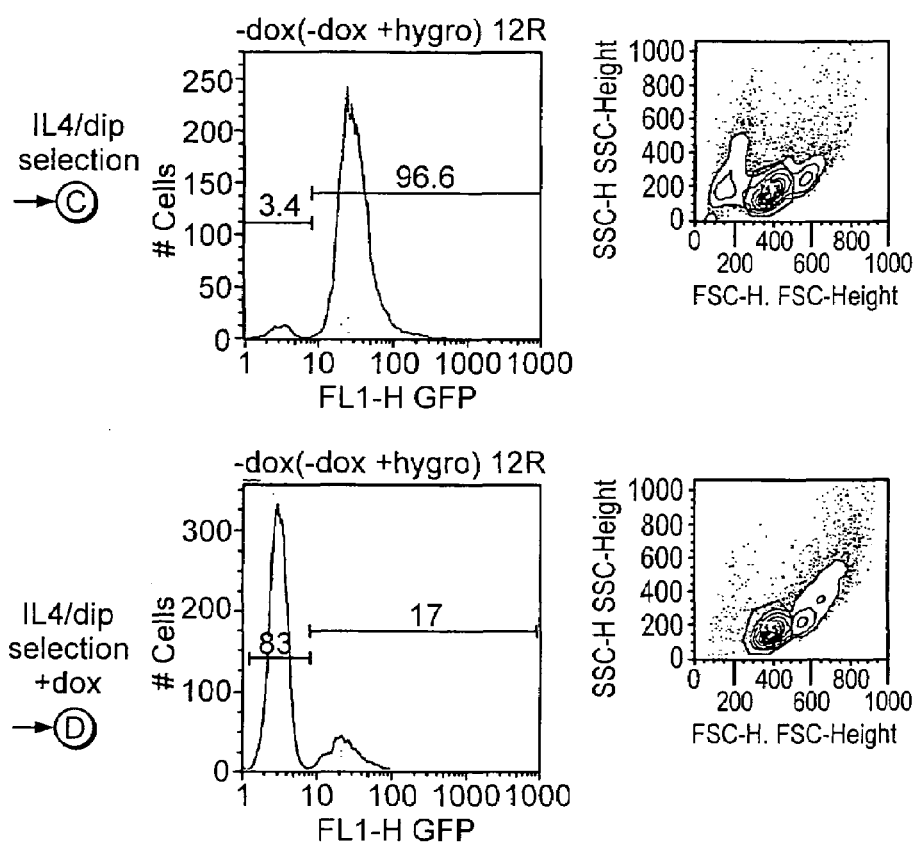

FIG. 15 depicts histograms indicating the amount of GFP fluorescence, in an experiment where IL4 responders were selected in the presence and absence of Dox in BH2-A5T cells spiked with cells infected with the retroviral construct TRA-SOCS1-ires-GFP. Cells were grown +/−dox for over 7 days. IL4/dip selection was performed in the presence or absence of dox. After selection, cells were grown without dox to allow for the SOCS1iresGFP expression.

Figure 16:
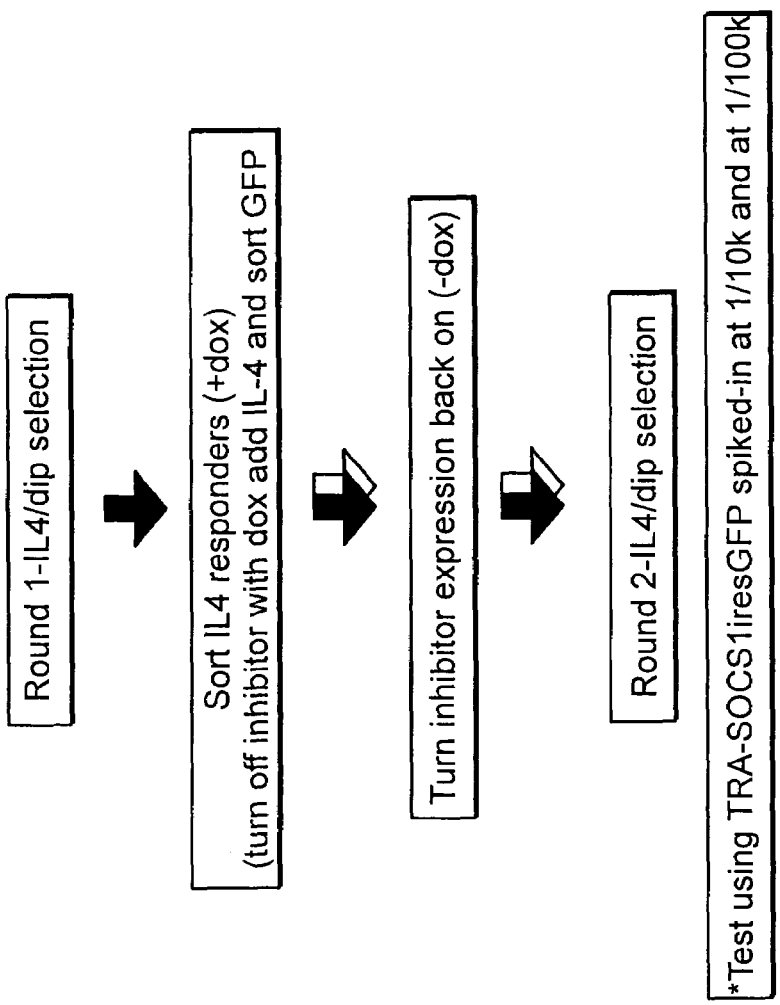

FIG. 16 depicts the round to round enrichment for cells expressing the known inhibitor SOCS1 by induction and repression of TRA-SOCS1-ires-GFP expression in BH2-A5T-4 cells using dox and sorting of the altered and parental cellular phenotype.

Figure 17:
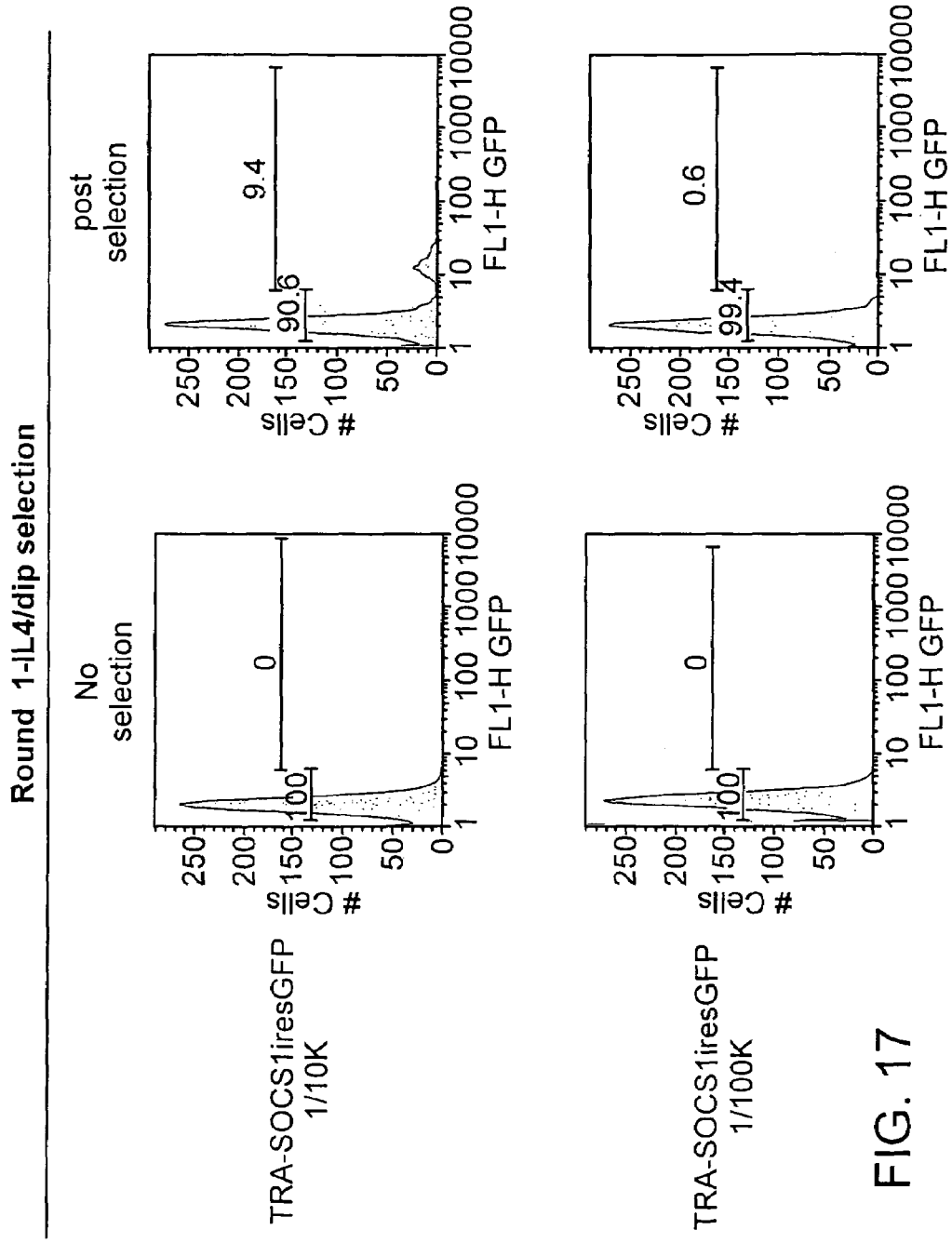

FIG. 17 depicts histograms indicating the amount of GFP fluorescence indicative of TRA-SOCS1-ires-GFP expression in cells after the first round of selection.

Figure 18:
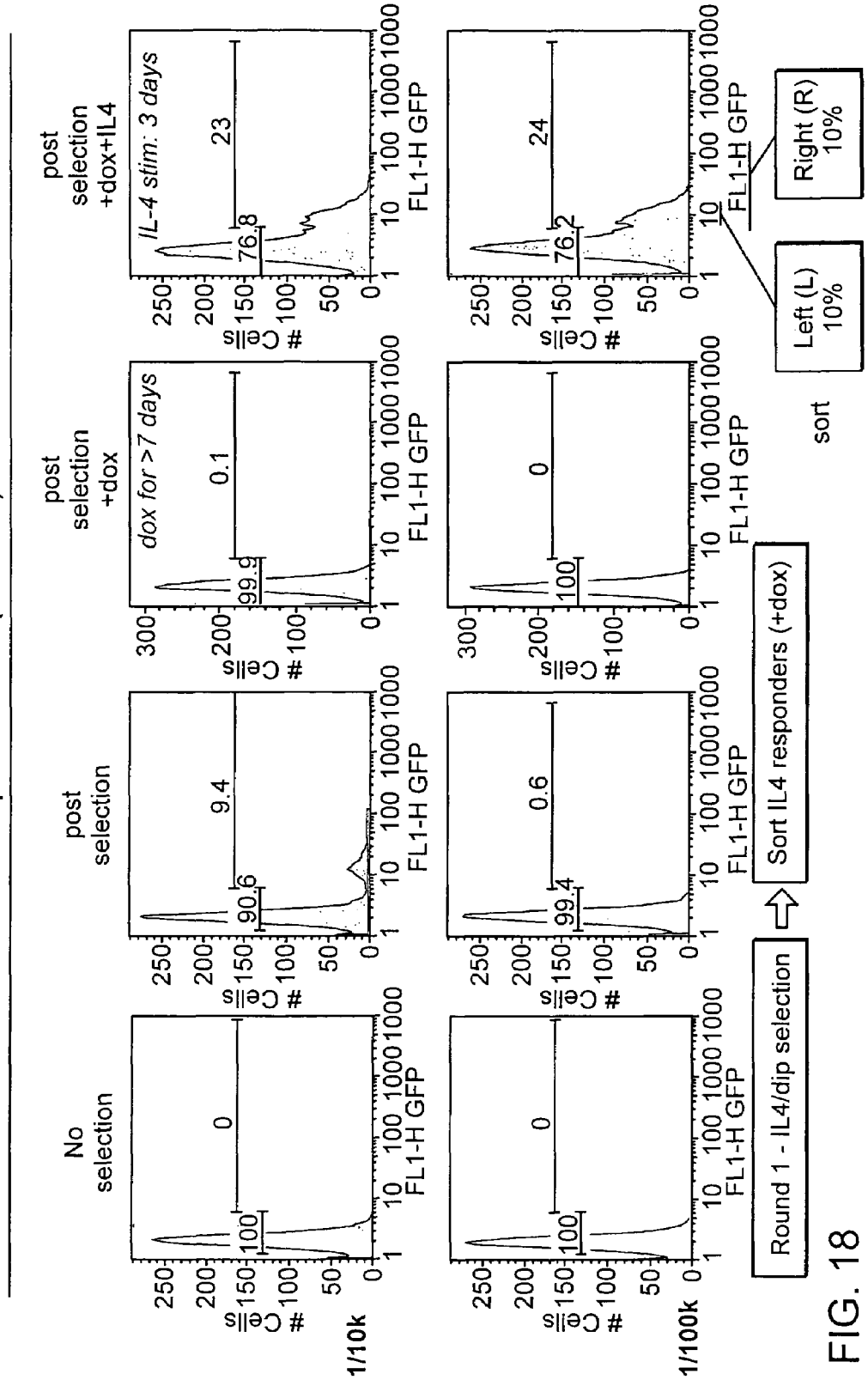

FIG. 18 depicts histograms showing the "Sort for IL4 responders" step in FIG. 16.

Figure 19A:
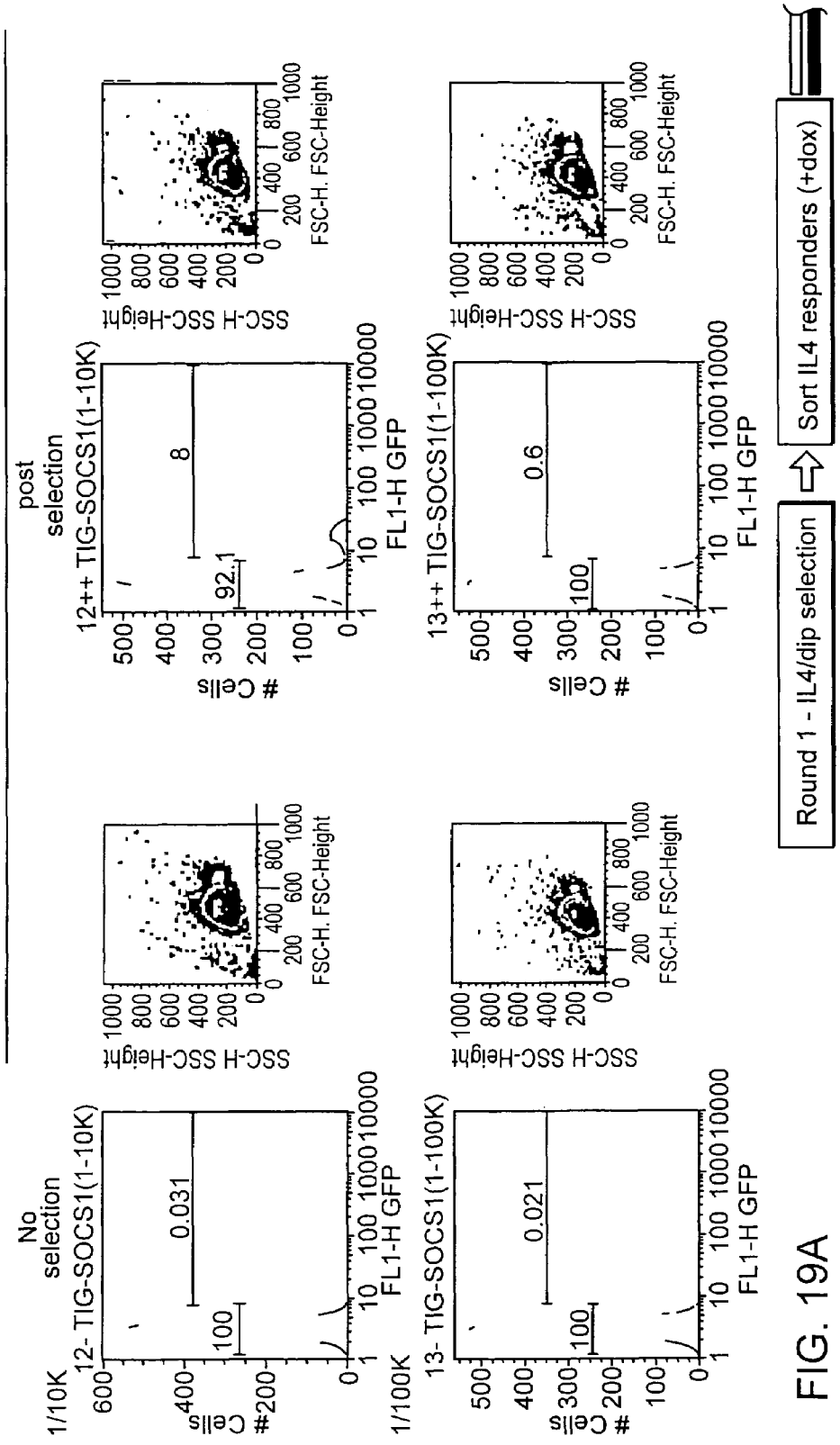
Figure 19B:
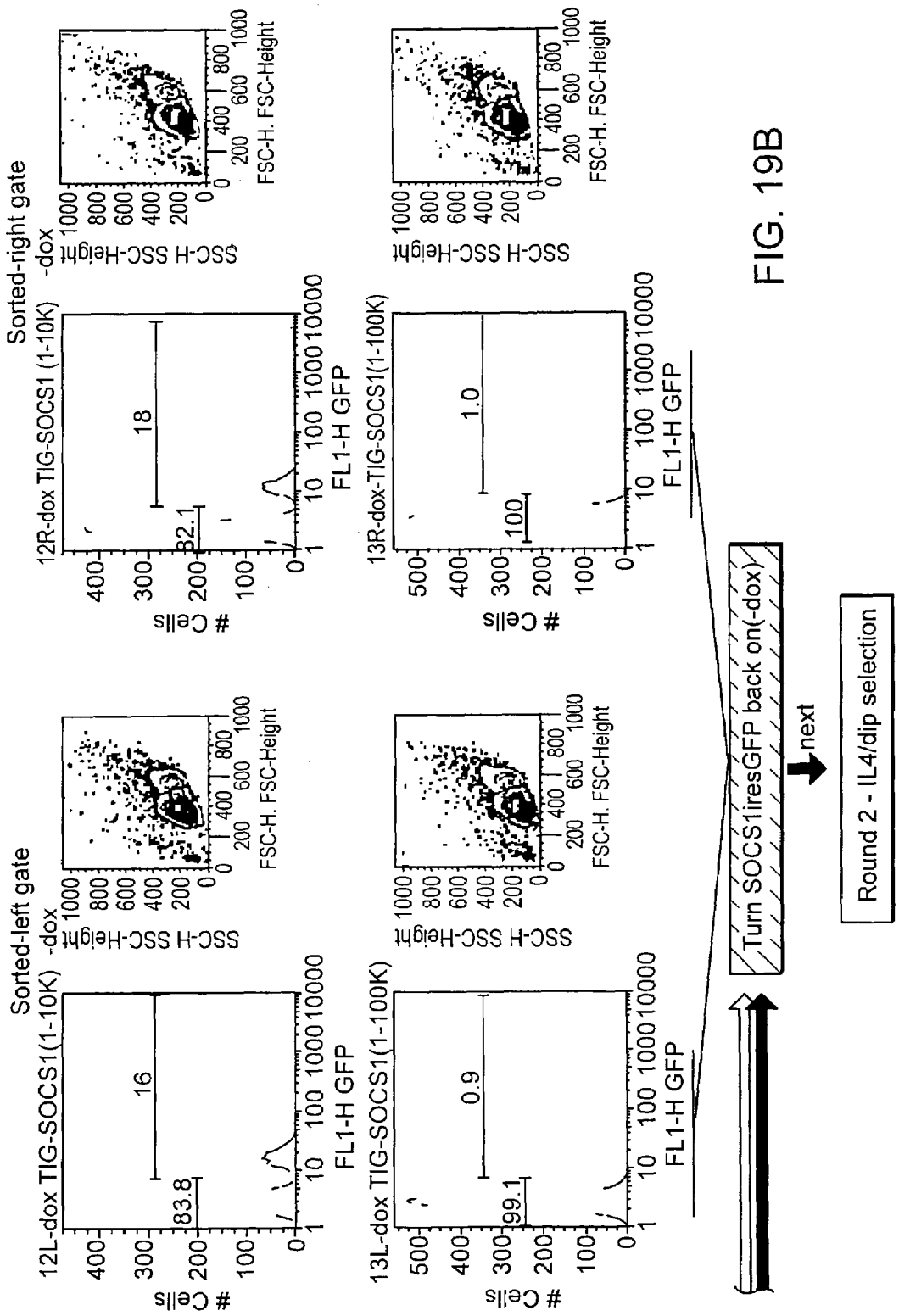

FIG. 19 depicts histograms showing the "Turn inhibitor expression back on" step in FIG. 16.

Figure 20B:
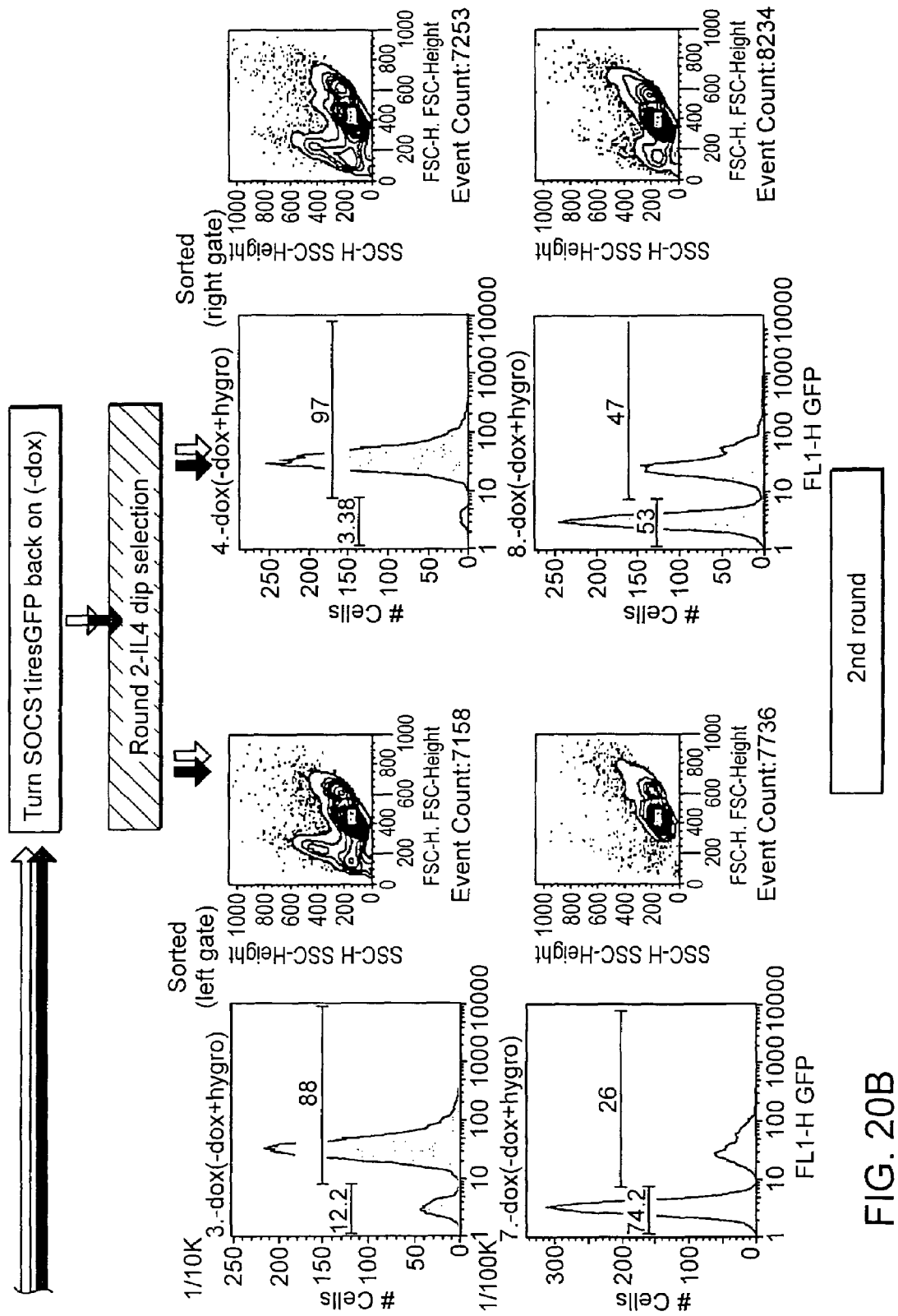

FIG. 20 depicts for the 1:10,000 dilution of cells, an 6.1% enrichment resulting from the first round of selection; for the second round of IL4/dip selection, a 88% enrichment from the de-doxed Left Gate cells and a 97% enrichment from de-doxed Right Gate cells from FIG. 19; and for the 1:100, 000 dilution of cells, an 0.3% enrichment resulting from the first round of selection; for the second round of IL4/dip selection, a 26% enrichment from the de-doxed Left Gate cells and 47% enrichment from de-doxed Right Gate cells resulting from the sorting of the cells cultured in the absence of Dox (FIG. 19).

Figure 21:
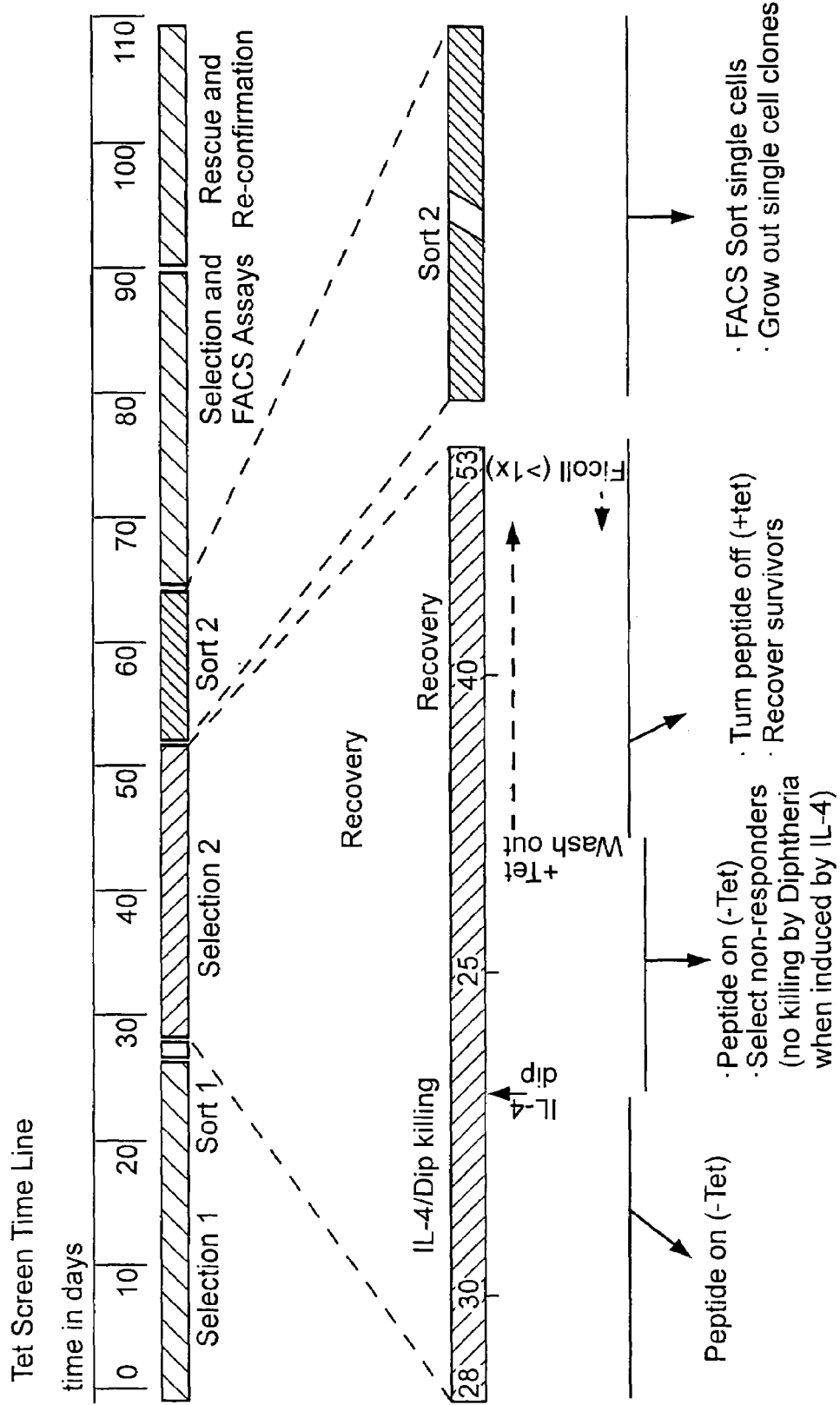

FIG. 21 schematically depicts an example of a timeline (in days) for a screening assay of the present invention, where the assay involves a first round of selection and sorting; a second round of selection and sorting; and thereafter single cell clones are grown. The single cell clones are then subjected to selection and FACS assays, the nucleic acid encoding the bioactive agent (e.g., a peptide inhibitor of IL4 signaling/induced expression) is then rescued and the phenotype is reconfirmed, e.g., by infecting naïve cells with the rescued nucleic acid and selection.

Figure 22:
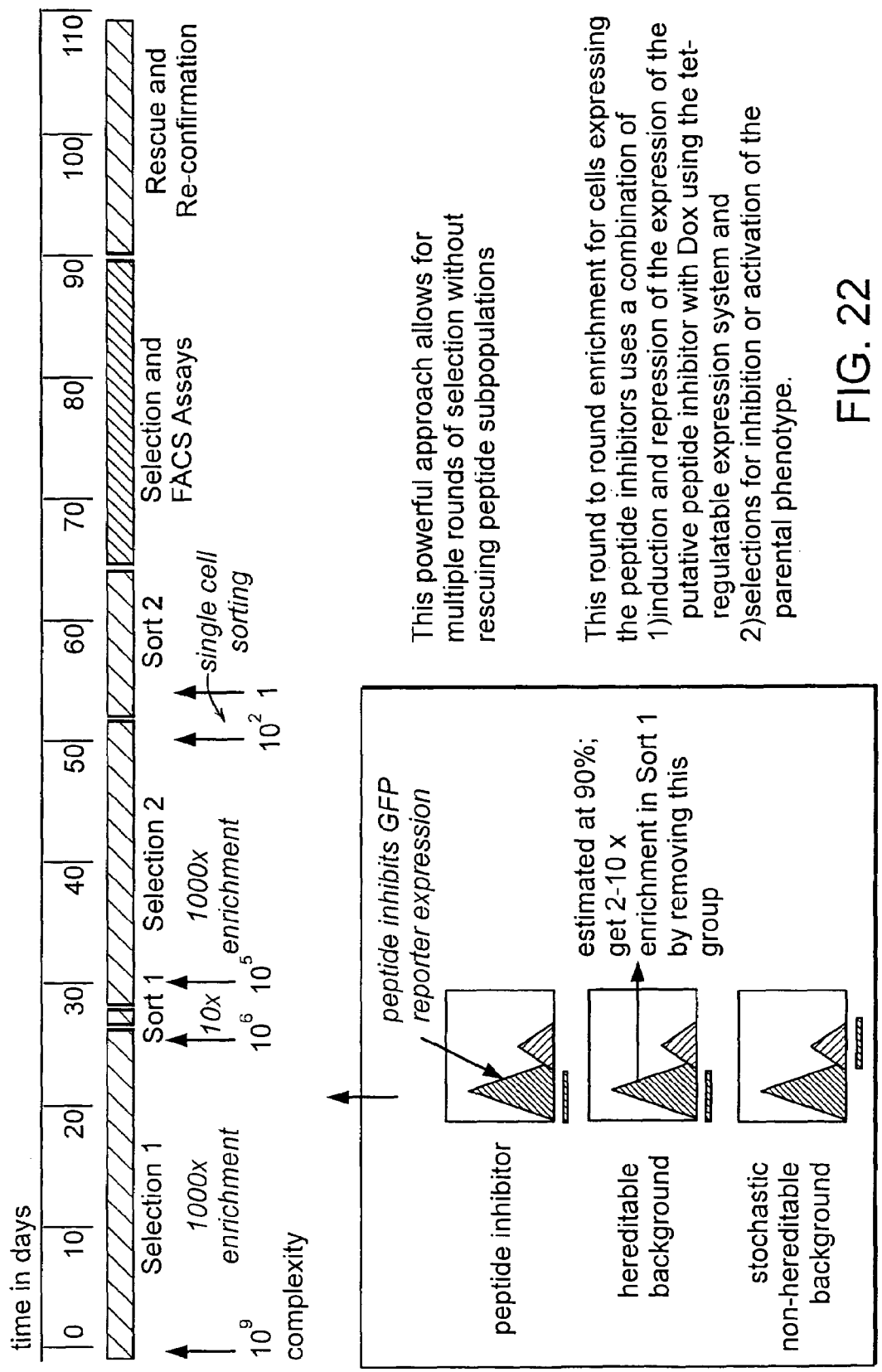

FIG. 22 schematically depicts an example of a timeline (in days) for a screening assay of the present invention (and as described for FIG. 21), where the complexity of the library of candidate bioactive agents (e.g., a peptide library), and the fold enrichment for the altered cellular phenotype, are indicated. Further, FIG. 22 schematically depicts the histogram profile of GFP fluorescence of false positives due to hereditable background or stochastic non-hereditable background; as compared to the histogram profile of GFP fluorescence of cells cultured in the presence (+Tet) or absence (−Tet) of Tet, after a first round of selection. This powerful approach allows for multiple rounds of selection without rescuing peptide subpopulations. This round to round enrichment for cells expressing the peptide inhibitors uses a combination of:

1. induction and repression of the expression of the putative peptide inhibitor with Dox using the tet-regulatable expression system and
2. selections for inhibition or activation of the parental phenotype.

Figure 23:
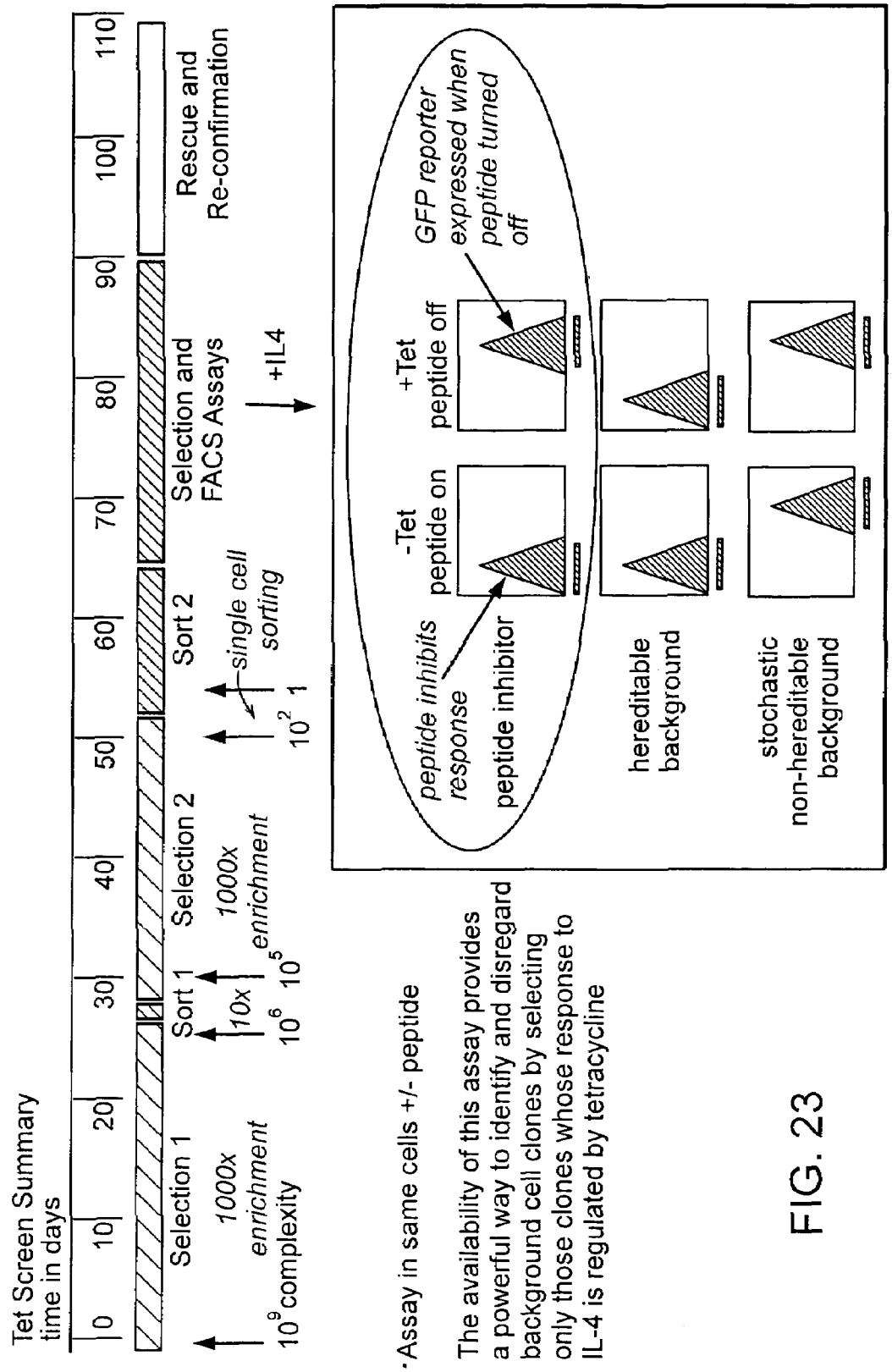

FIG. 23 schematically depicts an example of a timeline (in days) for a screening assay of the present invention (and as described for FIG. 21), where the complexity of the library of candidate bioactive agents (e.g., a peptide library), and the fold enrichment for the altered cellular phenotype, are indicated. Further, after a second of selection, cells are single cell cloned, aliquoted into microtiter plates, replica plated in duplicate microtiter plates and cultured in the presence or absence of Dox, and the single clones are contacted with IL4 for three days and their GFP fluorescence measured by FACS. Assay in same cells +/− peptide. The availability of this assay provides a powerful way to identify and disregard background cell clones by selecting only those clones whose response to IL-4 is regulated by tetracycline.

Figure 24:
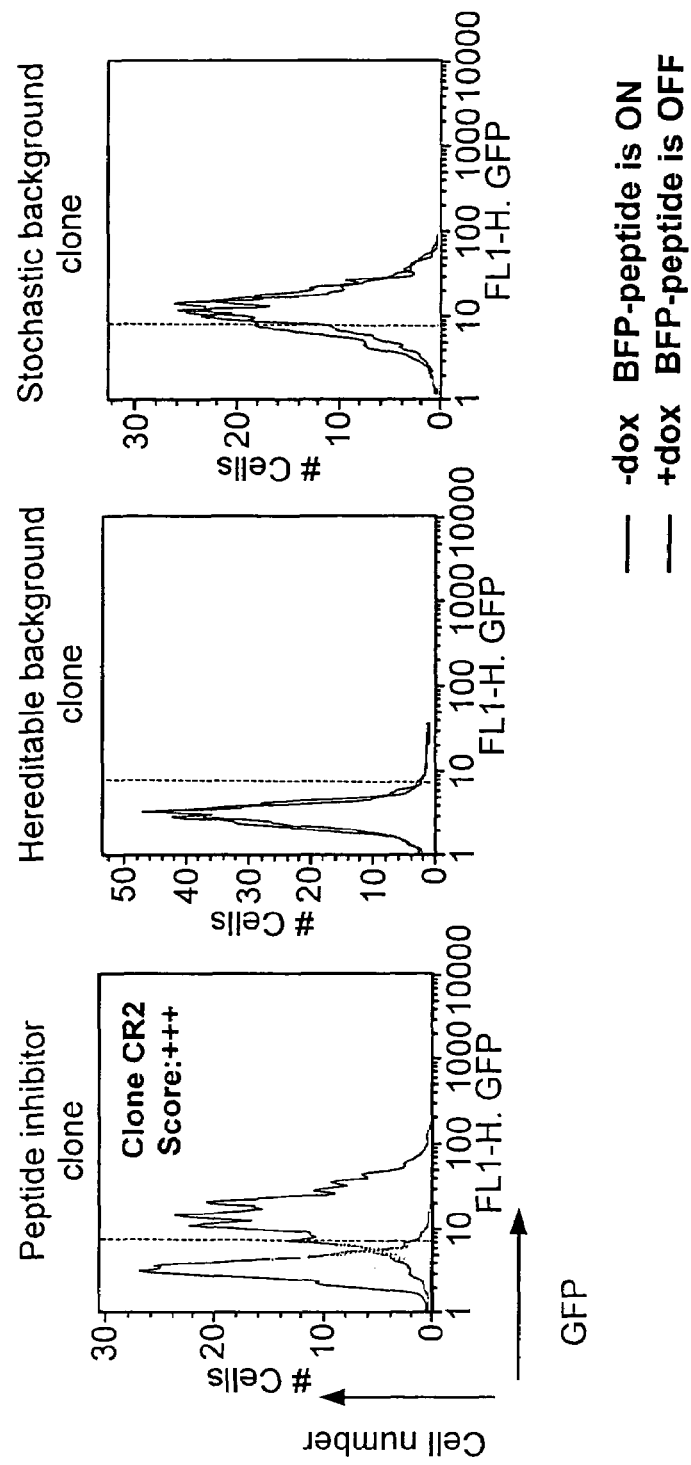

FIG. 24 depicts the histogram profile of GFP fluorescence of clones from a functional screen representing a BFP-peptide inhibitor clone, CR2 (left panel); a hereditable background clone (middle panel), and stochastic background clone (right panel), where the histograms from the clones cultured in the presence of Dox (+Dox) and the absence of Dox (−Dox) are overlayed.

Figure 25:
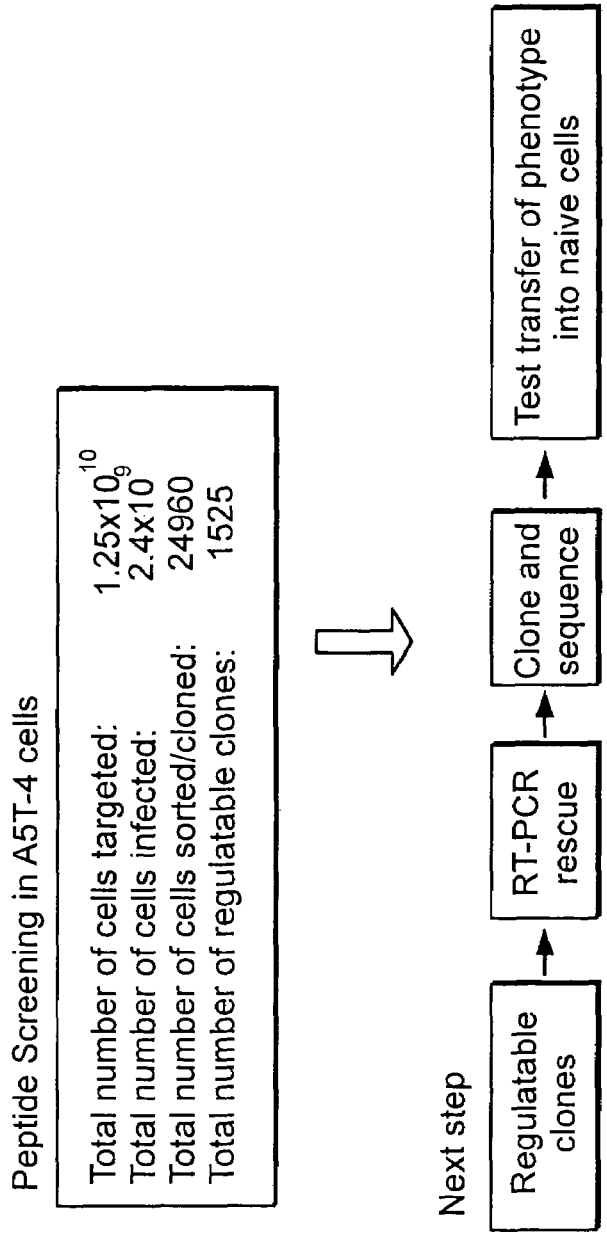

FIG. 25 depicts the summary of the results from the peptide screening in BH2-A5T-4 cells.

Figure 26A:
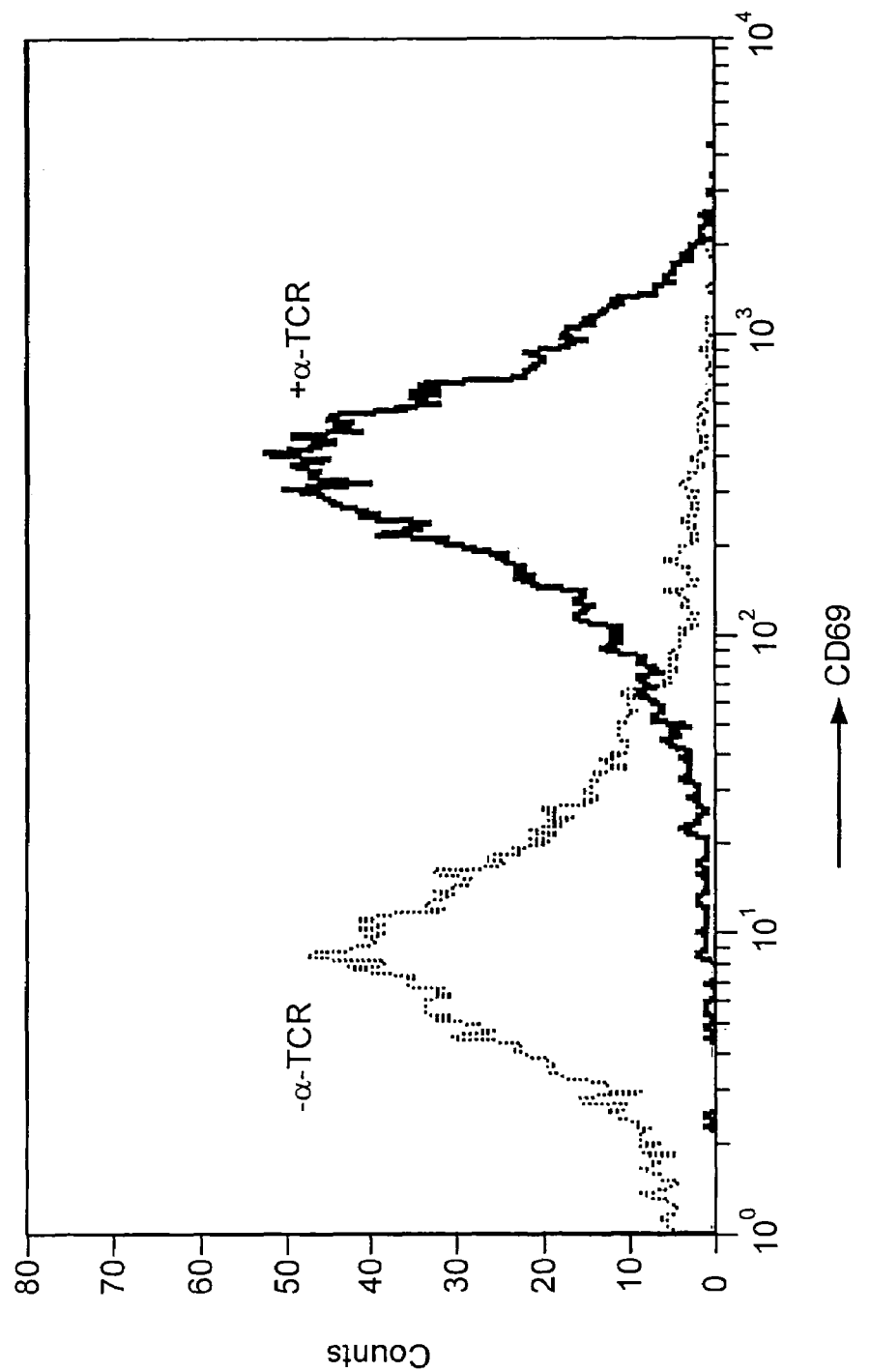
Figure 26B:
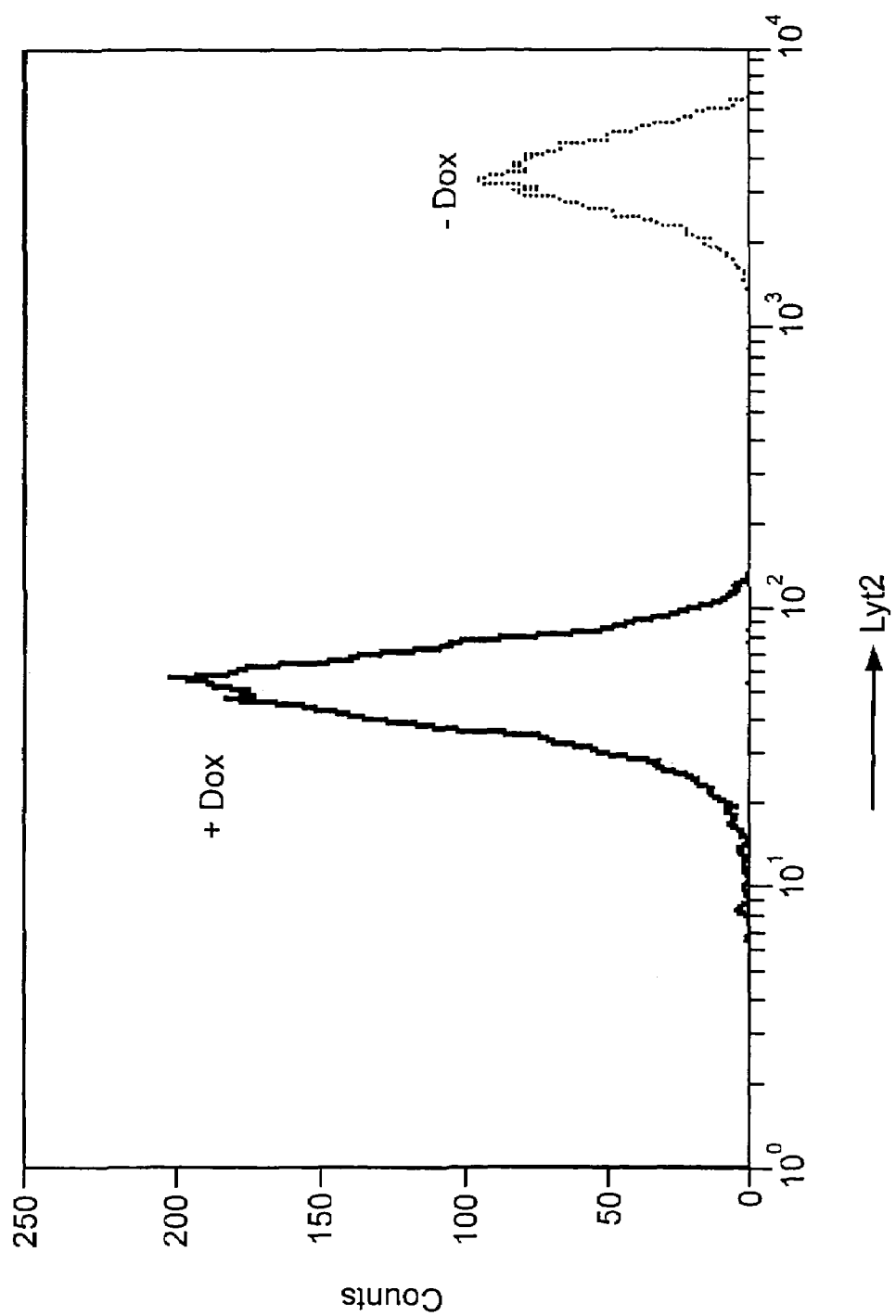

FIG. 26 depicts cell line and assay development. FIG. 26A depicts Jurkat cells stimulated with anti-T cell receptor (TCR) antibody C305 at 300 ng/ml and 24 hrs later, cells stained with anti-CD69APC and analyzed on a FACSCalibur. The dashed line indicates CD69 level before stimulation and the solid line after stimulation. FIG. 26B depicts Jurkat clone (4D9) with optimal CD69 expression profile infected with a retroviral construct which constitutively expresses a tetracycline transactivator protein (tTA) and a reporter construct which expresses Lyt2 driven by a tetracycline responsive element (TRE). The tTA-Jurkat cell clone 4D9#32 was obtained by sorting for high Lyt2 expression in the absence of Doxycycline (Dox) and low expression of Lyt2 in the presence Doxycycline (10 ng/ml). The solid line indicates Lyt2 level with Dox and dashed line without Dox.

FIG. 27 depicts dominant negative mutants of ZAP-70 inhibited TCR-induced CD69 expression. FIG. 27A depicts ZAP70 KI and ZAP70 SH2 (N+C) subcloned downstream of the internal ribosome entry site (IRES), followed by GFP in the Tet-regulated retroviral vector (TRE). FIG. 27B depicts after infecting tTA-Jurkat cells with retroviral constructs containing IRES-GFP, ZAP70 KI-IRES-GFP, or ZAP70 SH2 (N+C)-IRES-GFP, cells left unstimulated or stimulated with anti-TCR antibody for 24 hours. CD69 expression data were analyzed after gating on the GFP$^+$ population (infected population, shown in R1). The dashed line and the thin line indicate cells infected with IRES-GFP (vector) before and after TCR stimulation, respectively, and the thick line indicates cells infected with ZAP70 KI-IRES-GFP (top panel) or ZAP70 SH2 (N+C)-IRES-GFP (bottom panel), both after TCR stimulation. FIG. 27C depicts after infecting tTA-Jurkat cells with retroviral constructs containing IRES-GFP (vector) or ZAP70 SH2 (N+C)-IRES-GFP, cells treated with Dox for 6 days, and then left unstimulated or stimulated with anti-TCR antibody for 24 hrs. Addition of Dox turned off GFP expression, as shown by the loss of GFP$^+$ cells in the region R1. CD69 expression data were analyzed on the entire cell population. The dashed line and the thin line indicate cells infected with IRES-GFP (vector) before and after TCR stimulation, respectively, and the thick line indicates cells infected with ZAP70 SH2 (N+C)-IRES-GFP after TCR stimulation. FIG. 27D depicts tTA Jurkat cells containing different retroviral constructs (shown above the lanes) cultured in the absence (−) or presence (+) of Dox and lysed. Whole cell lysates were loaded (100:g each lane) and analyzed by Western blotting using anti-ZAP70 antibody (Upstate Biotechnology catalog # 05-253).

Figure 28A:
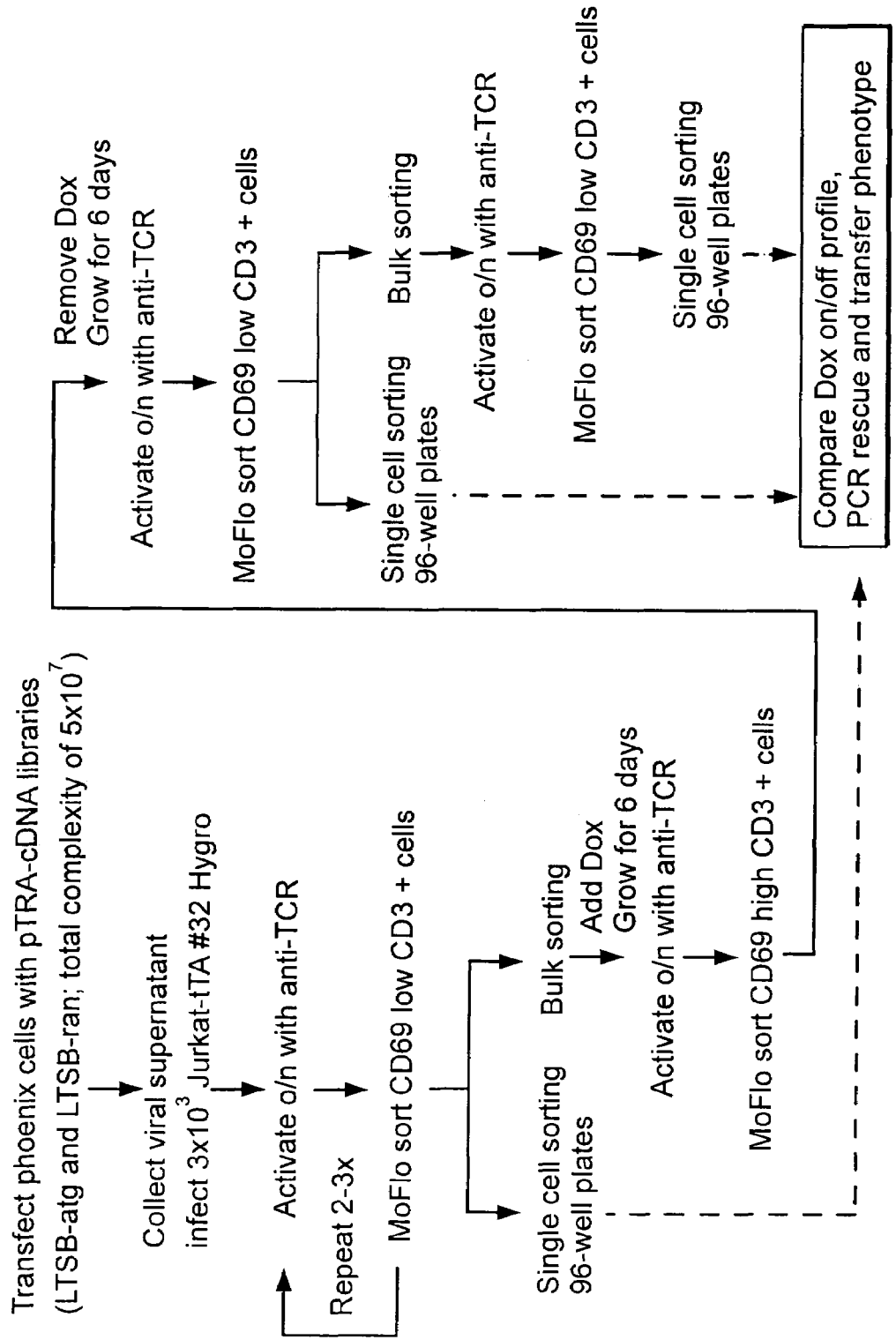
Figure 28B:
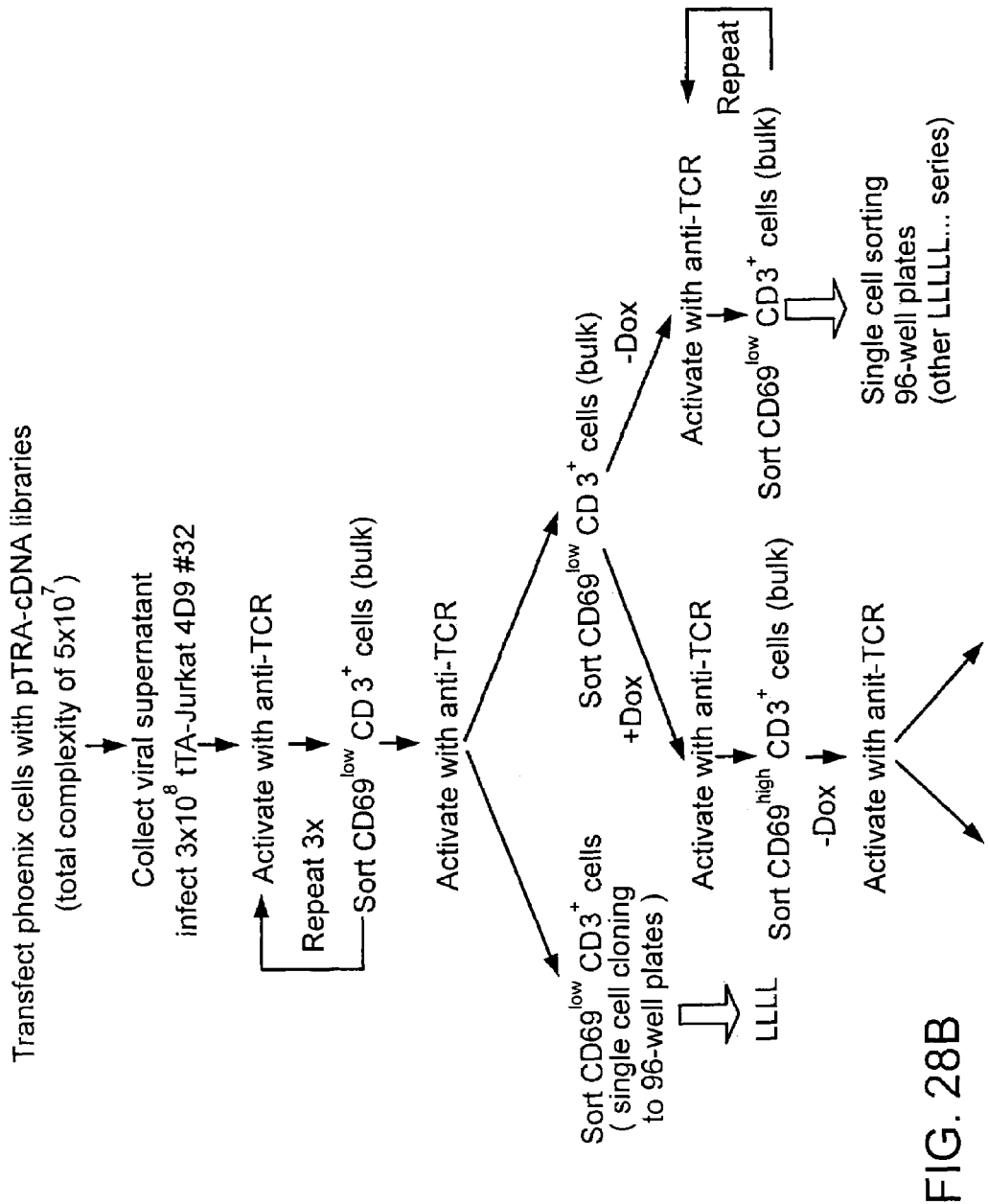

FIG. 28 depicts a screen for inhibitors of TCR-activation induced CD69 expression. FIG. 28A depicts a scheme of the functional genetic screen for inhibitors of TCR-activation induced CD69 expression. 3.5×10$^8$ cells were infected with pTRA-cDNA libraries. CD69$^{low}$CD3$^+$ cells represent cells expressing the lowest level of CD69 (bottom 3%) and still retaining CD3 expression after TCR stimulation, whereas CD69$^{high}$ cells are those expressing a high level of CD69 (top 10%) after grown with Dox and after TCR stimulation. Single cell cloning took place after at least 4 consecutive sorting of CD69$^{low}$CD3$^+$ with or without the placement of sorting of CD69$^{high}$ cells in between. FIG. 28B depicts phenotypic enrichment via iterative cell sorting. 7.1×10$^8$ cells were sorted with high-speed flow sorters (MoFlo) after stimulation and staining with anti-CD69-APC and anti-CD3-PE. The sort gate was set at the equivalent of 1% of the control cells that were stimulated but were never flow-sorted (shown as R2) to enrich for the CD69$^{low}$CD3$^+$ phenotype. After sorting, the desired cells were allowed to rest for a week before another round of stimulation and sorting. With reiterative sorting, not only the desired population was enriched (R2 cells from 1% to 23.2%), but also the overall population demonstrated a reduced CD69 level (shown as Y geo mean from >300 to 65). FIG. 28B depicts Dox regulation of the sorted population. Cells were split to two populations after the third round of sorting for the CD69$^{low}$CD3$^+$ phenotype (shown as R2). One half of the cells were grown in the absence of Dox (top left dot plot) while the other half in the presence of Dox (top right dot plot). A week later, CD69 expression was compared following anti-TCR stimulation. The dashed line indicates CD69 level without Dox and the solid line with Dox.

Figure 29A:
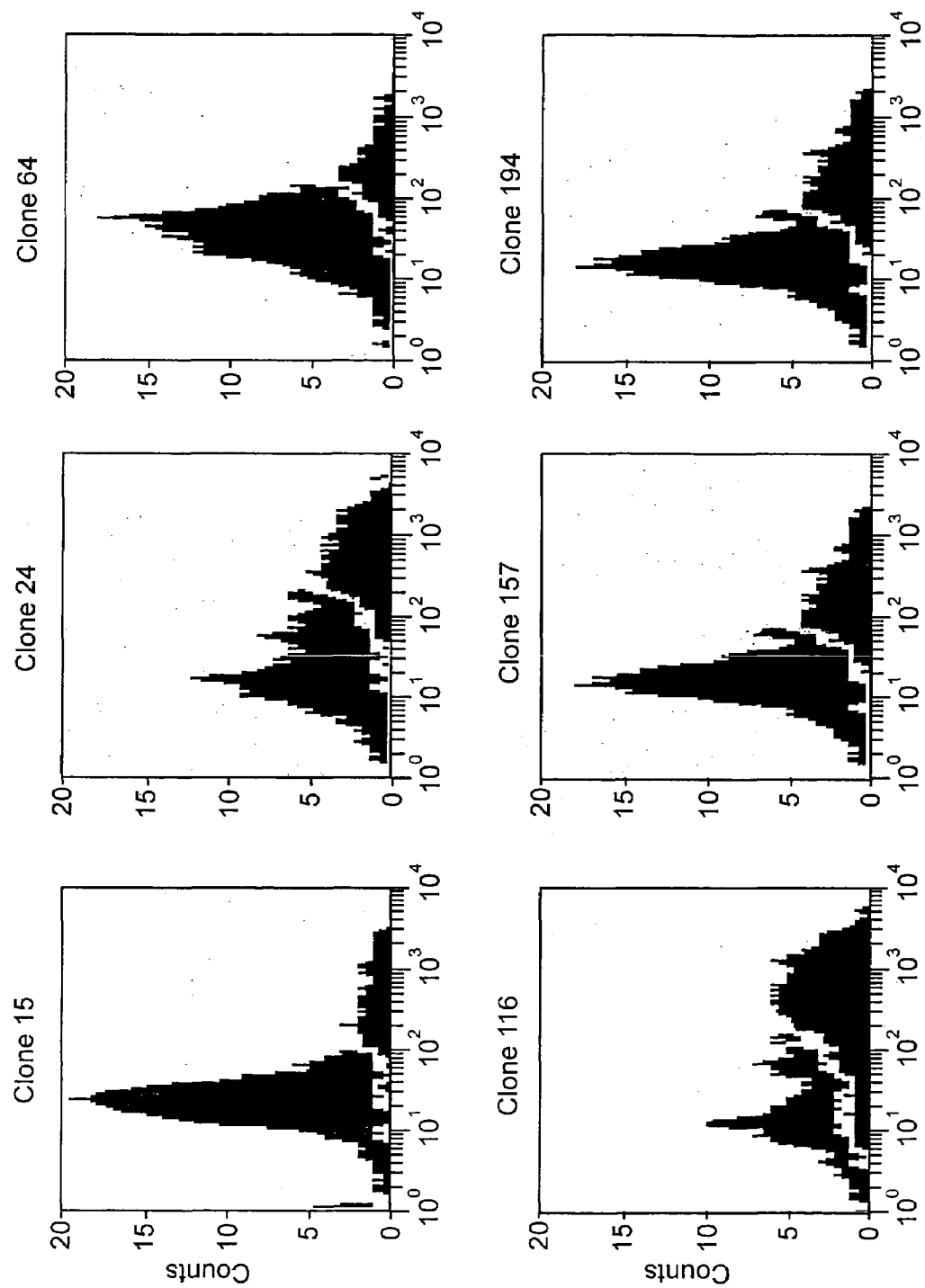
Figure 29B:
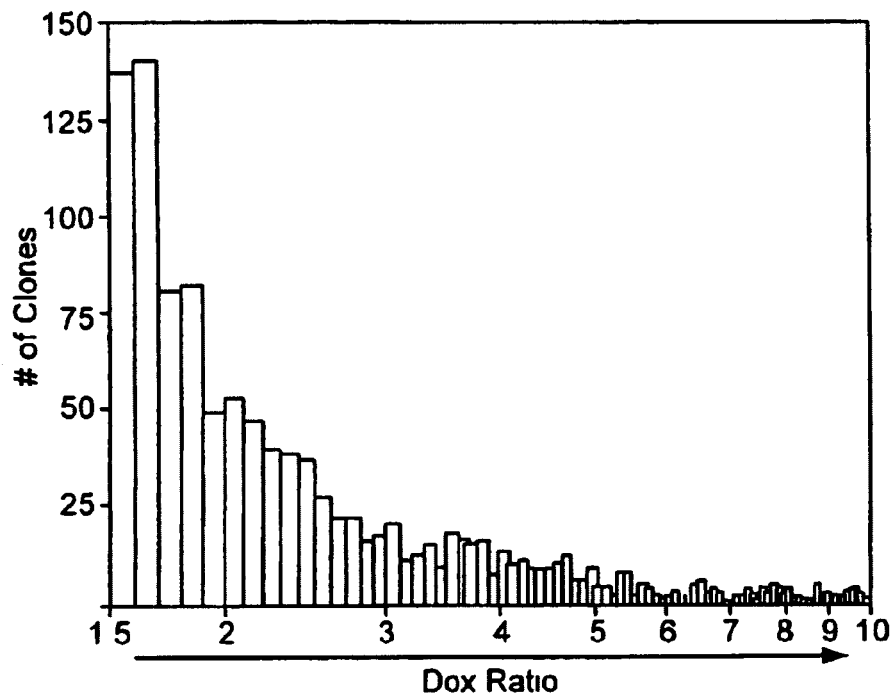
Figure 29C:
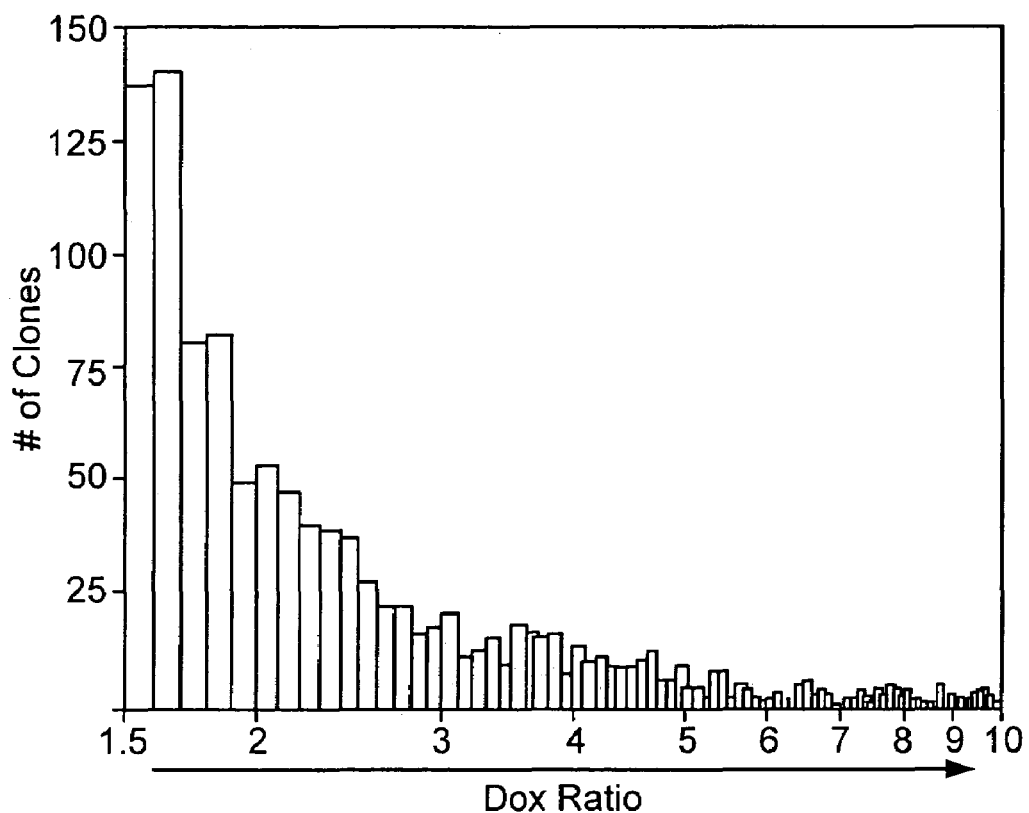

FIG. 29 depicts the identification of clones with desired altered phenotype. FIG. 29A depicts Individual clones grown in the presence or absence of Dox for a week and then stimulated overnight with anti-TCR antibody. Cells were stained with anti-CD69-APC and analyzed on a FACSCalibur. The filled peaks indicate CD69 expression level in the absence of Dox, when the cDNA hits were expressed. The open peaks indicate CD69 expression level in the presence of Dox, when the cDNA hits were not expressed. The geometric means of CD69 histograms are as follows: 490.68 (+Dox) and 28.60 (−Dox) for clone 15; 658.45 (+Dox) and 52.98 (−Dox) for clone 24; 553.46 (+Dox) and 40.09 (−Dox) for clone 64; 433.44 (+Dox) and 82.2 (−Dox) for clone 116; 1235.77 (+Dox) and 17.68 (−Dox) for clone 157; and finally, 245.81 (+Dox) and 26.43 (−Dox) for clone 194. The difference between filled and open peaks in any given clone is represented by the Dox ratio of the CD69 geometric means (using the +Dox values divided by the −Dox values), which reflects the dependence of the altered phenotype on the cDNA expression. FIG. 29B depicts 2,828 cell clones were assayed for CD69 expression after stimulation in the presence or absence of Dox. The geometric mean of CD69 fluorescent units in the presence of Dox was divided by those in the absence of Dox to give rise to the Dox Ratio for individual clones. A total of 1323 clones showed a Dox ratio of >1.5. The numbers of clones showing a Dox ratio between 1.5–10 was plotted against the Dox ratio themselves to illustrate the population distribution. FIG. 29C depicts DNA oligonucleotide primers specific to the library vector were designed (BstXTRA5G and BstXTRA3D) and used in RT-PCR reactions. The RT-PCR products were analyzed in an agarose gel followed by ethidium blue staining. Data from representative clones were shown along side the lkb DNA molecular weight ladder from New England BioLabs (Catalog # N3232S).

FIG. 30 depicts the functional transfer of the phenotype of known TCR signaling molecules. Diagrams of proteins predicted from the cDNA inserts and those from the corresponding wild-type genes were shown above the histograms. The left panel of histograms shows the Dox-regulatable phenotype of the original cell clones. The original cell clones were grown in the presence or absence of Dox for a week and then stimulated overnight with anti-TCR antibody. Cells were stained with anti-CD69-APC and analyzed by FACS. The filled peaks indicate CD69 expression level in the absence of Dox, when the cDNA hits were expressed. The open peaks indicate CD69 expression level in the presence of Dox, when the cDNA hits were not expressed. The Dox ratio was shown for each original mutant clone. The right top and bottom panels of histograms show the phenotypes after expressing the cDNA inserts (followed by IRES-GFP) in a naive tTAJurkat population. After retroviral infection, the tTA-Jurkat cells were either stimulated with the anti-TCR antibody (+"−TCR, solid line) or left unstimulated (−"−TCR, dashed line), and analyzed by FACS for CD69 induction after staining with anti-CD69-APC. The top right histogram in each group analyzed GFP$^-$ cells, which did not express the cDNA hit, whereas the bottom right histogram in each group analyzed GFP$^+$ cells, which expressed the cDNA hit. The following cDNA hits were analyzed: LCK (A), ZAP70 hit #1 (B), SYK (C), and PLCyl (D).

FIG. 31 depicts the functional transfer of phenotype of unknown TCR signaling molecules. Diagrams of proteins predicted from the cDNA inserts and those from the corresponding wild-type genes were shown above the histograms. The left panel of histograms shows the Dox-regulatable phenotypes of the original cell clones. The original cell clones were grown in the presence or absence of Dox for a week and then stimulated overnight with anti-TCR antibody. Cells were stained with anti-CD69-APC and analyzed by FACS. The filled peaks indicate CD69 expression level in the absence of Dox, when the cDNA hits were expressed. The open peaks indicate CD69 expression level in the presence of Dox, when the cDNA hits were not expressed. The Dox ratio was shown for each original mutant clone. The right top and bottom panels of histograms show the phenotypes after expressing the cDNA inserts (followed by IRES-GFP) in a naive tTAJurkat population. After retroviral infection, the tTA-Jurkat cells were either stimulated with the anti-TCR antibody (+"–TCR, solid line) or left unstimulated (–"–TCR, dashed line), and analyzed by FACS for CD69 induction after staining with anti-CD69-APC. The top right histogram in each group analyzed GFP⁻ cells, which did not express the cDNA hit, whereas the bottom right histogram in each group analyzed GFP⁺ cells, which expressed the cDNA hit. The following cDNA hits were analyzed: TCPTP (A), IL1 ORA (B), Integrin "2 (C), and GG2-l (D).

Figure 32A:
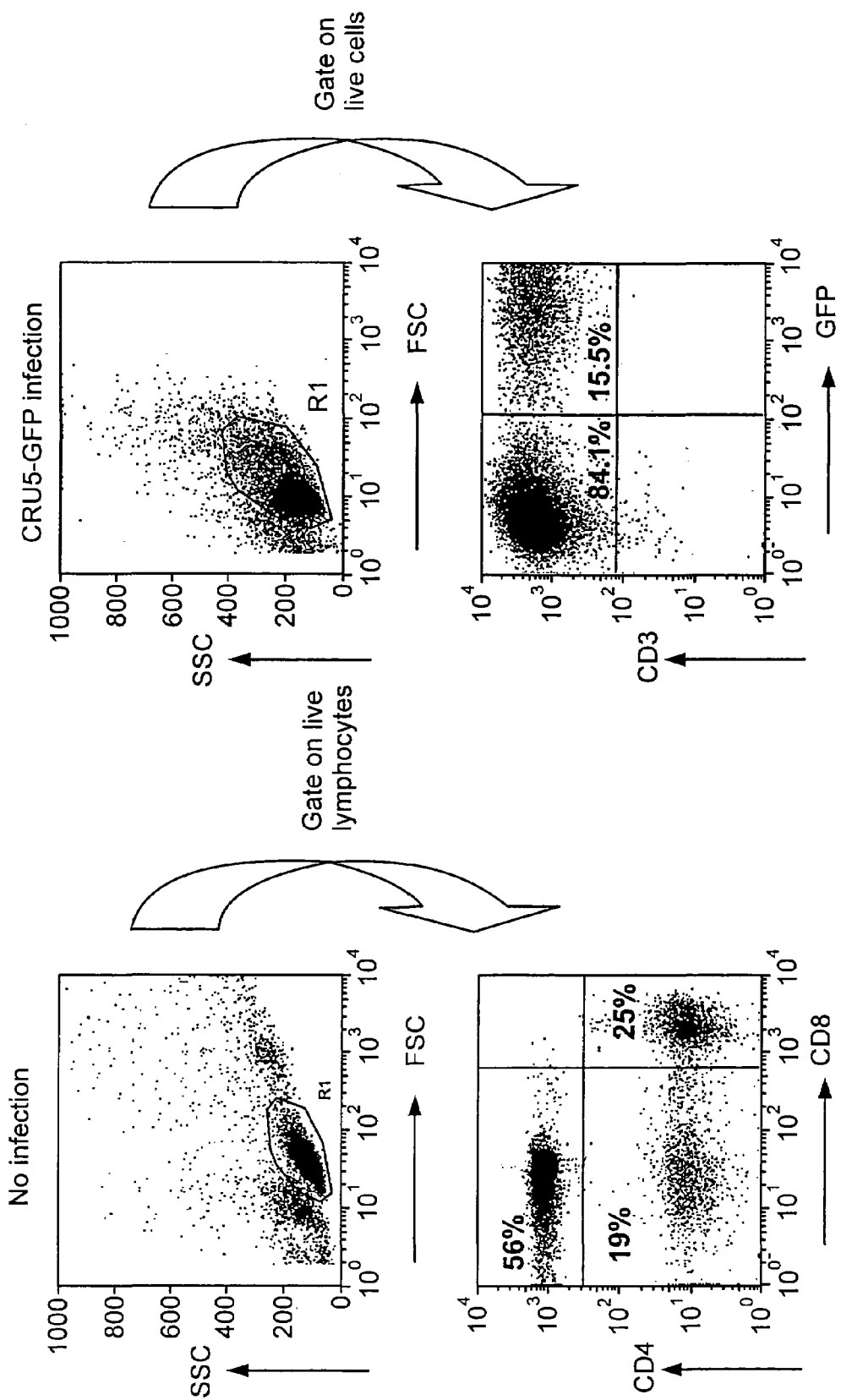
Figure 32B:
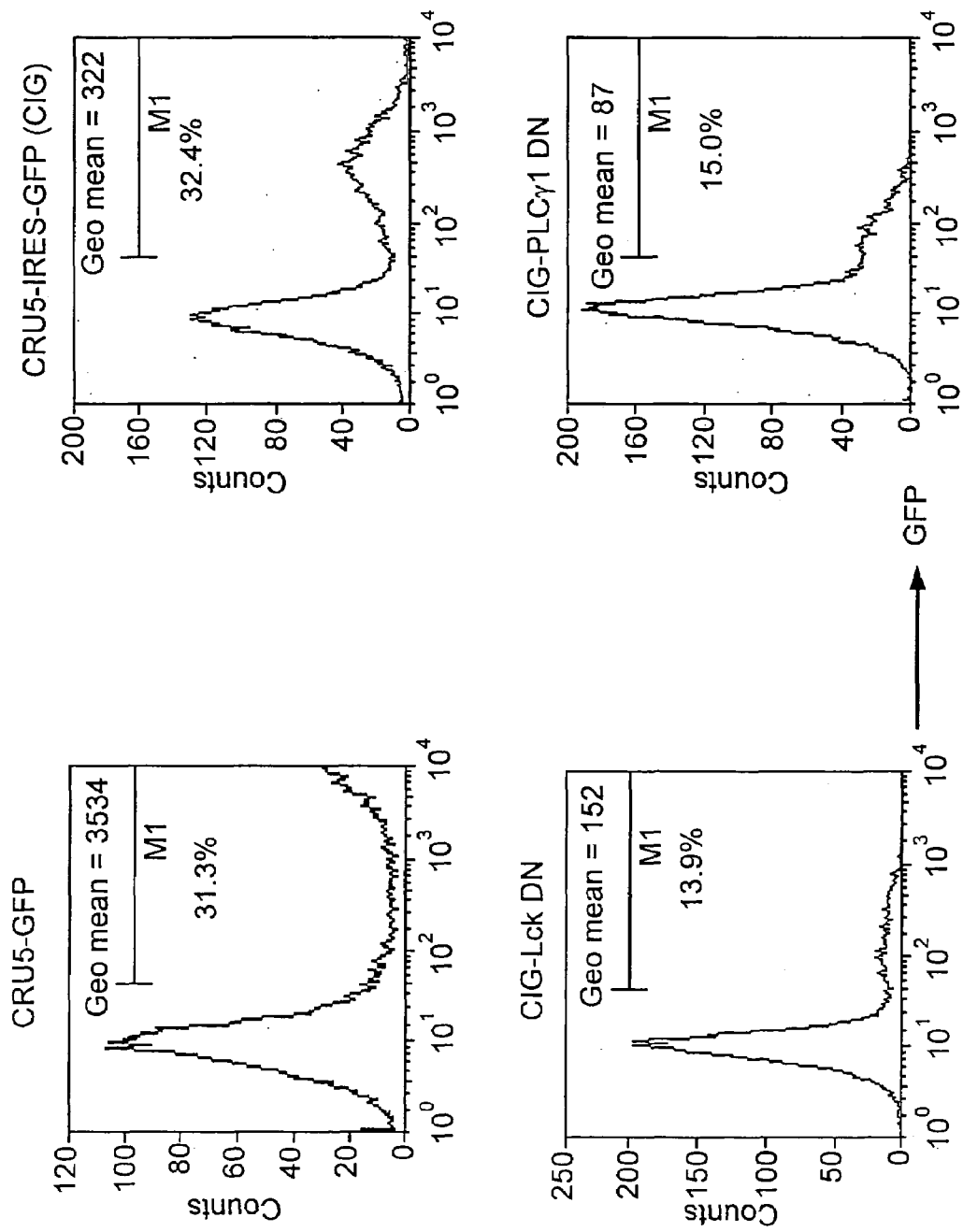
Figure 32C:
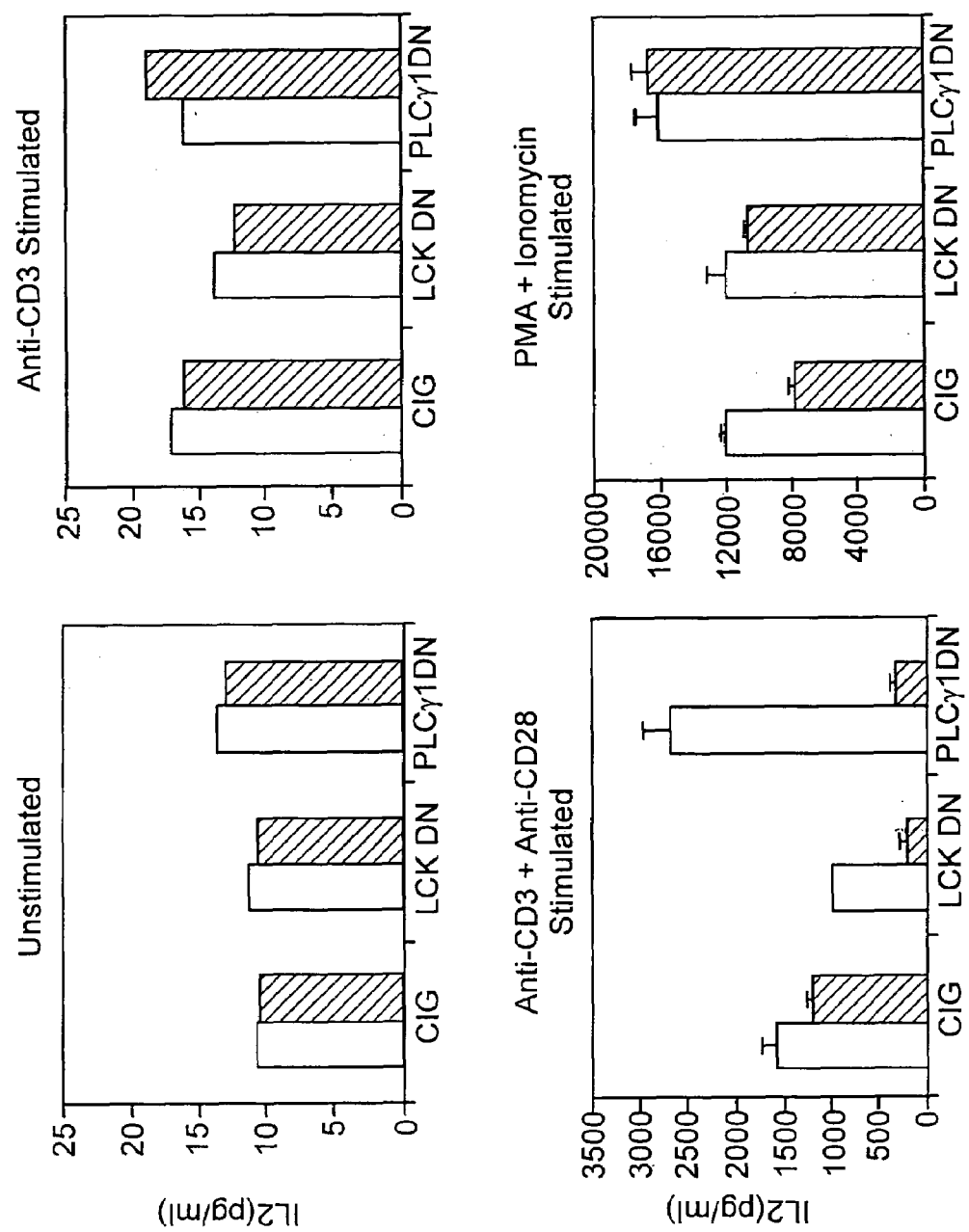

FIG. 32 depicts the cDNA hits from the screening methods of the present invention inhibited T cell activation in human primary T lymphocytes. FIG. 32A depicts retroviral infection of primary T lymphocytes. Primary T lymphocytes were cultured on anti-CD3 and anti-CD28 coated wells for 3 days and then infected with the retroviral CRU5-GFP vector, where GFP was expressed from the constitutively active retroviral LTR promoter. Cells were stained with anti-CD3-APC, or with anti-CD4-PE and anti-CD8-APC antibodies and analyzed by FACS. The percentage of cells in each quadrant is shown. FSC: forward scatter; and SSC: side scatter. FIG. 32B depicts human primary T lymphocytes were infected with vector alone (CRU5-GFP and CRU5-IRES-GFP or CIG) or with vector expressing the Lck and PLC(1 dominant negative (DN) hits. The infection rate was monitored by the percentage of GFP⁺ cells in M1. The geometric mean of GFP was shown above the marker. FIG. 32C depicts IL-2 production was inhibited by LCK DN and PLC(1 DN proteins in primary T lymphocytes. Infected primary T cells were allowed to rest and then sorted to give rise to GFP⁻ (filled bars) and GFP⁺ (open bars) populations. Equal numbers of cells were cultured in 96-well dish coated with anti-CD3 or anti-CD3+anti-CI)28 antibodies, cultured without antibodies or cultured with PMA+ionomycin. 40 hrs later the culture supernatants were harvest and assayed for IL-2 production by ELISA using commercial reagents (R&D Systems).

FIG. 33 depicts an overview of identified molecular targets as described in Example 7 and designated Table 2.

DETAILED DESCRIPTION OF THE INVENTION

The present invention provides methods and compositions for screening for an altered cellular phenotype due to the presence of a candidate bioactive agent. The methods of the present invention provide a significant improvement over conventional screening techniques because the methods allow the rapid and highly efficient screening of large numbers of candidate bioactive agents in cells without the need to collect or synthesize the candidate bioactive agents. In particular, the methods of the present invention afford significant advantages over conventional screening techniques because the methods permit the tightly controlled and highly specific expression of a candidate nucleic acid in cells, and rapid detection of a subpopulation of cells highly enriched for a cellular phenotype corresponding to the controlled expression of the candidate nucleic acid. In particular, multiple rounds of selection can be performed to achieve the desired enrichment of cells having an altered phenotype corresponding to the expression of a candidate nucleic acid. Thus, the advantages of the methods of the present invention include the ability to rapidly and efficiently screen diverse populations of cells for an altered cellular phenotype corresponding to the inducible expression of a candidate nucleic acid.

The invention provides compositions for use in the methods of the present invention. Specifically, the invention provides populations of cells having a parent phenotype and comprising a nucleic acid encoding a first element expressed in the cells. The first element is preferably a transactivator, and more preferably a Tet-dependent transactivator. The invention further provides libraries of fusion nucleic acids, where the fusion nucleic acids comprise a second element that is regulatable by the first element. The second element preferably comprises an operator sequence, and more preferably at least one Tet operator (TetO) sequence. The fusion nucleic acids further comprise a nucleic acid sequence operably linked to the second element. The nucleic acid sequence preferably encodes a candidate bioactive agent. The candidate bioactive agent is preferably a peptide or a nucleic acid. In addition, the invention provides a third element that induces or represses the expression of the nucleic acid sequence encoding the candidate bioactive agent. The third element is preferably Tet or an analogue thereof. Thus, the invention provides two approaches for screening for an altered cellular phenotype; in a first approach the third element induces ("turns on" expression; and in a second approach the third element represses ("turns off") expression.

Thus, generally, the invention works as follows. Cells exhibiting the parent phenotype are induced to express the candidate agents, and the cells are screened for those exhibiting an altered phenotype. Once identified and isolated as a first subpopulation, the expression of the candidate agent is turned off, and the first subpopulation is again screened for cells exhibiting the parent phenotype. This ensures a higher level of confidence that the altered phenotype is due to the candidate agent. This second subpopulation is again induced (or un-repressed, as the case may be) to express the candidate agent to result in the altered phenotype. Thus, by screening for "off-on-off" (or, in some cases as outlined herein, "on-off-on", etc., a more reproducible data set with a higher level of confidence is achieved. In addition, further reiterative rounds allow additional results. In general, this allows the elimination of non-responsive cells and thus "false positives".

Using either approach, in the methods of the present invention, the cells having an altered phenotype due to the presence of the candidate bioactive agent are distinguished and detected based on their responsiveness to the induction and repression of expression of the nucleic acid sequence encoding the candidate bioactive agent, by the third element. The responsive cells have the parent phenotype when expression of the nucleic acid sequence is repressed and have an altered phenotype when expression of the nucleic acid sequence is induced. The nonresponsive cells can be distinguished by having a phenotype that is not responsive to the induction and repression of expression of the nucleic acid sequence. As used herein, the term "parent phenotype" refers to the cellular phenotype of a cell in the uninduced state, i.e., the expression of a nucleic acid sequence operably linked to a second element is turned off or repressed in the cell. As used herein, the term "altered phenotype" refers to the cellular phenotype of a cell in the induced state, i.e., the expression of a nucleic acid sequence operably linked to a second element is turned on or induced in the cell.

In a preferred embodiment, the parent phenotype is due to the presence of a stimulator. In another preferred embodiment, the stimulator induces the parent phenotype. Examples of stimulators include, but are not limited to, cytokines, ligands or antibodies against cells surface receptors, growth factors, hormones, peptides, neuropeptides, drugs or compounds, LPS, viruses, bacteria, and so on. In a preferred embodiment, the stimulator is interleukin 4 (IL4), a cytokine, that has various biological activities, for example, IL-4 induces germline epsilon promoter (transcription) in B cells. In another preferred embodiment, the stimulator is anti-TCR (T cell receptor), a stimulator that activates T cell activation as monitored by CD69 upregulation.

In a preferred embodiment, the fusion nucleic acids further comprise a sequence encoding a reporter protein, and this sequence is operably linked to the nucleic acid sequence encoding the candidate bioactive agent. Thus, the expression of the reporter protein corresponds to the expression of the nucleic acid sequence encoding a candidate bioactive agent. Suitable reporter proteins are outlined below.

Cells having an altered phenotype may be sorted from cells having a parent phenotype using standard techniques known in the art for cell sorting. In the methods of the present invention, any chemical, physical, or physiological markers distinguishing an altered phenotype from a parent phenotype may be used to sort a population or subpopulation of cells having a parent phenotype from a subpopulation of cells having an altered phenotype. Thereby, a subpopulation of cells having an altered phenotype can be detected and collected. In a preferred embodiment, the fusion nucleic acids further comprise a sequence encoding a reporter protein that is an autofluorescent protein, for example GFP from a *Renilla* species, and the cells having an altered phenotype are sorted from the cells having a parent phenotype by fluorescence-activated cell sorting (FACS). In this embodiment, the sequence encoding the reporter protein is operably linked to a nucleic acid sequence encoding a candiate bioactive agent.

Using the first approach, the invention provides methods of screening for an altered cellular phenotype comprising the steps of: a) providing a population of cells having a parent phenotype and comprising a nucleic acid encoding a first element inducibly or constitutively expressed in the cells; b) introducing a library of fusion nucleic acids into the population of cells, where the fusion nucleic acids comprise a second element that is regulatable by the first element and further comprise a nucleic acid sequence encoding a candidate bioactive agent; c) inducing the expression of the nucleic acid sequence by contacting the cells with a third element; d) collecting a first subpopulation of cells having an altered phenotype; e) repressing the expression of the nucleic acid by modulating the contacting of the third element with the first subpopulation of cells; f) collecting a second population of cells having a parent phenotype; g) inducing the expression of the nucleic acid sequence by contacting the third element with the second subpopulation of cells; and g) detecting a third subpopulation of cells.

Using the second approach, the invention provides methods of screening for an altered cellular phenotype comprising the steps of: a) providing a population of cells having a parent phenotype and comprising a nucleic acid encoding a first element inducibly or constitutively expressed in the cells; b) introducing a library of fusion nucleic acids into the population of cells, where the fusion nucleic acids comprise a second element that is regulatable by the first element and further comprise a nucleic acid sequence encoding a candidate bioactive agent; c) inducing the expression of the nucleic acid sequence by expressing the first element; d) collecting a first subpopulation of cells having an altered phenotype; e) repressing the expression of the nucleic acid by contacting a third element with the first subpopulation of cells; f) collecting a second population of cells having a parent phenotype; g) inducing the expression of the nucleic acid sequence modulating the contacting the third element with the second subpopulation of cells; and h) detecting a third subpopulation of cells.

Using either approach, the invention provides methods of screening for an altered cellular phenotype further comprising collecting the responsive cells. The methods also further comprise repeating the induction or repression of expression and detecting the responsive cells and, further, collecting the cells to enrich for a subpopulation of cells having the altered phenotype. The inducing or repressing of expression, followed by detecting and, further, by collecting a subpopulation of cells responsive to the induction and represssion can be repeated multiple times to obtain a desired level of enrichment and detection of a subpopulation of cells having an altered cellular phenotype due to the presence of a candidate bioactive agent.

In a preferred embodiment, using the first approach, the present invention provides methods comprising the steps of: a) providing a population of cells having a parent phenotype and comprising a nucleic acid encoding a first element that is expressed in the cells, for example, a reverse tetracycline-dependent transactivator (rtTA); b) introducing into the population of cells a library of fusion nucleic acids, where the nucleic acids each comprise a second element that is regulatable by the first element, and a nucleic acid sequence that is operably linked to the first element, where the nucleic acid sequence encodes a candidate bioactive agent; c) inducing the expression of the nucleic acid sequence by contacting a third element with the population of cells, wherein the population of cells is expressing the first element; d) collecting a first subpopulation of cells having an altered phenotype; e) repressing the expression of the nucleic acid sequence by modulating the contacting of the third element with the first subpopulation of cells; f) collecting a second subpopulation of cells having the parent phenotype; g) inducing the expression of the nucleic acid sequence by contacting the third element with the second subpopulation of cells; and h) detecting a third subpopulation of cells having the altered phenotype.

In another preferred embodiment, using the first approach, the method further comprises: i) collecting the third subpopulation of cells having an altered phenotype; j) repressing the expression of the nucleic acid sequence by modulating the contacting of the third element with the third subpopulation of cells; and k) detecting a fourth subpopulation of cells having the parent phenotype.

In another additional preferred embodiment, using the first approach, the method further comprises: l) collecting the fourth subpopulation of cells having the parent phenotype; m) inducing the expression of the nucleic acid sequence by contacting the third element with the fourth subpopulation of cells; and n) detecting a fifth subpopulation of cells having the altered phenotype.

In another preferred embodiment, using the second approach, the invention provides a method of screening for cells having an altered phenotype comprising the steps of: a) providing a population of cells having a parent phenotype and comprising a nucleic acid encoding a first element, for example, a tetracycline-dependent transactivator; b) introducing into the population of cells a library of fusion nucleic acids, where the nucleic acids each comprise a second element that is regulatable by the first element, and a nucleic acid sequence that is operably linked to the first element, where the nucleic acid sequence encodes a candidate bioactive agent; c) inducing the expression of the nucleic acid sequence by expressing the first element in the population of cells; d) collecting a first subpopulation of cells having an altered phenotype; e) repressing the expression of the nucleic acid by contacting a third element with the first subpopulation of cells; f) collecting a second subpopulation of cells having the parent phenotype; g) inducing the expression of the nucleic acid sequence by modulating the contacting of the third element with the second subpopulation of cells; and h) detecting a third subpopulation of cells having the altered phenotype.

In another embodiment, using the second approach, the method further comprises: i) collecting the third subpopulation of cells having the altered phenotype; j) repressing the expression of the nucleic acid sequence by contacting the third element with the third subpopulation of cells; and k) detecting a fourth subpopulation of cells having the parent phenotype.

In another embodiment, using the second approach, the method further comprises: l) collecting the fourth subpopulation of cells having the parent phenotype; m) inducing the expression of the nucleic acid sequence by modulating the contacting of the third element with the fourth subpopulation of cells; and n) detecting a fifth subpopulation of cells having said altered phenotype.

Accordingly, the invention provides methods for screening cells having an altered phenotype as compared to a parent phenotype. As used herein, the term "parent phenotype" refers to the cellular phenotype of a cell in the uninduced state, i.e., the expression of a nucleic acid sequence operably linked to a second element is turned off or repressed in the cell. As used herein, the term "altered phenotype" refers to the cellular phenotype of a cell in the induced state, i.e., the expression of a nucleic acid sequence operably linked to a second element is turned on or induced in the cell.

In a preferred embodiment, the parent phenotype is due to the presence of a stimulator. A stimulator as used herein is an agent that can cause phenotypic changes. In another preferred embodiment, the stimulator induces the parent phenotype. Examples of stimulators include, but are not limited to, cytokines, ligands or antibodies against cells surface receptors, growth factors, hormones, peptides, neuropeptides, drugs or compounds, LPS, viruses, bacteria, and so on (see e.g., Lorens et al. (2001) Pharmaceutical Biotechnology, pp. 613–621). In a preferred embodiment, the stimulator is interleukin 4 (IL-4), a cytokine, that has various biological activities, for example, IL-4 induces germline epsilon promoter (transcription) in B cells. In another preferred embodiment, the stimulator is anti-TCR (T cell receptor), a stimulator that activates T cell activation as monitored by CD69 upregulation.

The methods provide populations of cells. As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive agent. As is more fully described below, cell types implicated in a wide variety of disease conditions are particularly useful because the methods of the present invention can be used to enrich for and detect cells that exhibit an altered phenotype as a consequence of the presence of a bioactive agent within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be genetically engineered, that is, contain exogenous nucleic acid, for example, to contain target molecules.

By a "plurality of cells" or a "population of cells" herein is meant roughly from about $10^3$ cells to $10^8$ or $10^9$, with from $10^6$ to $10^8$ being preferred. This plurality of cells comprises a cellular library, wherein generally each cell within the library contains a member of the retroviral molecular library, i.e., a different candidate nucleic acid, although as will be appreciated by those in the art, some cells within the library may not contain a retrovirus, and some may contain more than one. When methods other than retroviral infection are used to introduce the candidate nucleic acids into a plurality of cells, the distribution of candidate nucleic acids within the individual cell members of the cellular library may vary.

The methods rely on regulatable expression systems. Suitable regulatable expression systems for use in the methods of the present event are those having the following properties: a low level of basal expression in the non-induced state; inducers that do not promote pleiotropic effects; high levels of expression in the induced state; highly specific induction of expression of a candidate nucleic acid of interest; and modulation of the level of induced expression. Examples of regulatable expression systems having such properties include, but are not limited to: a Tet inducible system (see e.g., Gossen et al. (1992) Proc. Natl. Acad. Sci. USA 89:5547–5551; Gossen et al. (1995) Science 268:1766–1769); a FK506/rapamycin inducible system (see e.g., Spencer et al. (1993) Science 262:1019–1024; Belshaw et al. (1996) Proc. Natl. Acad. Sci. USA 93:4604–4607); a RU486/mifepristone inducible system; and an ecdysone inducible system (for review, see Rossi et al. (1989) Curr. Op. Biotech. 9:451–456).

In a preferred embodiment, a Tet inducible expression system is used in the methods of the present invention (see e.g., Gossen et al. (1992) Proc. Natl. Acad. Sci. USA 89:5547–5551; Gossen et al. (1995) Science 268:1766–1769). In a Tet inducible expression system, a Tet-dependent transactivator binds to a Tet operator (TetO) sequence and activates the expression of a nucleic acid sequence operably linked to the TetO sequence. Various Tet-dependent transactivators are known and either bind to the operator sequence in the presence or the absence of Tet or an analogue thereof. Thus, Tet or an analogue thereof, acts as an agent mediating the binding of a transactivator to the operator sequence and the expression of an operably linked nucleic acid sequence. An example of a tetracycline-dependent transactivator that binds to a TetO sequence in the presence of Tet, and not in the absence of Tet, is the reverse tetracycline-dependent transactivator (rtTA). An example of a tetracycline-dependent transactivator that binds to the Tet) sequence in the absence of Tet, and not in the presence of Tet, is the tetracycline-dependent transactivator (tTA).

In the methods of the present invention, the first element regulates a second element that is operably linked to a nucleic acid sequence encoding a candidate bioactive agent. Preferably, the first element is a transactivator. In a preferred embodiment, the first element comprises the rtTA. In another preferred embodiment, the first element comprises the tTA. The first element can be expressed inducibly, constitutively, stably, transiently; or in trans or in cis relative to a nucleic acid sequence that is operably linked to a second element. In another preferred embodiment, the transactivator is a polypeptide, and even more preferably, the transactivator is a fusion protein. Thus, one aspect of the invention relates to fusion proteins and nucleic acids encoding fusion proteins. The term "fusion protein" as used herein refers to at least two polypeptides which are operably linked, either directly or indirectly, using a linker.

In a preferred embodiment, the transactivator fusion protein comprises a first polypeptide that binds to a Tet operator sequence in the presence of tetracycline (Tet) or an analogue thereof; and a second polypeptide that activates expression of a nucleic acid sequence operably linked to an operator sequence. The first polypeptide of the transactivator fusion protein is preferably a mutated Tet repressor.

The wild-type Tet repressor (TetR) is a component of the *E. coli* tetracycline (Tc) resistance system. Wild-type TetR binds to TetO sequences in the absence of Tet or an analogue thereof and represses expression of nucleic acid sequences operably linked to the TetO sequences (Gatz, C. et al. (1992) Plant J. 2:397–404).

The term "mutated TetR" or "mutant TetR" as used herein includes polypeptides having an amino acid sequence which is similar to a wild-type TetR but which has at least one amino acid difference from the wild-type TetR. The term "wild-type TetR" as used herein describes a naturally occurring protein which represses transcription from TetO sequences in prokaryotic cells in the absence of Tet or an analogue thereof. The amino acid difference(s) between a mutated TetR and a wild-type TetR may be a substitution of one or more amino acids, deletion of one or more amino acids, or addition of one or more amino acids.

A suitable mutated TetR for use in the transactivator fusion proteins of the present invention binds to a TetO sequence, i.e., it retains the DNA binding specificity of a wild-type Tet repressor; and regulates expression in a reverse or opposite manner as compared to a wild-type TetR, i.e., the mutated TetR binds to a TetO sequence only in the presence of Tet or analogue thereof, rather than in the absence of Tet.

A mutated TetR having the functional properties described above can be constructed by substitution of amino acid residues in the sequence of a wild-type TetR. For example, a Tn10-derived TetR having amino acid substitutions at amino acid positions 71, 95, 101 and 102 has the desired functional properties and thus can be used as the first polypeptide in the transactivator fusion protein of the invention. These and other amino acid substitutions, deletions or additions at these or other amino acid positions which retain the desired functional properties of the mutated TetR are known in the art (see, e.g., U.S. Pat. Ser. No. 6,136,954).

Further, the crystal structure of a TetR-Tet complex, as described in Hinrichs, W. et al. (1994) Science 264:418–420, can be used for rational design of mutated Tet repressors. Amino acid positions 95, 101 and 102 are located within the conserved Tet binding pocket. Thus, the Tet binding pocket of a TetR may mutated to generate a mutated TetR suitable for inclusion in a transactivator fusion protein of the present invention.

Additional suitable mutated TetR can be constructed according to the teachings of the invention and in the references cited herein. A number of different classes of TetR have been described, e.g., A, B, C, D and E (of which the Tn10-encoded repressor is a class B repressor). The amino acid sequences of the different classes of TetR share a high degree of homology (i.e., 40–60% across the length of the proteins), including in the region encompassing the above-described mutations. The amino acid sequences of various classes of TetR are described in Tovar, K. et al. (1988) Mol. Gen. Genet. 215:76–80. Accordingly, equivalent mutations to those described above for the Tn10-derived TetR can be made in other classes of TetR for inclusion in a transactivator fusion protein of the invention. Suitable equivalent mutations will be apparent to those skilled in the art and can be constructed and tested for functionality by procedures described herein or in the cited references. Nucleotide and amino acid sequences of Tet repressors of the A, C, D and E classes are disclosed in Waters, S. H. et al. (1983) Nucl. Acids Res. 11:6089–6105, Unger, B. et al. (1984) Nucleic acid 31:103–108, Unger, B. et al. (1984) Nucl Acids Res. 12:7693–7703 and Tovar, K. et al. (1988) Mol. Gen. Genet. 215:76–80, respectively. These wild-type TetR sequences can be mutated according to the teachings herein and in the cited references, for inclusion in the transactivator fusion protein of the present invention.

Additional suitable mutated Tet repressors (i.e., having the desired functional properties described above) can be constructed by mutagenesis of a wild-type TetR using methods known in the art. The nucleotide and amino acid sequences of wild-type class B Tet repressors are disclosed in Hillen, W. and Schollmeier, K. (1983) Nucl. Acids Res. 11:525–539 and Postle, K. et al. (1984) Nucl. Acids Res. 12:4849–4863. The nucleotide and amino acid sequences of wild-type class A, C, D and E type repressors are cited above. A mutated TetR can be created and selected, for example as follows: a nucleic acid (e.g., DNA) encoding a wild-type TetR is subjected to random mutagenesis and the resultant mutated nucleic acids are incorporated into an expression vector and introduced into a host cell for screening. A screening assay is used which allows for selection of a TetR which binds to a Tet operator sequence only in the presence of Tet or an analogue thereof. For example, a library of mutated nucleic acids in an expression vector can be introduced into an *E. coli* strain in which TetO sequences control the expression of a nucleic acid encoding a Lac repressor and the Lac repressor controls the expression of a nucleic acid encoding an selectable marker (e.g., drug resistance). Binding of a TetR to TetO sequences in the bacteria will inhibit expression of the Lac repressor, thereby inducing expression of the selectable marker gene. Cells expressing the marker nucleic acid are selected based upon the selectable phenotype (e.g., drug resistance). For wild-type TetR, expression of the selectable marker nucleic acid will occur in the absence of Tet. A nucleic acid encoding a mutated TetR is selected using this system based upon the ability of the nucleic acid to induce expression of the selectable marker nucleic acid in the bacteria only in the presence of Tet.

As mentioned above, the first polypeptide of the transactivator fusion protein (e.g., the mutated TetR) has the property of binding specifically to a TetO sequence. Each class of TetR has a corresponding target TetO sequence. Accordingly, the term "Tet operator sequence" or "ATetO sequence" as used herein encompasses all classes of TetO sequences, e.g., class A, B, C, D, and E. Nucleotide sequences of these five classes of TetO sequences are described in Waters, S. H. et al. (1983) cited supra, Hillen, W. and Schollenmeier, K. (1983) cited supra, Stuber, D. and Bujard, H. (1981) Proc. Natl. Acad. Sci. USA 78:167–171, Unger, B. et al. (1984) cited supra and Tovar, K. et al. (1988) cited supra. In a preferred embodiment, the mutated TetR is a Tn10-encoded repressor (i.e., class B) and the TetO sequence is a class B Tet operator sequence. Alternatively, a mutated class A TetR can be used with a class A TetO sequence, and so on for the other classes of TetR and TetO sequences.

Another approach for creating a mutated TetR which binds to a class A Tet operator is to further mutate the already mutated Tn10-derived TetR described herein (a class B repressor) such that it no longer binds efficiently to a class B operator but instead binds efficiently to a class A operator as taught in the art (see, e.g., Wissman et al. (1988) J. Mol. Biol. 202:397–406; Altschmied et al. (1988) EMBO J. 7:4011–4017). Accordingly, one can alter the binding specificity of the mutated Tn10-derived TetR as described herein by additionally changing amino acid residue 40 from Thr to Ala by standard molecular biology techniques (e.g., site directed mutagenesis).

A mutated TetR having specific mutations can be constructed by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated TetR is identified by selection from a library, the mutated nucleic acid can be recovered from the library vector. To construct a transactivator fusion protein suitable for use in the methods of the present invention, a nucleic acid encoding a mutated TetR is then ligated in-frame to another nucleic acid encoding a transcriptional activation domain and the fusion construct is incorporated into a recombinant expression vector. The transactivator fusion protein can be expressed by introducing the recombinant expression vector into a host cell.

The first polypeptide of the transactivator fusion protein is operably linked to a second polypeptide. The second polypeptide directly or indirectly activates expression in eukaryotic cells of a nucleic acid sequence operably linked to a TetO sequence. To operably link the first and second polypeptides, the nucleic acid sequences encoding the first and second polypeptides are ligated to each other in-frame to create a chimeric nucleic acid encoding a transactivator fusion protein, although the first and second polypeptides can be operably linked by other means that preserve the function of each polypeptide (e.g., chemically crosslinked). In a preferred embodiment, the second polypeptide of the transactivator fusion protein itself possesses transcriptional activation activity (i.e., the second polypeptide directly activates expression). In another embodiment, the second polypeptide activates expression by an indirect mechanism, through recruitment of an activation protein to interact with the fusion protein.

Polypeptides that function to directly or indirectly activate gene expression in eukaryotic cells are well known in the art, and are suitable for use in the construction of the second polypeptide of the transactivator fusion protein. In particular, transcriptional activation domains of many DNA binding proteins have been described and have been shown to retain their activation function when the domain is transferred to a heterologous protein. A preferred polypeptide for use in the transactivator fusion protein of the invention is the herpes simplex virus virion protein 16 (referred to herein as VP16, the amino acid sequence of which is described in Triezenberg, S. J. et al. (1988) Genes Dev. 2:718–729). In one embodiment, the second polypeptide of the transactivator fusion protein comprises about 127 of the C-terminal amino acids of VP16 are used. In another embodiment, at least one copy of about 11 amino acids from the C-terminal region of VP16 which retain transcriptional activation ability is used as the second polypeptide. Preferably, a dimer of this region (i.e., about 22 amino acids) is used. Suitable C-terminal peptide portions of VP16 are described in Seipel, K. et al. (EMBO J. (1992) 13:4961–4968).

Other polypeptides with the ability to activate expression of nucleic acid sequences in eukaryotic cells can be used for construction of the second polypeptide of the transactivator fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (EMBO J. (1992) 13:4961–4968). In addition, novel activation domains can be identified and constructed using methods known in the art, and are within the scope of the invention.

In another embodiment, the second polypeptide of the transactivator fusion protein indirectly activates transcription by recruiting a transcriptional activator to interact with the fusion protein. For example, a mutated tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) Nature 340: 245–247; Chien et al. (1991) Proc. Natl. Acad. Sci. USA 88:9578–9582; Gyuris et al. (1993) Cell 75:791–803; and Zervos, A. S. (1993) Cell 72:223–232).

Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) Science 243:1681–1688), helix-loop-helix domains (Murre, C. et al. (1989) Cell 58:537–544) and zinc finger domains (Frankel, A. D. et al. (1988) Science 240: 70–73). Interaction of a dimerization domain present in the fusion protein with an endogenous nuclear factor results in recruitment of the transactivation domain of the nuclear factor to the fusion protein, and thereby to a Tet operator sequence to which the fusion protein is bound.

A nucleic acid encoding a transactivator fusion protein of the invention can be incorporated into a recombinant expression vector in a form suitable for expression of the fusion protein in a host cell. That is, the recombinant expression vector includes one or more regulatory sequences operably linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, Nucleic acid Expression Technology: Methods in Enzymology 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by viral genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. The human cytomegalovirus IE promoter is described in Boshart et al. (1985) Cell 41:521–530. Other ubiquitously expressing promoters which can be used include the HSV-Tk promoter (disclosed in McKnight et al. (1984) Cell 37:253–262) and .beta.-actin promoters (e.g., the human -actin promoter as described by Ng et al. (1985) Mol. Cell. Biol. 5:2720–2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230: 912–916), and mammary gland-specific promoters (e.g., milk whey promoter; U.S. Pat. No. 4,873,316 and European Application Publication No. 264,166).

Developmentally-regulated promoters are also encompassed, for example the murine hox promoters (Kessel and Gruss (1990) Science 249:374–379) and the -fetoprotein promoter (Campes and Tilghman (1989) Genes Dev. 3:537–546).

Alternatively, a self-regulating construct encoding a transactivator fusion protein can be constructed. To accomplish this, nucleic acid encoding the fusion protein is operably linked to a minimal promoter sequence and at least one Tet operator sequence. When this nucleic acid is introduced into a cell (e.g., in a recombinant expression vector), a small amount of basal transcription of the transactivator nucleic acid is likely to occur due to "leakiness". In the presence of Tet or analogue thereof this small amount of the transactivator fusion protein will bind to the Tet operator sequence(s) upstream of the candidate nucleic acid sequence encoding the transactivator and stimulate additional transcription of the nucleic acid sequence encoding the transactivator, thereby leading to further production of the transactivator fusion protein in the cell.

It will be appreciated by those skilled in the art that such a self-regulating promoter can also be used in conjunction with other tetracycline-regulated transactivators, such as the wild-type Tet repressor fusion protein (tTA) described in Gossen, M. and Bujard, H. (1992) Proc. Natl. Acad. Sci. USA 89:5547–5551, which binds to Tet operators in the absence of Tet. When used in conjunction with this transactivator, self-regulated transcription of the candidate nucleic acid sequence encoding this transactivator is stimulated in the absence of Tet. The plasmid pUHD15-3, which comprises candidate nucleic acid sequences encoding the tTA described in Gossen and Bujard (1992), cited supra, operably linked to a self-regulating promoter, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9280.

In one embodiment, the recombinant expression vector containing the transactivator fusion protein is a plasmid. Alternatively, the recombinant expression vector can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include .psi.Crip, .psi.Cre, .psi.2 and .psi.Am. The genome of adenovirus can be manipulated such that it encodes and expresses a transactivator fusion protein but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 eTet.) are well known to those skilled in the art. Alternatively, an adeno-associated virus vector such as that described in Tratschin et al. (1985) Mol. Cell. Biol. 5:3251–3260 can be used to express a transactivator fusion protein.

The fusion nucleic acids of the present invention comprise a second element that is regulatable by the first element. The second element is preferably an operator sequence, and more preferably a TetO sequence. In a preferred embodiment, the second element comprises an oligomer of a TetO sequence. The term "Tet operator sequence" as used herein encompasses all classes of Tet operators (e.g., A, B, C, D and E). A nucleic acid sequence can be operably linked to a single TetO sequence, or for an enhanced range of regulation, it can be operably linked to multiple TetO sequences (e.g., two, three, four, five, six, seven, eight, nine, ten or more operator sequences). In a preferred embodiment, the candidate nucleic acid sequence is operably linked to seven TetO sequences.

In a preferred embodiment, the transactivator fusion protein of the invention is used to regulate the expression of a nucleic acid sequence encoding a candidate bioactive agent. This nucleic acid sequence is operably linked to an operator sequence to which the transactivator fusion protein binds. In a preferred embodiment, the transactivator fusion protein regulates expression of a candidate nucleic acid sequence operably linked to at least one TetO sequence. Accordingly, another aspect of the invention relates to nucleic acid sequences that are operably linked to at least one TetO sequence. Such nucleic acid sequences are also referred to herein as "tet-regulated transcription units" or "transcription units". In a preferred embodiment, the transcription unit comprises a minimal promoter and candidate nucleic acid sequence. The minimal promoter sequence is operably linked to the candidate nucleic acid sequence in a 5' to 3' direction by phosphodiester bonds. Accordingly, as used herein, the terms "candidate nucleic acid sequence" or "nucleic acid sequence" comprise a nucleic acid sequence encoding a candidate bioactive agent and may include operably linked functional elements. Examples of functional elements, include but are not limited to, promoters (e.g., minimal promoters), enhancers, restriction enzyme sites, and nucleic acid sequences encoding a peptide or an RNA.

The term "minimal promoter" as used herein refers to a partial promoter sequence which defines the start site of transcription for an operably linked nucleic acid sequence but which by itself is not capable of initiating transcription efficiently. Thus, the activity of such a minimal promoter is dependent upon the binding of a transcriptional activator to an operably linked operator sequence (e.g., one or more TetO sequences). In one embodiment, the minimal promoter is from the human cytomegalovirus (as described in Boshart et al. (1985) Cell 41:521–530). Preferably, nucleotide positions between about +75 to −53 and +75 to −31 are used. Other suitable minimal promoters are known in the art or can be identified by standard techniques.

Within a transcription unit, the candidate nucleic acid sequence (including an upstream minimal promoter sequence) is operably linked to at least one TetO sequence. For example, the TetO sequence(s) is operably linked upstream or 5= of the minimal promoter sequence through a phosphodiester bond at a suitable distance to allow for transcription of the candidate nucleic acid sequence upon binding of a transactivator (e.g., rtTA or tTA) to the TetO sequence. That is, the transcription unit is comprised of, in a 5' to 3' direction: TetO sequence(s); a minimal promoter; and a candidate nucleic acid sequence. It will be appreciated by those skilled in the art that there is some flexibility in the permissible distance between the TetO sequence(s) and the minimal promoter, although typically the TetO sequences will be located within about 200–400 base pairs upstream of the minimal promoter. Suitable promoter sequences are known in the art and described for example, in Gossen, M. and Bujard, H. (1992) Proc. Natl. Acad. Sci. USA 89:5547–5551.

Alternatively, since regulatory elements have been observed in the art to function downstream of sequences to be transcribed, it is likely that the TetO sequence(s) can be operably linked downstream (i.e., 3') of the candidate nucleic acid sequence. Thus, in this conFiguration, the transcription unit is comprised of, in a 5' to 3' direction: a minimal promoter; a candidate nucleic acid sequence; and TetO sequence(s). Again, it will be appreciated that there is likely to be some flexibility in the permissible distance downstream at which the TetO sequence(s) can be linked.

A tet-regulated transcription unit can further be incorporated into a recombinant vector (e.g., a plasmid or viral vector) by standard recombinant DNA techniques. The transcription unit, or recombinant vector in which it is contained, can be introduced into a host cell by standard transfection techniques, such as those described herein. It should be appreciated that, after introduction of the transcription unit into a population of host cells, it may be necessary to select a host cell clone which exhibits low basal expression of the candidate nucleic acid sequence operably linked to the TetO sequence(s) (i.e., selection for a host cell in which the transcription unit has integrated at a site that results in low basal expression of the TetO-linked candidate nucleic acid sequence).

In one preferred embodiment, the candidate nucleic acid sequence of the tet-regulated transcription unit encodes a candidate bioactive agent that is a peptide, e.g., a cyclic peptide. Upon induction of expression of the candidate nucleic acid sequence and translation of the resultant mRNA, the peptide of interest is produced in a host cell. In another preferred embodiment, the candidate nucleic acid sequence of the tet-regulated transcription unit encodes a candidate bioactive agent that is an RNA, e.g., an antisense RNA or ribozyme. Upon induction of expression of the candidate nucleic acid sequence, the RNA of interest is produced in the host cell.

Thus, examples of candidate bioactive agents include, but are not limited to, nucleic acids and polypeptides. Further examples of bioactive agents are cyclic peptides, RNA, antisense RNA, and DNA. Additional examples of nucleic acid sequences encoding a candidate bioactive agent, include but are not limited to, random nucleic acid sequences, and biased random nucleic acid sequences. Examples of nucleic acid sequences encoding a candidate bioactive agent, also include but are not limited to, full-length cDNA sequences, subsequences of a full-length cDNA, and antisense sequences of a full-length cDNA. Another example of a nucleic acid sequence encoding a candidate bioactive agent is a nucleic acid sequence encoding an amino acid sequence that is in-frame or out-of-frame as compared to the open reading frame (ORF) encoded by the amino acid sequence of a full-length cDNA.

Alternatively, a transactivator of the invention can regulate transcription of an endogenous nucleic acid sequence to which a TetO sequence(s) is operably linked. An "endogenous" nucleic acid sequence is a nucleic acid sequence which is present within the genome of a host cell. An endogenous nucleic acid sequence can be operably linked to a TetO sequence(s) by homologous recombination between a TetO-containing recombination vector and the endogenous nucleic acid sequence. For example, a homologous recombination vector can be prepared which includes at least one TetO sequence and a miminal promoter sequence flanked at the 3' end by sequences representing the coding region of the endogenous nucleic acid sequence and flanked at the 5' end by sequences from the upstream region of the endogenous nucleic acid sequence by excluding the actual promoter region of the endogenous nucleic acid sequence. The flanking sequences are of sufficient length for successful homologous recombination of the vector DNA with the endogenous gene. Preferably, upon homologous recombination between the vector DNA and the endogenous nucleic acid sequence in a host cell, a region of the endogenous promoter is replaced by the vector DNA containing one or more TetO sequences operably linked to a minimal promoter. Thus, expression of the endogenous nucleic acid sequence is no longer under the control of its endogenous promoter but rather is placed under the control of the TetO sequence(s) and the minimal promoter.

In another embodiment, TetO sequences can be inserted elsewhere within an endogenous gene, preferably within a 5' or 3' regulatory region, via homologous recombination to create an endogenous nucleic acid whose expression can be regulated by a tet. An endogenous nucleic acid sequence having TetO sequences inserted into a non-critical regulatory region will retain the ability to be expressed in a normal constitutive and/or tissue-specific manner but, additionally, can be downregulated by a tetracycline-controlled transcriptional inhibitor protein (described infra) in a controlled manner. For example, constitutive expression of such a modified endogenous nucleic acid sequence can be inhibited by in the presence of Tet or analogue thereof using an inhibitor fusion protein that binds to TetO sequences in the presence of Tet or analogue thereof.

In the present invention, the expression of a candidate nucleic acid operably linked to a second element (e.g., an operator sequence) that is regulatable by a first element (e.g., a transactivator). Thus, these components, the first element and the candidate nucleic acid operably linked to an operator sequence, are present in a host cell, and can be contained on the same nucleic acid or separate nucleic acids. The presence of these components in the same host cell can be achieved in a number of different ways. For example, a host cell can be transfected with a first nucleic acid encoding, e.g., a first element, stably transfected cells can be selected, and then the transfected cells can be re-transfected (also referred to as "supertransfected") with a second nucleic acid comprising, e.g., the second element operably linked to a candidate nucleic acid. Two distinct selectable markers can be used for selection, e.g., uptake of the first nucleic acid can be selected with G418 and uptake of the second nucleic acid can be selected with hygromycin. Alternatively, a single population of cells can be transfected with nucleic acid corresponding to both components of the system.

Accordingly, in one aspect, the invention provides a first nucleic acid encoding a transactivator fusion protein and a second nucleic acid comprising a candidate nucleic acid sequence operably linked to at least one TetO sequence. The transactivator of the first nucleic acid comprises a first polypeptide and second polypeptide. The first polypeptide binds to a TetO sequence in the presence of Tet or analogue thereof and is operably linked to a second polypeptide which activates transcription in eukaryotic cells.

In one embodiment, the two nucleic acids are two separate molecules (e.g., two different vectors). Thus, in this embodiment a host cell is cotransfected with the two nucleic acid molecules or successively transfected first with one nucleic acid molecule and then the other nucleic acid molecule. In another embodiment, the two nucleic acids are linked (i.e., colinear) in the same nucleic acid molecule (e.g., a single vector). Thus, in this embodiment a host cell is transfected with the single nucleic acid molecule. Further, the host cell may be a cell cultured in vitro or a cell present in vivo.

The third element of the present invention, induces or represses the expression of a candidate nucleic acid. In a preferred embodiment, the third element is an agent which induces expression of a candidate nucleic acid, e.g., by binding to a transactivator (e.g., rtTA). In another preferred embodiment, the third element is an agent which represses expression of a candidate nucleic acid, e.g., by binding to a transactivator (e.g., tTA). In a preferred embodiment, the agent comprises tetracycline or an analogue thereof, e.g., doxycycline (Dox).

The term "tetracycline analogue" is intended to include compounds which are structurally related to Tet and which bind to the TetR with a $K_a$ of at least about $10^6$ $M^{-1}$. Preferably, the Tet analogue binds with an affinity of about $10^9$ $M^{-1}$ or greater. Examples of such Tet analogues include, but are not limited to, anhydrotetracycline, Dox, chlorotetracycline, oxytetracycline and others disclosed by Hlavka and Boothe, "The Tetracyclines," in Handbook of Experimental Pharmacology 78, R. K. Blackwood et al. (eds.), Springer-Verlag, Berlin-New York, 1985; L. A. Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; R. C. Evans, "The Technology of the Tetracyclines", Biochemical Reference Series 1, Quadrangle Press, New York, 1968; and H. F. Dowling, "Tetracycline", Antibiotic Monographs, no. 3, Medical Encyclopedia, New York, 1955. Preferred Tet analogues for high level stimulation of transcription are anhydrotetracycline and Dox. A Tet analogue can be chosen which has reduced antibiotic activity compared to Tet. Examples of such Tet analogues are anhydrotetracycline, epioxytetracycline and cyanotetracycline.

In a preferred embodiment, to induce or repress nucleic acid expression in a cell in vitro, the cell is contacted with Tet or a analogue thereof by culturing the cell in a medium containing the compound. Preferably, the concentration range of the Tet or analogue thereof in the cell medium is between about 10 and about 1000 ng/ml. Tet or analogue thereof can be directly added to media in which cells are already being cultured, or more preferably for high levels of nucleic acid induction. Additionally, the cells can be harvested from Tet-free media and cultured in fresh media containing Tet, or an analogue thereof, or vice versa.

The use of different Tet analogues allows for the modulation of the level of expression of a nucleic acid sequence operably linked to a TetO sequence, for example, by adjusting the concentration of Tet or an analogue thereof in contact with the cells. For example, anhydrotetracycline and doxycycline are known to be strong inducers of expression, e.g., in a system where a transactivator binds to a TetO sequence in the presence of Tet or analogue thereof. From the uninduced state to the induced state, the increase in expression of a nucleic acid operably linked to a TetO sequence is typically about 1000- to 2000-fold, and can be at least about 20,000 fold. In the same system, Tet, chlorotetracycline and oxytetracycline have been found to be weaker inducers of expression, i.e., from the uninducec state to the induced state, the increase in expression at least about 10-fold. Thus, an appropriate Tet analogue can be selected, for use in the methods of the present invention, based upon the desired level of induction or repression of expression of nucleic acid sequence operably linked to a TetO sequence. It is also possible to change the level of expression over time, in a host cell, of a nucleic acid operably linked to a TetO sequence, by changing the Tet analogue used to induce or repress expression. For example, in some situations it may be desirable to have a strong burst of expression initially and then have a sustained lower level of expression.

Accordingly, a first agent (e.g., a first Tet analogue) which stimulates a high levels of expression can be used initially as the third element in the methods of the present invention and then the third element can be switched to a second agent (e.g., a second analogue) which stimulates a lower level of expression. Moreover, when regulating the expression of multiple nucleic acid sequences (e.g., when one sequence is regulated by a one of class TetO sequence(s) and the other is regulated by another class of TetO sequence(s), it may be possible to independently vary the level of expression of each sequence depending upon which transactivator fusion protein is used to regulate transcription and which Tet analogue is used.

In a preferred embodiment, a host cell comprises an rtTA and a fusion nucleic acid comprising a nucleic acid sequence operably linked to a TetO sequence, and a high level expression of the nucleic acid sequence does not occur in the absence of a third element, for example, tetracycline or analogues thereof. The level of basal expression of the candidate nucleic acid sequence may vary depending upon the host cell and site of integration of the sequence, but is generally quite low or even undetectable in the absence of Tet. In order to induce expression, the host cell is contacted with Tet or analogue thereof. In order to repress expression, the contacting of Tet or analogue thereof with the cells is modulated. In a preferred embodiment, the contacting is modulated by adjusting the concentration of the Tet or analogue thereof, for example, in the cell medium. Accordingly, another aspect of the invention relates to methods for inducing or repressing expression of a nucleic acid sequence operably linked to a TetO sequence in a host cell which expresses a transactivator of the invention, by modulating the contacting of Tet or an analogue thereof with the host cell.

In a preferred embodiment, a host cell comprises an tTA and a fusion nucleic acid comprising a candidate nucleic acid sequence operably linked to a TetO sequence, high level expression of the candidate nucleic acid sequence occurs only in the presence of the rtTA and, expression is repressed in the presence of Tet or an analogue thereof. The level of basal expression of the candidate nucleic acid sequence may vary depending upon the host cell and site of integration of the sequence, but is generally quite low or even undetectable in the absence of tTA. In order to induce expression, tTA is expressed in the host cell. In order to repress expression, the cells are contacted with Tet or an analogue thereof. In a preferred embodiment, the contacting is modulated by adjusting the concentration of the Tet or analogue thereof, for example, in the cell medium. Accordingly, another aspect of the invention relates to methods for inducing or repressing expression of a nucleic acid sequence operably linked to a TetO sequence in a host cell comprising a transactivator of the invention, by modulating the contacting of Tet or an analogue thereof with the host cell.

Different transactivator fusion proteins are likely to exhibit different levels of responsiveness to Tet analogues. Thus, the level of induction or repression of expression by a particular combination of transactivator fusion protein and Tet analogue can be determined by techniques described herein or known in the art. Additionally, the level of expression can be modulated by varying the concentration of the Tet analogue. Thus, in the methods of the present invention, expression of a nucleic acid operably linked to a TetO sequence can be regulated by turning the expression on or off, but also by modulating the level of expression at intermediate levels (between induction and repression) depending on the type and concentration of the Tet analogue used in the methods.

Another aspect of the invention relates to inhibitor fusion proteins. The inhibitor fusion proteins are constructed similarly to the transactivator fusion proteins in that the fusion proteins comprise a first and second polypeptide, and the first polypeptide is a mutated TetR. However, in contrast to the transactivator fusion protein, the second polypeptide of the inhibitor fusion protein has a domain that inhibits expression (rather than activates expression as in the transactivator fusion protein) in eukaryotic cell of a nucleic acid sequence operably linked to a TetO sequence. Thus, inhibitor fusion proteins can be used to downregulate the expression of a nucleic acid sequence operably linked to a TetO sequence, and can be used in the methods of the present invention to screen for an altered cellular phenotype as described herein. For example, the level of basal, constitutive expression of a nucleic acid sequence operably linked to an operator sequence may vary depending upon the type of cell in which the nucleic acid is introduced or the site of integration of the nucleic acid. Therefore, the inhibitor fusion proteins of the invention can, in a controlled manner, inhibit the expression of a nucleic acid operably linked to an operator sequence.

In one embodiment, the inhibitor fusion protein comprises a first polypeptide that binds to Tet operator sequences in the absence, but not the presence, of Tet or an analogue thereof, operably linked to a heterologous second polypeptide that inhibits transcription in eukaryotic cells. In another embodiment, the inhibitor fusion protein comprises a first polypeptide that binds to a Tet operator sequence in the presence, but not the absence, of Tet or analogue thereof, operably linked to a heterologous second polypeptide that inhibits transcription in eukaryotic cells. The term "heterologous" is intended to mean that the second polypeptide is derived from a different protein than the first polypeptide. Like the transactivator fusion proteins, the inhibitor fusion proteins can be prepared using standard recombinant DNA techniques as described herein.

Proteins and polypeptide domains within proteins which can function to inhibit transcription in eukaryotic cells have been described in the art (for reviews see, e.g., Renkawitz, R. (1990) Trends in Genetics 6:192–197; and Herschbach, B. M. and Johnson, A. D. (1993) Annu. Rev. Cell. Biol. 9:479–509) have suitable inhibitor domains for use in the inhibitor fusion proteins of the present invention. Such transcriptional inhibitor domains have been referred to in the art as "silencing domains" or "repressor domains." Although the precise mechanism by which many of these polypeptide domains inhibit transcription is not known (and the invention is not intended to be limited by mechanism), there are several possible means by which repressor domains may inhibit transcription, including: competitive inhibition of binding of either activator proteins or the general transcriptional machinery; prevention of the activity of a DNA bound activator; and negative interference with the assembly of a functional preinitiation complex of the general transcription machinery. Thus, an inhibitor domain may have a direct inhibitory effect on the transcriptional machinery or may inhibit transcription indirectly by inhibiting the activity of activator proteins.

Accordingly, polypeptide containing an inhibitor domain can act either directly or indirectly to inhibit expression. As used herein a "reduction" in the level of expression of a nucleic acid sequence operably linked to an operator sequence refers to a diminution in the level or amount of expression of the nucleic acid compared to the level or amount prior to regulation by the transcriptional inhibitor protein. Transcriptional inhibition may be partial or complete. The terms "silencer", "repressor" and "inhibitor" are used interchangeably herein to describe an inhibitor protein, or domains thereof, that can inhibit expression of a nucleic acid sequence operably linked to an operator sequence.

A "repressor" or "silencer" domain as used herein is a polypeptide domain that retains its repressor function (e.g., repression of expression of a nucleic acid sequence operably linked to an operator sequence) when the domain is transferred to a heterologous protein. Proteins which have been demonstrated to have repressor domains that can function when transferred to a heterologous protein include the v-erbA onconucleic acid product (Baniahmad, A. et al. (1992) EMBO J. 11:1015–1023), the thyroid hormone receptor (Baniahmad, supra), the retinoic acid receptor (Baniahmad, supra), and the *Drosophila* Krueppel (Kr) protein (Licht, J. D. et al. (1990) Nature 346:76–79; Sauer, F. and Jackle, H. (1991) Nature 353:563–566; Licht, J. D. et al. (1994) Mol. Cell. Biol. 14:4057–4066). Non-limiting examples of other proteins which have transcriptional repressor activity in eukaryotic cells include the *Drosophila* homeodomain protein even-skipped (eve), the *S. cerevisiae* Ssn6/Tup1 protein complex (see Herschbach and Johnson, supra), the yeast SIR1 protein (see Chien, et al. (1993) Cell 75:531–541), NeP1 (see Kohne, et al. (1993) J. Mol. Biol. 232:747–755), the *Drosophila* dorsal protein (see Kirov, et al. (1994) Mol. Cell. Biol. 14:713–722; Jiang, et al. (1993) EMBO J. 12:3201–3209), TSF3 (s Chen, et. al. (1993) Mol. Cell. Biol. 13:831–840), SF1 (see Targa, et al. (1992) Biochem. Biophys. Res. Comm. 188:416–423), the *Drosophila* hunchback protein (see Zhang, et al. (1992) Proc. Natl. Acad. Sci. USA 89:7511–7515), the *Drosophila* knirps protein (see Gerwin, et al. (1994) Mol. Cell. Biol. 14:7899–7908), the WT1 protein (Wilm's tumor nucleic acid product) (see Anant, et al. (1994) Onconucleic acid 9:3113–3126; Madden et al., (1993) Onconucleic acid 8:1713–1720), Oct-2.1 (see Lillycrop, et al. (1994) Mol. Cell. Biol. 14:7633–7642), the *Drosophila* engrailed protein (see Badiani, et al. (1994) Genes Dev. 8:770–782; Han and Manley, (1993) EMBO J. 12:2723–2733), E4BP4 (see Cowell and Hurst, (1994) Nucleic Acids Res. 22:59–65) and ZF5 (see Numoto, et al. (1993) Nucleic Acids Res. 21:3767–3775), In additional aspects described below, the invention provides alternative approaches to regulating the expression of one or more nucleic acid sequences. These alternative approaches to regulating expression of nucleic acid sequences operably linked to TetO sequences are suitable for use in the methods of the present invention to screen for cells having an altered phenotype due to the presence of a candidate bioactive agent.

In addition to regulating nucleic acid expression using either a transactivator fusion protein or inhibitor fusion protein alone, these two types of proteins, can be used in combination to allow for both positive and negative regulation of expression of one or more nucleic acids in a host cell. Positive regulation of expression refers to induction or increase in expression, whereas negative regulation of expression refers to repression or reduction in expression. Thus, an inhibitor protein that binds to TetO either 1) in the absence, but not the presence, of Tet; or 2) in the presence, but not the absence, of Tet or analogue thereof, can be used in combination with a transactivator fusion protein that binds to TetO either 1 in the absence, but not the presence, of Tet or analogue thereof; or 2) in the presence, but not the absence, of Tet or analogue thereof. Transactivator proteins that bind to TetO in the absence, but not the presence, of Tet or analogue thereof are described herein, and in U.S. Pat. No. 5,464,758, U.S. Ser. No. 08/076,327 and U.S. Pat. No. 5,650,298. Transactivator proteins that bind to TetO in the presence, but not the absence, of Tet are described herein, and in U.S. Ser. No. 08/270,637 and U.S. Pat. No. 5,654,168.

When more than one TetR-containing fusion protein is expressed in a host cell, additional steps may be taken to inhibit heterodimerization between the different TetR-containing fusion proteins. For example, a transactivator composed of a TetR of one class may be used in combination with an inhibitor fusion protein composed of a TetR of a second, different class that does not heterodimerize with the first class of TetR. Alternatively, amino acid residues of the TetR involved in dimerization may be mutated to inhibit heterodimerization. However, even if some heterodimerization between transactivator and inhibitor fusion proteins occurs in a host cell, sufficient amounts of homodimers should be produced to allow for efficient positive and negative regulation as described herein.

It will be appreciated by those skilled in the art that various combinations of activator and inhibitor proteins can be used to regulate a single nucleic acid sequence operably linked to a TetO sequence in both a positive and negative manner or to regulate multiple nucleic acid sequences operably linked to TetO sequences in a coordinated manner or in an independent manner using the teachings described herein or known in the art. Several non-limiting examples of how the transactivator and inhibitor fusion proteins may be used in combination are described further below. However, many other possible combinations will be evident to the skilled artisan in view of the teachings herein and known in the art.

In one embodiment expression of a nucleic acid acid sequence operably linked to a TetO sequence in a host cell is regulated in both a negative and positive manner by the combination of an inhibitor fusion protein that binds to TetO in the absence, but not the presence, of Tet or analogue thereof (referred to as a Tet controlled silencing domain, or tSD) and an transactivator fusion protein that binds to TetO in the presence, but not the absence, of Tet or analogue thereof (e.g., rtTA). In addition to TetO sequences, the nucleic acid sequence is operably linked to a promoter, and may contain other positive regulatory elements (e.g., enhancer sequences) that contribute to basal level, constitutive expression of the nucleic acid in the host cell. Binding of tSD to the TetO sequences in the absence of Tet or analogue thereof inhibits the basal constitutive expression of the nucleic acid sequence, thus keeping the expression of the nucleic acid sequence in a repressed or uninduced state until expression is desired. When expression is desired, the concentration of Tet or analogue thereof in contact with the host cell is increased. Upon contacting a host cell with Tet or an analogue thereof, tSD loses the ability to bind to TetO sequences whereas the previously unbound rtTA acquires the ability to bind to TetO sequences. The resultant binding of rtTA to the TetO sequences operably linked to a nucleic acid sequence of interest thus induces expression of the nucleic acid sequence. The level of expression may be controlled by the concentration of Tet or analogue thereof, type of Tet analogue, duration of induction, and type of rtTA (e.g., class of TetR and transactivator domain, as described previously herein). It will be appreciated that the combination of transactivator and inhibitor fusion proteins (i.e., where the inhibitor binds in the presence but not the absence of Tet or analogue thereof, and the transactivator binds in the absence but not the presence of Tet or analogue thereof) can also be used in the methods of the present invention. In this case, expression of the nucleic acid sequence of interest is repressed by contacting the host cell with Tet (e.g., culture with Tet or analogue) and nucleic acid expression is activated by removal of the drug.

In another embodiment, the activator and inhibitor fusion proteins are used in combination to coordinately regulate, in both a positive and negative manner, two nucleic acid sequences operably linked to a TetO sequence but are expressed bidirectionally with respect to each other. In this case, a first nucleic acid and a second nucleic acid are linked to the same TetO sequence(s), but in opposite orientations. The inhibitor fusion protein is used to repress basal levels of expression of both the first nucleic acid and the second nucleic acid in a coordinate manner, whereas the transactivator fusion protein is used to stimulate expression of the first nucleic acid and the second nucleic acid in a coordinate manner.

In another embodiment, the activator and inhibitor fusion proteins are used to independently regulate two or more nucleic acid sequences each operably linked to their respective TetO sequence, where each TetO sequence is of a different class. In one embodiment, a transactivator fusion protein that binds to one class of TetO sequences (e.g., class A) in the presence, but not the absence of Tet or analogue is used in combination with an inhibitor fusion protein that binds to a second, different class of TetO sequences (e.g., class B) also in the presence, but not the absence, of Tet or analogue. For example, a host cell containing a first nucleic acid sequence operably linked to class A TetO sequences and second nucleic acid sequence operably linked to class B TetO sequences, both nucleic acid sequences will be expressed at basal levels in the absence of Tet or an analogue thereof, whereas expression of the first nucleic acid will be stimulated in the presence of Tet or an analogue thereof and expression of the second nucleic acid will be repressed in the presence of Tet or analogue thereof.

Alternatively, in another embodiment, the transactivator fusion protein binds to one class of TetO sequences (e.g., class A) in the presence, but not the absence, of Tet or analogue thereof and the inhibitor fusion protein binds to a second, different class of TetO sequences (e.g., class B) in the absence but not the presence of Tet or analogue. For example, in the host cell, the first nucleic acid sequence will be expressed at basal levels in the absence of Tet or an analogue thereof and will be stimulated in the presence of Tet or an analogue thereof, whereas the expression of the second nucleic acid sequence will be repressed in the absence of the Tet or an analogue thereof but will have basal levels expression in the presence of Tet or analogue thereof. Various other possible combinations will be apparent to the skilled artisan.

By "fusion nucleic acid" or grammatical equivalents thereof is meant a nucleic acid comprising functional elements that may or may not be operably linked. Examples of functional elements include, but are not limited to, a promoter, enhancer, operator sequence, restriction enzyme site, candidate nucleic acid, and nucleic acid encoding a polypeptide or RNA. In a preferred embodiment the fusion nucleic acid comprises a second element and a candidate nucleic acid. In another preferred embodiment, the fusion nucleic acid comprises a nucleic acid encoding a first element. As outlined herein, fusion nucleic acids, or other components of the system such as fusion partners as well as the vectors themselves, can include reporter proteins.

By "candidate nucleic acid" or grammatical equivalents thereof is meant a nucleic acid comprising a nucleic acid sequence encoding a candidate bioactive agent. The candidate nucleic acid of the present invention can also comprises functional elements, e.g., a promoter, enhancer, and restriction enzyme site. In another preferred embodiment, the candidate nucleic acid comprises and minimal promoter operably linked to a nucleic acid sequence encoding the bioactive agent.

By "candidate nucleic acid sequence" or grammatical equivalents thereof is meant a nucleic acid sequence comprising a nucleic acid sequence encoding a candidate bioactive agent.

By "candidate bioactive agents" or "candidate drugs" or "candidate expression products" or grammatical equivalents herein is meant the expression product of a candidate nucleic acid sequence which may be tested for the ability to alter the phenotype of a cell. As is described below, the candidate bioactive agents are the expression products of a candidate nucleic acid sequence, and encompass several chemical classes, including peptides and nucleic acids such as DNA, cDNA, messenger RNA (mRNA), antisense RNA, and ribozyme components. Thus, the candidate bioactive agents (expression products) may be either translation products of the candidate nucleic acid sequence, i.e., peptides, or transcription products of the candidate nucleic acid sequences, i.e., either DNA or RNA.

In a preferred embodiment, the candidate bioactive agents are translation products of candidate nucleic acid sequences. In this embodiment, a library of fusion nucleic acids each comprising a candidate nucleic acid sequence are introduced into the cells, and the cells express the nucleic acid sequence to form peptides. Thus, in this embodiment, the candidate bioactive agents are peptides. Generally, peptides ranging from about 4 amino acids in length to about 100 amino acids may be used, with peptides ranging from about 5 to about 50 being preferred, with from about 5 to about 30 being particularly preferred and from about 6 to about 20 being especially preferred.

In a preferred embodiment, the candidate bioactive agents are transcription products of candidate nucleic acid sequences and, thus, the candidate bioactive agents are also nucleic acids. The transcription products may be either primary transcripts or secondary translation products. That is, using the retroviral reverse transcriptase, primary DNA is made which is later converted into double stranded DNA. Additionally, using the primary DNA, RNA transcripts can be generated within the cell, including mRNA, antisense RNA and ribozymes or portions thereof.

At a minimum, the candidate bioactive agents comprise randomized expression products of the nucleic acid sequence of the fusion nucleic acids. That is, every candidate bioactive agent has a randomized portion, as defined below, that is the basis of the screening methods outlined herein. In addition, to the randomized portion, the candidate bioactive agent may also include a fusion partner.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e., not native to the host cell), or synthetic (not native to any cell). Suitable fusion partners include, but are not limited to: a)

presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In a preferred embodiment, the fusion partner is a presentation structure. By "resentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacological agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e., artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on -sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference, and FIG. 28). Using this system investigators have isolated peptides capable of high affinity interaction with the appropriate target. In general, coiled-coil structures allow for between 6 to 20 randomized positions.

A preferred coiled-coil presentation structure is as follows:

MGCAALESEVSALESEVASLESEVAALGRGDMP LAAVKSKLSAVKSKLASVKSKLAACGPP (SEQ ID NO:1). The underlined regions represent a coiled-coil leucine zipper region defined previously (see Martin et al., EMBO J. 13(22):5303–5309 (1994), incorporated by reference). The bolded GRGDMP region represents the loop structure and when appropriately replaced with randomized peptides (i.e., candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQATSGFTFSHFYMEWVRGGEYIAASR HKHNKYTTEYSASVKGRYIVSRDTSOSILYLQ KKKGPP (SEQ ID NO:2). The bold, underline regions are the regions which may be randomized. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "oped" with cysteine residues which, under the appropriate reDox conditions, may result in highly crosslinked structured conformations, similar to a presentation structure. Similarly, the randomization regions may be controlled to contain a certain number of residues to confer β-sheet or -helical structures.

In a preferred embodiment, the presentation structure is a reporter protein. In a preferred embodiment, the reporter protein can be used as a direct label, for example a detection protein for sorting the cells or for cell enrichment by FACS. In this embodiment, the protein product of the reporter gene itself can serve to distinguish cells that are expressing the reporter gene. In this embodiment, suitable reporter genes include those encoding green fluorescent protein (GFP;

Chalfie, M. et al. (1994) Science 263:802–05; and EGFP; Clontech—Genbank Accession Number U55762), blue fluorescent protein (BFP; Quantum Biotechnologies, Inc. 1801 de Maisonneuve Blvd. West, 8th Floor, Montreal (Quebec) Canada H3H 1J9; Stauber, R. H. (1998) Biotechniques 24:462–71; Heim, R. et al. (1996) Curr. Biol. 6:178–82), enhanced yellow fluorescent protein (EYFP; 1. Clontech Laboratories, Inc., 1020 East Meadow Circle, Palo Alto, Calif. 94303), *Renilla reniformis* GFP (WO 99/49019), *Ptilosarcus gurneyi* GFP (WO 99/49019; U.S. Ser. No. 60/164,592; U.S. Ser. No. 09/710,058; U.S. Ser. No. 60/290,287), *Renilla mulleris* GFP (WO 99/49019; U.S. Ser. No. 60/164,592; U.S. Ser. No. 09/710,058; U.S. Ser. No. 60/290,287), luciferases (for example, firefly, Kennedy, H. J. et al. (1999) J. Biol. Chem. 274:13281–91; *Renilla reniformis*, Lorenz, W. W. (1996) J Biolumin. Chemilumin. 11:31–37; *Renilla mulleris*, U.S. Pat. No. 6,232,107), b-galactosidase (Nolan, G. et al. (1988) Proc. Natl. Acad. Sci. USA 85:2603–07), b-glucouronidase (Jefferson, R. A. et al. (1987) EMBO J. 6:3901–07; Gallager, S., GUS Protocols: Using the GUS Gene as a reporter of gene expression, Academic Press, Inc., 1992), and secreted form of human placental alkaline phosphatase, SEAP (Cullen, B. R. et al. (1992) Methods Enzymol. 216:362–68). In a preferred embodiment, the codons of the reporter genes are optimized for expression within a particular organism, especially mammals, and particularly preferred for human cell expression (see Zolotukhin, S. et al. (1996) J. Virol. 70:4646–54; U.S. Pat. No. 5,968,750; U.S. Pat. No. 6,020,192; U.S. Ser. No. 60/290,287, all of which are expressly incorporate by reference).

In another embodiment, the reporter protein will bind a label that can be used as the basis of the cell enrichment (sorting); that is, the reporter protein serves as an indirect label or detection protein. In this embodiment, the reporter protein is a cell-surface protein. For example, the reporter protein may be any cell-surface protein not normally expressed on the surface of the cell, such that secondary binding agents serve to distinguish cells that contain the reporter protein from those that do not. Alternatively, albeit non-preferably, reporters comprising normally expressed cell-surface proteins could be used, and differences between cells containing the reporter construct and those without could be determined. Thus, secondary binding agents bind to the reporter protein. These secondary binding agents are preferably labeled, for example with fluors, and can be antibodies, haptens, etc. For example, fluorescently labeled antibodies to the reporter gene can be used as the label. Similarly, membrane-tethered streptavidin could serve as a reporter gene, and fluorescently-labeled biotin could be used as the label, i.e. the secondary binding agent. Alternatively, the secondary binding agents need not be labeled as long as the secondary binding agent can be used to distinguish the cells containing the construct; for example, the secondary binding agents may be used in a column, and the cells passed through, such that the expression of the reporter gene results in the cell being bound to the column, and a lack of the reporter gene (i.e. inhibition), results in the cells not being retained on the column. Other suitable reporter proteins/secondary labels include, but are not limited to, antigens and antibodies, enzymes and substrates (or inhibitors), etc.

In a preferred embodiment, the reporter gene is a survival gene that serves to provide a nucleic acid (or encode a protein) without which the cell cannot survive, such as drug resistance genes. In this embodiment, expressing the survival gene allows selection of cells expressing the fusion nucleic acid by identifying cells that survive, for example in presence of a selection drug. Examples of drug resistance genes include, but are not limited to, puromycin resistance (puromycin-N-acetyltransferase) (de la Luna, S. et al. (1992) Methods Enzymol. 216:376–85), G418 neomycin resistance gene, hygromycin resistance gene (hph), and blasticidine resistance genes (bsr, brs, and BSD; Pere-Gonzalez, et al.(1990) Gene, 86:129–34; Izumi, M. et al. (1991) Exp. Cell Res. 197:229–33; Itaya, M. et al. (1990) J. Biochem. 107: 799–801; Kimura, M. et al. (1994) Mol. Gen. Genet. 242: 121–29). In addition, generally applicable survival genes are the family of ATP-binding cassette transporters, including multiple drug resistance gene (MDR1) (see Kane, S. E. et. al. (1988) Mol. Cell. Biol. 8:3316–21 and Choi, K. H. et al. (1988) Cell 53:519–29), multi-drug resistance associated proteins (MRP) (Bera, T. K. et al. (2001) Mol. Med. 7:509–16), and breast cancer associated protein (BCRP or MXR) (Tan, B. et al. (2000) Curr. Opin. Oncol. 12:450–58). When expressed in cells, these selectable genes can confer resistance to a variety of toxic reagents, especially anti-cancer drugs (i.e. methotrexate, colchicine, tamoxifen, mitoxanthrone, and doxorubicin). As will be appreciated by those skilled in the art, the choice of the selection/survival gene will depend on the host cell type used.

In a preferred embodiment, the reporter gene encodes a death gene that causes the cells to die when expressed. Death genes fall into two basic categories: death genes that encode death proteins requiring a death ligand to kill the cells, and death genes that encode death proteins that kill cells as a result of high expression within the cell and do not require the addition of any death ligand. Preferred are cell death mechanisms that requires a two-step process: the expression of the death gene and induction of the death phenotype with a signal or ligand such that the cells may be grown expressing the death gene, and then induced to die. A number of death genes/ligand pairs are known, including, but not limited to, the Fas receptor and Fas ligand (Schneider, P. et al. (1997) J. Biol. Chem. 272:18827–33; Gonzalez-Cuadrado, S. et al. (1997) Kidney Int. 51:1739–46; Muruve, D. A. et al. (1997) Hum. Gene Ther. 8:955–63); p450 and cyclo-phosphamide (Chen, L. et al. (1997) Cancer Res. 57:4830–37); thymidine kinase and gangcylovir (Stone, R. (1992) Science 256:1513), tumor necrosis factor (TNF) receptor and TNF. Alternatively, the death gene need not require a ligand, and death results from high expression of the gene; for example, the overexpression of a number of programmed cell death (PCD) proteins known to cause cell death, including, but not limited to, caspases, bax, TRADD, FADD, SCK, MEK, etc.

In a preferred embodiment, death genes also include toxins that cause cell death, or impair cell survival or cell function when expressed by a cell. These toxins generally do not require addition of a ligand to produce toxicity. An example of a suitable toxin is campylobacter toxin CDT (Lara-Tejero, M. (2000) Science, 290:354–57). Expression of CdtB subunit, which has homology to nucleases, causes cell cycle arrest and ultimately cell death. Another toxin, the diphtheria toxin (and similar *Pseudomonas exotoxin*), functions by ADP ribosylating the ef-2 (elongation factor 2) molecule in the cell and preventing translation. Expression of the diphtheria toxin A subunit induces cell death in cells expressing the toxin fragment. Other useful toxins include cholera toxin and pertussis toxin (catalytic subunit-A ADP ribosylates the G protein regulating adenylate cyclase), pierisin from cabbage butterflys (induces apoptosis in mammalian cells; Watanabe, M. (1999) Proc. Natl. Acad. Sci. USA 96:10608–13), phospholipase snake venom toxins (Diaz, C. et al. (2001) Arch. Biochem. Biophys. 391:56–64), ribosome inactivating toxins (i.e. ricin A chain, Gluck, A. et al. (1992) J. Mol. Biol. 226:411–24; and nigrin, Munoz, R. et al. (2001) Cancer Lett. 167:163–69) and pore forming toxins (hemolysin and leukocidin). When the target cells are neuronal cells, neuronal specific toxins may be used to inhibit specific neuronal functions. These include bacterial toxins such as botulinum toxin and tetanus toxin, which are proteases that act on synaptic vesicle associated proteins (i.e. synaptobrevin) to prevent neurotransmitter release (see Binz, T. et al. (1994) J. Biol. Chem. 269:9153–58; Lacy, D. B. et al. (1998) Curr. Opin. Struct. Biol. 8:778–84).

Another preferred embodiment of a reporter molecule is a cell cycle gene, that is, a gene that causes alterations in the cell cycle. For example, Cdk interacting protein p21 (see Harper, J. W. et al. (1993) Cell 75:805–16), which inhibits cyclin dependent kinases, does not cause cell death but causes cell-cycle arrest. Thus, expressing p21 allows selecting for regulators of promoter activity or regulators of p21 activity based on detecting cells that grow out much more quickly due to low p21 activity, either through inhibiting promoter activity or inactivation of p21 protein activity. As will be appreciated by those in the art, it is also possible to conFigure the system to select cells based on their inability to grow out due to increased p21 activity. Similar mitotic inhibitors include p27, p57, p16, p15, p18 and p19, p19 ARF (human homolog p14 ARF). Other cell cycle proteins useful for altering cell cycle include cyclins (Cln), cyclin dependent kinases (Cdk), cell cycle checkpoint proteins (i.e. Rad17, p53), Cks1 p9, Cdc phosphatases (i.e Cdc 25) etc.

As is described generally in WO 00/20574, expressly incorporated by reference, the reporter gene or reporter protein can be part of a fusion nucleic acid or fusion polypeptide, and can be attached to a candidate agent at the B or C-terminus, or internally, with or without the use of linkers. In addition, rather than have the reporter gene be a fusion partner, it may be located anywhere in the vector being used, or attached to other components.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including a) subcellular locations such as the golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Arg Lys Val (SEQ ID NO:3)), Kalderon (1984), et al., Cell, 39:499–509; the human retinoic acid receptor-β nuclear localization signal (ARRRRP (SEQ ID NO:4)); NFkB p50 (EEVQRKRQKL (SEQ ID NO:5); Ghosh et al., Cell 62:1019 (1990); NFkB p65 (EEKRKRTYE (SEQ ID NO:6); Nolan et al., Cell 64:961 (1991); and others (see for example Boulikas, J. Cell. Biochem. 55(1):32–58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp (SEQ ID NO:7)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space; see FIG. 28. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:8); Nakauchi et al., PNAS USA 82:5126 (1985) and 1–21 in the case of ICAM-2 (MSSFGYRTLTVALFTLICCPG (SEQ ID NO:9); Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDCRPRGSVKGTGLDFACDIYIWA-PLAGICVALLLSLIITLICYHSR (SEQ ID NO:10); Nakauchi, supra) and 224–256 from ICAM-2 (MVIIVTVVSV-LLSLFVTSVLLCFIFGQHLRQQR (SEQ ID NO:11); Staunton, supra).

Alternatively, membrane anchoring sequences include the GPI anchor, which results in a covalent bond between the molecule and the lipid bilayer via a glycosyl-phosphatidylinositol bond for example in DAF PNKGSGTTSGTTRLLS-GHTCFTLTGLLGTLVTMGLLT (SEQ ID NO:12), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:13) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence LLQRLFSRQDCCGNCSD-SEEELPTRL (SEQ ID NO:14), with the bold cysteines being palmitolyated; Stoffel et al., J. Biol. Chem 269:27791 (1994)); from rhodopsin KQFRNCMLTSLCCGKNPLGD (SEQ ID NO:15); Barnstable et al., J. Mol. Neurosci. 5(3):207 (1994)); and the p21 H-ras 1 protein LNPPDES-GPGCMSCKCVLS (SEQ ID NO:16); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO;17); Dice, Ann. N.Y. Acad. Sci. 674:58 (1992); or lysosomal membrane sequences from Lamp-1 (MLIP-IAGFFALAGLVLIVLIAYLI*GRKRSHAGYQTI* (SEQ ID NO:18), Uthayakumar et al., Cell. Mol. Biol. Res. 41:405 (1995)) or Lamp-2 (LVPIAVGAALAGVLILVLLAYFIG *LKHHHAGYEQF* (SEQ ID NO;19), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:20); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:21); Schatz, supra); mitochondrial intermembrane space sequences (yeast cyto chrome c1; MFSMLSKRWAQRTL-SKSFYSTATGAASKS-
GKLTQKLVTAGVAAAGITASTLLYADSLTAEAMTA (SEQ ID NO:22); Schatz, supra) or mitochondrial outer membrane sequences (yeast 70 kD outer membrane protein; MKSFITRNKTAILATVAATG-
TAIGAYYYYNQLQQQQQRGKK (SEQ ID NO:23); Schatz, supra).

The target sequences may also be endoplasmic reticulum sequences, including the sequences from calreticulin (KDEL (SEQ ID NO:24); Pelham, Royal Society London Transactions B; 1–10 (1992)) or adenovirus E3/19K protein (LYLSRRSFIDEKKMP (SEQ ID NO:25); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO;16), with the bold cysteine farnesylated; Capon, supra); geranylgeranylation sequences (for example, protein rab-5A; LTEPTQPTRNQCCSN (SEQ ID NO:26), with the bold cysteines geranylgeranylated; Farnsworth, PNAS USA 91:11963 (1994)); or destruction sequences (cyclin B1; RTALGDIGN (SEQ ID NO:27); Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is conFigured to contain, in series, secretion signal peptide-presentation structure-randomized expression product region-presentation structure, see FIG. 28. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:28); Villinger et al., J. Immunol. 155:3946 (1995)), growth hormone (MATGSRTSLLLAFGLLCLP-WLQEGSAFPT (SEQ ID NO:29); Roskam et al., Nucleic Acids Res. 7:30 (1979)); preproinsulin (MALWMRLL-PLLALLALWGPDPAAAFVN (SEQ ID NO:30); Bell et al., Nature 284:26 (1980)); and influenza HA protein (MKAK-LLVLLYAFVAGDQI (SEQ ID NO:31); Sekikawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLACAGN-FVHG (SEQ ID NO:32).

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligocandidate nucleic acid sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky=s N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_n GGPP$ (SEQ ID NO:33), where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods.

The fusion partners may be placed anywhere (i.e., N-terminal, C-terminal, internal) in the structure as the biology and activity permits.

In a preferred embodiment, the fusion partner includes a linker or tethering sequence. Linker sequences between various targeting sequences (for example, membrane targeting sequences) and the other components of the constructs (such as the randomized candidate agents) may be desirable to allow the candidate agents to interact with potential targets unhindered. For example, when the candidate bioactive agent is a peptide, useful linkers include glycine-serine polymers (including, for example, $(GS)_n$, $(GSGGS)_n$ (SEQ ID NO:34) and $(GGGS)_n$ (SEQ ID NO:35), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, reporter sequences, rescue sequences, and stability sequences may be used, with or without linker sequences.

By "candidate nucleic acids" herein is meant nucleic acids comprising a candidate nucleic acid sequence encoding a candidate bioactive agent. The candidate nucleic acids can be expressed to form a candidate bioactive agent. Therefore, the candidate nucleic acids can further encode, for example, a fusion partner and contain sequences to effect translation or transcription. Where the candidate bioactive agents are randomized peptides in a peptide library, the candidate nucleic acid generally contains cloning sites which are placed to allow in frame expression of the randomized peptides, and any fusion partners, if present, such as presentation structures. For example, when presentation structures are used, the presentation structure will generally contain the initiating ATG, as a part of the parent vector. Where the candidate bioactive agents are RNAs in an RNA library, the candidate nucleic acids are generally constructed with an internal CMV promoter, tRNA promoter or cell specific promoter designed for immediate and appropriate expression of the RNA structure at the initiation site of RNA synthesis. The RNA is expressed anti-sense to the direction of retroviral synthesis and is terminated as known, for example with an orientation specific terminator sequence. Interference from upstream transcription is alleviated in the target cell with the self-inactivation deletion, a common feature of certain retroviral expression systems.

Generally, the candidate nucleic acids are expressed within the cells to produce expression products of the candidate nucleic acids. As outlined above, the expression products include translation products, i.e., peptides, or transcription products, i.e., nucleic acid. The candidate bioactive agents and candidate nucleic acids are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. As is more fully described below, the candidate nucleic acids which give rise to the candidate expression products are chemically synthesized, and thus may incorporate any nucleotide at any position. Thus, when the candidate nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized candidate nucleic acids.

The library should provide a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is necessary for completion of the signaling pathway. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, with libraries of $10^7$ $10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3/64, or 4.69%, chance that the codon will be a stop codon. Thus, in a peptide of 10 residues, there is an unacceptable high likelihood that 46.7% of the peptides will prematurely terminate. For free peptide structures this is perhaps not a problem. But for larger structures, such as those envisioned here, such termination will lead to sterile peptide expression. To alleviate this, random residues are encoded as NNK, where K=T or G. This allows for encoding of all potential amino acids (changing their relative representation slightly), but importantly preventing the encoding of two stop residues TAA and TGA. Thus, libraries encoding a 10 amino acid peptide will have a 15.6% chance to terminate prematurely. For candidate nucleic acids which are not designed to result in peptide expression products, this is not necessary.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate bioactive agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus oocytes* following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, biased SH-3 domain-binding oligonucleotides/peptides are made. SH-3 domains have been shown to recognize short target motifs (SH-3 domain-binding peptides), about ten to twelve residues in a linear sequence, that can be encoded as short peptides with high affinity for the target SH-3 domain. Consensus sequences for SH-3 domain binding proteins have been proposed. Thus, in a preferred embodiment, oligos/peptides are made with the following biases 1. XXXPPXPXX, wherein X is a randomized residue.

2. (within the positions of residue positions 11 to −2):
11 10 9 8 7 6 5 4 3 2 1
Met Gly aa11 aa10 aa9 aa8 aa7 Arg Pro Leu Pro Pro hyd
0 −1 −2
Pro hyd hyd Gly Gly Pro Pro STOP (SEQ ID NO:36)
atg ggc nnk nnk nnk nnk nnk aga cct ctg cct cca sbk
cct sbk sbk gga ggc cca cct TAA1 (SEQ ID NO:37).

In this embodiment, the N-terminus flanking region is suggested to have the greatest effects on binding affinity and is therefore entirely randomized. "Hyd" indicates a bias toward a hydrophobic residue, i.e.—Val, Ala, Gly, Leu, Pro, Arg. To encode a hydrophobically biased residue, "sbk" codon biased structure is used. Examination of the codons within the genetic code will ensure this encodes generally hydrophobic residues. s=g,c; b=t, g, c; v=a, g, c; m=a, c; k=t, g; n=a, t, g, c.

The candidate nucleic acids are introduced into the cells to screen for bioactive agents capable of altering the phenotype of a cell. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin7, electroporation, viral infection, etc. The candidate nucleic acids may stably integrate into the genome of the host cell (for example, with retroviral introduction, outlined below), or may exist either transiently or stably in the cytoplasm (i.e., through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the candidate nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

In a preferred embodiment, the candidate nucleic acids are introduced into the cells using retroviral vectors. Currently, the most efficient nucleic acid transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins -gag, pol, and env- that are required for packaging, processing, reverse transcription, and integration of recombinant genomes. Those RNA molecules that have in cis the R packaging signal are packaged into maturing virions. Retroviruses are preferred for a number of reasons. First, their derivation is easy. Second, unlike Adenovirus-mediated nucleic acid delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene therapy 7:1405–1413; Hofmann et al., PNAS USA 93:5185–5190; Choate et al., Human Gene therapy 7:2247 (1996); and WO 94/19478; and references cited therein, all of which are incorporated by reference.

In one embodiment of the invention, the library is generated in a retrovirus DNA construct backbone, as is generally described in the examples. Standard oligonucleotide synthesis is done to generate the random portion of the candidate bioactive agent, using techniques well known in the art (see Eckstein, Oligonucleotides and Analogues, A Practical Approach, IRL Press at Oxford University Press, 1991); libraries may be commercially purchased. Libraries with up to $10^9$ unique sequences can be readily generated in such DNA backbones. After generation of the DNA library, the library is cloned into a first primer. The first primer serves as a "cassette" which is inserted into the retroviral construct. The first primer generally contains a number of elements, including for example, the required regulatory sequences (e.g. translation, transcription, promoters, eTet), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene therapy 1:136 (1994)) and a modified MFG virus (Rivere et al., Genetics 92:6733 (1995)), and pBABE, outlined in the examples. A general schematic of the retroviral construct is depicted in FIG. 29.

In a preferred embodiment, a retroviral vector is designed to allow inducible expression of retroviral inserts after integration of a single vector in target cells. Importantly, the expression system is contained within the single retrovirus. For example, Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of Tet or analogues thereof. However, when using the the transactivator tTA, in the absence of Tet or an analogue thereof, expression is turned on, with uniform increased expression of the whole population of cells that harbor the inducible retrovirus, indicating that expression is regulated uniformly within the infected cell population. Further, using the transactivator rtTA, in the presence of Tet or an analogue thereof, expression is turned on.

In this manner the primers create a library of fragments, each containing a different random candidate nucleic acid sequence that may encode a different peptide (or candidate bioactive agent). The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PhiNX-eco and PhiNX-ampho or similar cell lines, which are two cells lines as follows. The cell lines are based on the BING and BOSC23 cell lines described in WO 94/19478, which are based on the 293T cell line (a human embryonic kidney line transformed with adenovirus E1a and carrying a temperature sensitive T antigen co-selected with neomycin). The unique feature of this cell line is that it is highly transfectable with either calcium phosphate mediated transfection or lipid-based transfection protocols—greater than 50% of 293T cells can be transiently transfected with plasmid DNA. Thus, the cell line could be a cellular milieu in which retroviral structural proteins and genomic viral RNA could be brought together rapidly for creation of helper-defective virus. 293T cells were therefore engineered with stably integrated defective constructs capable of producing gag-pol, and envelope protein for either ecotropic or amphotropic viruses. These lines are called BOSC23 and Bing, respectively. The utility of these lines are that one can produce small amounts of recombinant virus transiently for use in small-scale experimentation. The lines offer advantages over previously developed stable expression systems in that virus can be produced in days rather than months.

Although the BING and BOSC23 lines are useful in the present invention, the PhiNX second-generation lines are preferred. These lines are based on 293T cells as well, and contain the following improvements over the first-generation lines. First, the ability to monitor gag-pol production on a cell by cell basis was made by introducing an IRES-CD8 surface marker expression cassette downstream of the reading frame of the gag-pol construct (other surface markers besides CD8 are also useful). IRES (internal ribosome entry site) sequences allow secondary or tertiary protein translation from a single mRNA transcript. Thus, CD8 expression is a direct reflection of intracellular gag-pol and the stability of the producer cell population=s ability to produce gag-pol can be readily monitored by flow cytometry. Second, for both the gag-pol and envelope constructs non-Moloney promoters were used to minimize recombination potential with introduced retroviral constructs, and different promoters for gag-pol and envelope were used to minimize their inter-recombination potential. The promoters used were CMV and RSV. Two cell lines were created, PHEONIX-ECO and PHEONIX-AMPHO. Gag-pol was introduced with hygromycin as the co-selectable marker and the envelope proteins were introduced with diphtheria resistance as the co-selectable marker. Finally, the cells were screened to find a relatively rare cell type that produced gag-pol and env in a uniform distribution, although this is not required. In addition, a line termed PHEONIX-gp has been produced that expresses only gag-pol. This line is available for further pseudotyping of retroviral virions with other envelope proteins such as gibbon ape leukemia virus envelope or Vesicular Stomatitis VSV-G protein, Xenotropic, or retargeting envelopes can also be added.

Both PHEONIX-ECO and PHEONIX-AMPHO were tested for helper virus production and established as being helper-virus free. Both lines can carry episomes for the creation of stable cell lines which can be used to produce retrovirus. Both lines are readily testable by flow cytometry for stability of gag-pol (CD8) and envelope expression; after several months of testing the lines appear stable, and do not demonstrate loss of titre as did the first-generation lines BOSC23 and Bing (partly due to the choice of promoters driving expression of gag-pol and envelope). Both lines can also be used to transiently produce virus in a few days. Thus, these new lines are fully compatible with transient, episomal stable, and library generation for retroviral nucleic acid transfer experiments. Finally, the titres produced by these lines have been tested. Using standard polybrene-enhanced retroviral infection, titres approaching or above $10^7$ per ml were observed for both PHEONIX-eco and PHEONIX-ampho when carrying episomal constructs. When transiently produced virus is made, titres are usually 2 to ⅓ that value.

These lines are helper-virus free, carry episomes for long-term stable production of retrovirus, stably produce gag-pol and env, and do not demonstrate loss of viral titre over time. In addition, PhiNX-eco and PhiNX-ampho are capable of producing titres approaching or above $10^7$ per ml when carrying episomal constructs, which, with concentration of virus, can be enhanced to $10^8$ to $10^9$ per ml.

In a preferred embodiment, the cell lines disclosed above, and the other methods for producing retrovirus, are useful for production of virus by transient transfection. The virus can either be used directly or be used to infect another retroviral producer cell line for "expansion" of the library.

Concentration of virus may be done as follows. Generally, retroviruses are titred by applying retrovirus-containing supernatant onto indicator cells, such as NIH3T3 cells, and then measuring the percentage of cells expressing phenotypic consequences of infection. The concentration of the virus is determined by multiplying the percentage of cells infected by the dilution factor involved, and taking into account the number of target cells available to obtain a relative titre. If the retrovirus contains a reporter gene, such as lacZ, then infection, integration, and expression of the recombinant virus is measured by histological staining for lacZ expression or by flow cytometry (FACS). In general, retroviral titres generated from even the best of the producer cells do not exceed $10^7$ per ml, unless concentration by relatively expensive or exotic apparatus. However, as it has been recently postulated that since a particle as large as a retrovirus will not move very far by brownian motion in liquid, fluid dynamics predicts that much of the virus never comes in contact with the cells to initiate the infection process. However, if cells are grown or placed on a porous filter and retrovirus is allowed to move past cells by gradual gravitometric flow, a high concentration of virus around cells can be effectively maintained at all times. Thus, up to a ten-fold higher infectivity by infecting cells on a porous membrane and allowing retrovirus supernatant to flow past them has been seen. This should allow titres of $10^9$ after concentration.

The candidate nucleic acids, as part of the retroviral construct, are introduced into the cells to screen for bioactive agents capable of altering the phenotype of a cell, as described herein.

In a preferred embodiment, a first plurality of cells is screened using the methods of the present invention. That is, the cells into which the candidate nucleic acids are introduced are screened for an altered phenotype. Thus, in this embodiment, the effect of the bioactive agent is seen in the same cells in which it is made; i.e., an autocrine effect.

In one embodiment, the candidate nucleic acids are introduced into a first plurality of cells, and the effect of the candidate bioactive agents is screened in a second or third plurality of cells, different from the first plurality of cells, i.e., generally a different cell type. That is, the effect of the bioactive agents is due to an extracellular effect on a second cell; i.e., an endocrine or paracrine effect. Using standard techniques, for example, the first plurality of cells may be grown in or on one media, and the media allowed to touch a second plurality of cells, and the effect measured. Alternatively, there may be direct contact between the cells. Thus, "contacting" as used herein includes both direct and indirect contact and, thus, may be a functional contact. In this embodiment, the first plurality of cells may or may not be screened using the methods of the present invention.

In the methods of the present invention, the cells are treated to conditions suitable for inducing or repressing the expression of the candidate nucleic acids. The expression products of the candidate nucleic acids may be translation or transcription products.

Thus, the methods of the present invention comprise introducing a molecular library of randomized candidate nucleic acids into a plurality of cells, a cellular library. Each of the nucleic acids comprises a different, generally randomized, candidate nucleic acid sequence. The plurality of cells is then screened, as is more fully outlined below, for a cell exhibiting an altered phenotype. The altered cellular phenotype is due to the presence of a candidate bioactive agent.

By "altered cellular phenotype," "altered phenotype," or "changed physiology" or other grammatical equivalents herein is meant that the phenotype of the cell is altered in a manner that is detectable and/or measurable. In a preferred embodiment, the cellular phenotype is altered due to the presence of a candidate bioactive agent or corresponds to the the expression of a nucleic acid sequence encoding a candidate bioactive agent. As will be appreciated in the art, a strength of the present invention is the wide variety of cell types and potential phenotypic changes which may be detected using the present methods of screening.

Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e., half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens. By "capable of altering the phenotype" herein is meant that the bioactive agent can change the phenotype of the cell in a detectable and/or measurable way.

The altered phenotype may be detected and selected or sorted or collected from a parent phenotype, in a wide variety of ways, as is described more fully below, and will generally depend and correspond to the phenotype that is being changed. Generally, the altered phenotype is detected using, for example: microscopic analysis of cell morphology; standard cell viability assays, including both increased cell death and increased cell viability, e.g., cells that are now resistant to cell death via virus, bacteria, or bacterial or synthetic toxins; standard labeling assays such as fluorometric indicator assays for the presence or level of a particular cell or molecule, including FACS or other dye staining techniques; and other methods of biochemical known in the art for detection of the expression of the candidate nucleic acid sequence.

In a preferred embodiment, the candidate nucleic acid sequence is operably linked to a sequence encoding a reporter protein that is an autofluorescent protein, and the cells having an altered phenotype are sorted or detected or collected by FACs.

In preferred embodiments, the altered phenotype is detected in the cell in which the candidate nucleic acid is introduced. In other embodiments, the altered phenotype is detected in a second cell which is responding to a molecular signal from a first cell.

Exemplary assays are described in PCT US97/01019; WO 99/58663; WO 00/26241; WO 99/54494; WO 00/72088; and PCT US01/10906, all of which are expressly incorporated by reference.

In a preferred embodiment, once a cell with an altered phenotype is detected using the methods of the invention, the cell can be isolated. This may be performed in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes.

In a preferred embodiment, the candidate nucleic acid and/or the bioactive agent is isolated from the positive cell. This may be performed in a number of ways. In a preferred embodiment, primers complementary to DNA regions common to the retroviral constructs, or to specific components of the library such as a rescue sequence, defined above, are used to "rescue" the unique random sequence. Alternatively, the bioactive agent is isolated using a rescue sequence. Thus, for example, rescue sequences comprising epitope tags or purification sequences may be used to pull out the bioactive agent, using immunoprecipitation or affinity columns. In some instances, as is outlined below, this may also pull out the primary target molecule, if there is a sufficiently strong binding interaction between the bioactive agent and the target molecule. Alternatively, the peptide may be detected using mass spectroscopy.

Once rescued, the sequence of the bioactive agent and/or bioactive nucleic acid is determined. This information can then be used in a number of ways.

In a preferred embodiment, the bioactive agent is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive agent is used to generate more candidate bioactive agents. For example, the sequence of the bioactive agent may be the basis of a second round of (biased) randomization, to develop bioactive agents with increased or altered activities. Alternatively, the second round of randomization may change the affinity of the bioactive agent. Furthermore, it may be desirable to put the identified random region of the bioactive agent into other presentation structures, or to alter the sequence of the constant region of the presentation structure, to alter the conformation/shape of the bioactive agent. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive agent or the bioactive nucleic acid encoding it is used to identify target molecules, i.e., the molecules with which the bioactive agent interacts. As will be appreciated by those in the art, there may be primary target molecules, to which the bioactive agent binds or acts upon directly, and there may be secondary target molecules, which are part of the signalling pathway affected by the bioactive agent; these might be termed "validated targets".

In a preferred embodiment, the bioactive agent is used to pull out target molecules. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide bioactive agent and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signaling pathways may be elucidated. Similarly, bioactive agents specific for secondary target molecules may also be discovered, to allow a number of bioactive agents to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive agent is found, the undesirable effect may be reduced or eliminated and therefore the cells have an altered phenotype. Alternatively, with an eye towards elucidating the cellular mechanisms associated with the disease state or signaling pathway, normally desirable consequences may be reduced or eliminated and therefore the cells have an altered phenotype.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micrometastases. Thus, in a preferred embodiment, non-transformed cells can be transfected with these oncogenes, and then random libraries introduced into these cells, to select for bioactive agents which reverse or correct the transformed state. One of the signal features of onconucleic acid transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive agent will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive agents capable of blocking the ability of the growth factor or cytokine to stimulate the tumor cell. The introduction of random libraries into specific tumor cells with the addition of the growth factor or cytokine, followed by selection of bioactive agents which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have random libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the random libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of bioactive agents which restore the constitutive function of the brca-1 or brca-2 genes, and other tumor suppressor genes important in breast cancer such as the adenomatous polyposis coli nucleic acid (APC) and the *Drosophila* discs-large nucleic acid (Dlg), which are components of cell-cell junctions. Mutations of brca-1 are important in hereditary ovarian and breast cancers, and constitute an additional application of the present invention.

In a preferred embodiment, the methods of the present invention are used to create novel cell lines from cancers from patients. A retrovirally delivered short peptide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Epstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native conFiguration of the signaling pathways in these cells. By introducing nucleic acids encoding peptides which inhibit apoptosis, increased cell survival in vitro, and hence the opportunity to study signaling transduction pathways in primary human tumor cells, is accomplished. In addition, these methods may be used for culturing primary cells, i.e., non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive agents are inserted into cardiomyocytes, the cells are subjected to the insult, and bioactive agents are selected that prevent any or all of: apoptosis; membrane depolarization (i.e., decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive agents, followed by the application of arrythmogenic insults, with screening for bioactive agents that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive agents which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive agents are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive agents which will diminish the adhesion of platelets and leukocytes, and thus diminish the occlusion events. Adhesion in this setting can be inhibited by the libraries of the invention being inserted into endothelial cells (quiescent cells, or activated by cytokines, i.e., IL-1, and growth factors, i.e., PDGF/EGF) and then screening for peptides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive agents can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive agent libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive agent libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive agents can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive agents that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive agents that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive agents isolated which decrease the rate of growth of these cells.

In a preferred embodiment, the present methods are useful in the regulation or inhibition of keloid formation (i.e., excessive scarring). Candidate libraries inserted into skin connective tissue cells isolated from individuals with this condition, and bioactive agents isolated that decrease proliferation, collagen formation, or proline incorporation. Results from this work can be extended to treat the excessive scarring that also occurs in burn patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate libraries can be inserted into skin connective tissue cells, and bioactive agents isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive agents can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive agents isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a random, cyclized peptide library of the general sequence CNNNNNNNNNNC or C—(X)$_n$—C. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry. Viruses are known to enter cells using specific receptors to bind to cells (for example, HIV uses CD4, coronavirus uses CD13, murine leukemia virus uses transport protein, and measles virus uses CD44) and to fuse with cells (HIV uses chemokine receptor). Candidate libraries can be inserted into target cells known to be permissive to these viruses, and bioactive agents isolated which block the ability of these viruses to bind and fuse with specific target cells.

In a preferred embodiment, the present invention finds use with infectious organisms. Intracellular organisms such as *mycobacteria, listeria, salmonella, pneumocystis, yersinia, leishmania, T. cruzi,* can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive agents selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive agents can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive agents can be isolated that confer protection, when these cells are treated with these specific antibiotics.

Furthermore, the present invention finds use in screening for bioactive agents that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactive agents can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug=s effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive agents can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate libraries can be introduced into tumor cell lines (primary and cultured) that have demonstrated specific or multiple drug resistance. Bioactive agents can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactive agents selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1–17, may be selected, or agents that bind cytokines such as TNF-", before they bind their receptor.

Antigen processing by mononuclear leukocytes (ML) is an important early step in the immune system=s ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive agents selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive agents which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive agent sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e., within a signaling pathway, to localize the effects to a functional area of interest.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Construction of BH-1-4 and BH2-A5 cell lines for use in methods for screening for an altered cellular phenotype.

Cell line BH-1-4 The novel cell line, BH-1-4 was constructed by engineering the B cell line BJAB to contain the cDNA encoding the reporter protein heparin-binding epidermal-growth-factor-like growth factor (HBEGF) operably linked to an interleukin 4 (IL4) inducible germline promoter, the epsilon promoter (Pϵ) (see FIG. 1). The epsilon promoter was activated by contacting the cells with the stimulator IL4. In this cell line, IL4 binds to IL4 receptors (IL4R) expressed on the cell surface and the IL4R mediates transduction and activation of the epsilon promoter by IL4.

HBEGF functions as the receptor for diphtheria toxin ("dip" or "dt"). Diphtheria toxin is a 535 amino acid protein consisting of three domains. The receptor binding domain (residues 387–535) binds to BEGF. The transmembrane domain, T, comprising residues 200–378, is responsible for creating a channel in the cell membrane. The catalytic domain, comprising residues 1–188, is responsible for stopping potein production in the cell nd thereby causing cell death. Thus, in the novel BH-1-4 cell line, HBEGF confers high sensitivity to the killing of cells by diphtheria toxin following the induction of the expression of HBEGF by the addition of the stimulator IL4. Thus, in this example cell death is a marker for the expression of the reporter HBEGF in the presence of diphtheria toxin.

Cell line BH2-A5

Figure 2:
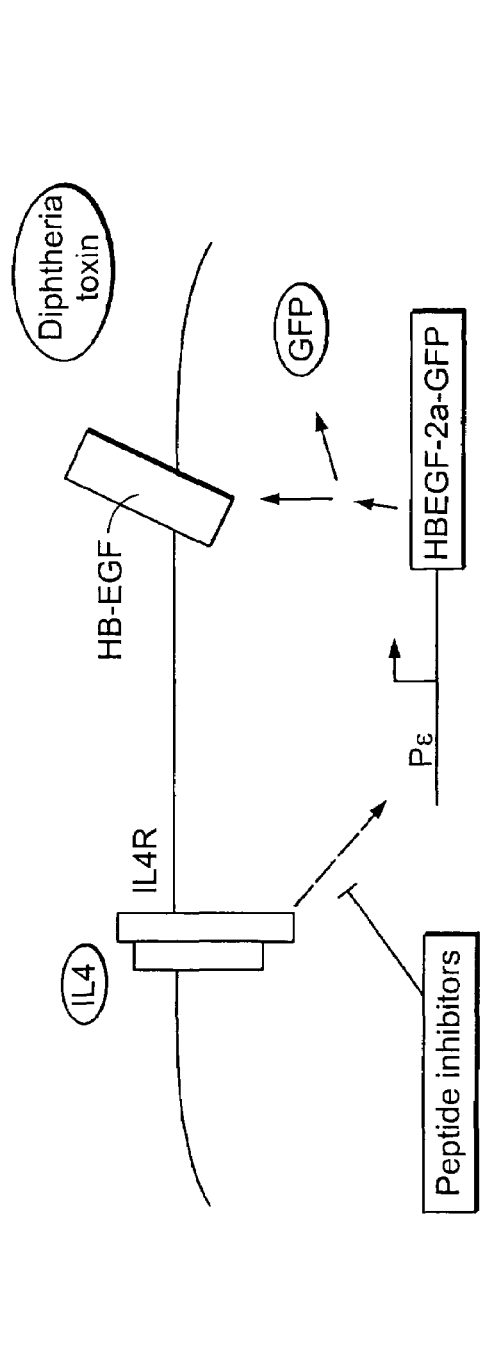
FIG. 2 schematically depicts the cell line BH2-A5 and HBEGF Diphtheria toxin selection in the cell line. The new cell line generated has a dual-function reporter driven by the germline ε promoter:
 1. HB-EGF functions as the receptor for diphtheria toxin and confers high sensitivity to diphtheria toxin killing following IL4 induction (for use in survival screening strategies)
 2. GFP to monitor IL4 induction of the Pε by fluorescence (FACS)

The novel cell line, BH2-A5 was constructed in the same manner as described above for the BH1-4 cell line, except that the DNA encodes the reporter protein Green Fluorescent Protein (GFP) operably linked to HBEGF via a cleavable peptide linker (2*a*) (see FIG. 2). Basically, the BH2-A5 cell line was constructed by engineering the B cell line BJAB to contain the DNA encoding the reporter (HBEGF) operably linked to an interleukin 4 (IL4) inducible germline promoter, the epsilon promoter (Pe), and the GFP reporter, where the HBEGF and GFP are linked by the cleavable peptide linker 2*a*. Similar to the BH1-4 cell line, the epsilon promoter was activated by contacting the cells with the stimulator IL4; IL4 binds to IL4 receptors (IL4R) expressed on the cell surface; and the IL4R mediates transduction and activation of the epsilon promoter by IL4. Also, in this cell line, HBEGF functions as the receptor for diphtheria . Thus, in the novel BH2-A5 cell line, HBEGF confers high sensitivity to the killing of cells by diphtheria toxin following the induction of the expression of HBEGF by the addition of the stimulator IL4. In addition, the concomitant expression of GFP was used to monitor IL4 induction of the epsilon promoter by fluorescence using FACS. Thus, the BH2-A5 cell line was engineered to contain the HBEGF and GFP dual-function reporter. In this example cell death is a marker for the expression of the reporter HBEGF in the presence of diphtheria toxin, whereas GFP is a marker for IL4 induced expression.

Thus, the BH1-4 and BH2-A5 were used to screen for an altered cellular phenotype due to the presence of a candidate bioactive agent. In this example, the candidate bioactive agent is a member of a peptide library (with a complexity of 1×10e9), where the peptide is operably linked to a GFP reporter; the parent phenotype is the result of contacting the cells with the stimulator IL4 and induction of expression of HBEGF; and the altered cellular phenotype is cell survival in the presence of diphtheria toxin in cells expressing HBEGF, where the altered cellular phenotype is due to the presence of a bioactive agent that inhibits the IL4-induced expression of HBEGF and thereby results in the survival of the cells in the presence of diphtheria toxin.

FIG. 3 depicts the conventional screening method which involved first infecting the cell lines with retroviral vectors encoding a candidate peptide operably linked to a GFP reporter and thereby expressing the peptide in the cells; culturing the infected cells in the presence of the stimulator IL4 to induce expression of HBEGF; contacting the cells with diphtheria toxin to kill cells expressing HBEGF (i.e., selecting the cells in the presence of diphtheria toxin); removing the IL4 and diphtheria toxin by washing the cells, concentrating them, and removing the dead cells ("debris"); from the surviving (selected) cells, rescue the retroviral population and infect naïve cells for a new fresh round of selection and perform clonal selection and analysis of the cloned retroviral population. However, this step requires that the complexity and representation of the population should be maintained as they are infected into naïve cells; and, further, this step is technically challenging. Thus, the present invention provides a novel approach that obviates these problems. The following examples further illustrate this novel approach for screening for altered cellular phenotypes.

Example 2

Screening for an altered cellular phenotype using known bioactive agents, SOCS1 and STAT6Δ (a C-terminal truncated version of STAT6), as positive controls for the method of screening.

STAT6 (signal transducer and activator of transcription 6) mediates the response of cytokines like IL4 and SOCS1 (suppressor of cytokine signaling) and STAT6? Are known inhibitors of IL4 signal transduction. In the BH1-4 or BH2-A5 cells lines of the present invention, SOCS1 and STAT6Δ each inhibit the IL4 inducible expression of HBEGF (and SOCS1 is a stronger inhibitor than STAT6Δ).

As depicted in FIG. 4, the following five different retroviral vectors were constructed as positive controls for the screening assay, and are the encoded GFP, SOCS1, STAT6Δ, and/or ires are operably linked to a promoter in the retroviral vector: the retroviral vector cGFP contains the GFP; the retroviral vector SOCS1-ires-GFP contains, from 5' to 3' (and operably linked), SOCS1, internal ribosomal entry site (IRES), and GFP; the retroviral vector GFP-SOCS1 contains, from 5' to 3' (and operably linked), GFP-SOCS1 fusion; the retroviral vector STAT6Δ-ires-GFP contains, from 5' to 3' (and operably linked), STAT6Δ, ires, and GFP; and the retroviral vector GFP-STAT6Δ contains, from 5' to 3' (and operably linked), GFP-STAT6Δ fusion.

As depicted in FIG. 5 the five retroviral vectors described above were assayed in BH1-4 cells using the following protocol: BH1-4 cells were infected with the retroviral constructs and cultured for 3 days in medium containing IL4 and diphtheria toxin; or alternatively, the infected cells were cultured in IL4 for 2 days followed by the addition of diphtheria toxin and culturing in the presence of IL4 and diphtheria. Three days after infections, a 1:10 dilution of the cell cultures was made with fresh medium (without IL4 and diphtheria toxin). On the day of infection, day 3, day 6 and day 7 GFP fluorescence of the cells was measured using FACS.

FIG. 6 depicts the effects of SOCS1 and STAT6 on IL4/diphtheria (IL4/dip) induced death of BH1-4 cells 6 days post infection for each of the five retroviral vectors, where the histogram panels under the column entitled "unstimulated" refers to a control assay where the cells were not stimulated/cultured with IL4; the column entitled "IL4" refers to a control assay where the cells were stimulated with IL4 but diphtheria toxin was not added to the medium; the column entitled "IL4/dip" refers to the assay where the cells were cultured in both IL4 and dip together for 3 days; and the column entitled "IL4 then dip" refers to the assay where the cells were cultured in IL4 for 2 days followed by the addition of diphtheria toxin. The histogram in each panel summarizes the FACS measurements for each assay. The histograms in the panels for the control assays entitled "unstimulated," "IL4," and "Dip" depict the fluorescent scattering pattern indicative of live or surviving cells, whereas the histograms in the panels for the assays entitled "IL4/dip" and "IL4 then dip" for retroviral vectors cGFP, STAT6-IRES-GFP, and GFP-STAT6 depict a the fluorescent scattering pattern indicative of dead or killed cells. In contrast, the histograms in the panels for the same assays, i.e., "IL4/dip" and "IL4 then dip," for retroviral vectors SOCS1-IRES-GFP and GFP-SOCS1 depict a fluorescent scattering pattern indicative of live cells. FIG. 7 depicts the same results except that the vertical axis indicates the number of cells, and the horizontal axis indicates the amount of GFP fluorescence.

These results indicate that the expression of SOCS1-ires-GFP and GFP-SOCS1 retroviral constructs inhibit IL4 signaling/induced expression of HBEGF. Further, the results indicate that the GFP report protein is an effective marker for monitoring SOCS1 expression in the screening assays of the present invention. Finally, these results indicate that the expression of GFP-STAT6Δ only partially inhibits IL4 signaling/induced expression of HBEGF.

Example 3

Enrichment of inhibitors of IL4 signaling in BH1-4 or BH2-A5 cell lines using SOCS1.

To examine the degree of enrichment that could be achieved by the above-described IL4-diphtheria selection assay, BH1-4 and BH2-A5 cell populations were "spiked" with BH1-4 and BH2-A5 cells that had been infected with the retroviral construct SOCS1-ires-GFP, and the following dilutions of the SOCS-infected cells with uninfected cells (i.e., BH2-A5 and BH1-4 cells not infected with a SOCS1 retroviral construct) were made:
1:10
1:100
1:1000
1:10,000.

As depicted in FIG. 8, the diluted spiked cell populations were then subjected to the following procedure: On the day of infection, 12×10e6 cells at 200 k/ml were stimulated with IL4 (at 30 units/ml) in a T175 flask; On day 1 post infection, diphtheria toxin (dip toxin) at 20 ng/ml was added to the cell culture (but prior to the addition of dip toxin, an aliquot of cells was taken as a "no dip control"); On day 3 post infection, the cell culture was washed ("washout") from IL4 and diphtheria toxin and the cells were grown in regular media; On days 4, 6, and 8 post infection, the GFP fluorescence of the cells were measured using FACS; On day 9 post infection, the "washout" dying cells were subjected to ficoll treatment to recover lice cells from dead cells; and On days 15 and 18 post infection, the GFP fluorescence of the cells were measured using FACS.

The results of this experiment indicate that the screening assay using L4-dip selection is validated. In particular, the "washout" treated cells ere enriched for the cells having the SOCS1 phenotype by approximately 1000 fold at the 1:10,000 seeding, from 0.01% to 10%. FIG. 9 schematically depicts the IL4-dip selection assay using BH1-4 cells and depicts the results of the assay starting with a 1:10 dilution of the SOCS1-infected cells. The results are depicted in histograms where the vertical axis indicates the number of cells and the horizontal axis indicates the amount of GFP fluorescence measured using FACS, the day of infection (day 1) and on days 4, 6, and 8 post-infection. GFP fluorescence was used to monitor SOCS1 expression. SOCS1 inhibits IL4-induced HBEGF expression making the cells expressing it resistant to cell death by IL4-dip treatment. The results indicate that by day 8 the majority of the surviving cells are SOCS1-ires-GFP expressing cells. FIG. 10 depicts the results for the assays using BH1-4 cells starting with the 1:10, 1:100, 1:1,000, and 1:10,000 dilution of the SOCS1-infected cells. The results are depicted in histograms where the vertical axis indicates the number of cells and the horizontal axis indicates the amount of GFP fluorescence measured using FACS, the day of infection (day 1) and on days 4, 6, and 8 post-infection. FIG. 11 depicts the results for both BH1-4 and BH2-A5 cells starting with the 1:10, 1:100, 1:1,000, and 1:10,000 dilution of the spiked cells. The results are depicted in histograms where the vertical axis indicates the number of cells and the horizontal axis indicates the amount of GFP fluorescence measured using FACS on day 15 post-infection.

FIG. 12 depicts the results of selection beginning with naïve cells in a first round of selection with IL4-Dip and then subjecting the surviving cells from the first round of selection to a second round of selection with IL4-Dip. The naïve cells are the spiked cells diluted 1:10 and 1:10,000 with unspiked cells. The first round of selection was performed as described above and the amount of fluorescence was measured using FACS on days 1, 4, and 18 post infection. For the 1:10,000 seeding, the surviving cells selected from the first round were subjected to a second round of selection performed in the same manner as the first round, and the amount for fluorescence was measured using FACS on the day IL4 was added to the medium to stimulate IL4 induced expression of HBEGF; and on days 4 and 8 thereafter.

The results of these SOCS1-infected cells spiking experiments demonstrate that the IL4-Dip selection in the BH1-4 and BH2-A5 cell lines result in enrichment of inhibitors of IL4 signaling/induced expression of HBEGF. At a 1:10,000 dilution of the spiked cells, the enrichment by the IL4-Dip selection is approximately 1000 fold (i.e., from 0.01% to 10%). However, in these experiments, the results indicate that most survivors of the first selection did not respond to a second round of IL4 stimulation. Thus, in this case a second round of selection lead to very little enrichment for the peptide inhibitors. The conventional or usual solution following selection is to rescue the retroviral population and infect naïve cells for a new and fresh round of selection. However, this step requires that the complexity and representation of the population should be maintained as they are infected into naïve cells; this requirement makes this step technically challenging. Thus, the present invention provides a novel approach that obviates these problems, as described in the following examples.

Example 4

Screening for an altered cellular phenotype using a Tet-regulatable expression system.

This example demonstrates a method of screening for an altered cellular phenotype where cells responsive to stimulation by IL4 ("IL4 responders") are separated from the population of cells that have undergone the first selection. These IL4 responders can then undergo an additional round of highly efficient selection by repressing (or "turning down") the expression of the peptide inhibitors of IL4 signaling using a Tet-regulatable (or "Tet inducible") expression system; and then sorting for the IL4 responders using a reporter protein, e.g., Green Fluorescent Protein ("GFP").

As depicted in FIG. 13, the screening assay in this example involves infecting. A novel cell line BH2-A5T (described below) with the peptide library BFP-C20 encoded by retroviral vectors (described below). Thereafter, the cells are stimulated with IL4, selected on IL4-dip, and then the cells are washed and the surviving cells recovered. The peptide encoded by the retroviral construct is expressed in the absence of Dox (a Tet analogue) and repressed in the presence of Dox. After the first round of IL4-dip selection, Dox is added to the cell culture medium containing the surviving cells and expression of the peptide is turned off. The cells are then stimulated with IL4 to induce expression of HBEGF-2a-GFP and thereafter sorted for GFP fluorescence (indicative of IL4 induced expression) using FACS. Thereafter, expression of the peptide is turned on by removing the Dox. The cells are then selected on IL4-Dip, washed, aliquoted into microtiter plates, sorted by FACS for single cell clones, replica plated in duplicate microtiter plates and cultured in the presence or absence of Dox, and the single clones are selected on the basis that the IL-4 induced GFP is inhibited by the presence of a BFP-peptide as measured by the BFP and GFP fluorescence using FACS.

As depicted in FIG. 14, the BH2-A5 cell line was further engineered to construct the cell line BH2A-5T (or "A5T" or "A5T-4") which expresses a Tet regulated transactivator (tTA or Tet transactivator) and allows for the Tet regulated expression of candidate bioactive agents introduced into the cells. As in the BH2-A5 cells, the BH2-A5T cells contain the HBEGF-2a-GFP construct that is driven by the epsilon promoter and is expression of HBEGF-2a-GFP is inducible by stimulation with IL4. In this example, the candidate bioactive agents are from a library of random sequence peptides, 20 amino acids in length, which are members of the BFP-C20 mer peptide library. The 20 mer peptides are expressed as carboxy-terminal peptides fused to the reporter protein, Blue Fluorescent Protein (BFP). These fusion peptides (BFP-C20mer library member) are operably linked to an oligomer of a Tet operator sequence (TRA or TetO sequence) and promoter as depicted in FIG. 14. In the absence of Tet or analogue thereof (e.g., Dox) the peptide is expressed in the BH2-A5T cells, whereas in the presence of Tet or analogue thereof, the expression of the peptide is repressed (or turned off).

FIG. 15 depicts histograms indicating the amount of GFP fluorescence, in an experiment where IL4responders were selected in the presence and absence of Dox in BH2-A5T cells spiked with cells infected with the retroviral construct TRA-SOCS1-ires-GFP. This construct contains the SOCS1-ires-GFP as described above and in addition is operably linked to a TRA and thus is regulatable by the tTA. In this experiment, the spiked cells were selected for over 7 days on IL4 and DIP, and 1) in the absence of Dox ("IL4/dip selection"); and 2) in the presence of Dox ("IL4/dip selections+Dox"). After selection, the cells were cultured in the absence of Dox to allow for the SOCS1-ires-GFP expression.

In summary, the BH2-A5T cell line (expressing tTA) was generated and quality controlled for Dox responsiveness, infectability, responsiveness to IL4 stimulation/induction of expression, and IL4/Dip induced cell death. These experiments established the fidelity of Dox regulation (turning peptide expression on and off) and kinetics. The results demonstrate that peptide expression levels can be 10–17 fold higher using a TRA containing vector in comparison to the LTR vectors described above. Further, results from the IL4/Dip selection in the presence or absence of Dox demonstrate the correlation of enrichment and SOCS1 expression, i.e., enrichment was regulated by the presence or absence of Dox.

Example 5

Screening for cells having an altered cellular phenotype by multiple rounds of sorting of cells responsive to IL4 induced expression of HBEGF-2a-GFP using an expression system regulatable by Dox, as depicted in FIG. 13 and further described above in Example 4.

As described above in Example 3, FIG. 12 depicts the results of a first round and second round of selection for cells responsive to IL4 induced expression, showing that most cells surviving selection fail to respond to IL4 due to the presence of false positives (i.e., stochastic or hereditary nonresponders). The following experiments illustrate by example how the methods of the present invention solve these problems by the round to round enrichment for cells expressing the peptide inhibitor using a combination of 1) induction and repression of the expression of the putative peptide inhibitor (or other candidate bioactive agent) via Dox with 2) selections for inhibition or activation of the parental phenotype.

FIG. 16 depicts the round to round enrichment for cells expressing the known inhibitor SOCS1 by induction and repression of TRA-SOCS1-ires-GFP expression in BH2-A5T-4 cells using dox and sorting of the altered and parental cellular phenotype. In this system, the expression of TRA-SOCS1-ires-GFP is turned off in the presence of Dox; and SOCS1-ires-GFP is expressed in the absence of Dox. In these experiments, BH2-A5T4 cells are infected with the retroviral construct TRA-SOCS1-ires-GFP (as described above); and the infected cells are then diluted at 1:10,000 and 1:100,000 with uninfected naive cells. In the first round of selection (Round 1) the cells are selected on IL4-Dip for the altered phenotype (as described above); the cells are then contacted with Dox to repress (or turn off) expression of TRA-SOCS1-ires-GFP and the cells are stimulated with IL4 and sorted for the parental phenotype using GFP fluorescence which is indicative of IL4 induced expression of HBEGF-2a-GFP. Thereafter, the cells responsive to IL4 induced expression are collected and cultured in medium without Dox in order to induce (or turn on) the expression of SOCS1-ires-GFP. The cells expressing TRA-SOCS1-ires-GFP are then subjected to a second round of selection for the altered phenotype on IL4-Dip achieving further efficient enrichment of SOCS1-expressing cells. FIGS. 17 and 18 show the results of these experiments.

FIG. 17 depicts histograms indicating the amount of GFP fluorescence indicative of TRA-SOCS1-ires-GFP expression in cells after the first round of selection. The column entitled "no selection" is a control where IL4 and Dip were not added to the cells; the column entitled "post selection" is a control where the cells were selected on IL4-Dip but were not cultured in the presence of Dox; The results of the first round selection are shown for both the selection starting with a 1:10,000 dilution of the spiked cells ("TRA-SOCS1-ires-GFP 1/10K") and 1:100,000 dilution of the spiked cells ("TRA-SOCS1-ires-GFP 1/100K"). For the selection starting with a 1:10,000 dilution of the spiked cells ("TRA-SOCS1-ires-GFP 1/10K"), the first round of selection resulted in about 1000-fold enrichment (from ~0.01% to ~9.4%) of cells expressing TRA-SOCS1-ires-GFP. For the selection starting with a 1:100,000 dilution of the spiked cells ("TRA-SOCS1-ires-GFP 1/100K"), the first round of selection did not result in a statistically measurable enrichment of cells expressing TRA-SOCS1-ires-GFP.

FIG. 18 depicts histograms showing the "Sort for IL4 responders" step in FIG. 16. The columns entitled "no selection" and "post selection" are the same as those in FIG. 17; the column "post selection+dox" depicts the turning off the expression of TRA-SOCS1-ires-GFP by contacting the cells with Dox for over 7 days in the cells that had been selected on IL4-Dip; the column "post selection +dox+IL4" shows the GFP profile of "post selection+dox" cells after being contacted with IL4 and Dox for 3 days. Since the SOCS1-ires-GFP expression is repressed by Dox, the GFP expression in this column is indicative of the IL4-induction of HBEGF-2a-GFP (which is the parental phenotype); thus 23% to 24% of the cells expressing GFP are IL4 responders. From these cell populations, the 10% highest expressing GFP cells (labeled Right (R) gate) and the next 10% (labeled Left (L) gate) were collected as depicted in FIG. 18 for subsequent steps shown in FIGS. 19 and 20.

FIG. 19 depicts histograms showing the "Turn inhibitor expression back on" step in FIG. 16. The columns entitled "no selection" and "post selection" are the same as those in FIG. 17 and 18; the panels "sorted-left gate" and "sorted-right gate" show histograms of the sorted populations from FIG. 18 after they have been cultured over 5 days in the absence of Dox (referred to as de-doxing). In this case, the GFP expression is indicative of the cells expressing TRA-SOCS1.-ires-GFP. As depicted in FIG. 19, there is a small enrichment of the cells expressing TRA-SOCS1-ires-GFP resulting from the sorting of the Left Gate and Right Gate subpopulation of cells cultured in the absence of Dox. FIG. 19 depicts for the 1:10,000 dilution of cells, an 8% enrichment resulting from the first round of selection, a 16% enrichment from Left Gate cells and 18% enrichment from Right Gate cells resulting from the sorting of the cells cultured in the absence of Dox; and for the 1:100,000 dilution of cells, an 0.6% enrichment resulting from the first round of selection, a 0.9% enrichment from Left Gate cells and 1.0% enrichment from Right Gate cells resulting from the sorting of the cells cultured in the absence of Dox. For the next step, these cell populations are subjected to a second round of IL4/dip selection as summarized in FIG. 20.

FIG. 20 depicts for the 1:10,000 dilution of cells, an 6.1% enrichment resulting from the first round of selection; for the second round of IL4/dip selection, a 88% enrichment from the de-doxed Left Gate cells and a 97% enrichment from de-doxed Right Gate cells from FIG. 19; and for the 1:100,000 dilution of cells, an 0.3% enrichment resulting from the first round of selection; for the second round of IL4/dip selection, a 26% enrichment from the de-doxed Left Gate cells and 47% enrichment from de-doxed Right Gate cells resulting from the sorting of the cells cultured in the absence of Dox (FIG. 19).

A summary of the screening assay in this example is schematically depicted in FIG. 20 where in the first round of selection the cells are selected on IL-4-Dip; and then the surviving cells are cultured in the presence of dox and sorted for responsiveness to IL4 induced expression of HBEGF-GFP (i.e., sorted for "IL4 responders"). From the population of IL4 responders, a Left Gate and Right Gate subpopulation of cells is collected and cultured in the absence of dox (or "dedoxing"). In the absence of dox, the expression of TRA-SOCS1-ires-GFP is turned back on and subjected to a second round of IL4-Dip selection as described above.

The results of these experiments demonstrate that cells harboring a petide causing an altered phenotype can be highly enriched and selected for by the methods of the present invention. Specifically, the round to round induction and repression of expression using Dox resulted in the enrichment and selection of cells responsive to IL4 induced expression having an altered cellular phenotype due to the presence of TRA-SOCS1-ires-GFP. Further, in screening experiments, the putative peptide inhibitor is operably linked to BFP, thus avoiding any potential conflicts between the sorting for GFP fluorescence indicative of P$\epsilon$-HBEGF-2a-GFP expression and sorting for BFP fluorescence indicative of the expression of the putative peptide inhibitor (or candidate bioactive agent).

Example 6

Methods for screening for an altered cellular phenotype using a Tet-regulatable expression system and a screening cell line, e.g., BH2-A5T.

FIG. 21 schematically depicts an example of a timeline (in days) for a screening assay of the present invention, where the assay involves a first round of selection and sorting; a second round of selection and sorting; and thereafter single cell clones are grown. The single cell clones are then subjected to selection and FACS assays, the nucleic acid encoding the bioactive agent (e.g., a peptide inhibitor of IL4 signaling/induced expression) is then rescued and the phenotype is reconfirmed, e.g., by infecting naïve cells with the rescued nucleic acid and selection.

FIG. 22 schematically depicts an example of a timeline (in days) for a screening assay of the present invention (and as described for FIG. 21), where the complexity of the library of candidate bioactive agents (e.g., a peptide library), and the fold enrichment for the altered cellular phenotype, are indicated. Further, FIG. 22 schematically depicts the histogram profile of GFP fluorescence of false positives due to hereditable background or stochastic non-hereditable background; as compared to the histogram profile of GFP fluorescence of cells cultured in the presence (+Tet) or absence (−Tet) of Tet, after a first round of selection.

FIG. 23 schematically depicts an example of a timeline (in days) for a screening assay of the present invention (and as described for FIG. 21), where the complexity of the library of candidate bioactive agents (e.g., a peptide library), and the fold enrichment for the altered cellular phenotype, are indicated. Further, after a second of selection, cells are single cell cloned, aliquoted into microtiter plates, replica plated in duplicate microtiter plates and cultured in the presence or absence of Dox, and the single clones are contacted with IL4 for three days and their GFP fluorescence measured by FACS. FIG. 23 schematically depicts the histogram profile of GFP fluorescence of false positive clones due to hereditable background or stochastic non-heritable background; as compared to the histogram profile of GFP fluorescence of cell clones harboring a peptide inhibitor cultured in the presence of Tet (+Tet) or absence of Tet (−Tet) (see panel of schematically depicted histograms). FIG. 23 depicts an example of a clone where in the presence of Tet the expression of the peptide inhibitor is turned off and thus the GFP reporter is expressed; and in the absence of Tet the peptide is expressed and thus the GFP reporter is inhibited in cells having an altered phenotype. Thus, this example demonstrates a powerful approach to identifying and eliminating (or disregarding) background cell clones (e.g., false positives) by selecting only those clones responsive to IL4 stimulation (i.e., IL4 induced expression) that is regulated by Tet.

FIG. 24 depicts the histogram profile of GFP fluorescence of clones from a functional screen representing a BFP-peptide inhibitor clone, CR2 (left panel); a hereditable background clone (middle panel), and stochastic background clone (right panel), where the histograms from the clones cultured in the presence of Dox (+Dox) and the absence of Dox (−Dox) are overlayed. In the presence of Dox the expression of the BFP-peptide is turned off; and in the absence of Dox the BFP-peptide is expressed.

FIG. 25 depicts the summary of the results from the peptide screening in BH2-A5T-4cells. In this screen, the total number of cells targeted with the retroviral vector peptide library was $1.25 \times 10^{10}$. From the total cells targeted, the total number of cells infected with a retroviral member of the library was $2.4 \times 10^9$. From the total cells infected, the total number of cells sorted/cloned was 24,960. From the total number of cells sorted/cloned, the total number of regulatable clones, was 1,525. FIG. 25 further depicts a protocol for characterizing the identified regulatable clones by rescuing the retroviral construct encoding the peptide from the clones, cloning and sequencing the nucleic acid encoding the peptide, and testing for the transfer of the altered cellular phenotype (conferred by the presence of the peptide) into naïve cells.

Example 7

Identification and validation of novel signaling molecules specific for T cell activation and effector function by screening for an altered cellular phenotype in activated T cells.

Abstract

T lymphocytes play crucial roles in immune responses, including the direct killing of virus-infected cells by cytotoxic T cells and facilitation of B-cell responses by helper T cells. The activation of T cells is mediated by the T cell receptor (TCR), which in turn activates specific membrane-associated and intracellular proteins. Identifying these signaling proteins downstream of TCR activation is crucial for developing therapeutic agents to inhibit or regulate immune responses in autoimmune diseases and organ transplantation. Using the methods and compositions of the present invention novel signaling molecules specific for T cell activation and effector function were identified and validated. A large library ($5 \times 10^7$) of cDNA clones were introduced into T cells from which an altered cellular phenotype was enriched for and identified. Using the screening methods of the present invention, 2,800 individual clones were obtained based on a reduction in T cell receptor activation-induced CD69 expression, and the causal relationship of cDNA expression and altered phenotype was established. In addition to many known signaling molecules such as LCK, ZAP70, SYK, and PLC(I, molecules previously unknown to this pathway were also discovered using the screening methods of the present invention. When selected for evaluation with primary human T lymphocytes, hits from the screen inhibited anti-CD3 and anti-CD28 stimulated IL-2 production. From these molecules, potential therapeutic targets may be identified that are effective in modulating immune-mediated processes.

Introduction

Activation of specific signaling pathways in lymphocytes determines the quality, magnitude and duration of immune responses. In transplantation, acute and chronic inflammatory diseases, and autoimmunity, it is these pathways that are responsible for the induction, maintenance and exacerbation of disease lymphocyte responses. In all cases, recognition of antigens presented by the Major Histocompatability Complex (MHC) by the T cell receptor (TCR) complex triggers the activation of T lymphocytes. Engagement of the TCR by antigen/MHC results in actin cytoskeleton rearrangement, induction of cyrokine and other gene transcription, and progression into the cell cycle[1,2]. The proximal events of TCR signaling include activation of src family kinases LCK, FYN, phosphorylation of TCR component (. ) and subsequent activation of ZAP70/SYK tyrosine kinases, as well as recruitment of adaptor molecules(CBL-B, LAT, SLP76), which couple to more distal signaling pathways including Ras and PLC($^{3-5}$. New components of the TCR signaling pathway have been discovered and reported, such as the new transmembrane adaptor PAG/CBP[6], albeit with a slower pace. It has become apparent that identifying additional signaling molecules requires novel approaches including functional genomics. Using the methods of the present invention, novel signaling molecules specific for T cell activation and effector function were identified and validated.

In this example, using the methods of the present invention, a novel approach to identifying new targets for immune suppressive drugs is presented. Following T cell activation, expression of numerous cell surface markers such as CD25, CD69, and CD40L are upregulated. CD69 has been shown to be an early activation marker in T, B, and NK cells[7-9]. CD69 is a disulphide-linked dimer. The cell surface marker is not expressed in resting lymphocytes but appears on T, B and NK cells after activation in vitro. The relevance of CD69 as a TCR signaling outcome has been validated using T cells deficient in certain key signaling molecules such as SLP76 and LAT[10,11]. Furthermore, re-introducing SLP76 or LAT into the deficient cells resulted in restoration of CD69 expression. The CD69 upregulation could then be used to monitor TCR signal transduction. The rationale of the functional genomics screen was to identify cell clones whose CD69 upregulation was repressed following introduction of a retroviral cDNA library. The library members conferring such repression would then represent immune modulators that function to block TCR signal transduction.

The use of retrovirus-mediated gene transfer has contributed to the cloning of T cell antigens[12], tumor antigens[3], various receptors[14-24], signaling molecules[25] and transcription factors[26]. In most of the cases, retroviral cDNA libraries were used for expressional cloning. The unique feature of the current study reported here, is the use of retroviruses as pharmaceutical tools for target discovery and validation a long a whole pathway of signal transduction, from ligand-receptor interaction on the plasma membrane, membrane-proximal signaling, actin-cytoskeleton rearrangement to gene transcription in the nucleus. Another feature of our screen was to build-in the functional relevance through partial and full-length cDNAs in the library. Expression of these library inserts was expected to have dominant effects over their endogenous counterparts by being competitive inhibitors of endogenous protein activity, or being constitutively active. Integration of several key technology innovations such as new cell lines, improved retroviral infection efficiency, high level and regulated expression of nucleic acids (e.g., of a nucleic acid library), and high throughput screening tools complemented successful execution of these screens.

Results and Discussion

Experimental design. Several T cell linesj-including Jurkat, HPB-ALL, HSB-2 and PEER were tested for the presence of surface CD3, CD25, CD28, CD40L, CD69, CD95, and CD95L. Those that expressed CD3 were cultured with anti-CD3 or anti-TCR to crosslink the TCR and examined for the upregulation of CD69. A Jurkat T cell line was selected for its ability to upregulate CD69 in response to TCR crosslinking with kinetics mimicking that of primary T lymphocytes (data not shown). The population of Jurkat cells was sorted for low basal and highly inducible CD69 expression following anti-TCR stimulation. Clone 4D9 was selected because CD69 in this clone was uniformly and strongly induced following TCR stimulation in 24 hours (FIG. 26A).

In order to regulate the expression of the retroviral library, the Tet-Off system was used. The cDNA inserts in the retroviral library were cloned in a manner to operably link the inserts to the tetracycline regulatory element (TRE) and the minimal promoter of TK. Transcription of the cDNA inserts was then dependent on the presence of tetracycline-controlled trans-activator (tTA)[27], a fusion of Tet repression protein and the VP16 activation domain, and the absence of tetracycline or its derivatives such as doxycycline (Dox). To shut off the cDNA expression, one can simply add doxycycline in the medium. To obtain a Jurkat clone that stably expresses tTA, a retroviral LTR-driven tTA in conjunction with a TRE-dependent reporter construct was introduced, i.e., TRA-Lyt2. Through sorting of Lyt2 positive cells in the absence of Dox and Lyt2 negative cells in the presence of Dox, coupled with clonal evaluation, we obtained a derivative of Jurkat clone 4D9, called 4D9#32, that showed the best Dox regulation of Lyt2 expression, as seen in FIG. 26B.

Figure 27A:
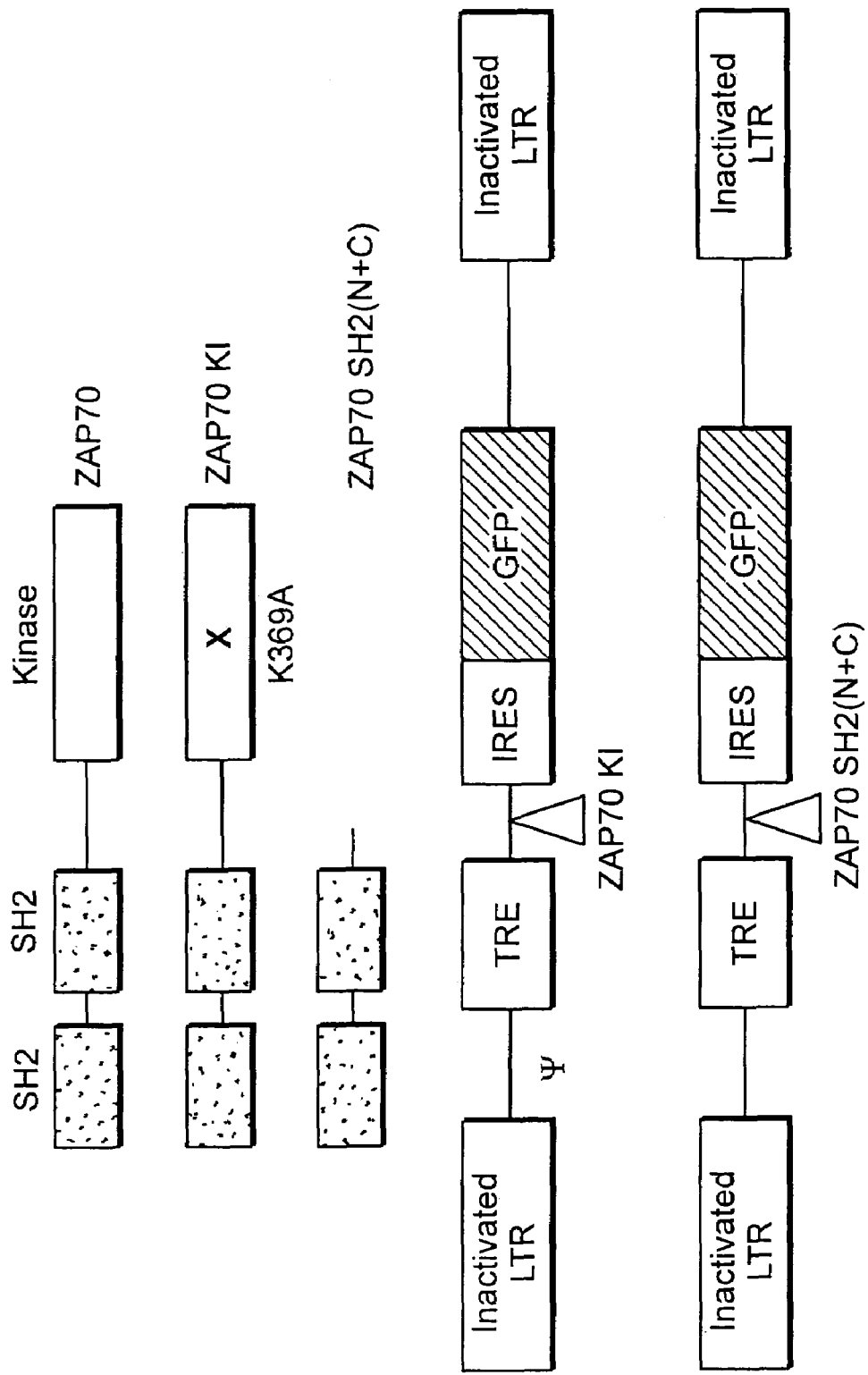
Figure 27B:
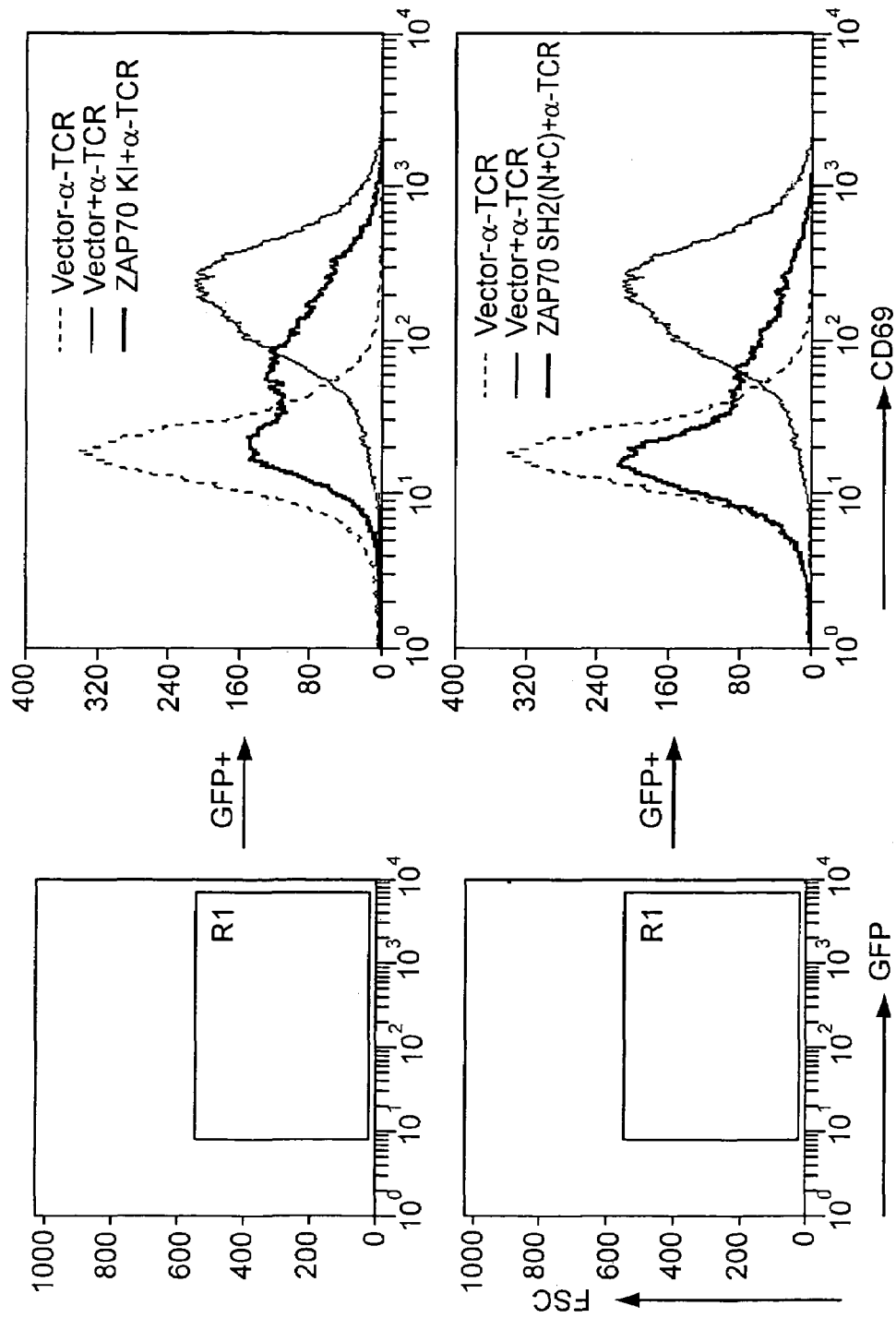

Positive controls. ZAP70 is a positive regulator of T cell activation[28]. A kinase-inactive (KI) ZAP70 and a truncated ZAP70 (SH2 N+C)[29] were subcloned into the retroviral vector under TRE control (FIG. 27A). As seen in FIG. 27B, ZAP70 SH2 (N+C) and ZAP70 KI both inhibited TCR-induced CD69 expression. Consistent with the published report of dominant negative forms of ZAP70 on NFAT activity 29, the truncated protein is also a more potent inhibitor of CD69 induction compared to the K protein, which had a single point mutation in the catalytic domain. In addition, with higher protein expression, as measured by higher levels of GFP from the bi-cistronic ZAP70 SH2 (N+C)-1RES-GFP and ZAP70 KI-IRES-GFP constructs, inhibition of CD69 induction was stronger (data not shown).

Figure 27C:
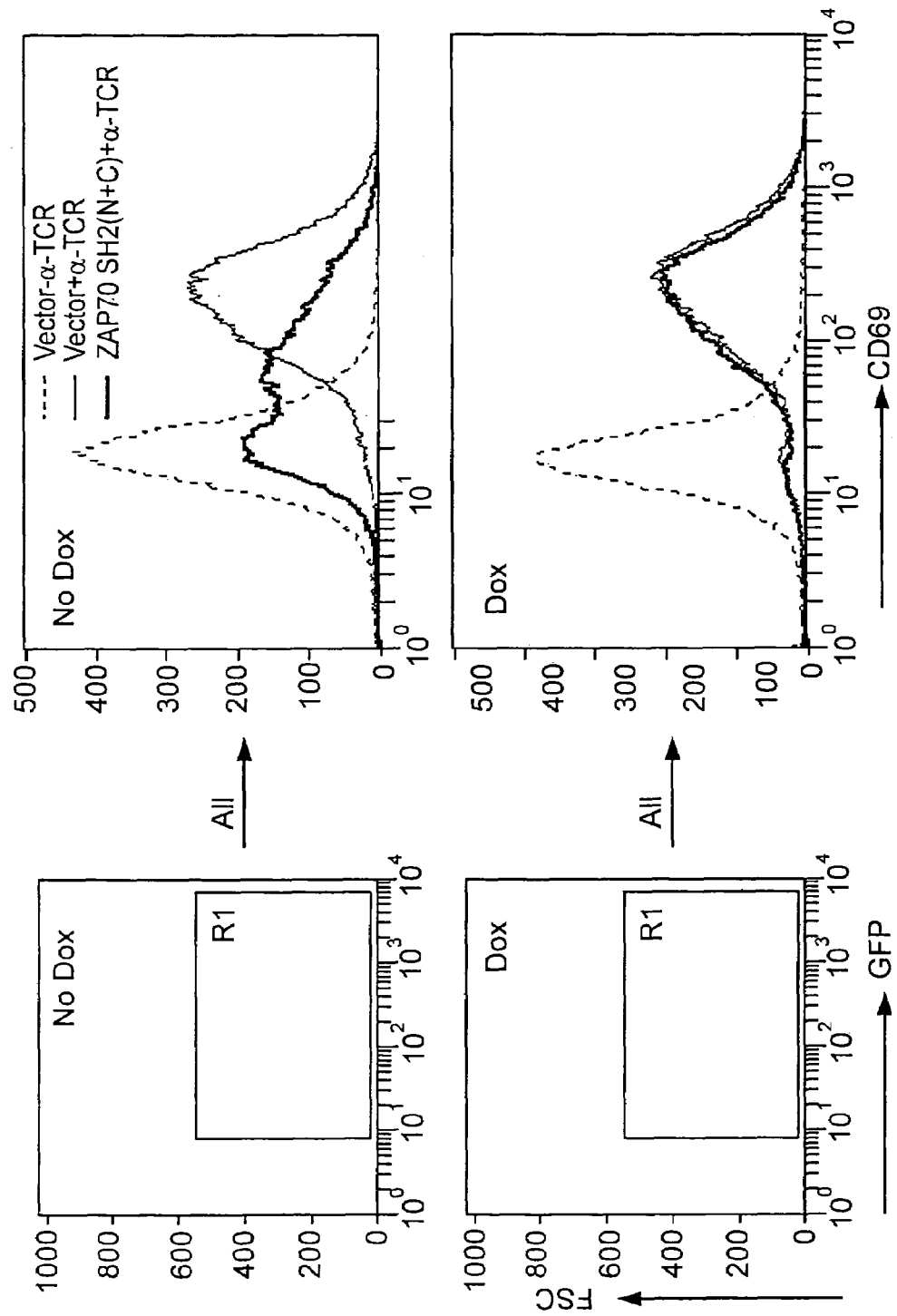
Figure 27D:
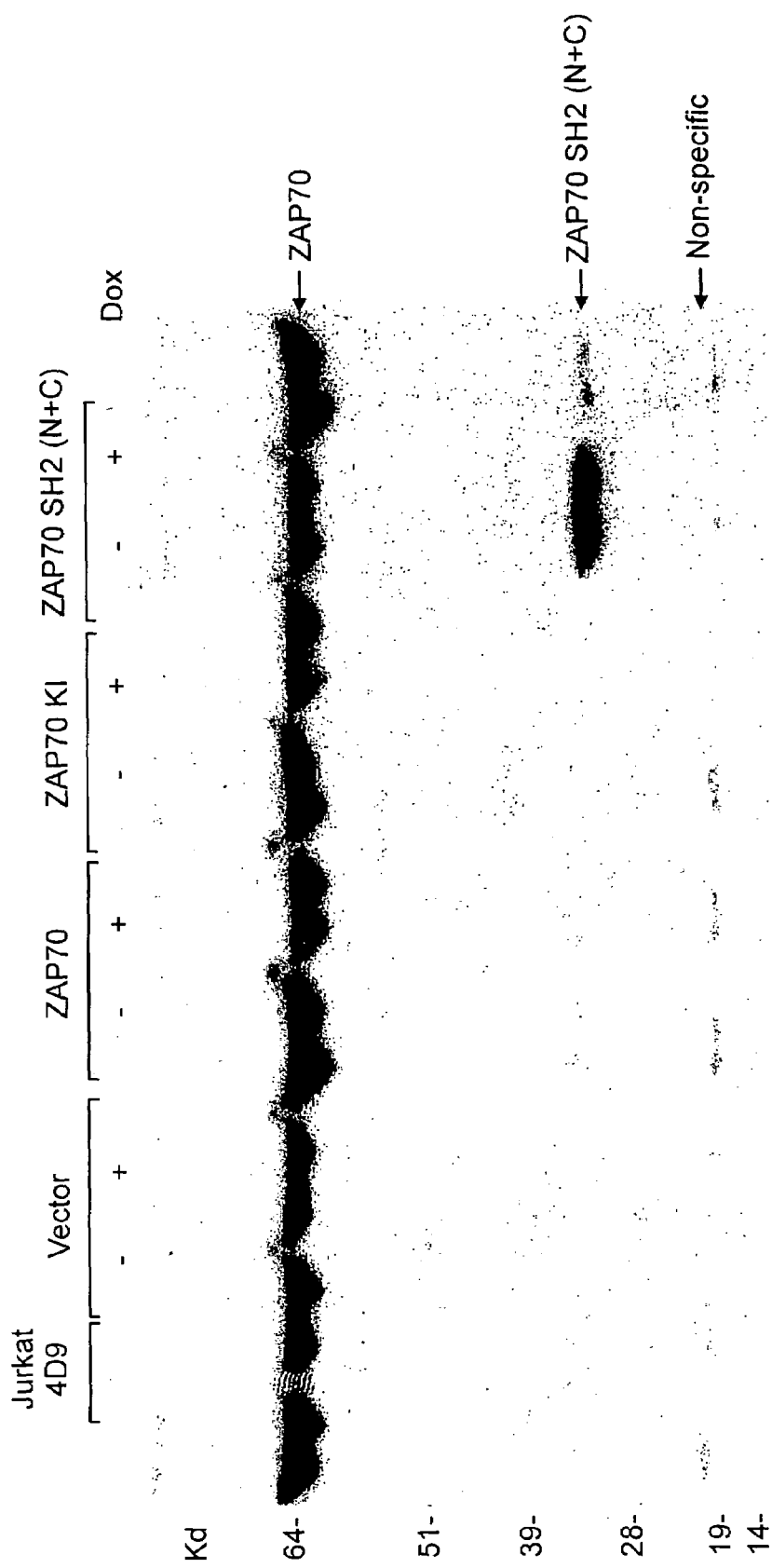

The CD69 inhibitory phenotype is dependent on expression of dominant negative forms of ZAP70. As shown in FIG. 27C, when Dox was added before TCR was stimulated, there was no inhibition of CD69 expression. FACS analysis of cellular GFP expression revealed a lack of GFP+cells, supporting the notion that the bi-cistronic ZAP70 SH2 (N+C)-IRES-GFP mRNA was not transcribed. The lack of ZAP70 SH2 (N+C) protein expression in the presence of Dox was confirmed by Western (FIG. 27D). In the absence of Dox, each cell population contained roughly 50% of GFP−cells that did not express the retrovirally introduced ZAP70 variants. Thus, FIG. 27D showed that it took on average 4–5 fold higher level of ZAP70 SH2 (N+C) than the endogenous ZAP70 to achieve a dominant-negative effect.

Screening for cells lacking CD69 upregulation. FIG. 28A diagrams the scheme to obtain cell clones with CD69 inhibitory phenotype. Jurkat 4D9#32 cells were infected with cDNA libraries made form primary human lymphoid organs such as thymus, spleen, lymph node and bone marrow. The library complexity was $5 \times 10^7$ and was built on the TRE vector. The infection rate was 52%, as judged by infection with TRA-dsGFP in parallel experiment using the same host cells (data not shown). TRA-dsGFP was another TRE-dependent reporter construct using the same vector backbone as that used by the cDNA libraries or TRALyt2. After library infection, cells were stimulated with the anti-TCR antibody C305 overnight. A total of $7.1 \times 10^8$ cells were stained with anti-CD69 antibody conjugated to allophycocyanin (APC) and anti-CD3 antibody conjugated to phycoerythrin (PE) and screened using flow cytometry. Even though there was a significant reduction of CD3/TCR complex on the surface due to receptor-mediated internalization, compared to unstimulated cells (data not shown), the CD3− population was distinguishable from the CD3+ population. Greater than 2% cells lacking the CD3-PE staining (CD3−) (>2% of total cells had lost TCR/CD3 complex) were consistently observed, which explained their unresponsiveness to stimulation and, consequently, low CD69 expression. Based on this fact, only cells with the lowest CD69 expression which still retained the CD3 expression were selected. The desired altered phenotype was termed CD69$^{low}$ CD3$^+$ (FIG. 28A), which represented 1% of the total stained cells (FIG. 28B). The 1% sorting gate also translated as 100-fold enrichment in the first round of sorting alone, based on cell numbers. The recovered cells were allowed to rest in complete medium for 5 days before being stimulated again for a new round of sorting. In subsequent rounds of sorting, the sorting gate was always maintained to contain the equivalent of 1% of the control cells that were stimulated but were never flow-sorted. As shown in FIG. 28B, an enrichment was achieved after 3 rounds of reiterative sorting. Cells with the desired CD69$^{low}$ CD3$^+$ phenotype increased from 1% to 23.2%. In addition, the overall population's geometric mean for the CD69 fluorescent intensity was also reduced (from >300 to 65).

In order to ascertain that the phenotype was due to expression of the cDNA library rather than to spontaneous or retroviral insertion-mediated somatic mutation, the cells recovered after the third round of sorting were split into two populations. One half of the cells were grown in the absence of Dox while the other half in the presence of Dox for 6 days. CD69 expression was analyzed following anti-TCR stimulation overnight.

Figure 28C:
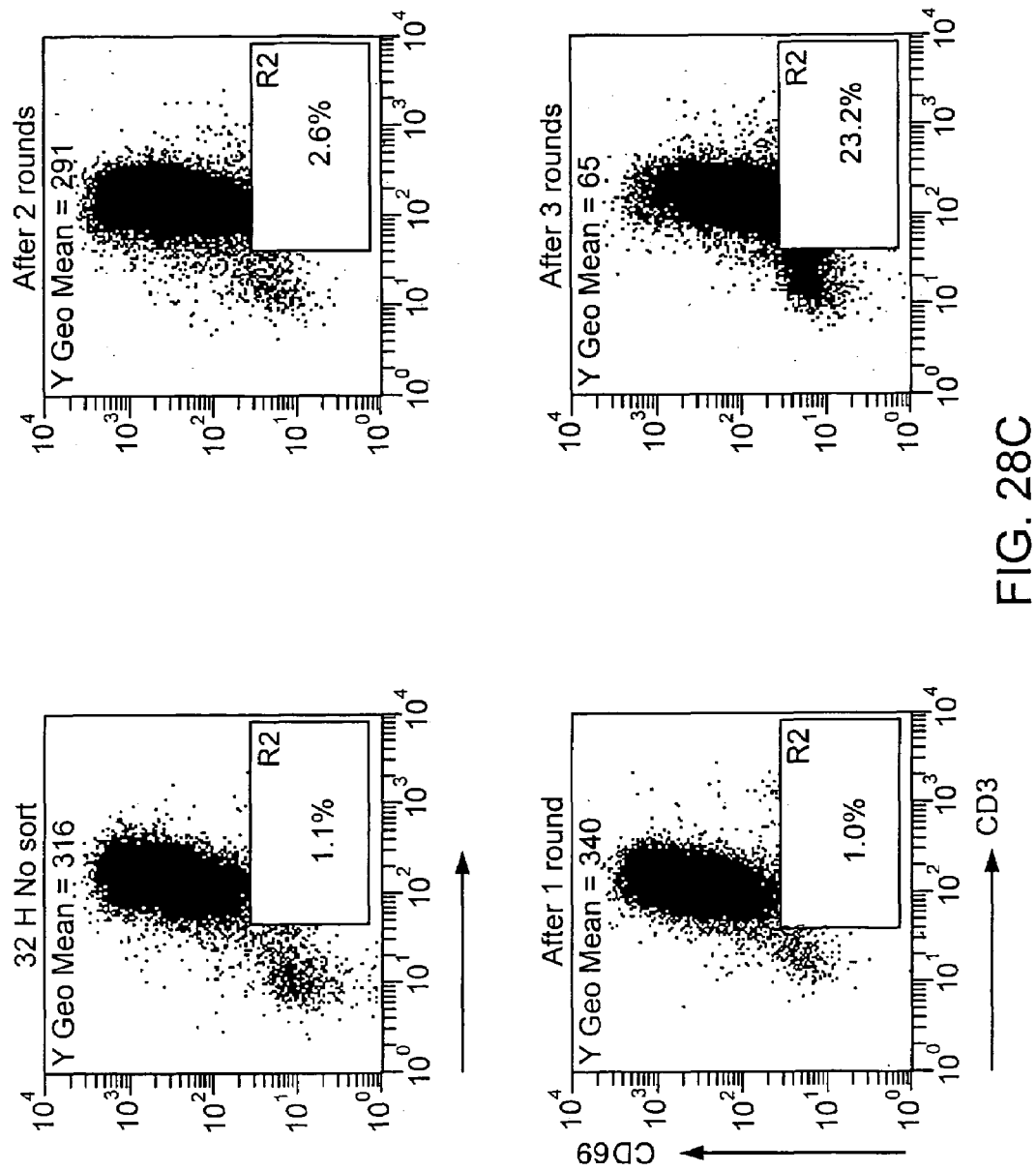

As shown in FIG. 28C, cells with the CD69$^{low}$ CD3$^+$ phenotype decreased from 24.0% to 13.0% with the addition of Dox, demonstrating that a significant number of cells (11%) had lost the CD69$^{low}$ CD3$^+$ phenotype in the presence of Dox. These data suggested that the CD69$^{low}$ CD3$^+$ phenotype in a significant number of cells in the population was indeed caused by the expression of the cDNA library members. Single cell clones were deposited in conjunction with the fourth round of CD69$^{low}$ CD3$^+$ sorting. The cells from three consecutive rounds of CD69$^{low}$ CD3$^+$ sorting were referred to as LLL, and those from four consecutive rounds of CD69[low] CD3[+] sorting were referred to as LLLL. Overall, cells from up to 7 rounds of sorting (LLLLLLL) were collected.

In order to reduce the number of cells whose phenotype was not Dox-regulatable, the population of the cells grown in the presence of Dox were subjected to a different round of sorting. The purpose for this round of sorting was to enrich for cells having normal CD69 expression when the library cDNA expression was switched off in the presence of Dox. This sorting variation was termed LLLH where H means CD69[high]. The cells recovered from LLLH sort were cultured in the absence of Dox for subsequence sorting of the CD69[low] CD3[+] phenotype. Single cell clones with the CD69[low] CD3[+] phenotype were deposited in 96-well plates from both the LLLHL and LLLL sorting variations. Table 1 showed that indeed a higher percentage of Dox-regulatable clones with the LLLHL sorting variation than with LLLL was achieved.

Functional Analysis of Single Cell Clones. After single cell clones started to grow into individual colonies in 96-well plates, their cellular phenotype was characterized with the cDNA expression turned on or off, by growing the cells in the presence or absence of Doxcycline (Dox). FIG. 29A shows some examples of the Dox-regulatable phenotypes for individual clones. Dox regulation of CD69 expression was expressed as the ratio of geometric mean fluorescent intensity (GMFI) in the presence of Dox divided by the CD69 GMFI in the absence of Dox after TCR stimulation. This ratio of (+Dox)/GMFI (−Dox) was termed the Dox ratio. In uninfected cells, Dox had little or no effect on the induction of CD69 expression so that the Dox ratio for individual clones on all occasions was consistently 1.00+/−0.25 (standard deviation). Therefore, the 2× standard deviation was used as a cut-off criterion and designated clones with a ratio above 1.5 as Dox regulated clones. Out of 2828 clones analyzed, 1323 had a Dox-regulatable cellular phenotype as judged by the above criteria, representing 46.8% of analyzed clones. FIG. 29B shows the distribution of clones with the Dox ratio between 1.5 and 10, which contained 1186 clones. Interestingly, the majority of clones have a Dox ratio below 10 whereas rare clones were discovered with a Dox ratio up to 70.

RNA samples were prepared from clones with Dox-regulatable phenotypes. Using primers specific for the vector sequence flanking the cDNA library insert, we captured the cDNA insert of selected clones by RT-PCR. FIG. 29C showed the pattern of RT-PCR products. Most clones generated only one DNA band, whereas a few clones generated two or more bands. Sequencing analysis revealed that the additional bands were usually caused by double or multiple insertions of retroviruses. Occasionally, the two PCR products in the same lane represented different fragments of the same gene product. The results of the cDNA analysis are summarized in Table 2.

Characterization of proteins critical for T cell activation. As shown in Table 2, known TCR regulators such as LCK. ZAP70, SYK, and PLC(1 were obtained using the methods of the present invention.

Figure 30A:
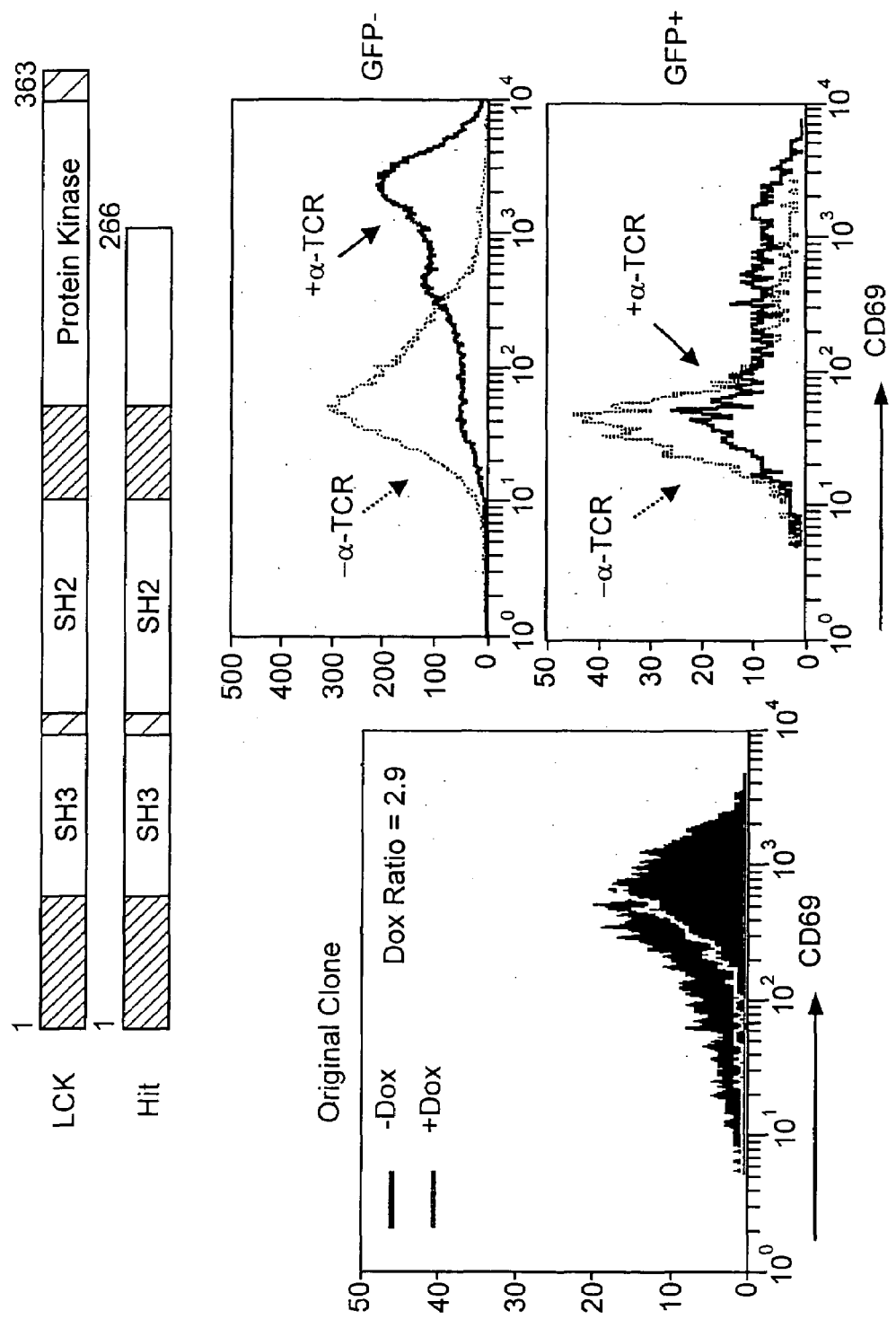

LCK is a non-receptor protein tyrosine kinase[30,31]. Its role in T cell development and activation has been widely documented[32-34]. To date, dominant negative forms of LCK have not been reported. The discovery by the present inventors that over expression of the kinase-truncated form of LCK caused inhibition of CD69, similar to the phenotype of Jurkat somatic mutant lacking LCK 35, suggests that kinase deletion of LCK could also work as a dominant negative form of LCK (FIG. 30A).

Figure 30B:
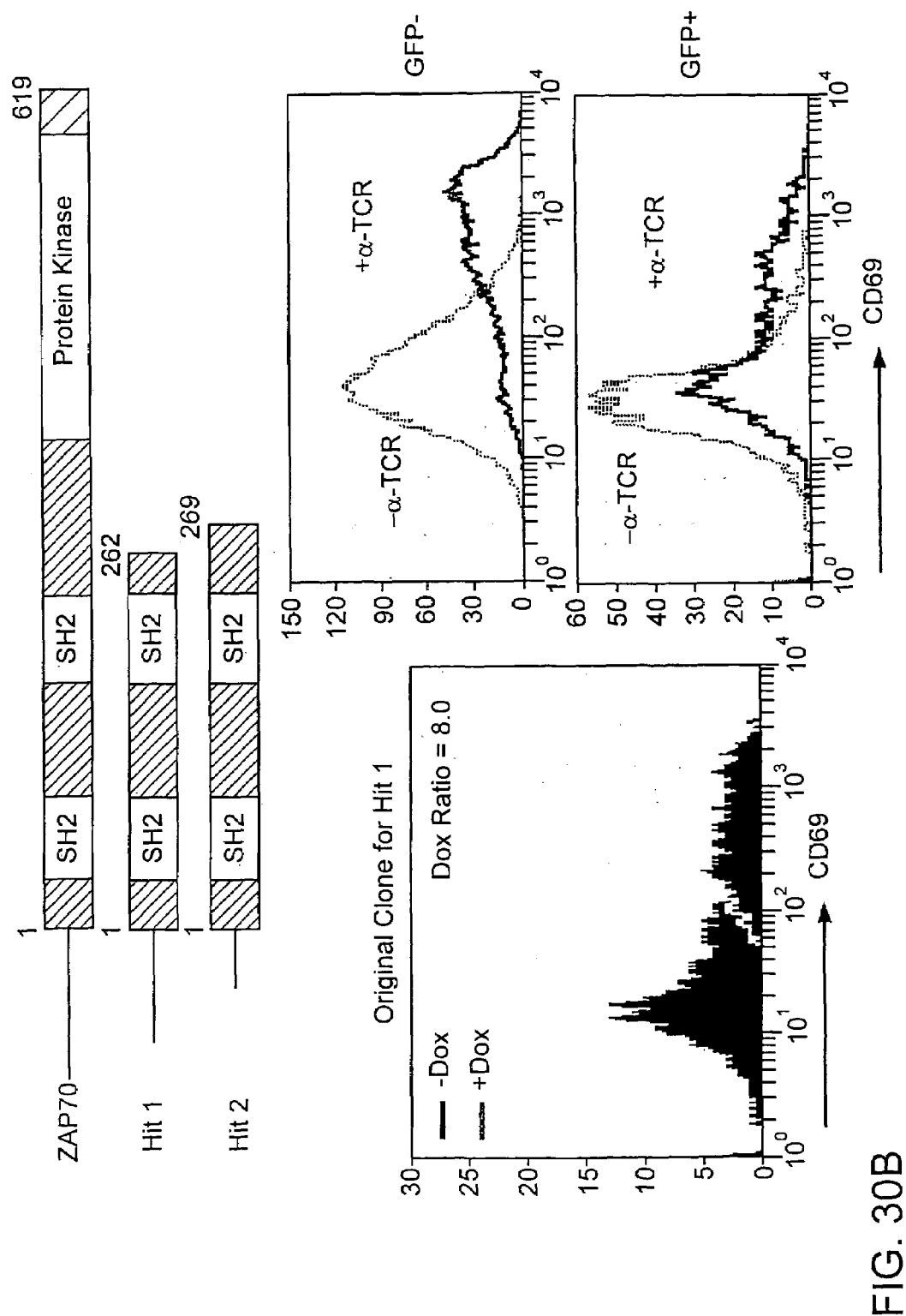

The two ZAP70 hits both contained the endogenous ATG initiation codon and ended at aa 262 and 269, respectively (FIG. 30B). They both are missing the catalytic domain. The deletions are very close to the positive control for the screen, ZAP70 SH2 (N+C), which ended at aa 276[29]. Since ZAP70 SH2 (N+C) was shown to be a dominant negative protein 29 (also see FIG. 27), the two ZAP70 hits are believed to also behave as dominant negative proteins of ZAP70 (FIG. 30B).

Figure 30C:
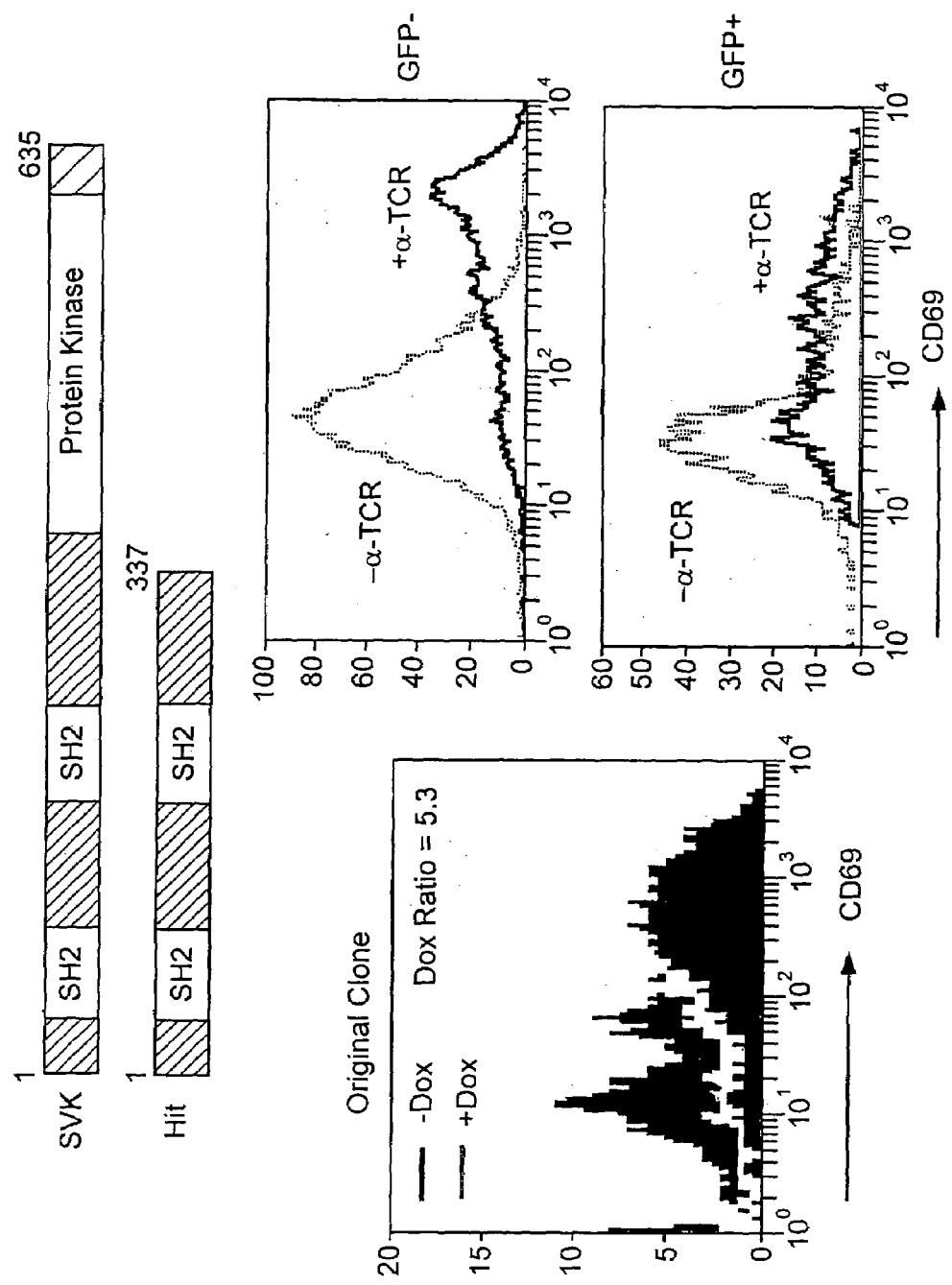

SYK is a non-receptor tyrosine kinase belonging to the SYK/ZAP70 family of kineses[36]. Since it has also been shown that the lack of SYK expression in Jurkat cells did not appear to significantly alter the TCR-mediated responses compared with Jurkat clones expressing SYK[37], the SYK hit obtained from the present screen is believed to function mainly in blocking ZAP70 function (FIG. 30C and data not shown). SYK's similarity to ZAP70, its ability to associate with phosphorylated TCR; chain and its ability to reconstitute the ZAP70-deficient Jurkat T-cell line also support this notion[38].

Figure 30D:
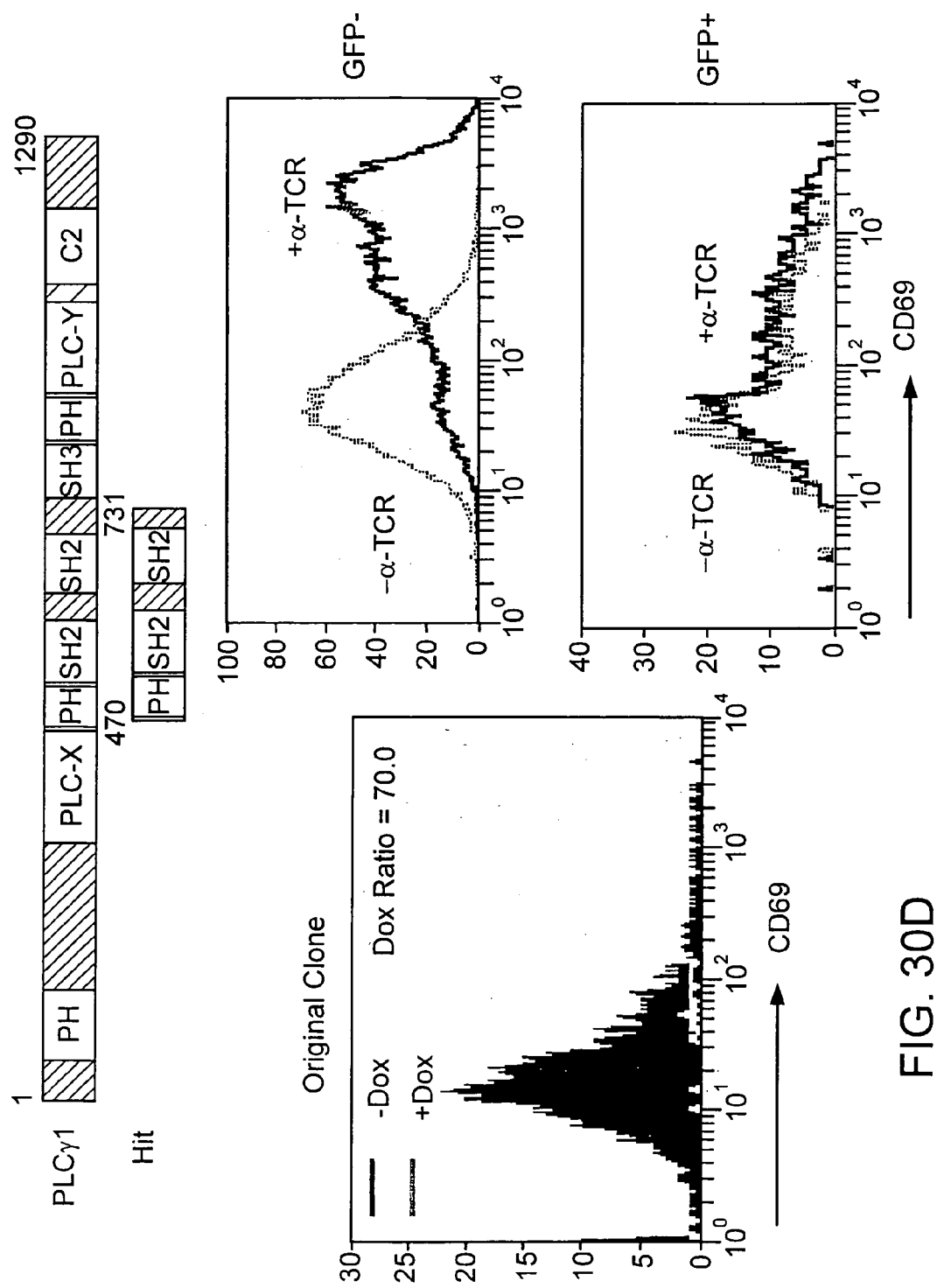

PLC(I plays a crucial role in coupling T cell receptor ligation to IL-2 gene expression in activated T lymphocytes[1]. TCR engagement leads to rapid tyrosine phosphorylation and activation of PLC(I[39]. The activated enzyme converts phosphatidylinositol-4,5-bisphosphate (PIP2) to inositol-1,3,5-trisphosphate (IP3) and diacylglycerol (DAG). IP3 triggers intracellular $Ca^{2+}$ increase and DAG is a potent activator of protein kinase C (PKC). PLC(1 has a split catalytic domain comprised of conserved X and Y subdomains (FIG. 30D). Single point mutation in the catalytic X box completely abolished the enzyme activity and also blocked IL-2 reporter gene expression when introduced into PLC(I-deficient Jurkat cells[40]. The hit contained the PH domain and the N and C terminal SH2 domains of PLC(I (FIG. 30D). Significantly this hit also deleted the crucial tyrosine Y783 between the SH2 (C) and SH3 domains. It was reported that Y783 was essential for coupling of TCR stimulation to IL-2 promoter activation and that mutation of Y783 to F (phenoalanine) generated a very potent dominant negative form of PLC(I[40]. Indeed, the original clone encoding the PLC(I hit had the highest Dox ratio for CD69 expression among all clones from the cDNA screen, indicating the strong repression of CD69 induction by the PLC(1 hit as well as the total de-repression in the absence of the hit expression. When introduced to naive Jurkat cells, this fragment caused severe block of TCR-induced CD69 expression (FIG. 30D).

Other signaling molecules known to involve in TCR signaling pathway were also discovered using the methods of the present invention. They included PAG[6], CSK[41,42,43], SHP-1[44] and nucleolin[45] (Table 2 and data not shown). Raf is a MAP kinase kinase kinase. It interacts with Ras and leads to activation of the MAP kinase pathway[46]. Raf-1 was reported to participate in TCR signaling[47,48]. The Raf hit obtained corresponds to the truncated form of A-raf, missing the kinase domain. It is likely that this A-raf hit is a dominant negative form of the Raf-1 kinase[49,50]. Alternatively, our result suggests that A-Raf is also critical for TCR signaling leading to CD69 activation.

In addition to the known signaling molecules, using the methods of the present invention the function of genes whose identity were reported previously, but whose involvement in TCR signaling was not documented, was discovered. For example, SH2-B was originally identified by its ability to associate with the immunoreceptor tyrosine-based activation motif (ITAM) of the FcgR (chain[51]. It belongs to a superfamily of intracellular signaling molecules including LNK and APS[52,53]. Recently, LNK was shown to be crucial for B cell production 54. It is conceivable that SH2-B plays an analogous immune modulatory role in T cell activation (Table 2).

Figure 31A:
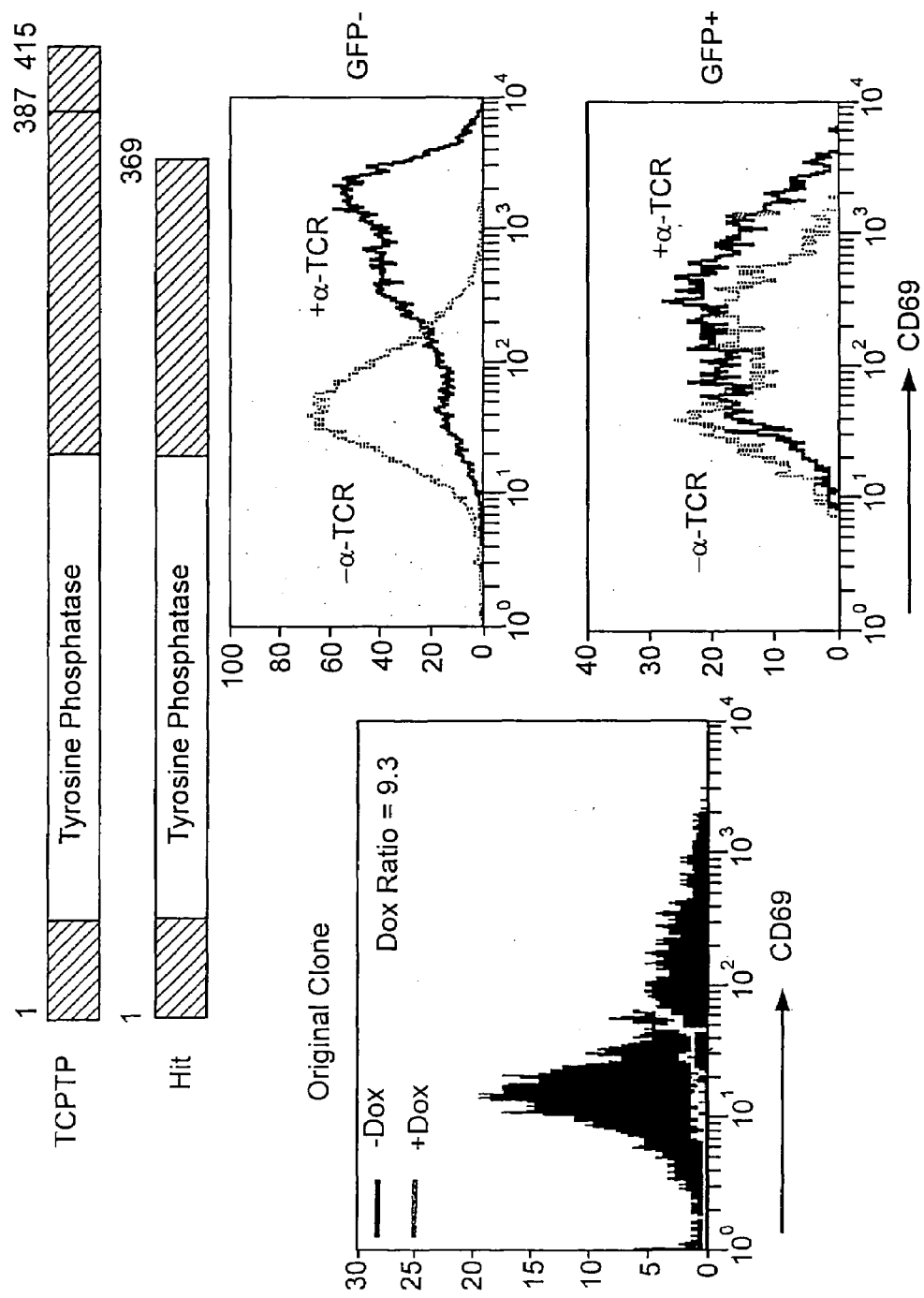
Figure 31B:
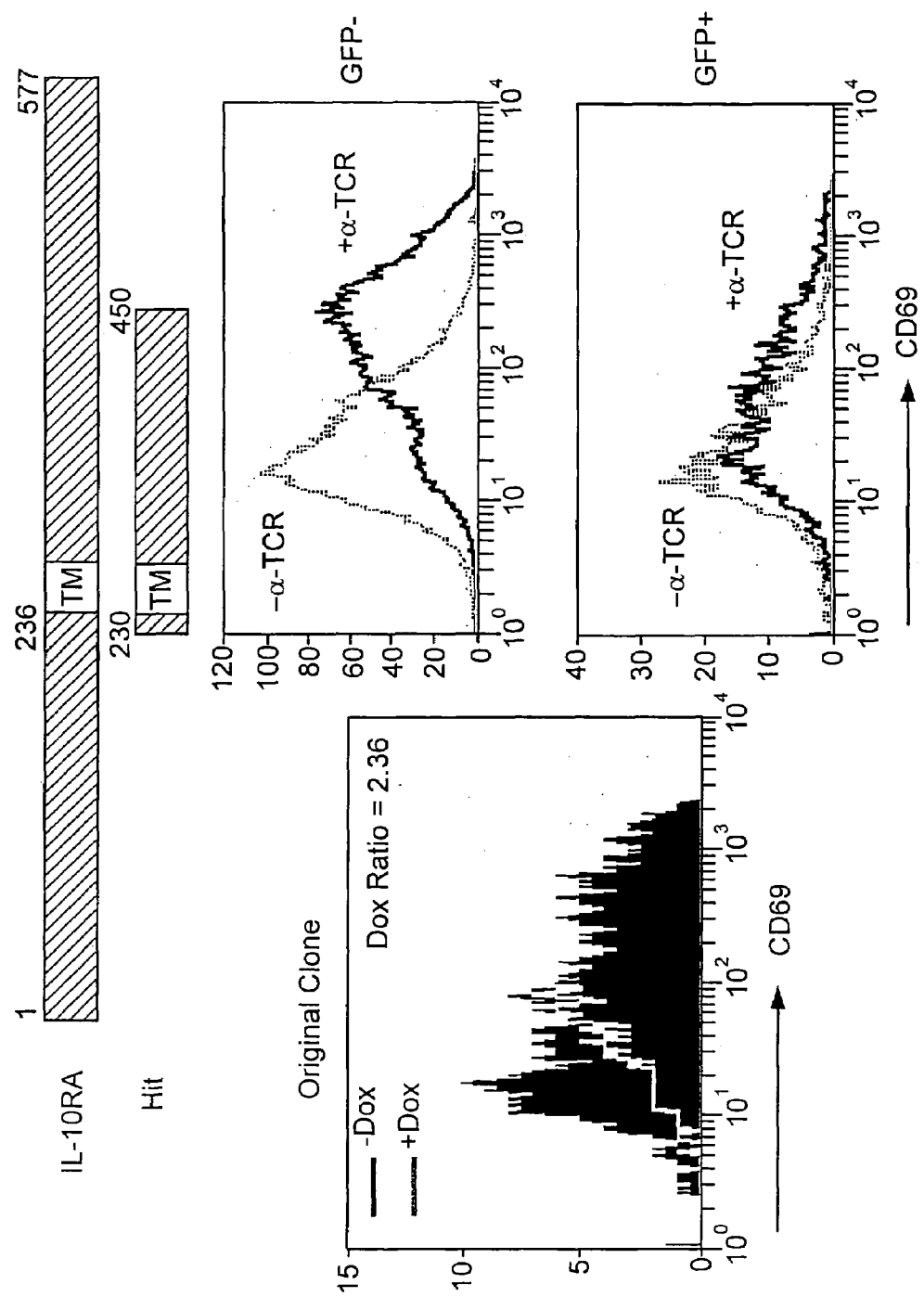

TCPTP (T cell protein tyrosine phosphatase) is also called PTPN2 for protein tyrosine phosphatase nonreceptor-2[55]. It was reported to be highly expressed in T cells but its function in TCR signal transduction was not elucidated. The hit obtained from the using the screening methods of the present invention contained a C-terminal truncation and an intact phosphatase domain (FIG. 31A). Constitutively active TCPTP was reported to have a C-terminal truncation due to protease cleavage at aa. 387[56]. Interestingly, the hit ends at aa 369, just 18 aa shorter than the protease cleavage product. It is conceivable that the hit is a constitutively activate TCPTP and that activated TCPTP is a negative regulator of TCR signaling.

Figure 31C:
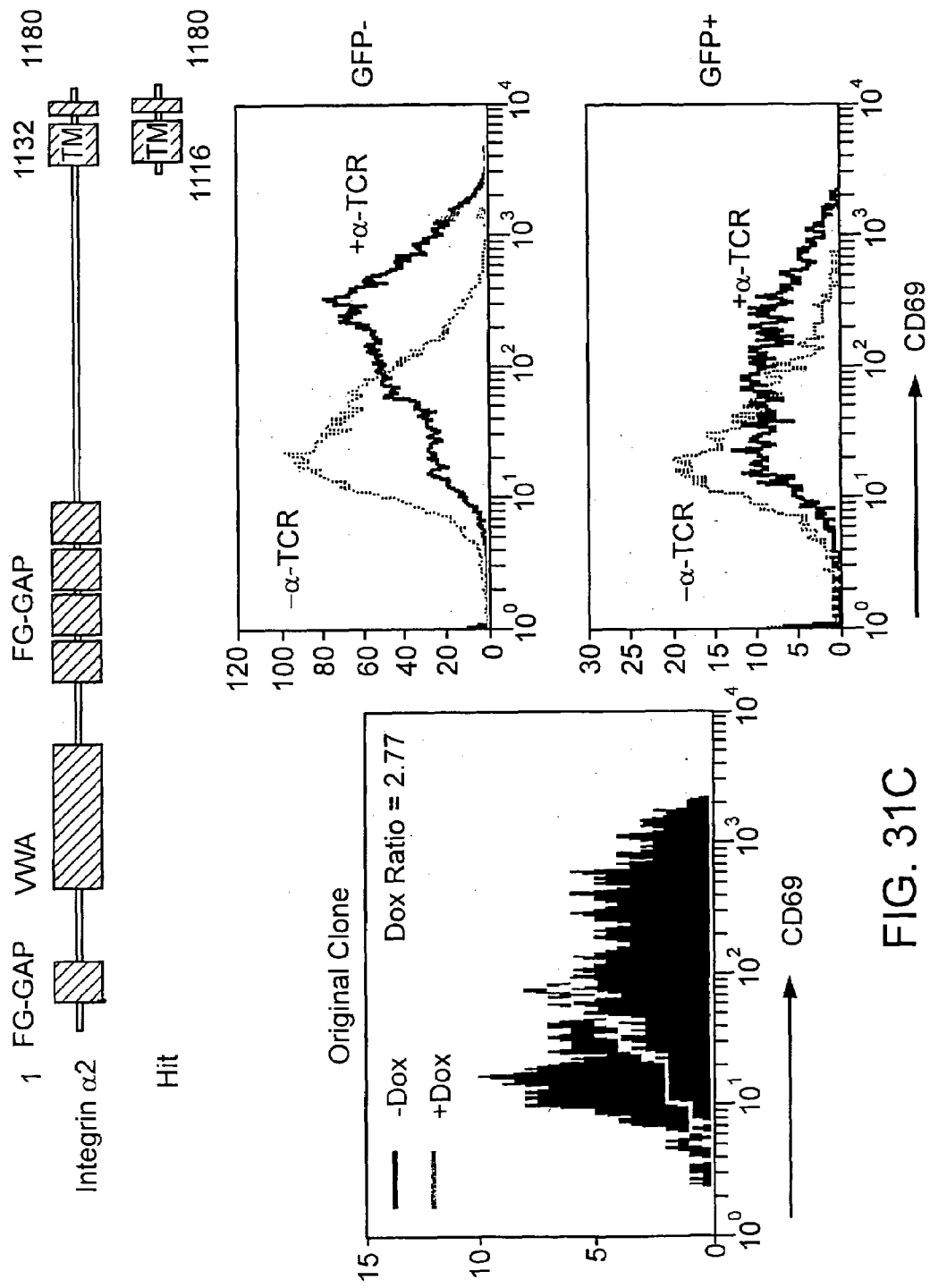
Figure 31D:
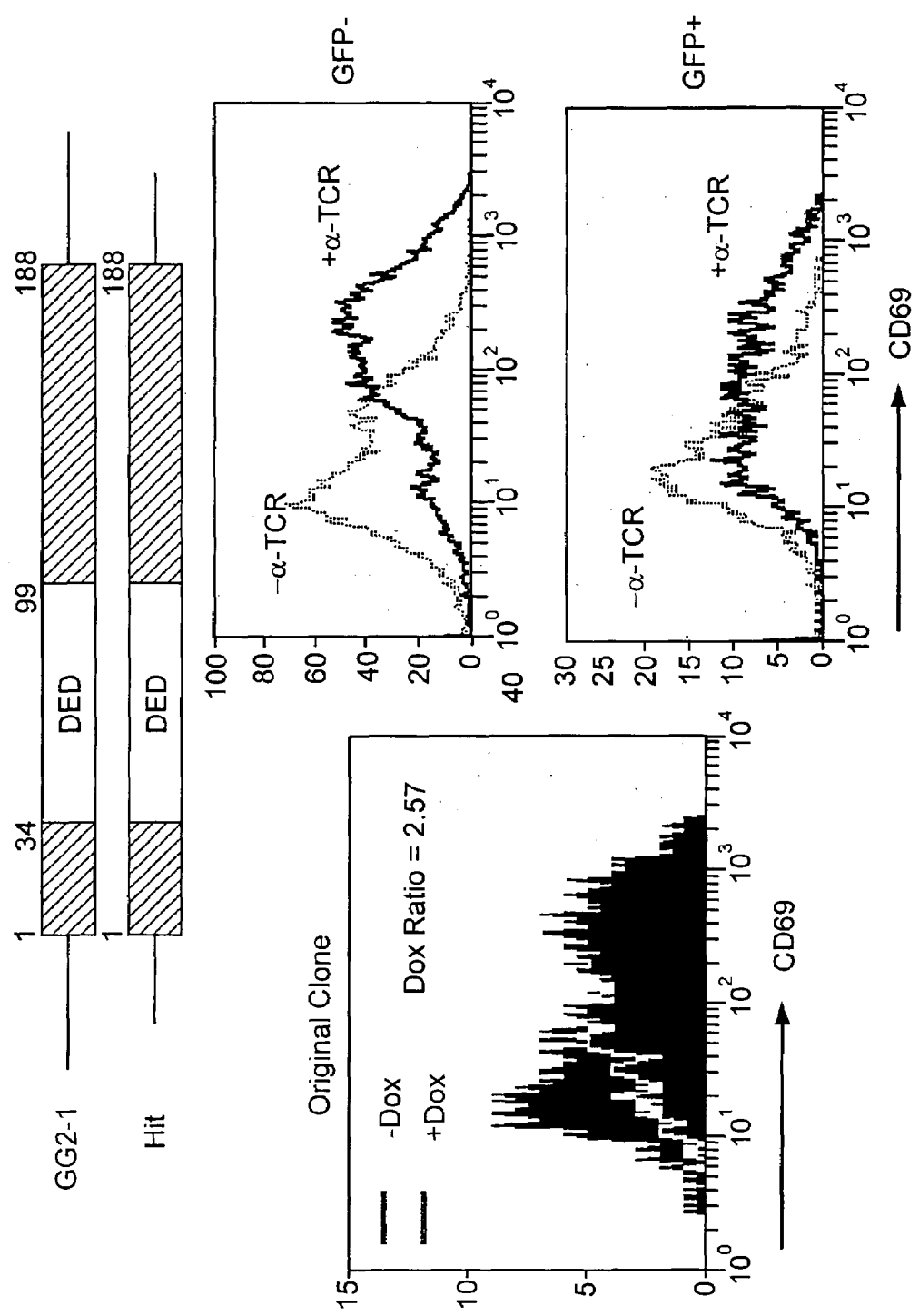

IL-10 receptor[57] and Integrin "2[58] are both transmembrane proteins. The cytoplasmic regions of these two receptors were identified as inhibitors of TCR-induced CD69 expression (FIG. 31B and FIG. 31C), using the methods of the present invention. Although the mechanisms of the inhibition were not clear, these transmembrane molecules may serve as specific "sinks" for other positive signaling molecules. Alternatively, a more appealing explanation is that these transmembrane molecules specifically modulate T cell activation. For example, stimulation of T cells via the CD3-TCR complex resulted in rapid increase in $1 integrin-mediated adhesion. Integrins are capable of inside-out signal transduction[59] and have been reported to bind to SLP-76[60]. The hematopoietic-specific adaptor SLAP-130/Fyb was also shown to be important for coupling TCR-mediated actin cytoskeletal rearrangement with activation of integrinfunction, and for T cells to respond fully to activating signals[61]. Recently, it has been reported that the Tec family tyrosine kinase ITK[62] regulated the inside-out signaling events from TCR to integrins[63]. Furthermore, Integrin "2$1 mediates p38" activation and upregulation of collagen gene transcription by a mechanism involving the "2 cytoplasmic tail, Cdc42, MKK3 and MKK4[64]. Taken together, our discovery of the dominant negative effect of the cytoplasmic tail of" integrin strengthened integrin's role in functionally modulating T cell activation (FIG. 31C).

In addition to uncovering truncated cDNAs encoding dominant negative mutants of the positive regulators and constitutively active mutants of the negative regulators of T cell activation, using the screening methods of the present invention a clone encoding the full-length open reading frame of the gene GG2-1 (Table 2 and FIG. 31D) was also identified. GG2-1, also called SCC S2, was independently discovered as a transcript upregulated with TNF"[65,66]. GG21/SCC-S2 contained a sequence in the amino terminus that shows a significant homology to death effector domain 11 of the cell death regulatory protein FLIP. Unlike FLIP, the GG2-1/SCC-S2 open reading frame contains only one death effector domain and lacks the carboxyl-terminal caspase-like homology domain. The significance of the GG2-1 hit from our T cell activation screen awaits further studies.

Function in primary T lymphocytes. The relevance of the cDNA hits, identified by the methods of the present invention, to the physiological function of T cells was investigated in primary T lymphocytes. The hits were subcloned into a retroviral vector under a constitutively active promoter embedded in the retroviral LTR, followed by IRES-GFP. A protocol was developed to couple successful retroviral infection to subsequence T cell activation. Primary T lymphocytes are at the quiescent stage when isolated from healthy donors. In order to be infected by a retrovirus, primary lymphocytes need to be activated to progress into the cell cycle. As shown in FIG. 32A, fresh peripheral blood lymphocytes (PBL) contained typically T cells and B cells. The combined CD4+ and CD8+ cells represented total T cells, which were 81% in this particular donor. The remaining 19% CD4+ and CD8+ cells were B cells as stained by CD19 (data not shown). Upon culturing on anti-CD3 and anti-CD28 coated dishes, primary T lymphocytes were expanded and primary B cells and other cell types gradually died off in the culture. FIG. 32 showed that after infection, the culture contained virtually all T cells. Furthermore, primary T lymphocytes were successfully infected by retroviruses (FIG. 32A and B). As seen with Jurkat cells (data not shown), GFP translated by way of IRKS was not as abundant as GFP translated using the conventional Kozak sequence (comparing GFP geometric mean from CRU5-IRES-GFP and CRU5-GFP). Nevertheless the percentage infection remained similar. Insertion of a gene in front of IRES-GFP further reduced the expression level of GFP, which was observed with many cell lines (data not shown) and here in primary T lymphocytes (FIG. 32B). After allowing cells to rest following infection, we flow sorted cells into two populations: GFP− and GFP+. The sorted cells were immediately put into culture. As seen in FIG. 32C, anti-CD3 alone did not induce IL-2 production. This observation was consistent with previous report on freshly isolated primary T lymphocytes and confirmed the notion that prior culture and retroviral infection did not damage the physiological properties of these primary T lymphocytes. Addition of anti-CD28 in conjunction with anti-CD3 led to robust IL-2 production with vector-infected cells and the GFP− population of LckDN and PLC(IDN-infected cells. The GFP+ cell population from LckDN and PLC(IDN-infected cells, however, were severed impaired in IL-2 production following anti-CD3 and anti-CD28 stimulation (FIG. 32C). As expected, the defect caused by LckDN and PLC(IDN can be completely rescued by stimulation using PMA and ionomycin (FIG. 32C). Taken together, these results showed that LCK and PLC(1 play crucial role in IL-2 production from primary T lymphocytes, consistently with their involvement in membrane proximal signaling events of T cell activation. These results also demonstrated a quick system to further validate hits using the methods of the present invention as a functional genetic screen in primary cells.

In conclusion, the methods of the present invention used in this study demonstrates a successful approach to discover and validate in a functionally relevant context important immune regulators on a genome-wide scale. This approach, which requires no prior sequence information, provides a tool for functional cloning of regulators in numerous signal transduction pathways. For example, B cell activation-induced CD69 expression (Holland et al., in press) and IL-4-induced IgE class switch are all amendable to the genetic perturbation following introduction of retroviral cDNA libraries. The methods of the present invention are less biased compared to forced introduction of a handful of signaling molecules discovered in other contexts such as growth factor signal transduction. The present invention also open the door for discovering peptide inhibitors of immune modulatory proteins by screening random peptide libraries expressed from retroviral vectors using the screening methods of the present invention.

Experimental Protocol

Preparation of cDNA libraries. mRNA extracted from human lymph nodes, thymus, spleen and bone marrow was used to produce two cDNA libraries; both randomly primed.

One library (−ATG) inserts were directionally cloned and the second (+ATG) non-directionally cloned and provided with 3 exogenous ATG in 3 frames. cDNAs were cloned into the pTRA-exs vector to give rise to robust Doxycycline-regulatable transcription from the TRE enhancer and the minimal promoter in cell lines expressing tTA. The total combined library complexity was 5×107 independent clones.

Cell lines. Phoenix A cells were cultured in DMEM supplemented with 10% fetal calf serum, penicillin and streptomycin. Human T cell leukemia line Jurkat was obtained from Novartis and was routinely cultured in RPMI 1640 medium supplemented with 10% fetal calf serum, penicillin and streptomycin. To obtain the clone with optimal CD69 induction, Jurkat cells were sorted for low basal CD69 expression and high induction of CD69 expression following TCR stimulation. To produce the tTA-Jurkat cell line, Jurkat clone (4D9) with optimal CD69 expression profile was infected with retroviral construct which constitutively expresses the tetracycline transactivator protein (tTA) and a reporter construct which expresses Lyt2 driven by a tetracycline responsive element (TRE). The tTA-Jurkat cell clone 4D9#32 was obtained by sorting for high Lyt2 expression in the absence of Doxycycline and low expression of Lyt2 in the presence Doxycycline (10 ng/ml).

Transfection and infection. Phoenix A packaging cells were transfected with retroviral vectors using calcium phosphate for 6 hours following standard protocols. After 24 hours, supernatant was replaced with complete RPMI medium and virus was allowed to accumulate for 24 hours at 32EC. Viral supernatant was collected, filtered through a 0.2 M filter and mixed with Jurkat cells at a density of $5\times10^5$ cells/mi. Cells were spun at room temperature for 3 hours at 2500 rpm, followed by overnight incubation at 37EC. Transfection and infection efficiencies were monitored by flow cytometry. Functional analysis was carried out 2–4 days after infection.

Stimulation. For CD69 upregulation experiment, Jurkat cells were split to $2.5\times10^5$ cells/ml 24 hours prior to stimulation. Cells were spun and resuspended at $5\times10^5$ cells/ml in fresh complete RPMI medium in the presence of 300 ng/ml C305 (anti-Jurkat clonotypic TCR) hybridoma supernatant for 20–26 hours at 37EC, and then assayed for surface CD69 expression.

Antibodies and Flow cytometry. Jurkat cells or human peripheral blood lymphocytes were stained with FITC-conjugated monoclonal anti-mouse CD8" (Lyt2), APC conjugated mouse monoclonal anti-human CD3, anti-human CD8, or anti-human CD69 antibodies, and PE-conjugated mouse monoclonal anti-human CD3 or anti-CD4 antibodies (all from Caltag) at 4EC for 20 minutes and analyzed using a FACSCalibur instrument (Becton Dickinson) with the CellQuest software. Fluorescent-activated cell sortings were performed on the MoFlo instruments (Cytomation).

cDNA library screen. Phoenix A packaging cells were transfected with a mixture of the two tTA regulated retroviral cDNA libraries (total complexity $5\times10^7$). Supernatant containing packaged viral particles was used to infect $3.5\times10^8$ tTA-Jurkat cells with an efficiency of 52% based on parallel infection with TRA-GFP. After 4 days of cDNA expression, library infected cells were stimulated with 300 ng/ml C305 for 20–30 hours, stained with APC-conjugated anti-CD69 and PE-conjugated anti-CD3, and 1% of total cells expressing the lowest CD69 level and still positive for CD3 expression were isolated using a fluorescence activated cell sorter (Cytomation). Sorting was repeated multiple rounds with a 6-day rest period between stimulations until the population was significantly enriched for the desired phenotype of $CD69^{low}CD3^+$. Following 3 consecutive sorting for the $CD69^{low}$ $CD3^+$ phenotype after TCR stimulation in the absence of Dox, half of the cells were cultured and stimulated in the presence of Dox and sorted for the top 10% of the CD69 level (so called $CD69^{high}$ henotype) to enrich for clones whose phenotype was dependent on cDNA expression. Single cells were deposited from 8 separate rounds of sorting with different variations of the placement of the $CD69^{high}$ sort. Cell clones were expanded in the presence and absence of Dox, stimulated and analyzed for CD69 upregulation.

Isolation of cDNA inserts. PCR primers were designed to amplify cDNA inserts from both libraries and did not amplify Lyt2 that was also under TRE regulation. The primers used contained flanking BstXI sites for subsequent cloning to the pTRA-IRES-GFP and CRU5-IRES-GFP vectors. BstXTRA5G: 5'TTGCAGAACCACCACCT-TGGGCTCTTAACCTAGGCCGATC3' (SEQ ID NO:38). BstXTRA3D: 5'TTGCAGAACCAATTTAATGGCGGC-CAGTCAGGCCATCGTCG3' (SEQ ID NO:39). RT-PCR cloning was achieved with kits from Clontech or Life Technologies. The gel-purified RT-PCR products were sequenced. The purified RT-PCR fragments were also digested for subcloning. Dominant negative ZAP70 (KI) and ZAP70SH2 (N+C) as well as selected hits from cDNA screens were subcloned to the retroviral pTRA-IRES-GFP vector. Selected hits form cDNA screens were also subcloned to CRU5-IRES-GFP for infection of human primary T lymphocytes.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of screening for cells having an altered phenotype, the method comprising the steps of:
   a) providing a population of cells having a parent phenotype, said population of cells comprising a nucleic acid sequence encoding a first element expressed in said population of cells;
   b) introducing into said population of cells a library of fusion nucleic acids, said fusion nucleic acids each comprising:
      (1) a second element that is regulatable by said first element; and
      (2) a nucleic acid sequence encoding a candidate bioactive agent, wherein said nucleic acid sequence is operably linked to said second element;
   c) modulating the expression of said nucleic acid sequence encoding the candidate bioactive agent by contacting said population of cells with a third element, wherein said modulation is selected from the group consisting of induction and repression of said nucleic acid sequence encoding the candidate bioactive agent;
   d) collecting a first subpopulation of cells having an altered phenotype;
   e) modulating in the opposite direction of step (c) the expression of said nucleic acid sequence by modulating said contacting of first subpopulation of cells with said third element;
   f) collecting a second subpopulation of cells having said parent phenotype;
   g) modulating in the same direction as in step (c) the expression of said nucleic acid sequence by contacting said second subpopulation of cells with said third element; and
   h) detecting a third subpopulation of cells having said altered phenotype.

2. The method according to claim 1 further comprising:
   i) collecting said third subpopulation of cells having said altered phenotype;
   j) modulating in the opposite direction of step (c) the expression of said nucleic acid sequence by modulating said contacting of said third subpopulation of cells with said third element; and k) detecting a fourth subpopulation of cells having said parent phenotype.

3. The method according to claim 2 further comprising:
   I) collecting said fourth subpopulation of cells having said parent phenotype;
   m) modulating in the same direction as in step (c) the expression of said nucleic acid sequence by contacting said fourth subpopulation of cells with said third element; and
   n) detecting a fifth subpopulation of cells having said altered phenotype.

4. A method of screening for cells having an altered phenotype, the method comprising the steps of:
   a) providing a population of cells having a parent phenotype, said population of cells comprising a nucleic acid sequence encoding a first element expressed in said population of cells;
   b) introducing into said population of cells a library of fusion nucleic acids, said fusion nucleic acids each comprising:
      1) a second element that is regulatable by said first element; and
      2) a nucleic acid sequence encoding a candidate bioactive agent, wherein said nucleic acid sequence is operably linked to said second element;
   c) inducing the expression of said nucleic acid sequence encoding the candidate bioactive agent by contacting said population of cells with a third element;
   d) collecting a first subpopulation of cells having an altered phenotype;
   e) repressing the expression of said nucleic acid sequence by modulating said contacting of first subpopulation of cells with said third element;
   f) collecting a second subpopulation of cells having said parent phenotype;
   g) inducing the expression of said nucleic acid sequence by contacting said second subpopulation of cells with said third element; and
   h) detecting a third subpopulation of cells having said altered phenotype.

5. The method according to claim 4 further comprising:
   i) collecting said third subpopulation of cells having said altered phenotype;

j) repressing the expression of said nucleic acid sequence by modulating said contacting of said third subpopulation of cells with said third element; and k) detecting a fourth subpopulation of cells having said parent phenotype.

6. A method of screening for cells having an altered phenotype, the method comprising the steps of:
   a) providing a population of cells having a parent phenotype, said population of cells comprising a nucleic acid sequence encoding a first element;
   b) introducing into said population of cells a library of fusion nucleic acids, said fusion nucleic acids each comprising:
      (1) a second element that is regulatable by said first element; and
      (2) a nucleic acid sequence encoding a candidate bioactive agent, wherein said nucleic acid sequence is operably linked to said second element;
   c) inducing the expression of said nucleic acid sequence encoding the candidate bioactive agent by expressing said first element in said population of cells;
   d) collecting a first subpopulation of cells having an altered phenotype;
   e) repressing the expression of said nucleic acid sequence by contacting said first subpopulation of cells with a third element;
   f) collecting a second subpopulation of cells having said parent phenotype;
   g) inducing the expression of said nucleic acid sequence by modulating said contacting of said second subpopulation of cells with said third element; and
   h) detecting a third subpopulation of cells having said altered phenotype.

7. The method according to claim 6 further comprising:
   i) collecting said third subpopulation of cells having said altered phenotype;
   j) repressing the expression of said nucleic acid sequence by contacting said third subpopulation of cells with said third element; and
   k) detecting a fourth subpopulation of cells having said parent phenotype.

8. The method according to claim 7 further comprising:
   l) collecting said fourth subpopulation of cells having said parent phenotype;
   m) inducing the expression of said nucleic acid sequence by modulating said contacting said fourth subpopulation of cells with said third element; and n) detecting a fifth subpopulation of cells having said altered phenotype.

9. The method according to any one of claims 4–5, wherein said first element comprises a reverse tetracycline-dependent transactivator (rtTA).

10. The method according to any one of claims 6–8, wherein said first element comprises a tetracycline-dependent transactivator (tTA).

11. The method according to any one of claims 4–5 and 6–8, wherein said second element comprises an tetracycline operator sequence (TetO).

12. The method according to any one of claims 4–5 and 6–8, wherein said second element comprises an oligomer of a tetracycline operator sequence (TetO).

13. The method according to any one of claims 4–5 and 6–8, wherein said third element comprises tetracycline (Tet).

14. The method according to any one of claims 4–5 and 6–8, wherein said third element comprises a tetracycline analogue.

15. The method according to any one of claims 4–5 and 6–8, wherein said third element comprises doxycycline (Tet).

16. The method according to any one of claims 4–5, wherein:
   said first element comprises a reverse tetracycline-dependent activator (rtTA);
   said second element comprises an oligomer of a tetracycline operator sequence (TetO); and
   said third element comprises tetracycline or doxycycline.

17. The method according to any one of claims 6–8, wherein:
   said first element comprises a tetracycline-dependent activator (rtTA);
   said second element comprises an oligomer of a tetracycline operator sequence (TetO); and
   said third element comprises tetracycline (Tet) or doxycycline (Dox).

18. The method according to any one of claims 4–5 and 6–8, wherein said population of cells comprise a stimulator and said parent phenotype is due to the presence of said stimulator.

19. The method according to any one of claims 4–5 and 6–8, wherein said fusion nucleic acids are each a component of a retroviral vector.

20. The method according to any one of claims 4–5 and 6–8, wherein said candidate bioactive agent is a polypeptide.

21. The method according to any-one of claims 4–5 and 6–8, wherein said candidate bioactive agent is a cyclic polypeptide.

22. The method according to any one of claims 4–5 and 6–8, wherein said first element is expressed stably or transiently.

23. The method according to any one of claims 4–5 and 6–8, wherein said first element is expressed constitutively.

24. The method according to any one of claims 4–5 and 6–8, wherein said first element is expressed in trans or in cis relative to said candidate bioactive agent.

25. The method according to any one of claims 4–5 and 6–8, wherein the expression of said first element is inducible.

26. The method according to any one of claims 4–5 and 6–8, wherein said fusion nucleic acids comprise said nucleic acid encoding said first element.

27. The method according to any one of claims 4–5 and 6–8, wherein said candidate bioactive agent is an RNA.

28. The method according to any one of claims 4–5 and 6–8, wherein said candidate bioactive agent is an antisense RNA.

29. The method according to any one of claims 4–5 and 6–8, wherein said candidate bioactive agent is a DNA.

30. The method according to any one of claims 4–5 and 6–8, wherein said nucleic acid sequence encoding the candidate bioactive agent comprises a full-length cDNA.

31. The method according to any one of claims 4–5 and 6–8, wherein said nucleic acid sequence encoding the candidate bioactive agent comprises a subsequence of a full-length cDNA.

32. The method according to any one of claims 4–5 and 6–8, wherein said nucleic acid sequence encoding the candidate bioactive agent comprises an antisense sequence of a full-length cDNA.

33. The method according to any one of claims 4–5 and 6–8, wherein said nucleic acid sequence encoding the candidate bioactive agent comprises an antisense sequence that is a subsequence of a full-length cDNA.

34. The method according to any one of claims 4–5 and 6–8, wherein said nucleic acid sequence encodes an amino acid sequence that is in-frame or out-of-frame as compared to the open reading frame (ORF)encoded by the amino acid sequence of a full-length cDNA, said amino acid sequence encoding said candidate bioactive agent.

35. The method according to any one of claims 4–5 and 6–8, wherein said library of fusion nucleic acids comprises about $10^3$ to $10^9$ different said nucleic acid sequences.

36. The method according to any one of claims 1–3 and 6–8, wherein said nucleic acid sequence encoding the candidate bioactive agent is a random nucleic acid sequence.

37. The method according to any one of claims 4–5 and 6–8, wherein said nucleic acid sequence encoding the candidate bioactive agent is a biased random nucleic acid sequence.

38. The method according to any one of claims 4–5 and 6–8, wherein said library comprises about $10^4$ to $10^8$ random nucleic acid sequences.

39. The method according to any one of claims 4–5 and 6–8, wherein said fusion nucleic acid further comprises a sequence encoding a reporter protein, wherein said reporter protein is operably linked to said nucleic acid sequence.

40. The method according to any one of claims 4–5 and 6–8, wherein said fusion nucleic acid further comprises a sequence encoding a reporter protein that is an autofluorescentprotein, wherein said reporter protein is operably linked to said nucleic acid sequence.

41. The method according to any one of claims 4–5 and 6–8, wherein said fusion nucleic acid further comprises a sequence encoding a reporter protein that is green fluorescent protein (GFP), wherein said reporter protein is operably linked to said nucleic acid sequence.

42. The method according to any one of claims 4–5 and 6–8, wherein said fusion nucleic acid further comprises a sequence encoding a reporter protein that is green fluorescent protein (GFP) from Aqueorea, wherein said reporter protein is operably linked to said nucleic acid sequence.

43. The method according to any one of claims 4–5 and 6–8, wherein said fusion nucleic acid further comprises a sequence encoding a reporter protein that is green fluorescent protein (GFP) from a *Renilla* species, wherein said reporter protein is operably linked to said nucleic acid sequence.

44. The method according to any of claims 4–5 and 6–8, wherein said collecting is by fluorescence-activated cell sorting (FACS).

45. The method according to any one of claims 4–5 and 6–8, wherein said fusion nucleic acid further comprises a third nucleic acid sequence encoding a reporter protein that is green fluorescent protein (GFP) from a *Renilla* species, wherein said reporter protein is operably linked to said third nucleic acid sequence; and wherein said collecting is by fluorescence-activated cell sorting (FACS).

46. The method according to any one of claims 4–5 and 6–8, wherein said cells of said population are mammalian cells.

47. The method according to any one of claims 4–5 and 6–8, wherein said altered phenotype comprises the modulation of cell cycle regulation due to the presence of said candidate bioactive agent.

48. The method according to any one of claims 4–5 and 6–8, wherein said altered phenotype comprises the modulation of exocytosis due to the presence of said candidate bioactive agent.

49. The method according to any of claims 4–5 and 6–8, wherein said altered phenotype comprises the modulation of T cell activation due to the presence of said candidate bioactive agent.

50. The method according to any one of claims 4–5 and 6–8, wherein said altered phenotype comprises the modulation of IgE synthesis due to the presence of said candidate bioactive agent.

51. The method according to any one of claims 4–5 and 6–8, wherein said altered phenotype comprises the modulation of IgE secretion due to the presence of said candidate bioactive agent.

52. The method according to any one of claims 4–5 and 6–8, wherein said altered phenotype comprises the modulation of antigen-induced B cell differentiation due to the presence of said candidate agent.

53. The method according to any one of claims 4–5 and 6–8, wherein said altered phenotype comprises the modulation of antigen-induced B cell isotype switching due the presence of said candidate agent.

54. The method according to any one of claims 4–5 and 6–8, wherein said altered phenotype comprises the modulation of IgE switching due to the presence of said candidate bioactive agent.

55. The method according to any one of claims 4–5 and 6–8, wherein said altered phenotype comprises the modulation of apoptosis due to the presence of said candidate bioactive agent.

56. The method according to any one of claims 4–5 and 6–8, wherein said altered phenotype comprises the modulation of angiogenesis due to the presence of said candidate bioactive agent.

57. The method according to any one of claims 4–5 and 6–8, wherein said altered phenotype comprises the modulation of T cell receptor (TCR) activation due to the presence of said candidate bioactive agent.

58. The method according to any one of claims 4–5 and 6–8, wherein said altered phenotype comprises the modulation of a T cell surface marker due to the presence of said candidate bioactive agent, wherein said marker is selected from a group of markers consisting of CD3, CD25, CD28, CD40L, CD69, CD95, and CD95L.

59. The method according to claim 5 further comprising:
k) collecting said fourth subpopulation of cells having said parent phenotype;
l) the expression of said nucleic acid sequence by contacting said fourth subpopulation of cells with said third element; and
m) detecting a fifth subpopulation of cells having said altered phenotype.

* * * * *